United States Patent
Aebi et al.

(10) Patent No.: US 9,260,408 B2
(45) Date of Patent: Feb. 16, 2016

(54) DIHYDROQUINOLINE-2-ONE DERIVATIVES

(75) Inventors: Johannes Aebi, Binningen (CH); Kurt Amrein, Itingen (CH); Benoit Hornsperger, Altkirch (FR); Henner Knust, Rheinfelden (DE); Bernd Kuhn, Reinach BL (CH); Yongfu Liu, Shanghai (CN); Hans P. Maerki, Basel (CH); Alexander V. Mayweg, Shanghai (CN); Peter Mohr, Basel (CH); Xuefei Tan, Shanghai (CN); Mingwei Zhou, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 302 days.

(21) Appl. No.: 13/612,956

(22) Filed: Sep. 13, 2012

(65) Prior Publication Data

US 2013/0072679 A1    Mar. 21, 2013

(30) Foreign Application Priority Data

Sep. 15, 2011   (WO) ................ PCT/CN2011/079673

(51) Int. Cl.
*C07D 401/04* (2006.01)
*C07D 401/14* (2006.01)
*C07D 405/14* (2006.01)
*C07D 413/14* (2006.01)
*C07D 417/14* (2006.01)
*C07D 471/04* (2006.01)
*C07D 471/06* (2006.01)
*C07D 487/10* (2006.01)
*C07F 7/18* (2006.01)
*A61P 13/12* (2006.01)
*A61P 9/04* (2006.01)
*A61P 9/12* (2006.01)

(52) U.S. Cl.
CPC ............ *C07D 401/04* (2013.01); *C07D 401/14* (2013.01); *C07D 405/14* (2013.01); *C07D 413/14* (2013.01); *C07D 417/14* (2013.01); *C07D 471/04* (2013.01); *C07D 471/06* (2013.01); *C07D 487/10* (2013.01); *C07F 7/1856* (2013.01)

(58) Field of Classification Search
CPC ......................... C07D 215/227; A61K 31/4704
USPC ......................................... 544/156; 514/312
See application file for complete search history.

(56) References Cited

U.S. PATENT DOCUMENTS

| | | | |
|---|---|---|---|
| 4,710,507 | A | 12/1987 | Campbell et al. |
| 2008/0176830 | A1 | 7/2008 | Adams et al. |
| 2010/0292225 | A1 | 11/2010 | Chamoin et al. |
| 2011/0112067 | A1 | 5/2011 | Hartmann et al. |

FOREIGN PATENT DOCUMENTS

| | | |
|---|---|---|
| FR | 2580646 | 10/1986 |
| WO | 2009135651 | 11/2009 |
| WO | 2010130773 | 11/2010 |

OTHER PUBLICATIONS (International Search Report for PCT/EP2012/067744 Nov. 16, 2012).
The English translation of the Taiwanese Office Action, issued on Dec. 4, 2013, in the corresponding Taiwanese application No. 101133381.
Lucas et al., Journal of Medicinal Chemistry (XP55040241), 54(7):2307-2319( 2011).
Intl Search Report for PCT/EP2012/067744 dated Oct. 12, 2012.
The Japanese Office Action mailed on Jan. 6, 2015 in the related Japanese patent application No. 2014-530184.
The English Translation of the Colombian Office Action, issued on Nov. 28, 2014, in the related Colombian patent application No. 14-040.934.

*Primary Examiner* — Susanna Moore

(57) ABSTRACT

The invention provides novel compounds having the general formula (I)

wherein $R^1$, $R^2$, $R^3$, $R^4$, $R^5$, $R^6$, $R^7$, $A^1$, $A^2$ and $A^3$ are as described herein, compositions including the compounds and methods of using the compounds. These compounds are useful for therapy or prophylaxis in a mammal, and in particular as aldosterone synthase (CYP11B2 or CYP11B1) inhibitors for the treatment or prophylaxis of chronic kidney disease, congestive heart failure, hypertension, primary aldosteronism and Cushing syndrome.

43 Claims, No Drawings

DIHYDROQUINOLINE-2-ONE DERIVATIVES

PRIORITY TO RELATED APPLICATION(S)

This application claims the benefit of International Patent Application PCT/CN2011/079673, which is hereby incorporated by reference in its entirety.

FIELD OF THE INVENTION

The present invention relates to organic compounds useful for therapy or prophylaxis in a mammal, and in particular to aldosterone synthase (CYP11B2 or CYP11B1) inhibitors for the treatment or prophylaxis of chronic kidney disease, congestive heart failure, hypertension, primary aldosteronism and Cushing syndrome.

BACKGROUND OF THE INVENTION

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

SUMMARY OF THE INVENTION

The present invention provides novel compounds of formula (I)

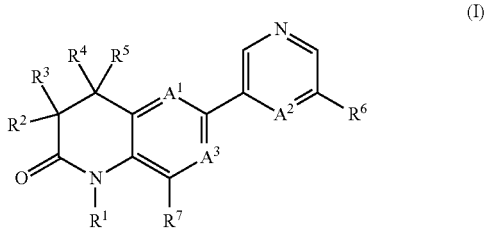

wherein
$R^1$ is H, alkyl, haloalkyl, cycloalkyl or halocycloalkyl;
$R^2$ is H, alkyl, haloalkyl, cycloalkyl or halocycloalkyl;
$R^3$ is H, alkyl, haloalkyl, cycloalkyl or halocycloalkyl;
$R^4$ is H, alkyl, haloalkyl, cycloalkyl or halocycloalkyl;
or $R^3$ and $R^4$ together with the carbon atoms to which they are attached form a double bond;
$R^5$ is H, alkyl, haloalkyl, cycloalkyl or halocycloalkyl;
$R^6$ is H or $R^8$, wherein in case $R^6$ is H then at least one of $A^1$ and $A^3$ is N;
$R^7$ is H, halogen, alkyl, haloalkyl, cycloalkyl or halocycloalkyl;
or $R^1$ and $R^7$ together with the nitrogen and carbon atoms to which they are attached form a heterocycloalkyl substituted with one to three substituents independently selected from H, alkyl, haloalkyl, cycloalkyl or halocycloalkyl;
$R^8$ is $-O_m-(CR^9R^{10})_n-(CR^{11}R^{12})_p-(CR^{13}R^{14})_q-NR^{15}R^{16}$,
$-N_mR^{17}-(CR^9R^{10})_n-(CR^{11}R^{12})_p-(CR^{13}R^{14})_q-NR^{15}R^{16}$ or
$-S_m(O)_r-(CR^9R^{10})_n-(CR^{11}R^{12})_p-(CR^{13}R^{14})_q-NR^{15}R^{16}$;
$R^9$ is H, alkyl, haloalkyl, cycloalkyl or halocycloalkyl;
$R^{10}$ is H, alkyl, haloalkyl, cycloalkyl or halocycloalkyl;
$R^{11}$ is H, alkyl, haloalkyl, cycloalkyl or halocycloalkyl;
or $R^{10}$ and $R^{11}$ together with the carbon atoms to which they are attached form a double bond;
$R^{12}$ is H, alkyl, haloalkyl, cycloalkyl or halocycloalkyl;
or $R^{11}$ and $R^{12}$ together with the carbon atom to which they are attached form a cycloalkyl or a heterocycloalkyl;
$R^{13}$ is H, alkyl, haloalkyl, cycloalkyl or halocycloalkyl;
$R^{14}$ is H, alkyl, haloalkyl, cycloalkyl or halocycloalkyl;
or $R^{10}$ and $R^{14}$ together form $-(CH_2)_t-$;
$R^{15}$ is H, alkyl, haloalkyl, cycloalkyl, halocycloalkyl, alkoxyalkyl, haloalkoxyalkyl or hydroxyalkyl;
$R^{16}$ is H, alkyl, haloalkyl, cycloalkyl, halocycloalkyl, hydroxyalkyl, alkoxyalkyl, haloalkoxyalkyl, phenylalkyl, substituted phenylalkyl, aryl, substituted aryl, heterocycloalkyl, substituted heterocycloalkyl, heteroaryl, substituted heteroaryl, $-S(O)_2R^{18}$, $-S(O)R^{18}$, $-S(O)_2OR^{18}$, $-S(O)_2NR^{18}R^{19}$, $-C(O)R^{18}$, $-C(O)OR^{18}$ or $-C(O)NR^{18}R^{19}$, wherein substituted phenylalkyl, substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl, wherein in case $R^{15}$ is H or alkyl and $R^{16}$ is H or alkyl, then the sum of n, p and q is at least 1;
or $R^{15}$ and $R^{16}$ together with the nitrogen atom to which they are attached form a substituted heterocycloalkyl or a substituted heteroaryl, wherein substituted heterocycloalkyl and substituted heteroaryl are substituted with $R^{23}$, $R^{24}$ and $R^{25}$;
or $R^{13}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;
or $R^{11}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;
or $R^9$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;
$R^{17}$ is H, alkyl, haloalkyl, cycloalkyl or halocycloalkyl;
$R^{18}$ is alkyl, cycloalkyl, haloalkyl, halocycloalkyl, hydroxyalkyl, halohydroxyalkyl, alkoxyalkyl, haloalkoxyalkyl, alkylcarbonyloxyalkyl, aryl, substituted aryl, heterocycloalkyl, substituted heterocycloalkyl, heteroaryl, substituted heteroaryl, wherein substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;
$R^{19}$ is H, alkyl, haloalkyl, cycloalkyl or halocycloalkyl;
$A^1$ is $CR^{20}$ or N;
$A^2$ is $CR^{21}$ or N;
$A^3$ is $CR^{22}$ or N;
$R^{20}$ is H, halogen, alkyl, haloalkyl, cycloalkyl or halocycloalkyl;
$R^{21}$ is H, halogen, alkyl, haloalkyl, cycloalkyl or halocycloalkyl;
$R^{22}$ is H, halogen, alkyl, haloalkyl, cycloalkyl or halocycloalkyl;
$R^{23}$, $R^{24}$ and $R^{25}$ are each independently selected from H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, $-S(O)_2R^{18}$, $-C(O)R^{18}$, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

wherein in case m is zero and $R^9$ and $R^{15}$, or $R^{11}$ and $R^{15}$ or $R^{13}$ and $R^{15}$ or $R^{15}$ and $R^{16}$ together with the nitrogen and carbon atoms to which they are attached form a substituted heterocycloalkyl or a substituted heteroaryl, then at least one of $R^{23}$, $R^{24}$, $R^{25}$ and $R^{16}$ is different from H, alkyl, haloalkyl, alkoxy, haloalkoxy, halogen, hydroxy, cyano, amino, substituted amino, aminocarbonyl, substituted aminocarbonyl, wherein substituted amino and substituted aminocarbonyl are substituted on the nitrogen atom with one to two alkyl, and —C(O)$R^{18}$, —S(O)$_2R^{18}$, wherein $R^{18}$ is alkyl, haloalkyl, hydroxyalkyl, halohydroxyalkyl, alkoxyalkyl or haloalkoxyalkyl;

m is zero or 1, wherein in case m is 1, then the sum of n and p is 2, 3 or 4;
n is zero, 1 or 2;
P is zero, 1 or 2;
q is zero, 1 or 2;
r is zero, 1 or 2, wherein in case m is zero then r is zero;
t is zero, 1 or 2;
or pharmaceutically acceptable salts or esters thereof.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and tert-butoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl and ethoxypropyl. Particular alkoxyalkyl group include methoxymethyl and methoxyethyl. More particular alkoxyalkyl group is methoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is methoxy or tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, and tert-butyl. Particular alkyl groups include methyl, isopropyl or ethyl. More particular alkyl group is methyl.

The term "alkylcarbonyl" of the formula —C(O)—R', wherein R' is an alkyl group. Examples of alkylcarbonyl groups include groups of the formula —C(O)—R', wherein R' is methyl or ethyl.

The term "alkylcarbonylamino" denotes an amino group wherein one of the hydrogen atoms of the —NH$_2$ group is replaced by an alkylcarbonyl group. Examples of alkylcarbonylamino groups include groups wherein R' is methyl or ethyl.

The term "alkylcarbonylaminoalkyl" denotes an aminoalkyl group wherein one of the hydrogen atoms of the —NH$_2$ group is replaced by an alkylcarbonyl group. Examples of alkylcarbonylaminoalkyl groups include groups wherein R' is methyl or ethyl.

The term "alkylcarbonyloxyalkyl" denotes a hydroxyalkyl group wherein the hydrogen atom of the —OH group is replaced by an alkylcarbonyl group. Examples of alkylcarbonyloxyalkyl groups include alkylcarbonyloxymethyl and alkylcarbonyloxyethyl. Particular alkylcarbonyloxyalkyl group is alkylcarbonyloxymethyl. More particular alkylcarbonyloxyalkyl group is methylcarbonyloxymethyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "amino" denotes a —NH$_2$ group.

The term "aminoalkyl" denotes an alkyl group wherein at least one of the hydrogen atoms of the alkyl group has been replaced by an amino group. Examples of aminoalkyl include aminomethyl, aminoethyl, aminopropyl, aminomethylpropyl and diaminopropyl.

The term "aminocarbonyl" of the formula —C(O)—NH$_2$

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylcarbonylamino" denotes an amino group wherein one of the hydrogen atoms of the —NH$_2$ group is replaced by a cycloalkylcarbonyl group. Examples of alkylcarbonylamino groups include groups wherein R' is cyclopropyl.

The term "cycloalkylcarbonylaminoalkyl" denotes an aminoalkyl group wherein one of the hydrogen atoms of the —NH$_2$ group is replaced by a cycloalkylcarbonyl group. Examples of alkylcarbonylaminoalkyl groups include groups wherein R' is cyclopropyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2-difluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2-difluoroethoxyethyl The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "halohydroxyalkyl" denotes an alkyl group wherein at least one of the hydrogen atoms of the alkyl group has been replaced by same or different halogen atoms and at least one of the hydrogen atoms of the alkyl group has been replaced by hydroxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, isoxazolyl and isothiazolyl. More particular heteroaryl groups include imidazolyl, oxazolyl, thiazolyl, oxadiazolyl, thiadiazolyl, tetrazolyl, pyridinyl, pyrazinyl, pyrazolyl, pyridazinyl, pyrimidinyl, isoxazolyl and isothiazolyl.

In particular in the definition of $R^{18}$, particular heteroaryl groups include imidazolyl, oxazolyl, furanyl, oxadiazolyl, pyridinyl, pyrazinyl, pyrazolyl, pyridazinyl, pyrimidinyl and isoxazolyl. More particularly oxazolyl, pyridinyl and pyrazolyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl and thiazinanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, 3-thia-9-aza-bicyclo[3.3.1]nonyl and 2,6-diaza-spiro[3.3]heptanyl. Examples for partly unsaturated heterocycloalkyl are dihydrofuryl, imidazolinyl, dihydro-oxazolyl, tetrahydro-pyridinyl, or dihydropyranyl. More particular examples of heterocycloalkyl group are pyrrolidinyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, thiazinanyl and 2,6-diaza-spiro[3.3]heptanyl. More particular examples of a heterocycloalkyl are pyrrolydinyl, piperidinyl, thiomorpholinyl, thiazinanyl and 2,6-diaza-spiro[3.3]heptanyl.

In particular in the definition of $R^{16}$, particular heterocycloalkyl group is oxetanyl.

In particular, the heterocycloalkyl formed by $R^9$ and $R^{15}$ together with the nitrogen and carbon atoms to which they are attached is azetidinyl, pyrrolidinyl, piperidinyl or tetrahydropyridinyl. More particularly, pyrrolidinyl.

In particular, the heterocycloalkyl formed by $R^{11}$ and $R^{15}$ together with the nitrogen and carbon atoms to which they are attached is azetidinyl or pyrrolidinyl.

In particular, the heterocycloalkyl formed by $R^{15}$ and $R^{16}$ together with the nitrogen and carbon atoms to which they are attached is pyrrolidinyl, piperidinyl, thiomorpholinyl, thiazinanyl, isothiazolidinyl, 1,1-dioxo-thiomorpholin-4-yl or 2,6-diaza-spiro[3.3]heptanyl. More particularly, thiomorpholinyl or 1,1-dioxo-thiomorpholin-4-yl. Further particularly, pyrrolidinyl or 1,1-dioxo-thiomorpholin-4-yl.

In particular, the heterocycloalkyl formed by $R^{11}$ and $R^{12}$ together with the nitrogen and carbon atoms to which they are attached is oxetanyl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular example is hydroxymethyl.

The term "oxo" denotes a divalent oxygen atom =O.

The term "phenylalkyl" denotes an alkyl group wherein one of the hydrogen atoms of the alkyl group has been replaced by a phenyl. Examples of phenylalkyl are benzyl and phenylethyl. Particular example of phenylalkyl is benzyl.

The term "tetrazolylalkyl" denotes an alkyl group wherein one of the hydrogen atoms of the alkyl group has been replaced by a tetrazolyl. Examples of tetrazolylalkyl are tetrazolylmethyl and tetrazolylethyl. Particular example of tetrazolylalkyl is tetrazolylmethyl.

The term "triazolylalkyl" denotes an alkyl group wherein one of the hydrogen atoms of the alkyl group has been replaced by a triazolyl. Examples of triazolylalkyl are triazolylmethyl and triazolylethyl. Particular example of triazolylalkyl is triazolylmethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc). The abbreviation uM means microMolar and is equivalent to the symbol μM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H ("T"), $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^2$H atom are also an embodiment of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The present invention provides novel compounds of formula (I)

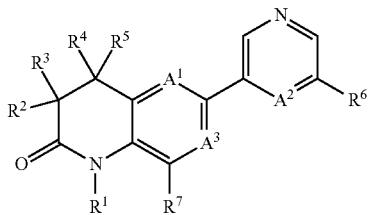

(I)

wherein
$R^1$ is H, alkyl, haloalkyl, cycloalkyl or halocycloalkyl;
$R^2$ is H, alkyl, haloalkyl, cycloalkyl or halocycloalkyl;
$R^3$ is H, alkyl, haloalkyl, cycloalkyl or halocycloalkyl;
$R^4$ is H, alkyl, haloalkyl, cycloalkyl or halocycloalkyl;
or $R^3$ and $R^4$ together with the carbon atoms to which they are attached form a double bond;
$R^5$ is H, alkyl, haloalkyl, cycloalkyl or halocycloalkyl;
$R^6$ is H or $R^8$, wherein in case $R^6$ is H then at least one of $A^1$ and $A^3$ is N;
$R^7$ is H, halogen, alkyl, haloalkyl, cycloalkyl or halocycloalkyl;
or $R^1$ and $R^7$ together with the nitrogen and carbon atoms to which they are attached form a heterocycloalkyl substituted with one to three substituents independently selected from H, alkyl, haloalkyl, cycloalkyl or halocycloalkyl;
$R^8$ is $-O_m-(CR^9R^{10})_n-(CR^{11}R^{12})_p-(CR^{13}R^{14})_q-NR^{15}R^{16}$,
$-N_mR^{17}-(CR^9R^{10})_n-(CR^{11}R^{12})_p-(CR^{13}R^{14})_q-NR^{15}R^{16}$ or
$-S_m(O)_r-(CR^9R^{10})_n-(CR^{11}R^{12})_p-(CR^{13}R^{14})_q-NR^{15}R^{16}$;
$R^9$ is H, alkyl, haloalkyl, cycloalkyl or halocycloalkyl;
$R^{10}$ is H, alkyl, haloalkyl, cycloalkyl or halocycloalkyl;
$R^{11}$ is H, alkyl, haloalkyl, cycloalkyl or halocycloalkyl;
or $R^{10}$ and $R^{11}$ together with the carbon atoms to which they are attached form a double bond;
$R^{12}$ is H, alkyl, haloalkyl, cycloalkyl or halocycloalkyl;
or $R^{11}$ and $R^{12}$ together with the carbon atom to which they are attached form a cycloalkyl or a heterocycloalkyl;
$R^{13}$ is H, alkyl, haloalkyl, cycloalkyl or halocycloalkyl;
$R^{14}$ is H, alkyl, haloalkyl, cycloalkyl or halocycloalkyl;
or $R^{10}$ and $R^{14}$ together form $-(CH_2)_t-$;
$R^{15}$ is H, alkyl, haloalkyl, cycloalkyl, halocycloalkyl, alkoxyalkyl, haloalkoxyalkyl or hydroxyalkyl;
$R^{16}$ is H, alkyl, haloalkyl, cycloalkyl, halocycloalkyl, hydroxyalkyl, alkoxyalkyl, haloalkoxyalkyl, phenylalkyl, substituted phenylalkyl, aryl, substituted aryl, heterocycloalkyl, substituted heterocycloalkyl, heteroaryl, substituted heteroaryl, $-S(O)_2R^{18}$, $-S(O)R^{18}$, $-S(O)_2OR^{18}$, $-S(O)_2NR^{18}R^{19}$, $-C(O)R^{18}$, $-C(O)OR^{18}$ or $-C(O)NR^{18}R^{19}$, wherein substituted phenylalkyl, substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl, wherein in case $R^{15}$ is H or alkyl and $R^{16}$ is H or alkyl, then the sum of n, p and q is at least 1; or $R^{15}$ and $R^{16}$ together with the nitrogen atom to which they are attached form a substituted heterocycloalkyl or a substituted heteroaryl, wherein substituted heterocycloalkyl and substituted heteroaryl are substituted with $R^{23}$, $R^{24}$ and $R^{25}$;
or $R^{13}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;

or $R^{11}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;

or $R^9$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;

$R^{17}$ is H, alkyl, haloalkyl, cycloalkyl or halocycloalkyl;

$R^{18}$ is alkyl, cycloalkyl, haloalkyl, halocycloalkyl, hydroxyalkyl, halohydroxyalkyl, alkoxyalkyl, haloalkoxyalkyl, alkylcarbonyloxyalkyl, aryl, substituted aryl, heterocycloalkyl, substituted heterocycloalkyl, heteroaryl, substituted heteroaryl, wherein substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

$R^{19}$ is H, alkyl, haloalkyl, cycloalkyl or halocycloalkyl;

$A^1$ is $CR^{20}$ or N;

$A^2$ is $CR^{21}$ or N;

$A^3$ is $CR^{22}$ or N;

$R^{20}$ is H, halogen, alkyl, haloalkyl, cycloalkyl or halocycloalkyl;

$R^{21}$ is H, halogen, alkyl, haloalkyl, cycloalkyl or halocycloalkyl;

$R^{22}$ is H, halogen, alkyl, haloalkyl, cycloalkyl or halocycloalkyl;

$R^{23}$, $R^{24}$ and $R^{25}$ are each independently selected from H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, —S(O)$_2$R$^{18}$, —C(O)R$^{18}$, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

wherein in case m is zero and $R^9$ and $R^{15}$, or $R^{11}$ and $R^{15}$ or $R^{13}$ and $R^{15}$ or $R^{15}$ and $R^{16}$ together with the nitrogen and carbon atoms to which they are attached form a substituted heterocycloalkyl or a substituted heteroaryl, then at least one of $R^{23}$, $R^{24}$, $R^{25}$ and $R^{16}$ is different from H, alkyl, haloalkyl, alkoxy, haloalkoxy, halogen, hydroxy, cyano, amino, substituted amino, aminocarbonyl, substituted aminocarbonyl, wherein substituted amino and substituted aminocarbonyl are substituted on the nitrogen atom with one to two alkyl, and —C(O)R$^{18}$, —S(O)$_2$R$^{18}$, wherein R$^{18}$ is alkyl, haloalkyl, hydroxyalkyl, halohydroxyalkyl, alkoxyalkyl or haloalkoxyalkyl;

m is zero or 1, wherein in case m is 1, then the sum of n and p is 2, 3 or 4;

n is zero, 1 or 2;

P is zero, 1 or 2;

q is zero, 1 or 2;

r is zero, 1 or 2, wherein in case m is zero then r is zero;

t is zero, 1 or 2;

or pharmaceutically acceptable salts or esters thereof.

A particular embodiment of the present invention are compounds according to formula (I) or pharmaceutically acceptable salts thereof.

A further embodiment of the present invention are compounds according to formula (I) as described herein, wherein $R^1$ is H, alkyl, haloalkyl, cycloalkyl or halocycloalkyl;

$R^2$ is H, alkyl, haloalkyl, cycloalkyl or halocycloalkyl;

$R^3$ is H, alkyl, haloalkyl, cycloalkyl or halocycloalkyl;

$R^4$ is H, alkyl, haloalkyl, cycloalkyl or halocycloalkyl;

$R^5$ is H, alkyl, haloalkyl, cycloalkyl or halocycloalkyl;

$R^6$ is H or $R^8$, wherein in case $R^6$ is H then at least one of $A^1$ and $A^3$ is N;

$R^7$ is H, halogen, alkyl, haloalkyl, cycloalkyl or halocycloalkyl;

$R^8$ is —O$_m$—(CR$^9$R$^{10}$)$_n$—(CR$^{11}$R$^{12}$)$_p$—(CR$^{13}$R$^{14}$)$_q$—NR$^{15}$R$^{16}$,

—N$_m$R$^{17}$—(CR$^9$R$^{10}$)$_n$—(CR$^{11}$R$^{12}$)$_p$—(CR$^{13}$R$^{14}$)$_q$—NR$^{15}$R$^{16}$ or

—S$_m$(O)$_r$—(CR$^9$R$^{10}$)$_n$—(CR$^{11}$R$^{12}$)$_p$—(CR$^{13}$R$^{14}$)$_q$—NR$^{15}$R$^{16}$;

$R^9$ is H, alkyl, haloalkyl, cycloalkyl or halocycloalkyl;

$R^{10}$ is H, alkyl, haloalkyl, cycloalkyl or halocycloalkyl;

$R^{11}$ is H, alkyl, haloalkyl, cycloalkyl or halocycloalkyl;

$R^{12}$ is H, alkyl, haloalkyl, cycloalkyl or halocycloalkyl;

or $R^{11}$ and $R^{12}$ together with the carbon atom to which they are attached form a cycloalkyl;

$R^{13}$ is H, alkyl, haloalkyl, cycloalkyl or halocycloalkyl;

$R^{14}$ is H, alkyl, haloalkyl, cycloalkyl or halocycloalkyl;

or $R^{10}$ and $R^{14}$ together form —(CH$_2$)$_t$—;

$R^{15}$ is H, alkyl, haloalkyl, cycloalkyl, halocycloalkyl, alkoxyalkyl, haloalkoxyalkyl or hydroxyalkyl;

$R^{16}$ is H, alkyl, haloalkyl, cycloalkyl, halocycloalkyl, hydroxyalkyl, alkoxyalkyl, haloalkoxyalkyl, phenylalkyl, substituted phenylalkyl, aryl, substituted aryl, heterocycloalkyl, substituted heterocycloalkyl, heteroaryl, substituted heteroaryl, —S(O)$_2$R$^{18}$, —S(O)$_2$OR$^{18}$, —S(O)$_2$NR$^{18}$R$^{19}$, —C(O)R$^{18}$, —C(O)OR$^{18}$ or —C(O)NR$^{18}$R$^{19}$, wherein substituted phenylalkyl, substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl, wherein in case $R^{15}$ is H or alkyl and $R^{16}$ is H or alkyl, then the sum of n, p and q is at least 1;

or $R^{15}$ and $R^{16}$ together with the nitrogen atom to which they are attached form a substituted heterocycloalkyl or a substituted heteroaryl, wherein substituted heterocycloalkyl and substituted heteroaryl are substituted with $R^{23}$, $R^{24}$ and $R^{25}$;

or $R^{13}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;

or $R^{11}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;

or $R^9$ and $R^{15}$ together with the nitrogen and carbon atoms to which they are attached form a $R^{24}$ substituted heterocycloalkyl, wherein substituted heterocycloalkyl is substituted with $R^{23}$, $R^{24}$ and $R^{25}$;

$R^{17}$ is H, alkyl, haloalkyl, cycloalkyl or halocycloalkyl;

$R^{18}$ is alkyl, cycloalkyl, haloalkyl, halocycloalkyl, hydroxyalkyl, halohydroxyalkyl, alkoxyalkyl, haloalkoxyalkyl, alkylcarbonyloxyalkyl, aryl, substituted aryl, heterocycloalkyl, substituted heterocycloalkyl, heteroaryl, substituted heteroaryl, wherein substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

$R^{19}$ is H, alkyl, haloalkyl, cycloalkyl or halocycloalkyl;

$A^1$ is $CR^{20}$ or N;

$A^2$ is $CR^{21}$ or N;

$A^3$ is $CR^{22}$ or N;

$R^{20}$ is H, halogen, alkyl, haloalkyl, cycloalkyl or halocycloalkyl;

$R^{21}$ is H, halogen, alkyl, haloalkyl, cycloalkyl or halocycloalkyl;

$R^{22}$ is H, halogen, alkyl, haloalkyl, cycloalkyl or halocycloalkyl;

$R^{23}$, $R^{24}$ and $R^{25}$ are each independently selected from H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, —S(O)$_2$R$^{18}$, —C(O)R$^{18}$, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

wherein in case m is zero, then at least one of $R^{23}$, $R^{24}$ and $R^{25}$ is different from H, alkyl, haloalkyl, alkoxy, haloalkoxy, halogen, hydroxy, cyano, amino, substituted amino, aminocarbonyl or substituted aminocarbonyl, wherein substituted amino and substituted aminocarbonyl are substituted on the nitrogen atom with one to two alkyl;

m is zero or 1, wherein in case m is 1, then the sum of n and p is 2, 3 or 4;

n is zero, 1 or 2;

P is zero, 1 or 2;

q is zero, 1 or 2;

r is zero, 1 or 2, wherein in case m is zero then r is zero;

t is zero, 1 or 2;

or pharmaceutically acceptable salts or esters.

A further embodiment of the present invention are compounds according to formula (I) as described herein, wherein $R^1$ is H, alkyl, haloalkyl, cycloalkyl or halocycloalkyl.

A further embodiment of the present invention are compounds according to formula (I) as described herein, wherein $R^1$ is H or alkyl.

A particular embodiment of the present invention are compounds according to formula (I) as described herein, wherein $R^1$ is alkyl.

In a further embodiment of the present invention are compounds according to formula (I) as described herein, wherein $R^1$ is methyl.

Another further embodiment of the present invention are compounds according to formula (I) as described herein, wherein $R^2$ is H.

Another embodiment of the present invention are compounds according to formula (I) as described herein, wherein $R^3$ is H, alkyl, haloalkyl, cycloalkyl or halocycloalkyl.

Another embodiment of the present invention are compounds according to formula (I) as described herein, wherein $R^3$ is H.

The present invention also relates to compounds according to formula (I) as described herein, wherein $R^4$ is H, alkyl, haloalkyl, cycloalkyl or halocycloalkyl.

The present invention also relates to compounds according to formula (I) as described herein, wherein $R^4$ is H or alkyl.

A further particular embodiment of the present invention are compounds according to formula (I) as described herein, wherein $R^4$ is H.

A more particular embodiment of the present invention are compounds according to formula (I) as described herein, wherein $R^5$ is H or alkyl.

Also an embodiment of the present invention are compounds according to formula (I) as described herein, wherein $R^5$ is H.

The present invention also relates to compounds according to formula (I) as described herein, wherein $R^6$ is H and at least one of $A^1$ and $A^3$ is N.

Another embodiment of the present invention are compounds according to formula (I) as described herein, wherein $R^6$ is $R^8$.

A further particular embodiment of the present invention are compounds according to formula (I) as described herein, wherein is $R^7$ is H, halogen, alkyl, haloalkyl, cycloalkyl or halocycloalkyl.

A further particular embodiment of the present invention are compounds according to formula (I) as described herein, wherein is $R^7$ is H.

A further particular embodiment of the present invention are compounds according to formula (I) as described herein, wherein $R^1$ and $R^7$ together with the nitrogen and carbon atoms to which they are attached form a heterocycloalkyl substituted with one to three substituents independently selected from H, alkyl, haloalkyl, cycloalkyl or halocycloalkyl.

A particular embodiment of the present invention are compounds according to formula (I) as described herein, wherein $R^8$ is $-O_m-(CR^9R^{10})_n-(CR^{11}R^{12})_p-(CR^{13}R^{14})_q-NR^{15}R^{16}$.

Also an embodiment of the present invention are compounds according to formula (I) as described herein, wherein $R^9$H, alkyl, haloalkyl, cycloalkyl or halocycloalkyl.

The present invention also relates to compounds according to formula (I) as described herein, wherein $R^9$ is H, alkyl or cycloalkyl.

The present invention also relates to compounds according to formula (I) as described herein, wherein $R^9$ is H or alkyl.

The present invention also relates to compounds according to formula (I) as described herein, wherein $R^9$ is H.

Another embodiment of the present invention are compounds according to formula (I) as described herein, wherein $R^{10}$ is H, alkyl, haloalkyl, cycloalkyl or halocycloalkyl.

Another embodiment of the present invention are compounds according to formula (I) as described herein, wherein $R^{10}$ is H or alkyl.

The present invention also relates to compounds according to formula (I) as described herein, wherein $R^{10}$ is H.

Also an embodiment of the present invention are compounds according to formula (I) as described herein, wherein $R^{11}$ is H, alkyl, haloalkyl, cycloalkyl or halocycloalkyl.

Also an embodiment of the present invention are compounds according to formula (I) as described herein, wherein $R^{11}$ is H.

Also an embodiment of the present invention are compounds according to formula (I) as described herein, wherein $R^{10}$ and $R^{11}$ together with the carbon atoms to which they are attached form a double bond.

Another embodiment of the present invention are compounds according to formula (I) as described herein, wherein $R^{12}$ is H.

Also an embodiment of the present invention are compounds according to formula (I) as described herein, wherein $R^{11}$ and $R^{12}$ together with the carbon atom to which they are attached form a cycloalkyl.

A particular embodiment of the present invention are compounds according to formula (I) as described herein, wherein $R^{13}$ is H.

A further particular embodiment of the present invention are compounds according to formula (I) as described herein, wherein $R^{14}$ is H, alkyl, haloalkyl, cycloalkyl or halocycloalkyl.

A more particular embodiment of the present invention are compounds according to formula (I) as described herein, wherein $R^{14}$ is H.

Also a particular embodiment of the present invention are compounds according to formula (I) as described herein, wherein $R^{10}$ and $R^{14}$ together form $-(CH_2)_t-$.

Also a particular embodiment of the present invention are compounds according to formula (I) as described herein, wherein $R^{15}$ is H, alkyl, haloalkyl, cycloalkyl, halocycloalkyl, alkoxyalkyl, haloalkoxyalkyl or hydroxyalkyl.

Also a particular embodiment of the present invention are compounds according to formula (I) as described herein, wherein $R^{15}$ is H, alkyl or alkoxyalkyl.

Also a particular embodiment of the present invention are compounds according to formula (I) as described herein, wherein $R^{15}$ is H or alkyl.

Another embodiment of the present invention are compounds according to formula (I) as described herein, wherein $R^{15}$ is H.

Also a particular embodiment of the present invention are compounds according to formula (I) as described herein, wherein $R^9$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$.

Another embodiment of the present invention are compounds according to formula (I) as described herein, wherein $R^{16}$ is H, alkyl, haloalkyl, cycloalkyl, halocycloalkyl, hydroxyalkyl, alkoxyalkyl, haloalkoxyalkyl, phenylalkyl, substituted phenylalkyl, aryl, substituted aryl, heterocycloalkyl, substituted heterocycloalkyl, heteroaryl, substituted heteroaryl, $-S(O)_2R^{18}$, $-S(O)_2OR^{18}$, $-S(O)_2NR^{18}R^{19}$, $-C(O)R^{18}$, $-C(O)OR^{18}$ or $-C(O)NR^{18}R^{19}$, wherein substituted phenylalkyl, substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl, wherein in case $R^{15}$ is H or alkyl and $R^{16}$ is H or alkyl, then the sum of n, p and q is at least 1.

Also an embodiment of the present invention are compounds according to formula (I) as described herein, wherein $R^{16}$ is H, hydroxyalkyl, phenylalkyl, heterocycloalkyl substituted with alkyl, $-S(O)R^{18}$, $-S(O)_2R^{18}$, $-C(O)R^{18}$ or $-C(O)OR^{18}$, wherein in case $R^{15}$ is H or alkyl and $R^{16}$ is H or alkyl, then the sum of n, p and q is at least 1. Also an embodiment of the present invention are compounds according to formula (I) as described herein, wherein $R^{16}$ is H, hydroxyalkyl, phenylalkyl, $-S(O)_2R^{18}$, $-C(O)R^{18}$ or $-C(O)OR^{18}$, wherein in case $R^{15}$ is H or alkyl and $R^{16}$ is H or alkyl, then the sum of n, p and q is at least 1.

Also an embodiment of the present invention are compounds according to formula (I) as described herein, wherein $R^{16}$ is hydroxyalkyl, $-S(O)_2R^{18}$, $-C(O)R^{18}$ or $-C(O)OR^{18}$.

Also an embodiment of the present invention are compounds according to formula (I) as described herein, wherein $R^{16}$ is H, hydroxyalkyl or phenylalkyl, wherein in case $R^{15}$ is H or alkyl and $R^{16}$ is H or alkyl, then the sum of n, p and q is at least 1.

Also an embodiment of the present invention are compounds according to formula (I) as described herein, wherein $R^{16}$ is H, hydroxyethyl, hydroxymethylbutyl or benzyl, wherein in case $R^{15}$ is H or alkyl and $R^{16}$ is H or alkyl, then the sum of n, p and q is at least 1.

Also an embodiment of the present invention are compounds according to formula (I) as described herein, wherein $R^{16}$ is hydroxyalkyl or $-S(O)_2R^{18}$.

A further embodiment of the present invention are compounds according to formula (I) as described herein, wherein $R^{16}$ is hydroxyalkyl.

Also an embodiment of the present invention are compounds according to formula (I) as described herein, wherein $R^{16}$ is hydroxyethyl, hydroxymethylbutyl or benzyl.

Another embodiment of the present invention are compounds according to formula (I) as described herein, wherein $R^{16}$ is —S(O)$_2$R$^{18}$.

Another embodiment of the present invention are compounds according to formula (I) as described herein, wherein $R^{16}$ is —C(O)R$^{18}$.

A further embodiment of the present invention are compounds according to formula (I) as described herein, wherein $R^{15}$ and $R^{16}$ together with the nitrogen atom to which they are attached form a substituted heterocycloalkyl or a substituted heteroaryl, wherein substituted heterocycloalkyl and substituted heteroaryl are substituted with $R^{23}$, $R^{24}$ and $R^{25}$.

A particular embodiment of the present invention are compounds according to formula (I) as described herein, wherein $R^{15}$ and $R^{16}$ together with the nitrogen atom to which they are attached form a substituted heterocycloalkyl wherein substituted heterocycloalkyl is substituted with one to three substituents independently selected from hydroxyalkyl, alkoxyalkyl, haloalkoxyalkyl, alkoxycarbonyl, oxo, triazolylalkyl and substituted aminoalkyl, wherein substituted aminoalkyl is substituted on the nitrogen atom with one to two alkyl.

A further particular embodiment of the present invention are compounds according to formula (I) as described herein, wherein $R^{15}$ and $R^{16}$ together with the nitrogen atom to which they are attached form a substituted heterocycloalkyl wherein substituted heterocycloalkyl is substituted with one to three substituents independently selected from hydroxyalkyl and oxo.

A more particular embodiment of the present invention are compounds according to formula (I) as described herein, wherein the heterocycloalkyl formed by $R^{15}$ and $R^{16}$ together with the nitrogen atom to which they are attached is selected from pyrrolydinyl, piperidinyl, thiomorpholinyl, thiazinanyl, isothiazolidinyl and 2,6-diaza-spiro[3.3]heptanyl. A more particular embodiment of the present invention are compounds according to formula (I) as described herein, wherein the heterocycloalkyl formed by $R^{15}$ and $R^{16}$ together with the nitrogen atom to which they are attached is selected from pyrrolydinyl, piperidinyl, thiomorpholinyl, thiazinanyl and 2,6-diaza-spiro[3.3]heptanyl.

Another embodiment of the present invention are compounds according to formula (I) as described herein, wherein $R^{15}$ and $R^{16}$ together with the nitrogen atom to which they are attached form 2-hydroxymethyl-pyrrolidin-1-yl, 2-hydroxymethyl-5-oxo-pyrrolidin-1-yl or isothiazolidinyl substituted on the sulfur atom by two oxo.

Another embodiment of the present invention are compounds according to formula (I) as described herein, wherein $R^{15}$ and $R^{16}$ together with the nitrogen atom to which they are attached form 2-hydroxymethyl-pyrrolidin-1-yl or 2-hydroxymethyl-5-oxo-pyrrolidin-1-yl.

Another particular embodiment of the present invention are compounds according to formula (I) as described herein, wherein $R^{18}$ is alkyl, cycloalkyl, haloalkyl, hydroxyalkyl, alkylcarbonyloxyalkyl, aryl, substituted aryl, heterocycloalkyl, substituted heterocycloalkyl, heteroaryl, substituted heteroaryl, wherein substituted aryl, substituted heterocycloalkyl and substituted heteroaryl are substituted with one to three substituents independently selected from alkyl, hydroxyalkyl, haloalkyl, cycloalkyl and halogen.

Another particular embodiment of the present invention are compounds according to formula (I) as described herein, wherein $R^{18}$ is alkyl, cycloalkyl, hydroxyalkyl, alkylcarbonyloxyalkyl or heterocycloalkyl substituted with one to three alkoxy.

Another particular embodiment of the present invention are compounds according to formula (I) as described herein, wherein $R^{18}$ is alkyl, cycloalkyl, hydroxyalkyl, alkylcarbonyloxyalkyl or heteroaryl substituted with one to three alkoxy.

A particular embodiment of the present invention are compounds according to formula (I) as described herein, wherein $R^{18}$ is alkyl or heteroaryl substituted with one to three substituents independently selected from alkyl and halogen.

A particular embodiment of the present invention are compounds according to formula (I) as described herein, wherein $R^{18}$ is heteroaryl substituted with one to three substituents independently selected from alkyl and halogen.

A particular embodiment of the present invention are compounds according to formula (I) as described herein, wherein $R^{18}$ is alkyl.

Also an embodiment of the present invention are compounds according to formula (I) as described herein, wherein $R^{18}$ is ethyl.

Another embodiment of the present invention are compounds according to formula (I) as described herein, wherein $A^1$ is CR$^{20}$.

The present invention also relates to compounds according to formula (I) as described herein, wherein $A^2$ is CR$^{21}$.

A further embodiment of the present invention are compounds according to formula (I) as described herein, wherein $A^3$ is CR$^{22}$.

A embodiment of the present invention are compounds according to formula (I) as described herein, wherein $R^{20}$ is H or halogen.

A embodiment of the present invention are compounds according to formula (I) as described herein, wherein $R^{20}$ is H.

A embodiment of the present invention are compounds according to formula (I) as described herein, wherein $R^{21}$ is H, alkyl or halogen.

A embodiment of the present invention are compounds according to formula (I) as described herein, wherein $R^{21}$ is H or alkyl.

Also an embodiment of the present invention are compounds according to formula (I) as described herein, wherein $R^{21}$ is H.

The present invention also relates to compounds according to formula (I) as described herein, wherein $R^{22}$ is H or halogen.

A further embodiment of the present invention are compounds according to formula (I) as described herein, wherein $R^{23}$, $R^{24}$ and $R^{25}$ are each independently selected from hydrogen, hydroxyalkyl, alkoxy, alkoxyalkyl, haloalkoxyalkyl, alkoxycarbonyl, oxo, triazolylalkyl and substituted aminoalkyl, wherein substituted aminoalkyl is substituted on the nitrogen atom with one to two alkyl.

The present invention also relates to compounds according to formula (I) as described herein, wherein $R^{22}$ is H.

Also an embodiment of the present invention are compounds according to formula (I) as described herein, wherein $R^{23}$, $R^{24}$ and $R^{25}$ are each independently selected from hydrogen, hydroxyalkyl, alkoxyalkyl, haloalkoxyalkyl, alkoxycarbonyl, oxo, triazolylalkyl and substituted aminoalkyl, wherein substituted aminoalkyl is substituted on the nitrogen atom with one to two alkyl.

A further embodiment of the present invention are compounds according to formula (I) as described herein, wherein $R^{23}$, $R^{24}$ and $R^{25}$ are each independently selected from hydrogen, hydroxyalkyl and oxo.

The present invention also relates to compounds according to formula (I) as described herein, wherein at least one of $R^{23}$, $R^{24}$ and $R^{25}$ is different from hydrogen.

The present invention also relates to compounds according to formula (I) as described herein, wherein $A^1$ is N.

The present invention also relates to compounds according to formula (I) as described herein, wherein $A^2$ is N.

The present invention also relates to compounds according to formula (I) as described herein, wherein $A^3$ is N.

Another embodiment of the present invention are compounds according to formula (I) as described herein, wherein m is zero or 1, wherein in case m is 1, then the sum of n, p and q is 2, 3, 4, 5 or 6.

A further embodiment of the present invention are compounds according to formula (I) as described herein, wherein m is 1.

A further embodiment of the present invention are compounds according to formula (I) as described herein, wherein m is zero.

Also a further embodiment of the present invention are compounds according to formula (I) as described herein, wherein n is zero or 1.

A particular embodiment of the present invention are compounds according to formula (I) as described herein, wherein n is zero.

Another embodiment of the present invention are compounds according to formula (I) as described herein, wherein p is zero or 1.

A further embodiment of the present invention are compounds according to formula (I) as described herein, wherein q is zero or 1.

A further embodiment of the present invention are compounds according to formula (I) as described herein, wherein q is zero.

A further embodiment of the present invention are compounds according to formula (I) as described herein, wherein r is zero and m is zero.

A further embodiment of the present invention are compounds according to formula (I) as described herein, wherein t is 2.

A further embodiment of the present invention are compounds according to formula (I) as described herein, wherein t is zero.

Particular examples of compounds of formula (I) as described herein are selected from Ethanesulfonic acid [5-(1-methyl-2-oxo-1,2,3,4-tetrahydro-quinolin-6-yl)-pyridin-3-yl]-amide;

Acetic acid [5-(1-methyl-2-oxo-1,2,3,4-tetrahydro-quinolin-6-yl)-pyridin-3-ylcarbamoyl]-methyl ester;

2-Hydroxy-N-[5-(1-methyl-2-oxo-1,2,3,4-tetrahydro-quinolin-6-yl)-pyridin-3-yl]-acetamide;

6-[5-(2-Hydroxy-ethylamino)-pyridin-3-yl]-1-methyl-3,4-dihydro-1H-quinolin-2-one;

6-[5-((S)-2-Hydroxymethyl-pyrrolidin-1-yl)-pyridin-3-yl]-1-methyl-3,4-dihydro-1H-quinolin-2-one;

6-[5-((R)-2-Hydroxymethyl-pyrrolidin-1-yl)-pyridin-3-yl]-1-methyl-3,4-dihydro-1H-quinolin-2-one;

6-[5-((S)-2-Hydroxymethyl-pyrrolidin-1-ylmethyl)-pyridin-3-yl]-1-methyl-3,4-dihydro-1H-quinolin-2-one;

6-[5-((S)-2-Hydroxymethyl-5-oxo-pyrrolidin-1-ylmethyl)-pyridin-3-yl]-1-methyl-3,4-dihydro-1H-quinolin-2-one;

6-[5-((S)-2-Ethylaminomethyl-pyrrolidin-1-yl)-pyridin-3-yl]-1-methyl-3,4-dihydro-1H-quinolin-2-one;

6-[5-((S)-2-Methoxymethyl-pyrrolidin-1-yl)-pyridin-3-yl]-1-methyl-3,4-dihydro-1H-quinolin-2-one;

1-Methyl-6-[5-((S)-2-[1,2,4]triazol-1-ylmethyl-pyrrolidin-1-yl)-pyridin-3-yl]-3,4-dihydro-1H-quinolin-2-one;

6-(5-Benzylamino-pyridin-3-yl)-1-methyl-3,4-dihydro-1H-quinolin-2-one;

6-[5-((S)-2-Hydroxymethyl-5-oxo-pyrrolidin-1-yl)-pyridin-3-yl]-1-methyl-3,4-dihydro-1H-quinolin-2-one;

1-Methyl-6-[5-(2-oxo-pyrrolidin-1-yl)-pyridin-3-yl]-3,4-dihydro-1H-quinolin-2-one;

Ethanesulfonic acid [5-(1-methyl-2-oxo-1,2,3,4-tetrahydro-quinolin-6-yl)-pyridin-3-ylmethyl]-amide;

Ethanesulfonic acid [5-(7-fluoro-1-methyl-2-oxo-1,2,3,4-tetrahydro-quinolin-6-yl)-pyridin-3-ylmethyl]-amide;

Ethanesulfonic acid [5-(1,4,4-trimethyl-2-oxo-1,2,3,4-tetrahydro-quinolin-6-yl)-pyridin-3-ylmethyl]-amide;

1-Methyl-6-[5-(2-oxo-pyrrolidin-1-ylmethyl)-pyridin-3-yl]-3,4-dihydro-1H-quinolin-2-one;

1-Methyl-6-[5-(2-oxo-piperidin-1-ylmethyl)-pyridin-3-yl]-3,4-dihydro-1H-quinolin-2-one;

6-[5-(1,1-Dioxo-1$\lambda^6$-thiomorpholin-4-ylmethyl)-pyridin-3-yl]-1-methyl-3,4-dihydro-1H-quinolin-2-one;

6-[5-((S)-2-Methoxymethyl-pyrrolidin-1-ylmethyl)-pyridin-3-yl]-1-methyl-3,4-dihydro-1H-quinolin-2-one;

(S)-1-[5-(1-Methyl-2-oxo-1,2,3,4-tetrahydro-quinolin-6-yl)-pyridin-3-ylmethyl]-pyrrolidine-2-carboxylic acid methyl ester;

1-Methyl-6-{5-[(S)-2-(2,2,2-trifluoro-ethoxymethyl)-pyrrolidin-1-ylmethyl]-pyridin-3-yl}-3,4-dihydro-1H-quinolin-2-one;

6-[6-(2-Hydroxy-ethylamino)-pyrazin-2-yl]-1-methyl-3,4-dihydro-1H-quinolin-2-one;

6-(6-Benzylamino-pyrazin-2-yl)-1-methyl-3,4-dihydro-1H-quinolin-2-one;

7-Fluoro-6-[6-(2-hydroxy-ethylamino)-pyrazin-2-yl]-1-methyl-3,4-dihydro-1H-quinolin-2-one;

6-(6-Benzylamino-pyrazin-2-yl)-7-fluoro-1-methyl-3,4-dihydro-1H-quinolin-2-one;

6-[6-(1-Methyl-2-oxo-1,2,3,4-tetrahydro-quinolin-6-yl)-pyrazin-2-yl]-2,6-diaza-spiro[3.3]heptane-2-carboxylic acid tert-butyl ester;

6-[5-(1-Methyl-2-oxo-1,2,3,4-tetrahydro-quinolin-6-yl)-pyridin-3-yl]-2,6-diaza-spiro[3.3]heptane-2-carboxylic acid tert-butyl ester;

6-[5-((R)-1-Hydroxymethyl-2-methyl-propylamino)-pyridin-3-yl]-1-methyl-3,4-dihydro-1H-quinolin-2-one;

6-[6-((R)-1-Hydroxymethyl-2-methyl-propylamino)-pyrazin-2-yl]-1-methyl-3,4-dihydro-1H-quinolin-2-one;

Ethanesulfonic acid [5-(5-methyl-6-oxo-5,6,7,8-tetrahydro-[1,5]naphthyridin-2-yl)-pyridin-3-ylmethyl]-amide;

6-Pyridin-3-yl-3,4-dihydro-1H-[1,5]naphthyridin-2-one;

1-Methyl-6-pyridin-3-yl-3,4-dihydro-1H-[1,5]naphthyridin-2-one;

1-Methyl-6-pyridin-3-yl-3,4-dihydro-1H-[1,7]naphthyridin-2-one;

6-(5-Aminomethyl-pyridin-3-yl)-1-methyl-3,4-dihydro-1H-quinolin-2-one;

N-[5-(1-Methyl-2-oxo-1,2,3,4-tetrahydro-quinolin-6-yl)-pyridin-3-ylmethyl]-propionamide;

Propane-2-sulfonic acid [5-(1-methyl-2-oxo-1,2,3,4-tetrahydro-quinolin-6-yl)-pyridin-3-ylmethyl]-amide;

{2-[5-(1-Methyl-2-oxo-1,2,3,4-tetrahydro-quinolin-6-yl)-pyridin-3-yloxy]-ethyl}-carbamic acid tert-butyl ester;

3-Methoxy-isoxazole-5-carboxylic acid [5-(1-methyl-2-oxo-1,2,3,4-tetrahydro-quinolin-6-yl)-pyridin-3-ylmethyl]-amide;

Cyclopropanecarboxylic acid [5-(1-methyl-2-oxo-1,2,3,4-tetrahydro-quinolin-6-yl)-pyridin-3-ylmethyl]-amide;
6-[5-(2-Amino-ethoxy)-pyridin-3-yl]-1-methyl-3,4-dihydro-1H-quinolin-2-one hydrochloride;
N-{2-[5-(1-Methyl-2-oxo-1,2,3,4-tetrahydro-quinolin-6-yl)-pyridin-3-yloxy]-ethyl}-propionamide;
6-[5-(1,1-Dioxo-1λ$^6$-[1,2]thiazinan-2-ylmethyl)-pyridin-3-yl]-1-methyl-3,4-dihydro-1H-quinolin-2-one;
and pharmaceutically acceptable salts thereof.

Also particular examples of compounds of formula (I) as described herein are selected from
(S)-2-[5-(1-Methyl-2-oxo-1,2,3,4-tetrahydro-quinolin-6-yl)-pyridin-3-yloxymethyl]-azetidine-1-carboxylic acid tert-butyl ester;
(R)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester;
3-[5-(1-Methyl-2-oxo-1,2,3,4-tetrahydro-quinolin-6-yl)-pyridin-3-yloxy]-azetidine-1-carboxylic acid tert-butyl ester;
(S)-3-[5-(1-Methyl-2-oxo-1,2,3,4-tetrahydro-quinolin-6-yl)-pyridin-3-yloxy]-pyrrolidine-1-carboxylic acid tert-butyl ester;
(S)-3-[5-(1-Methyl-2-oxo-1,2,3,4-tetrahydro-quinolin-6-yl)-pyridin-3-yloxy]-piperidine-1-carboxylic acid tert-butyl ester;
4-[5-(1-Methyl-2-oxo-1,2,3,4-tetrahydro-quinolin-6-yl)-pyridin-3-yloxy]-piperidine-1-carboxylic acid tert-butyl ester;
(S)-2-[5-(1-Methyl-2-oxo-1,2,3,4-tetrahydro-quinolin-6-yl)-pyridin-3-yloxymethyl]-pyrrolidine-1-carboxylic acid tert-butyl ester;
(S)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester;
(R)-3-[5-(1-Methyl-2-oxo-1,2,3,4-tetrahydro-quinolin-6-yl)-pyridin-3-yloxy]-pyrrolidine-1-carboxylic acid tert-butyl ester;
(R)-2-Methyl-propane-2-sulfinic acid {3-[5-(1-methyl-2-oxo-1,2,3,4-tetrahydro-quinolin-6-yl)-pyridin-3-yl]-oxetan-3-yl}-amide;
Ethanesulfonic acid [5-(2-oxo-1,2,3,4-tetrahydro-quinolin-6-yl)-pyridin-3-ylmethyl]-amide;
(R)-2-Methyl-propane-2-sulfinic acid {(S or R)-1-[5-(1-methyl-2-oxo-1,2,3,4-tetrahydro-quinolin-6-yl)-pyridin-3-yl]-ethyl}-amide;
(R) 2-Methyl-propane-2-sulfinic acid {(R or S)-1-[5-(1-methyl-2-oxo-1,2,3,4-tetrahydro-quinolin-6-yl)-pyridin-3-yl]-ethyl}-amide;
{(trans)-4-[5-(1-Methyl-2-oxo-1,2,3,4-tetrahydro-quinolin-6-yl)-pyridin-3-yloxy]-cyclohexyl}-carbamic acid tert-butyl ester;
6-[5-(1-Amino-cyclopropyl)-pyridin-3-yl]-1-methyl-3,4-dihydro-1H-quinolin-2-one;
1-Methyl-6-[5-((S)-pyrrolidin-3-yloxy)-pyridin-3-yl]-3,4-dihydro-1H-quinolin-2-one hydrochloride;
1-Methyl-6-[5-((S)-piperidin-3-yloxy)-pyridin-3-yl]-3,4-dihydro-1H-quinolin-2-one;
1-Methyl-6-[5-(piperidin-4-yloxy)-pyridin-3-yl]-3,4-dihydro-1H-quinolin-2-one hydrochloride;
6-[5-((S)-1-Azetidin-2-ylmethoxy)-pyridin-3-yl]-1-methyl-3,4-dihydro-1H-quinolin-2-one;
6-[5-((S or R)-1-Amino-ethyl)-pyridin-3-yl]-1-methyl-3,4-dihydro-1H-quinolin-2-one hydrochloride;
6-[5-((R or S)-1-Amino-ethyl)-pyridin-3-yl]-1-methyl-3,4-dihydro-1H-quinolin-2-one hydrochloride;
1-Methyl-6-[5-((S)-1-pyrrolidin-2-ylmethoxy)-pyridin-3-yl]-3,4-dihydro-1H-quinolin-2-one hydrochloride;
7-Fluoro-1-methyl-6-[5-((R)-pyrrolidin-3-yloxy)-pyridin-3-yl]-3,4-dihydro-1H-quinolin-2-one hydrochloride;
1-Methyl-6-[5-((R)-pyrrolidin-3-yloxy)-pyridin-3-yl]-3,4-dihydro-1H-quinolin-2-one hydrochloride;
6-[5-(3-Amino-oxetan-3-yl)-pyridin-3-yl]-1-methyl-3,4-dihydro-1H-quinolin-2-one hydrochloride;
6-[5-(Azetidin-3-yloxy)-pyridin-3-yl]-1-methyl-3,4-dihydro-1H-quinolin-2-one hydrochloride;
6-[5-((trans)-4-Amino-cyclohexyloxy)-pyridin-3-yl]-1-methyl-3,4-dihydro-1H-quinolin-2-one hydrochloride;
6-[5-(1-Amino-1-methyl-ethyl)-pyridin-3-yl]-1-methyl-3,4-dihydro-1H-quinolin-2-one;
6-(5-Aminomethyl-pyridin-3-yl)-7-fluoro-1-methyl-3,4-dihydro-1H-quinolin-2-one;
6-{6-[6-(3-Methoxy-isoxazole-5-carbonyl)-2,6-diaza-spiro[3.3]hept-2-yl]-pyrazin-2-yl}-1-methyl-3,4-dihydro-1H-quinolin-2-one;
3,5-Dimethyl-isoxazole-4-carboxylic acid [5-(1-methyl-2-oxo-1,2,3,4-tetrahydro-quinolin-6-yl)-pyridin-3-ylmethyl]-amide;
6-[5-((S)-1-Cyclopropanecarbonyl-pyrrolidin-3-yloxy)-pyridin-3-yl]-1-methyl-3,4-dihydro-1H-quinolin-2-one;
3-Methyl-N-[5-(1-methyl-2-oxo-1,2,3,4-tetrahydro-quinolin-6-yl)-pyridin-3-ylmethyl]-butyramide;
3,3,3-Trifluoro-N-[5-(1-methyl-2-oxo-1,2,3,4-tetrahydro-quinolin-6-yl)-pyridin-3-ylmethyl]-propionamide;
2-Hydroxy-2-methyl-N-[5-(1-methyl-2-oxo-1,2,3,4-tetrahydro-quinolin-6-yl)-pyridin-3-ylmethyl]-propionamide;
5-Methyl-[1,3,4]oxadiazole-2-carboxylic acid [5-(1-methyl-2-oxo-1,2,3,4-tetrahydro-quinolin-6-yl)-pyridin-3-ylmethyl]-amide;
1-Methyl-6-[5-((S)-1-propionyl-piperidin-3-yloxy)-pyridin-3-yl]-3,4-dihydro-1H-quinolin-2-one;
2-Methoxy-pyrimidine-5-carboxylic acid [5-(1-methyl-2-oxo-1,2,3,4-tetrahydro-quinolin-6-yl)-pyridin-3-ylmethyl]-amide,
1-Methyl-1H-imidazole-2-carboxylic acid [5-(1-methyl-2-oxo-1,2,3,4-tetrahydro-quinolin-6-yl)-pyridin-3-ylmethyl]-amide;
5-Trifluoromethyl-furan-3-carboxylic acid [5-(1-methyl-2-oxo-1,2,3,4-tetrahydro-quinolin-6-yl)-pyridin-3-ylmethyl]-amide;
Pyridazine-3-carboxylic acid [5-(1-methyl-2-oxo-1,2,3,4-tetrahydro-quinolin-6-yl)-pyridin-3-ylmethyl]-amide;
Pyrimidine-5-carboxylic acid [5-(1-methyl-2-oxo-1,2,3,4-tetrahydro-quinolin-6-yl)-pyridin-3-ylmethyl]-amide;
1-Methyl-1H-pyrazole-4-carboxylic acid [5-(1-methyl-2-oxo-1,2,3,4-tetrahydro-quinolin-6-yl)-pyridin-3-ylmethyl]-amide;
1-Methyl-6-[5-(1-propionyl-piperidin-4-yloxy)-pyridin-3-yl]-3,4-dihydro-1H-quinolin-2-one;
Pyridazine-4-carboxylic acid [5-(1-methyl-2-oxo-1,2,3,4-tetrahydro-quinolin-6-yl)-pyridin-3-ylmethyl]-amide;
1-Methyl-6-[5-((S)-1-propionyl-pyrrolidin-3-yloxy)-pyridin-3-yl]-3,4-dihydro-1H-quinolin-2-one;
6-[5-((S)-1-Cyclopropanecarbonyl-azetidin-2-ylmethoxy)-pyridin-3-yl]-1-methyl-3,4-dihydro-1H-quinolin-2-one;
3-Methyl-isoxazole-4-carboxylic acid [5-(1-methyl-2-oxo-1,2,3,4-tetrahydro-quinolin-6-yl)-pyridin-3-ylmethyl]-amide;
4-Fluoro-2,6-dimethyl-N-[5-(1-methyl-2-oxo-1,2,3,4-tetrahydro-quinolin-6-yl)-pyridin-3-ylmethyl]-benzamide;
1-Methyl-6-[5-((S)-1-propionyl-azetidin-2-ylmethoxy)-pyridin-3-yl]-3,4-dihydro-1H-quinolin-2-one;

3,6-Dichloro-pyridazine-4-carboxylic acid [5-(1-methyl-2-oxo-1,2,3,4-tetrahydro-quinolin-6-yl)-pyridin-3-ylmethyl]-amide;

3-Cyclopropyl-1-(2,2,2-trifluoro-ethyl)-1H-pyrazole-4-carboxylic acid [5-(1-methyl-2-oxo-1,2,3,4-tetrahydro-quinolin-6-yl)-pyridin-3-ylmethyl]-amide;

Pyridine-2-carboxylic acid [5-(1-methyl-2-oxo-1,2,3,4-tetrahydro-quinolin-6-yl)-pyridin-3-ylmethyl]-amide;

1,3-Dimethyl-1H-pyrazole-4-carboxylic acid [5-(1-methyl-2-oxo-1,2,3,4-tetrahydro-quinolin-6-yl)-pyridin-3-ylmethyl]-amide;

Pyrimidine-2-carboxylic acid [5-(1-methyl-2-oxo-1,2,3,4-tetrahydro-quinolin-6-yl)-pyridin-3-ylmethyl]-amide;

6-Methoxy-pyridazine-3-carboxylic acid [5-(1-methyl-2-oxo-1,2,3,4-tetrahydro-quinolin-6-yl)-pyridin-3-ylmethyl]-amide;

5-Methyl-isoxazole-4-carboxylic acid [5-(1-methyl-2-oxo-1,2,3,4-tetrahydro-quinolin-6-yl)-pyridin-3-ylmethyl]-amide;

3,5-Dimethyl-isoxazole-4-carboxylic acid {2-[5-(1-methyl-2-oxo-1,2,3,4-tetrahydro-quinolin-6-yl)-pyridin-3-yloxy]-ethyl}-amide;

1-Methyl-1H-pyrazole-4-carboxylic acid {2-[5-(1-methyl-2-oxo-1,2,3,4-tetrahydro-quinolin-6-yl)-pyridin-3-yloxy]-ethyl}-amide;

6-Chloro-pyridazine-3-carboxylic acid [5-(1-methyl-2-oxo-1,2,3,4-tetrahydro-quinolin-6-yl)-pyridin-3-ylmethyl]-amide;

3-Chloro-6-methyl-pyridazine-4-carboxylic acid [5-(1-methyl-2-oxo-1,2,3,4-tetrahydro-quinolin-6-yl)-pyridin-3-ylmethyl]-amide;

1-Methyl-6-[5-((S)-1-propionyl-pyrrolidin-2-ylmethoxy)-pyridin-3-yl]-3,4-dihydro-1H-quinolin-2-one;

5-Cyclopropyl-isoxazole-4-carboxylic acid [5-(1-methyl-2-oxo-1,2,3,4-tetrahydro-quinolin-6-yl)-pyridin-3-ylmethyl]-amide;

2-Methyl-5-trifluoromethyl-oxazole-4-carboxylic acid [5-(1-methyl-2-oxo-1,2,3,4-tetrahydro-quinolin-6-yl)-pyridin-3-ylmethyl]-amide;

2-Methyl-oxazole-4-carboxylic acid [5-(1-methyl-2-oxo-1,2,3,4-tetrahydro-quinolin-6-yl)-pyridin-3-ylmethyl]-amide;

5-Cyclopropyl-oxazole-4-carboxylic acid [5-(1-methyl-2-oxo-1,2,3,4-tetrahydro-quinolin-6-yl)-pyridin-3-ylmethyl]-amide;

2,5-Dimethyl-oxazole-4-carboxylic acid [5-(1-methyl-2-oxo-1,2,3,4-tetrahydro-quinolin-6-yl)-pyridin-3-ylmethyl]-amide;

5-Methyl-oxazole-4-carboxylic acid [5-(1-methyl-2-oxo-1,2,3,4-tetrahydro-quinolin-6-yl)-pyridin-3-ylmethyl]-amide;

3,5-Dimethyl-isoxazole-4-carboxylic acid {1-[5-(1-methyl-2-oxo-1,2,3,4-tetrahydro-quinolin-6-yl)-pyridin-3-yl]-cyclopropyl}-amide;

6-Chloro-pyridine-2-carboxylic acid [5-(1-methyl-2-oxo-1,2,3,4-tetrahydro-quinolin-6-yl)-pyridin-3-ylmethyl]-amide;

3-Methyl-pyridine-2-carboxylic acid [5-(1-methyl-2-oxo-1,2,3,4-tetrahydro-quinolin-6-yl)-pyridin-3-ylmethyl]-amide;

3,6-Dichloro-pyridine-2-carboxylic acid [5-(1-methyl-2-oxo-1,2,3,4-tetrahydro-quinolin-6-yl)-pyridin-3-ylmethyl]-amide;

6-Methyl-pyridine-2-carboxylic acid [5-(1-methyl-2-oxo-1,2,3,4-tetrahydro-quinolin-6-yl)-pyridin-3-ylmethyl]-amide;

3-Chloro-pyridine-2-carboxylic acid [5-(1-methyl-2-oxo-1,2,3,4-tetrahydro-quinolin-6-yl)-pyridin-3-ylmethyl]-amide;

3-Fluoro-pyridine-2-carboxylic acid [5-(1-methyl-2-oxo-1,2,3,4-tetrahydro-quinolin-6-yl)-pyridin-3-ylmethyl]-amide;

5-Chloro-3-methyl-pyridine-2-carboxylic acid [5-(1-methyl-2-oxo-1,2,3,4-tetrahydro-quinolin-6-yl)-pyridin-3-ylmethyl]-amide;

1-Methyl-6-[5-((R)-1-propionyl-pyrrolidin-3-yloxy)-pyridin-3-yl]-3,4-dihydro-1H-quinolin-2-one;

7-Fluoro-1-methyl-6-[5-((S)-1-propionyl-pyrrolidin-3-yloxy)-pyridin-3-yl]-3,4-dihydro-1H-quinolin-2-one;

5-Trifluoromethyl-pyrimidine-2-carboxylic acid [5-(1-methyl-2-oxo-1,2,3,4-tetrahydro-quinolin-6-yl)-pyridin-3-ylmethyl]-amide;

5-Methyl-pyrazine-2-carboxylic acid [5-(1-methyl-2-oxo-1,2,3,4-tetrahydro-quinolin-6-yl)-pyridin-3-ylmethyl]-amide;

5-Chloro-pyrazine-2-carboxylic acid [5-(1-methyl-2-oxo-1,2,3,4-tetrahydro-quinolin-6-yl)-pyridin-3-ylmethyl]-amide;

5-Trifluoromethyl-pyrazine-2-carboxylic acid [5-(1-methyl-2-oxo-1,2,3,4-tetrahydro-quinolin-6-yl)-pyridin-3-ylmethyl]-amide;

3,5-Dimethyl-isoxazole-4-carboxylic acid [5-(7-fluoro-1-methyl-2-oxo-1,2,3,4-tetrahydro-quinolin-6-yl)-pyridin-3-ylmethyl]-amide;

1-Methyl-6-[5-((R)-1-propionyl-pyrrolidin-2-ylmethoxy)-pyridin-3-yl]-3,4-dihydro-1H-quinolin-2-one;

1-Methyl-6-[5-(1-propionyl-azetidin-3-yloxy)-pyridin-3-yl]-3,4-dihydro-1H-quinolin-2-one;

N-{3-[5-(1-Methyl-2-oxo-1,2,3,4-tetrahydro-quinolin-6-yl)-pyridin-3-yl]-oxetan-3-yl}-propionamide;

3-Chloro-pyridine-2-carboxylic acid [5-(7-fluoro-1-methyl-2-oxo-1,2,3,4-tetrahydro-quinolin-6-yl)-pyridin-3-ylmethyl]-amide;

3,6-Dichloro-pyridazine-4-carboxylic acid [5-(7-fluoro-1-methyl-2-oxo-1,2,3,4-tetrahydro-quinolin-6-yl)-pyridin-3-ylmethyl]-amide;

7-Fluoro-1-methyl-6-[5-((R)-1-propionyl-pyrrolidin-3-yloxy)-pyridin-3-yl]-3,4-dihydro-1H-quinolin-2-one;

5-Chloro-3-methoxy-pyrazine-2-carboxylic acid [5-(1-methyl-2-oxo-1,2,3,4-tetrahydro-quinolin-6-yl)-pyridin-3-ylmethyl]-amide;

3,5-Dimethyl-isoxazole-4-carboxylic acid {(R or S)-1-[5-(1-methyl-2-oxo-1,2,3,4-tetrahydro-quinolin-6-yl)-pyridin-3-yl]-ethyl}-amide;

3-Methyl-5-trifluoromethyl-isoxazole-4-carboxylic acid [5-(1-methyl-2-oxo-1,2,3,4-tetrahydro-quinolin-6-yl)-pyridin-3-ylmethyl]-amide;

3-Chloro-pyridine-2-carboxylic acid {1-[5-(1-methyl-2-oxo-1,2,3,4-tetrahydro-quinolin-6-yl)-pyridin-3-yl]-cyclopropyl}-amide;

3-Chloro-pyridine-2-carboxylic acid {1-methyl-1-[5-(1-methyl-2-oxo-1,2,3,4-tetrahydro-quinolin-6-yl)-pyridin-3-yl]-ethyl}-amide;

3,5-Dimethyl-isoxazole-4-carboxylic acid {1-methyl-1-[5-(1-methyl-2-oxo-1,2,3,4-tetrahydro-quinolin-6-yl)-pyridin-3-yl]-ethyl}-amide;

3-Chloro-pyridine-2-carboxylic acid [5-(2-oxo-1,2,3,4-tetrahydro-quinolin-6-yl)-pyridin-3-ylmethyl]-amide;

3,5-Dimethyl-isoxazole-4-carboxylic acid [5-(2-oxo-1,2,3,4-tetrahydro-quinolin-6-yl)-pyridin-3-ylmethyl]-amide;

3-Chloro-pyridine-2-carboxylic acid {1-[5-(7-fluoro-1-methyl-2-oxo-1,2,3,4-tetrahydro-quinolin-6-yl)-pyridin-3-yl]-cyclopropyl}-amide;

3-Methyl-pyridine-2-carboxylic acid {1-[5-(1-methyl-2-oxo-1,2,3,4-tetrahydro-quinolin-6-yl)-pyridin-3-yl]-cyclopropyl}-amide;
N-{(trans)-4-[5-(1-Methyl-2-oxo-1,2,3,4-tetrahydro-quinolin-6-yl)-pyridin-3-yloxy]-cyclohexyl}-propionamide;
5-Trifluoromethyl-isoxazole-4-carboxylic acid [5-(1-methyl-2-oxo-1,2,3,4-tetrahydro-quinolin-6-yl)-pyridin-3-ylmethyl]-amide;
7-Fluoro-1-methyl-6-[5-((S)-pyrrolidin-3-yloxy)-pyridin-3-yl]-3,4-dihydro-1H-quinolin-2-one;
(R)-2-[5-(1-Methyl-2-oxo-1,2,3,4-tetrahydro-quinolin-6-yl)-pyridin-3-yloxymethyl]-pyrrolidine-1-carboxylic acid tert-butyl ester;
1-Methyl-6-[5-((R)-1-pyrrolidin-2-ylmethoxy)-pyridin-3-yl]-3,4-dihydro-1H-quinolin-2-one hydrochloride;
6-(5-Aminomethyl-pyridin-3-yl)-3,4-dihydro-1H-quinolin-2-one;
6-[5-(1-Amino-cyclopropyl)-pyridin-3-yl]-7-fluoro-1-methyl-3,4-dihydro-1H-quinolin-2-one; Ethanesulfonic acid {2-[5-(1-methyl-2-oxo-1,2,3,4-tetrahydro-quinolin-6-yl)-pyridin-3-yloxy]-ethyl}-amide;
3-Chloro-N-[5-(1-methyl-2-oxo-1,2,3,4-tetrahydro-quinolin-6-yl)-pyridin-3-ylmethyl]-benzenesulfonamide;
6-Methoxy-pyridine-3-sulfonic acid [5-(1-methyl-2-oxo-1,2,3,4-tetrahydro-quinolin-6-yl)-pyridin-3-ylmethyl]-amide;
3,5-Dimethyl-isoxazole-4-sulfonic acid [5-(1-methyl-2-oxo-1,2,3,4-tetrahydro-quinolin-6-yl)-pyridin-3-ylmethyl]-amide;
Cyclopropanesulfonic acid [5-(1-methyl-2-oxo-1,2,3,4-tetrahydro-quinolin-6-yl)-pyridin-3-ylmethyl]-amide;
3,4-Dichloro-N-[5-(1-methyl-2-oxo-1,2,3,4-tetrahydro-quinolin-6-yl)-pyridin-3-ylmethyl]-benzenesulfonamide;
1-Methyl-1H-imidazole-4-sulfonic acid [5-(1-methyl-2-oxo-1,2,3,4-tetrahydro-quinolin-6-yl)-pyridin-3-ylmethyl]-amide;
6-Chloro-pyridine-3-sulfonic acid [5-(1-methyl-2-oxo-1,2,3,4-tetrahydro-quinolin-6-yl)-pyridin-3-ylmethyl]-amide;
1-Methyl-1H-pyrazole-4-sulfonic acid [5-(1-methyl-2-oxo-1,2,3,4-tetrahydro-quinolin-6-yl)-pyridin-3-ylmethyl]-amide;
6-[5-((S)-1-Ethanesulfonyl-piperidin-3-yloxy)-pyridin-3-yl]-1-methyl-3,4-dihydro-1H-quinolin-2-one;
6-[5-(1-Ethanesulfonyl-piperidin-4-yloxy)-pyridin-3-yl]-1-methyl-3,4-dihydro-1H-quinolin-2-one;
2,2,2-Trifluoro-ethanesulfonic acid [5-(1-methyl-2-oxo-1,2,3,4-tetrahydro-quinolin-6-yl)-pyridin-3-ylmethyl]-amide;
C,C,C-Trifluoro-N-[5-(1-methyl-2-oxo-1,2,3,4-tetrahydro-quinolin-6-yl)-pyridin-3-ylmethyl]-methanesulfonamide;
6-[5-((S)-1-Ethanesulfonyl-pyrrolidin-3-yloxy)-pyridin-3-yl]-1-methyl-3,4-dihydro-1H-quinolin-2-one;
6-[5-((S)-1-Ethanesulfonyl-azetidin-2-ylmethoxy)-pyridin-3-yl]-1-methyl-3,4-dihydro-1H-quinolin-2-one;
Ethanesulfonic acid {1-[5-(1-methyl-2-oxo-1,2,3,4-tetrahydro-quinolin-6-yl)-pyridin-3-yl]-cyclopropyl}-amide;
6-[5-((S)-1-Ethanesulfonyl-pyrrolidin-2-ylmethoxy)-pyridin-3-yl]-1-methyl-3,4-dihydro-1H-quinolin-2-one;
6-[5-((R)-1-Ethanesulfonyl-pyrrolidin-3-yloxy)-pyridin-3-yl]-7-fluoro-1-methyl-3,4-dihydro-1H-quinolin-2-one;
6-[5-((R)-1-Ethanesulfonyl-pyrrolidin-3-yloxy)-pyridin-3-yl]-1-methyl-3,4-dihydro-1H-quinolin-2-one;
6-[5-(1-Ethanesulfonyl-azetidin-3-yloxy)-pyridin-3-yl]-1-methyl-3,4-dihydro-1H-quinolin-2-one; Ethanesulfonic acid {1-[5-(7-fluoro-1-methyl-2-oxo-1,2,3,4-tetrahydro-quinolin-6-yl)-pyridin-3-yl]-cyclopropyl}-amide;
Ethanesulfonic acid {(trans)-4-[5-(1-methyl-2-oxo-1,2,3,4-tetrahydro-quinolin-6-yl)-pyridin-3-yloxy]-cyclohexyl}-amide;
Ethanesulfonic acid {(R or S)-1-[5-(1-methyl-2-oxo-1,2,3,4-tetrahydro-quinolin-6-yl)-pyridin-3-yl]-ethyl}-amide;
Ethanesulfonic acid {(S or R)-1-[5-(1-methyl-2-oxo-1,2,3,4-tetrahydro-quinolin-6-yl)-pyridin-3-yl]-ethyl}-amide;
1-Methyl-1H-pyrazole-4-carboxylic acid [5-(7-fluoro-1-methyl-2-oxo-1,2,3,4-tetrahydro-quinolin-6-yl)-pyridin-3-ylmethyl]-amide;
(rac)-Ethanesulfonic acid {2-methyl-1-[5-(1-methyl-2-oxo-1,2,3,4-tetrahydro-quinolin-6-yl)-pyridin-3-yl]-propyl}-amide;
(rac)-Ethanesulfonic acid {cyclopropyl-[5-(1-methyl-2-oxo-1,2,3,4-tetrahydro-quinolin-6-yl)-pyridin-3-yl]-methyl}-amide;
(rac)-Ethanesulfonic acid {1-[5-(7-fluoro-1-methyl-2-oxo-1,2,3,4-tetrahydro-quinolin-6-yl)-pyridin-3-yl]-ethyl}-amide;
6-[5-(1,1-Dioxo-1$\lambda$6-isothiazolidin-2-ylmethyl)-pyridin-3-yl]-1-methyl-3,4-dihydro-1H-quinolin-2-one;
(rac)-Ethanesulfonic acid {1-[5-(1-methyl-2-oxo-1,2,3,4-tetrahydro-quinolin-6-yl)-pyridin-3-yl]-propyl}-amide;
Ethanesulfonic acid ethyl-[5-(1-methyl-2-oxo-1,2,3,4-tetrahydro-quinolin-6-yl)-pyridin-3-ylmethyl]-amide;
Ethanesulfonic acid methyl-[5-(1-methyl-2-oxo-1,2,3,4-tetrahydro-quinolin-6-yl)-pyridin-3-ylmethyl]-amide;
Ethanesulfonic acid {1-methyl-1-[5-(1-methyl-2-oxo-1,2,3,4-tetrahydro-quinolin-6-yl)-pyridin-3-yl]-ethyl}-amide;
Ethanesulfonic acid isopropyl-[5-(1-methyl-2-oxo-1,2,3,4-tetrahydro-quinolin-6-yl)-pyridin-3-ylmethyl]-amide;
Ethanesulfonic acid (2-ethoxy-ethyl)-[5-(1-methyl-2-oxo-1,2,3,4-tetrahydro-quinolin-6-yl)-pyridin-3-ylmethyl]-amide;
(rac)-Ethanesulfonic acid methyl-{1-[5-(1-methyl-2-oxo-1,2,3,4-tetrahydro-quinolin-6-yl)-pyridin-3-yl]-ethyl}-amide;
(rac)-Ethanesulfonic acid ethyl-{1-[5-(1-methyl-2-oxo-1,2,3,4-tetrahydro-quinolin-6-yl)-pyridin-3-yl]-ethyl}-amide;
3,5-Dimethyl-isoxazole-4-carboxylic acid methyl-[5-(1-methyl-2-oxo-1,2,3,4-tetrahydro-quinolin-6-yl)-pyridin-3-ylmethyl]-amide;
6-{5-[2-(1,1-Dioxo-1$\lambda$6-isothiazolidin-2-yl)-ethoxy]-pyridin-3-yl}-1-methyl-3,4-dihydro-1H-quinolin-2-one;
Ethanesulfonic acid {(R or S)-1-[5-(7-fluoro-1-methyl-2-oxo-1,2,3,4-tetrahydro-quinolin-6-yl)-pyridin-3-yl]-ethyl}-amide;
Ethanesulfonic acid {(S or R)-1-[5-(7-fluoro-1-methyl-2-oxo-1,2,3,4-tetrahydro-quinolin-6-yl)-pyridin-3-yl]-ethyl}-amide;
Ethanesulfonic acid [5-(7-fluoro-1-methyl-2-oxo-1,2,3,4-tetrahydro-quinolin-6-yl)-4-methyl-pyridin-3-ylmethyl]-amide;
Ethanesulfonic acid [4-chloro-5-(1-methyl-2-oxo-1,2,3,4-tetrahydro-quinolin-6-yl)-pyridin-3-ylmethyl]-amide;
Ethanesulfonic acid [4-methyl-5-(1-methyl-2-oxo-1,2,3,4-tetrahydro-quinolin-6-yl)-pyridin-3-ylmethyl]-amide;
Ethanesulfonic acid methyl-{2-[5-(1-methyl-2-oxo-1,2,3,4-tetrahydro-quinolin-6-yl)-pyridin-3-yloxy]-ethyl}-amide;
3-Chloro-pyridine-2-carboxylic acid methyl-[5-(1-methyl-2-oxo-1,2,3,4-tetrahydro-quinolin-6-yl)-pyridin-3-ylmethyl]-amide;
N-Methyl-N-{2-[5-(1-methyl-2-oxo-1,2,3,4-tetrahydro-quinolin-6-yl)-pyridin-3-yloxy]-ethyl}-propionamide;
1-Methyl-1H-pyrazole-4-carboxylic acid methyl-[5-(1-methyl-2-oxo-1,2,3,4-tetrahydro-quinolin-6-yl)-pyridin-3-ylmethyl]-amide;

3-Methyl-pyridine-2-carboxylic acid methyl-[5-(1-methyl-2-oxo-1,2,3,4-tetrahydro-quinolin-6-yl)-pyridin-3-ylmethyl]-amide;

3-Chloro-pyridine-2-carboxylic acid [5-(7-fluoro-1-methyl-2-oxo-1,2,3,4-tetrahydro-quinolin-6-yl)-pyridin-3-ylmethyl]-methyl-amide;

3-Chloro-pyridine-2-carboxylic acid methyl-{1-[5-(1-methyl-2-oxo-1,2,3,4-tetrahydro-quinolin-6-yl)-pyridin-3-yl]-cyclopropyl}-amide;

1-Methyl-1H-pyrazole-4-carboxylic acid [5-(7-fluoro-1-methyl-2-oxo-1,2,3,4-tetrahydro-quinolin-6-yl)-pyridin-3-ylmethyl]-methyl-amide;

Ethanesulfonic acid [5-(8-chloro-2-oxo-1,2,3,4-tetrahydro-quinolin-6-yl)-pyridin-3-ylmethyl]-amide;

3-Chloro-pyridine-2-carboxylic acid [5-(8-chloro-2-oxo-1,2,3,4-tetrahydro-quinolin-6-yl)-pyridin-3-ylmethyl]-amide;

3,5-Dimethyl-isoxazole-4-carboxylic acid [5-(8-chloro-2-oxo-1,2,3,4-tetrahydro-quinolin-6-yl)-pyridin-3-ylmethyl]-amide;

6-{5-[(3-Ethyl-oxetan-3-ylamino)-methyl]-pyridin-3-yl}-1-methyl-3,4-dihydro-1H-quinolin-2-one;

Ethanesulfonic acid [5-(7-chloro-1-methyl-2-oxo-1,2,3,4-tetrahydro-quinolin-6-yl)-pyridin-3-ylmethyl]-amide;

Ethanesulfonic acid [5-(8-fluoro-1-methyl-2-oxo-1,2,3,4-tetrahydro-quinolin-6-yl)-pyridin-3-ylmethyl]-amide;

Ethanesulfonic acid [5-(8-chloro-1-methyl-2-oxo-1,2,3,4-tetrahydro-quinolin-6-yl)-pyridin-3-ylmethyl]-amide;

Ethanesulfonic acid [5-(5-fluoro-1-methyl-2-oxo-1,2,3,4-tetrahydro-quinolin-6-yl)-pyridin-3-ylmethyl]-amide;

Ethanesulfonic acid [5-(7-fluoro-1-methyl-2-oxo-1,2,3,4-tetrahydro-quinolin-6-yl)-pyridin-3-ylmethyl]-methyl-amide;

N-[5-(7-Fluoro-1-methyl-2-oxo-1,2,3,4-tetrahydro-quinolin-6-yl)-pyridin-3-ylmethyl]-propionamide;

(rac)-N-{1-[5-(7-Fluoro-1-methyl-2-oxo-1,2,3,4-tetrahydro-quinolin-6-yl)-pyridin-3-yl]-ethyl}-propionamide;

(S)-3-[5-(2-oxo-1,2,3,4-tetrahydro-quinolin-6-yl)-pyridin-3-yloxy]-pyrrolidine-1-carboxylic acid tert-butyl ester;

3-Chloro-pyridine-2-carboxylic acid methyl-[5-(2-oxo-1,2,3,4-tetrahydro-quinolin-6-yl)-pyridin-3-ylmethyl]-amide;

3-Chloro-pyridine-2-carboxylic acid [5-(8-chloro-2-oxo-1,2,3,4-tetrahydro-quinolin-6-yl)-pyridin-3-ylmethyl]-methyl-amide;

(R)-2-Methyl-propane-2-sulfinic acid [4-chloro-5-(1-methyl-2-oxo-1,2,3,4-tetrahydro-quinolin-6-yl)-pyridin-3-ylmethyl]-amide;

6-(5-Aminomethyl-4-chloro-pyridin-3-yl)-1-methyl-3,4-dihydro-1H-quinolin-2-one hydrochloride;

3,5-Dimethyl-isoxazole-4-carboxylic acid [4-chloro-5-(1-methyl-2-oxo-1,2,3,4-tetrahydro-quinolin-6-yl)-pyridin-3-ylmethyl]-amide;

3-Chloro-pyridine-2-carboxylic acid [4-chloro-5-(1-methyl-2-oxo-1,2,3,4-tetrahydro-quinolin-6-yl)-pyridin-3-ylmethyl]-amide;

(R)-2-Methyl-propane-2-sulfinic acid [4-methyl-5-(1-methyl-2-oxo-1,2,3,4-tetrahydro-quinolin-6-yl)-pyridin-3-ylmethyl]-amide;

6-(5-Aminomethyl-4-methyl-pyridin-3-yl)-1-methyl-3,4-dihydro-1H-quinolin-2-one hydrochloride;

3,5-Dimethyl-isoxazole-4-carboxylic acid [4-methyl-5-(1-methyl-2-oxo-1,2,3,4-tetrahydro-quinolin-6-yl)-pyridin-3-ylmethyl]-amide;

3-Chloro-pyridine-2-carboxylic acid [4-methyl-5-(1-methyl-2-oxo-1,2,3,4-tetrahydro-quinolin-6-yl)-pyridin-3-ylmethyl]-amide;

(R)-2-Methyl-propane-2-sulfinic acid [5-(7-fluoro-1-methyl-2-oxo-1,2,3,4-tetrahydro-quinolin-6-yl)-4-methyl-pyridin-3-ylmethyl]-amide;

6-(5-Aminomethyl-4-methyl-pyridin-3-yl)-7-fluoro-1-methyl-3,4-dihydro-1H-quinolin-2-one hydrochloride;

3-Chloro-pyridine-2-carboxylic acid [5-(7-fluoro-1-methyl-2-oxo-1,2,3,4-tetrahydro-quinolin-6-yl)-4-methyl-pyridin-3-ylmethyl]-amide;

3-Chloro-pyridine-2-carboxylic acid [4-chloro-5-(1-methyl-2-oxo-1,2,3,4-tetrahydro-quinolin-6-yl)-pyridin-3-ylmethyl]-methyl-amide;

3-Chloro-pyridine-2-carboxylic acid methyl-[4-methyl-5-(1-methyl-2-oxo-1,2,3,4-tetrahydro-quinolin-6-yl)-pyridin-3-ylmethyl]-amide;

3-Chloro-pyridine-2-carboxylic acid {(R or S)-1-[5-(1-methyl-2-oxo-1,2,3,4-tetrahydro-quinolin-6-yl)-pyridin-3-yl]-ethyl}-amide;

5'-(1-Methyl-2-oxo-1,2,3,4-tetrahydro-quinolin-6-yl)-5,6-dihydro-4H-[3,3']bipyridinyl-1-carboxylic acid tert-butyl ester;

{2-[5-(7-Fluoro-1-methyl-2-oxo-1,2,3,4-tetrahydro-quinolin-6-yl)-pyridin-3-yloxy]-ethyl}-carbamic acid tert-butyl ester;

3-Chloro-pyridine-2-carboxylic acid {2-[5-(1-methyl-2-oxo-1,2,3,4-tetrahydro-quinolin-6-yl)-pyridin-3-yloxy]-ethyl}-amide;

Ethanesulfonic acid [5-(4-oxo-1,2,5,6-tetrahydro-4H-pyrrolo[3,2,1-ij]quinolin-8-yl)-pyridin-3-ylmethyl]-amide;

Ethanesulfonic acid [5-(3-oxo-2,3,6,7-tetrahydro-1H,5H-pyrido[3,2,1-ij]quinolin-9-yl)-pyridin-3-ylmethyl]-amide;

3-Chloro-pyridine-2-carboxylic acid [5-(4-oxo-1,2,5,6-tetrahydro-4H-pyrrolo[3,2,1-ij]quinolin-8-yl)-pyridin-3-ylmethyl]-amide;

3-Chloro-pyridine-2-carboxylic acid methyl-[5-(4-oxo-1,2,5,6-tetrahydro-4H-pyrrolo[3,2,1-ij]quinolin-8-yl)-pyridin-3-ylmethyl]-amide;

6-[5-(2-Amino-ethoxy)-pyridin-3-yl]-7-fluoro-1-methyl-3,4-dihydro-1H-quinolin-2-one hydrochloride;

(R)-2-Methyl-propane-2-sulfinic acid {(R or S)-1-[4-methyl-5-(1-methyl-2-oxo-1,2,3,4-tetrahydro-quinolin-6-yl)-pyridin-3-yl]-ethyl}-amide;

6-[5-((R or S)-1-Amino-ethyl)-4-methyl-pyridin-3-yl]-1-methyl-3,4-dihydro-1H-quinolin-2-one hydrochloride;

3-Chloro-pyridine-2-carboxylic acid {(R or S)-1-[4-methyl-5-(1-methyl-2-oxo-1,2,3,4-tetrahydro-quinolin-6-yl)-pyridin-3-yl]-ethyl}-amide;

3,5-Dimethyl-isoxazole-4-carboxylic acid {(R or S)-1-[4-methyl-5-(1-methyl-2-oxo-1,2,3,4-tetrahydro-quinolin-6-yl)-pyridin-3-yl]-ethyl}-amide;

Ethanesulfonic acid {2-[5-(7-fluoro-1-methyl-2-oxo-1,2,3,4-tetrahydro-quinolin-6-yl)-pyridin-3-yloxy]-ethyl}-amide;

3-Chloro-pyridine-2-carboxylic acid {2-[5-(7-fluoro-1-methyl-2-oxo-1,2,3,4-tetrahydro-quinolin-6-yl)-pyridin-3-yloxy]-ethyl}-amide;

N-{(trans)-4-[5-(1-Methyl-2-oxo-1,2,3,4-tetrahydro-quinolin-6-yl)-pyridin-3-yloxy]-cyclohexyl}-methanesulfonamide;

3,5-Dimethyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide;

5-(1-Methyl-2-oxo-1,2,3,4-tetrahydro-quinolin-6-yl)-3',6'-dihydro-2'H-[3,4']bipyridinyl-1'-carboxylic acid tert-butyl ester;

Ethanesulfonic acid {2-[5-(7-fluoro-1-methyl-2-oxo-1,2,3,4-tetrahydro-quinolin-6-yl)-pyridin-3-yloxy]-ethyl}-methyl-amide;

(R)-2-Methyl-propane-2-sulfinic acid {(R or S)-1-[4-chloro-5-(1-methyl-2-oxo-1,2,3,4-tetrahydro-quinolin-6-yl)-pyridin-3-yl]-ethyl}-amide;
6-[5-((R or S)-1-Amino-ethyl)-4-chloro-pyridin-3-yl]-1-methyl-3,4-dihydro-1H-quinolin-2-one hydrochloride;
3-Chloro-pyridine-2-carboxylic acid {(R or S)-1-[4-chloro-5-(1-methyl-2-oxo-1,2,3,4-tetrahydro-quinolin-6-yl)-pyridin-3-yl]-ethyl}-amide;
(R)-2-Methyl-propane-2-sulfinic acid {(R or S)-1-[5-(7-fluoro-1-methyl-2-oxo-1,2,3,4-tetrahydro-quinolin-6-yl)-4-methyl-pyridin-3-yl]-ethyl}-amide;
6-[5-((R or S)-1-Amino-ethyl)-4-methyl-pyridin-3-yl]-7-fluoro-1-methyl-3,4-dihydro-1H-quinolin-2-one hydrochloride;
6-[5-((S)-1-Acetyl-pyrrolidin-3-yloxy)-pyridin-3-yl]-1-methyl-3,4-dihydro-1H-quinolin-2-one;
1-Methyl-6-{5-[(S)-1-(1-methyl-1H-pyrazole-4-carbonyl)-pyrrolidin-3-yloxy]-pyridin-3-yl}-3,4-dihydro-1H-quinolin-2-one;
(S)-3-[5-(1-Methyl-2-oxo-1,2,3,4-tetrahydro-quinolin-6-yl)-pyridin-3-yloxy]-pyrrolidine-1-carboxylic acid ethyl ester;
3,5-Dimethyl-isoxazole-4-carboxylic acid {(R or S)-1-[4-chloro-5-(1-methyl-2-oxo-1,2,3,4-tetrahydro-quinolin-6-yl)-pyridin-3-yl]-ethyl}-amide;
3-Chloro-pyridine-2-carboxylic acid {(R or S)-1-[5-(7-fluoro-1-methyl-2-oxo-1,2,3,4-tetrahydro-quinolin-6-yl)-4-methyl-pyridin-3-yl]-ethyl}-amide;
5-Methyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide;
5-(1-Methyl-2-oxo-1,2,3,4-tetrahydro-quinolin-6-yl)-3',4',5',6'-tetrahydro-2'H-[3,4]bipyridinyl-1'-carboxylic acid tert-butyl ester;
N-{(R or S)-1-[4-Chloro-5-(1-methyl-2-oxo-1,2,3,4-tetrahydro-quinolin-6-yl)-pyridin-3-yl]-ethyl}-propionamide;
6-[5-(1-Amino-cyclopropyl)-pyridin-3-yl]-1-methyl-1H-quinolin-2-one;
Ethanesulfonic acid [5-(8-fluoro-1-methyl-2-oxo-1,2-dihydro-quinolin-6-yl)-pyridin-3-ylmethyl]-amide;
N-{(R or S)-1-[5-(7-Fluoro-1-methyl-2-oxo-1,2,3,4-tetrahydro-quinolin-6-yl)-4-methyl-pyridin-3-yl]-ethyl}-propionamide;
N-[4-Chloro-5-(1-methyl-2-oxo-1,2,3,4-tetrahydro-quinolin-6-yl)-pyridin-3-ylmethyl]-propionamide;
N-{(R or S)-1-[4-Methyl-5-(1-methyl-2-oxo-1,2,3,4-tetrahydro-quinolin-6-yl)-pyridin-3-yl]-ethyl}-propionamide;
3,5-Dimethyl-isoxazole-4-carboxylic acid {2-[5-(7-fluoro-1-methyl-2-oxo-1,2,3,4-tetrahydro-quinolin-6-yl)-pyridin-3-yloxy]-ethyl}-amide;
and pharmaceutically acceptable salts thereof.

Further particular examples of compounds of formula (I) as described herein are selected from
6-[5-(2-Hydroxy-ethylamino)-pyridin-3-yl]-1-methyl-3,4-dihydro-1H-quinolin-2-one;
6-[5-((S)-2-Hydroxymethyl-pyrrolidin-1-yl)-pyridin-3-yl]-1-methyl-3,4-dihydro-1H-quinolin-2-one;
6-[5-((S)-2-Hydroxymethyl-pyrrolidin-1-ylmethyl)-pyridin-3-yl]-1-methyl-3,4-dihydro-1H-quinolin-2-one;
6-[5-((S)-2-Hydroxymethyl-5-oxo-pyrrolidin-1-ylmethyl)-pyridin-3-yl]-1-methyl-3,4-dihydro-1H-quinolin-2-one;
Ethanesulfonic acid [5-(1-methyl-2-oxo-1,2,3,4-tetrahydro-quinolin-6-yl)-pyridin-3-ylmethyl]-amide;
Ethanesulfonic acid [5-(7-fluoro-1-methyl-2-oxo-1,2,3,4-tetrahydro-quinolin-6-yl)-pyridin-3-ylmethyl]-amide;
1-Methyl-6-[5-(2-oxo-pyrrolidin-1-ylmethyl)-pyridin-3-yl]-3,4-dihydro-1H-quinolin-2-one;
6-[5-((R)-1-Hydroxymethyl-2-methyl-propylamino)-pyridin-3-yl]-1-methyl-3,4-dihydro-1H-quinolin-2-one;
and pharmaceutically acceptable salts thereof.

Also further particular examples of compounds of formula (I) as described herein are selected from
3,5-Dimethyl-isoxazole-4-carboxylic acid [5-(1-methyl-2-oxo-1,2,3,4-tetrahydro-quinolin-6-yl)-pyridin-3-ylmethyl]-amide;
1-Methyl-6-[5-((S)-1-propionyl-pyrrolidin-3-yloxy)-pyridin-3-yl]-3,4-dihydro-1H-quinolin-2-one;
5-Methyl-isoxazole-4-carboxylic acid [5-(1-methyl-2-oxo-1,2,3,4-tetrahydro-quinolin-6-yl)-pyridin-3-ylmethyl]-amide;
3,5-Dimethyl-isoxazole-4-carboxylic acid {2-[5-(1-methyl-2-oxo-1,2,3,4-tetrahydro-quinolin-6-yl)-pyridin-3-yloxy]-ethyl}-amide;
1-Methyl-1H-pyrazole-4-carboxylic acid {2-[5-(1-methyl-2-oxo-1,2,3,4-tetrahydro-quinolin-6-yl)-pyridin-3-yloxy]-ethyl}-amide;
3-Chloro-pyridine-2-carboxylic acid [5-(1-methyl-2-oxo-1,2,3,4-tetrahydro-quinolin-6-yl)-pyridin-3-ylmethyl]-amide;
3-Chloro-pyridine-2-carboxylic acid [5-(7-fluoro-1-methyl-2-oxo-1,2,3,4-tetrahydro-quinolin-6-yl)-pyridin-3-ylmethyl]-amide;
7-Fluoro-1-methyl-6-[5-((R)-1-propionyl-pyrrolidin-3-yloxy)-pyridin-3-yl]-3,4-dihydro-1H-quinolin-2-one;
3-Chloro-pyridine-2-carboxylic acid {1-[5-(1-methyl-2-oxo-1,2,3,4-tetrahydro-quinolin-6-yl)-pyridin-3-yl]-cyclopropyl}-amide;
3-Chloro-pyridine-2-carboxylic acid {1-methyl-1-[5-(1-methyl-2-oxo-1,2,3,4-tetrahydro-quinolin-6-yl)-pyridin-3-yl]-ethyl}-amide;
3-Chloro-pyridine-2-carboxylic acid {1-[5-(7-fluoro-1-methyl-2-oxo-1,2,3,4-tetrahydro-quinolin-6-yl)-pyridin-3-yl]-cyclopropyl}-amide;
Ethanesulfonic acid {(trans)-4-[5-(1-methyl-2-oxo-1,2,3,4-tetrahydro-quinolin-6-yl)-pyridin-3-yloxy]-cyclohexyl}-amide;
1-Methyl-1H-pyrazole-4-carboxylic acid [5-(7-fluoro-1-methyl-2-oxo-1,2,3,4-tetrahydro-quinolin-6-yl)-pyridin-3-ylmethyl]-amide;
Ethanesulfonic acid {1-methyl-1-[5-(1-methyl-2-oxo-1,2,3,4-tetrahydro-quinolin-6-yl)-pyridin-3-yl]-ethyl}-amide;
6-{5-[2-(1,1-Dioxo-1λ6-isothiazolidin-2-yl)-ethoxy]-pyridin-3-yl}-1-methyl-3,4-dihydro-1H-quinolin-2-one;
Ethanesulfonic acid {(R or S)-1-[5-(7-fluoro-1-methyl-2-oxo-1,2,3,4-tetrahydro-quinolin-6-yl)-pyridin-3-yl]-ethyl}-amide;
Ethanesulfonic acid {(S or R)-1-[5-(7-fluoro-1-methyl-2-oxo-1,2,3,4-tetrahydro-quinolin-6-yl)-pyridin-3-yl]-ethyl}-amide;
Ethanesulfonic acid methyl-{2-[5-(1-methyl-2-oxo-1,2,3,4-tetrahydro-quinolin-6-yl)-pyridin-3-yloxy]-ethyl}-amide;
Ethanesulfonic acid [5-(4-oxo-1,2,5,6-tetrahydro-4H-pyrrolo[3,2,1-ij]quinolin-8-yl)-pyridin-3-ylmethyl]-amide;
N-{(trans)-4-[5-(1-Methyl-2-oxo-1,2,3,4-tetrahydro-quinolin-6-yl)-pyridin-3-yloxy]-cyclohexyl}-methanesulfonamide;
3,5-Dimethyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide;
5-(1-Methyl-2-oxo-1,2,3,4-tetrahydro-quinolin-6-yl)-3',6'-dihydro-2'H-[3,4]bipyridinyl-1'-carboxylic acid tert-butyl ester;
Ethanesulfonic acid {2-[5-(7-fluoro-1-methyl-2-oxo-1,2,3,4-tetrahydro-quinolin-6-yl)-pyridin-3-yloxy]-ethyl}-methyl-amide;
3,5-Dimethyl-isoxazole-4-carboxylic acid {2-[5-(7-fluoro-1-methyl-2-oxo-1,2,3,4-tetrahydro-quinolin-6-yl)-pyridin-3-yloxy]-ethyl}-amide;

1-Methyl-6-{5-[(S)-1-(1-methyl-1H-pyrazole-4-carbonyl)-pyrrolidin-3-yloxy]-pyridin-3-yl}-3,4-dihydro-1H-quinolin-2-one;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:

AcOH=acetic acid, BOC=t-butyloxycarbonyl, BuLi=butyllithium, CDI=1,1-carbonyldiimidazole, CH$_2$Cl$_2$=dichloromethane, DBU=2,3,4,6,7,8,9,10-octahydro-pyrimido[1,2-a]azepine, DCE=1,2-dichloroethane, DCM=dichloromethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, Et$_2$O=diethylether, Et$_3$N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, IPC=in process control, LAH=lithium aluminium hydride, LDA=lithium diisopropylamide, LiBH$_4$=lithium borohydride, MeOH=methanol, NaBH$_3$CN, sodium cyanoborohydride, NaBH$_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Scheme 1a

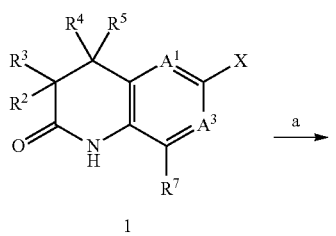

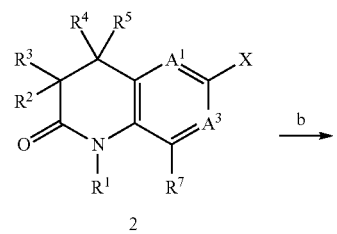

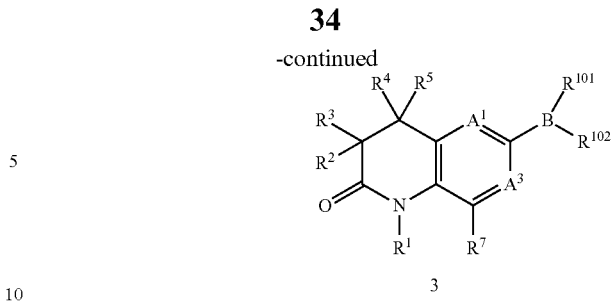

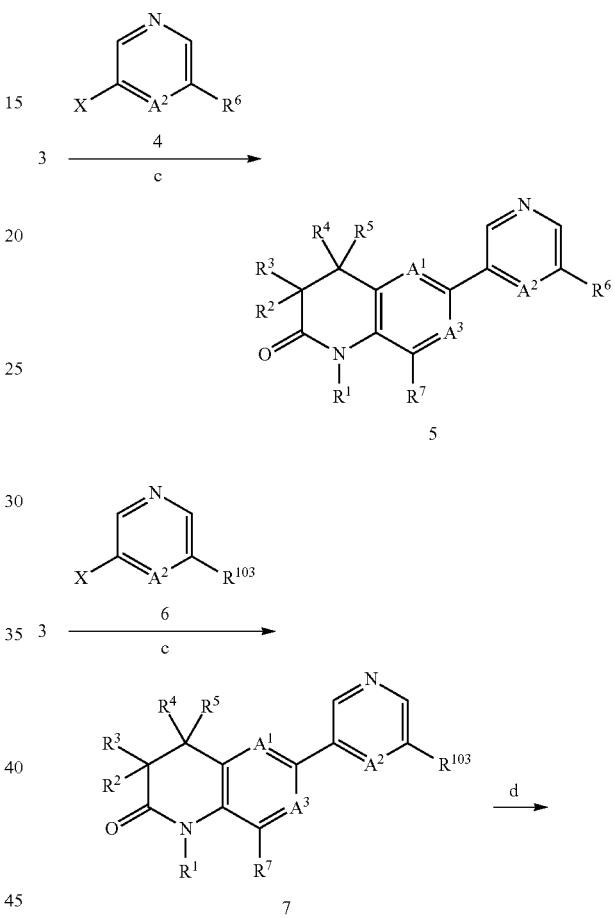

X is Halogen or OSO$_2$CF$_3$

R$^{101}$ and R$^{102}$ e.g.
together with the boron atom to which they are attached form 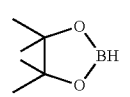

R$^{103}$ stands for substituents as e.g. shown in Schemes 2a and 2b, which allow further transformation into R$^6$ at a later stage in the synthesis Lactam compounds 1 (Scheme 1a) are known or can be prepared by methods described herein or known to the man skilled in the art (see also Scheme 1b for alternative syntheses of compounds 5 and 7); compounds 1 can be alkylated at nitrogen using a base like sodium hydride or sodium or potassium tert-butoxide, followed by addition of an alkylating agent of formula $R^1$—X, wherein Y is halogen, tosylate or mesylate, in a solvent like DMF or THF preferably in a temperature range between 0° C. and about 80° C. giving N-alkylated lactams 2 (step a).

Reaction of lactams 2 with e.g. 4,4,4',4',5,5,5',5'-octamethyl-2,2'-bi(1,3,2-5 dioxaborolane) in solvents like dimethylsulfoxide or dioxane in the presence of potassium acetate and catalysts like (1,1'-bis-diphenylphosphino)-ferrocene) palladium-(II)dichloride (1:1 complex with dichloromethane) at temperatures up to about 100° C. gives boronic ester compounds 3 (step b). Condensation of boronic ester compounds 3 with suitable aryl halides 4 or 6 (for possible syntheses of aryl halides 4 or 6, see Schemes 2) can be performed using Suzuki conditions, e.g. in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non-aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130° C. leading to adducts 5 or 7 (steps c). Compounds 7 can be further transformed into compounds of the general formula 5 by methods described in the following Schemes, the examples or by methods well known to persons skilled in the art (step d).

Halo-nitro pryridine compounds 8 (Scheme 1b) with at least one hydrogen substituent $R^7$ ortho to the nitro group react with 1-chloro-1-$R^5$-methanesulfonyl-4-methyl-benzene in solvents like THF and in the presence of a base like tert-BuOK in a temperature range between −78° C. and room temperature to give regioisomeric sulfones 9 and 10 (step a). Treatment of sulfones 9 and 10 with a haloacetic acid ester compound in a solvent like N,N-dimethylformamide and in the presence of a weak base as e.g. sodium or potassium carbonate preferably in a temperature range between room temperature and about 80° C. gives acetic acid ester adducts 11 and 16 (step b). Suzuki reactions of adducts 11 and 16 with suitable heteroaryl-boronic acid derivatives under conditions as described for step c (Scheme 1a) gives adducts 12 and 17 containing acrylic ester moieties by concomitant elimination of the 4-methyl-benzene-sulfonyl groups (step c). Catalytic hydrogenation e.g. using Pd/C and AcOH in methanol at elevated temperature and with $H_2$ pressure of about 50-200 psi gives lactam compounds 13 and 18 (step d). Treatment of lactam compounds 13 and 18 with an alkylating agent like an alkyl or cycloalkyl halide, alkyl or cycloalkyl tosylate or an alkyl or cycloalkyl mesylate in a solvent like THF or N,N-dimethylformamide in the presence of a base like sodium or potassium hydride preferable around 0° C. gives alkylated lactam compounds 14 and 19 (step e). Alkylated lactam compounds 14 and 19 can be further transformed into compounds of the general formula 15 or 20 by methods described in the following Schemes, the examples or by methods well known to persons skilled in the art (step f).

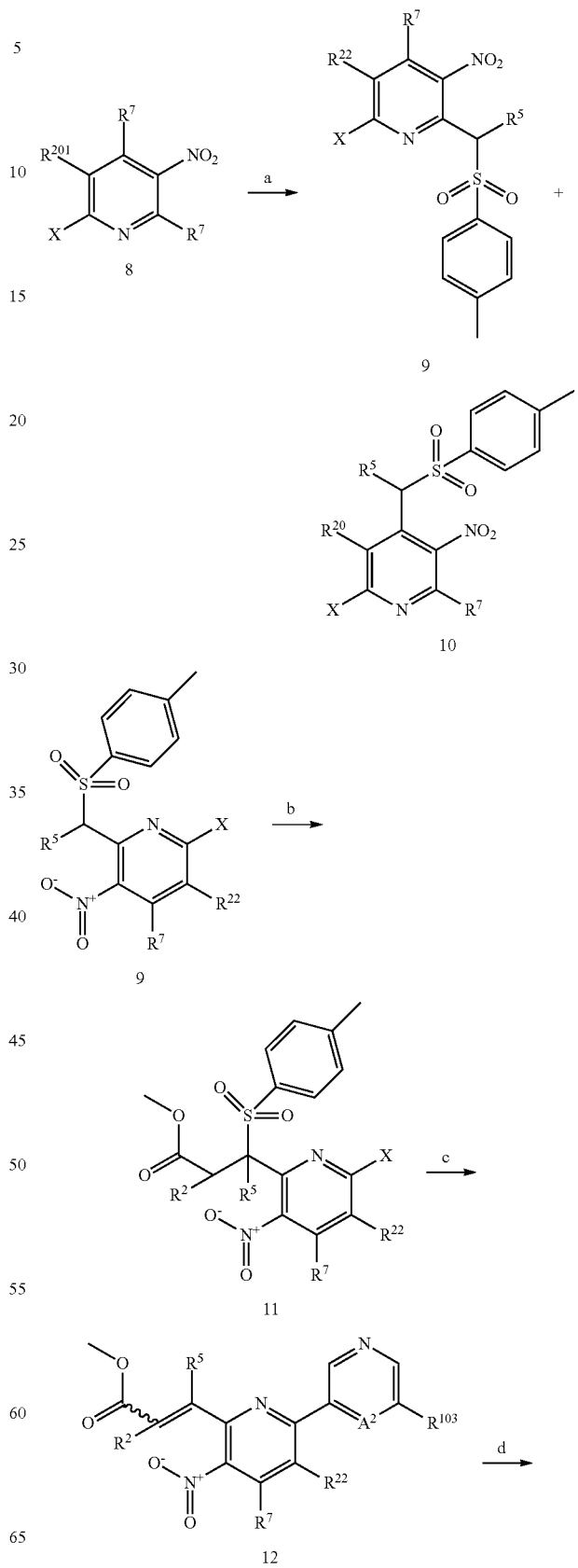

Scheme 1b

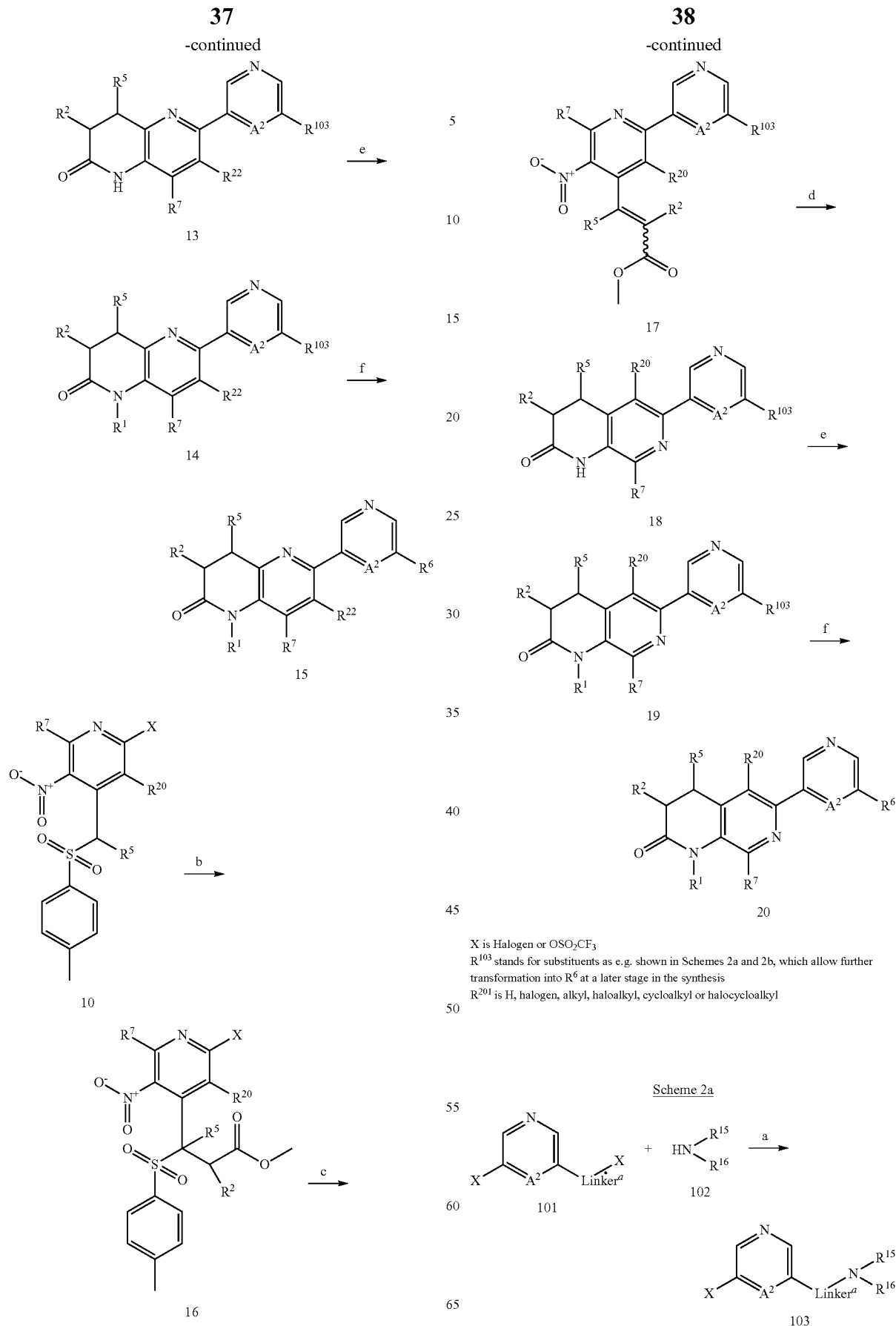
X is Halogen or OSO$_2$CF$_3$
R$^{103}$ stands for substituents as e.g. shown in Schemes 2a and 2b, which allow further transformation into R$^6$ at a later stage in the synthesis
R$^{201}$ is H, halogen, alkyl, haloalkyl, cycloalkyl or halocycloalkyl
Scheme 2a

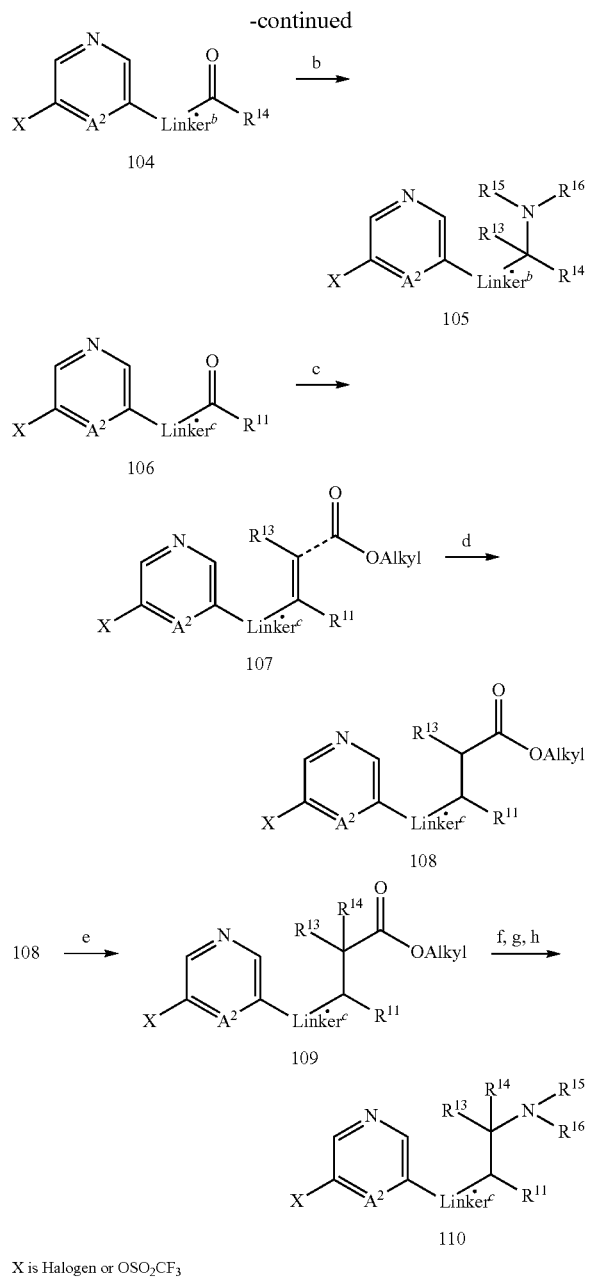

X is Halogen or OSO$_2$CF$_3$

Schemes 2a and 2b describe possible syntheses of aryl halide compounds 103, 105, 110, 114, 117 and 121 which correspond to aryl halides 4 and 6 in Scheme 1. The terms linker used in Scheme 2a are defined as follows:
Linker$^a$=—O$_m$—(CR$^9$R$^{10}$)$_n$—(CR$^{11}$R$^{12}$)$_p$—(CR$^{13}$R$^{14}$)$_q$—, N$_m$R$^{17}$—(CR$^9$R$^{10}$)$_n$—(CR$^{11}$R$^{12}$)$_p$—(CR$^{13}$R$^{14}$)$_q$— or —S$_m$(O)$_r$—(CR$^9$R$^{10}$)$_n$—(CR$^{11}$R$^{12}$)$_p$—(CR$^{13}$R$^{14}$)$_q$—;

Linker$^b$=—O$_m$—(CR$^9$R$^{10}$)$_n$—(CR$^{11}$R$^{12}$)$_p$—, —N$_m$R$^{17}$—(CR$^9$R$^{10}$)$_n$—(CR$^{11}$R$^{12}$)$_p$— or —S$_m$(O)$_r$—(CR$^9$R$^{10}$)$_n$—(CR$^{11}$R$^{12}$)$_p$—;

Linker$^c$=—O$_m$—(CR$^9$R$^{10}$)$_n$—, —N$_m$R$^{17}$—(CR$^9$R$^{10}$)$_n$— or —S$_m$(O)$_n$—(CR$^9$R$^{10}$)$_n$—.

Compounds 101 (Scheme 2a) carrying an aliphatic Linker$^a$ react with amino compounds 102 either per se or after anion formation e.g. with sodium hydride in solvents like N,N'-dimethylformamide in a temperature range between 0° C. and about 100° C. to form adducts 103 (step a). Compounds 101 in which Linker$^a$ is absent react with amino compounds 102 (R$^{16}$ is H, alkyl, haloalkyl, cycloalkyl, halocycloalkyl, hydroxyalkyl, alkoxyalkyl, haloalkoxyalkyl, phenylalkyl, substituted phenylalkyl, aryl, substituted aryl, heterocycloalkyl, substituted heterocycloalkyl, heteroaryl or substituted heteroaryl) either directly in the presence of a base like Hunig's base in a solvent like butanol and elevated temperature or by using Pd(0)-catalyzed amination reactions (Buchwald-Hartwig coupling) under an inert atmosphere such as argon or nitrogen in the presence of a palladium catalyst such as tris(dibenzylideneacetone)dipalladium(0) (Pd$_2$(dba)$_3$) or palladium(II) acetate (Pd(COOCH$_3$)$_2$), a phosphine ligand like triphenylphosphine, rac-2,2'-bis(diphenylphosphino)-1,1'-binaphthalene (rac-BINAP) or (R)-(−)-1-[(S)-2-(dicyclohexylphosphino)ferrocenyl]ethyldi-tert-butylphosphine and a base such as Cs$_2$CO$_3$ or KOtert-Bu in a solvent like toluene, ethanol or water or mixtures thereof at room temperature or elevated temperatures, whereby heating might be achieved conventionally or by microwave irradiation to give substituted adducts 103 in which Linker$^a$ is absent (step a).

Compounds 101 in which Linker$^a$ is absent react with amino compounds 102 (R$^{16}$ is —S(O)$_2$R$^{18}$, —S(O)$_2$OR$^{18}$, —S(O)$_2$NR$^{18}$R$^{19}$, —C(O)R$^{18}$, —C(O)OR$^{18}$ or —C(O)NR$^{18}$R$^{19}$) in solvents like 1,4-dioxane, in the presence of copper (I) iodide, potassium or cesium carbonate, and a chelating 1,2-diamino compound like N,N'-dimethylethylenediamine or trans-1,2-diamino-hexane, at elevated temperatures, preferable with the aide of microwave heating to give substituted adducts 103 in which Linker$^a$ is absent (step a).

Suitable reductive amination procedures as e.g. treatment of aldehydes or ketones 104 and suitable amino-moieties with NaBH(OAc)$_3$ in a one step procedure in a solvent like methanol preferably around room temperature or in a two step procedure by first treatment with titanium (IV) isopropoxide in solvents like methanol or toluene preferably at temperatures between room temperature and the reflux temperature of the solvents followed by reaction with NaBH$_4$ preferably between 0° C. and room temperature converts aldehydes or ketones 104 into amino compounds 105; alternatively imines obtained after treatment with titanium (IV) isopropoxide can be evaporated, then be re-dissolved in a solvent like THF and being treated with a Grignard reagent R$^{13}$MgX, preferably between −40° C. and 0° C. leading to amino compounds 105 carrying the specific R$^{13}$ substituent (step b).

Aldehydes and ketones 106 react in Horner-Emmons reactions using e.g. reagents like dimethyl(methoxycarbonyl)methylphosphonate, optionally carrying an additional R$^{13}$ substituted at the methylene group, and a base like sodium hydride in a solvent like tetrahydrofuran preferable between about 0° C. and the reflux temperature of the solvent to give unsaturated esters 107 (step c). Reduction of the double bond in unsaturated esters 107 can be performed e.g. by using a mixture of nickel chloride and sodiumborohydride as reducing agents in solvents like methanol preferably between about 0° C. and room temperature leading to ester compounds 108 (step d). Alpha mono- or di-substituted esters 109 can be synthesized from esters 108, by treatment with a base like LDA or HMDS in solvents like tetrahydrofuran or 1,2-dimethoxyethane, followed by addition of one or sequentially two different alkyl halides, a reaction preferably performed between −78° C. and room temperature (step e). Esters 109 can be further transformed into amino compounds 110 suitable to function as compounds 4 or 6 in Scheme 1, e.g. by amide formation with ammonia in methanol around room temperature, Hofmann rearrangement, treatment with sodium hydroxide, and bromine in a solvent like ethanol preferably between about 0° C. and the reflux temperature of the solvent and subsequent introduction of $R^{15}$ and $R^{16}$ substituents (steps f, g, h) by methods known to the man skilled in the art.

Amino compounds 110 can also be obtained by hydrolysis of esters 109 to the corresponding acids followed by treatment with diphenylphosphoryl azide, TEA in a solvent like toluene preferably at reflux and subsequent treatment with e.g. sodium trimethylsilanoate in a solvent like THF preferably around RT followed by subsequent introduction of $R^{15}$ and $R^{16}$ substituents (steps f, g, h) by methods known to the man skilled in the art.

Di-halogen or di-triflate substituted heteroaromatic compounds 111 (Scheme 2b) react with unsaturated boronic acid derivatives 112 under Suzuki conditions as described in Scheme 1, step c, to adducts 113 (step i). Removal of the double bond in compounds 113 e.g. by catalytic hydrogenation, followed by additional standard synthetic modifications transforms compounds 113 into synthons 114 (step k).

Reaction of compounds 111 with amino compounds 115, performed under conditions as described for the transformation of compounds 101 in which Linker$^a$ is absent into compounds 103, is giving compounds 116 or 117 (step l). Compounds 116 can be transformed by additional standard synthetic modifications into synthons 117 (step m).

Phenols or thiophenols 118 react with alcohols 119 under Mitsunobu conditions e.g. with triphenylphosphine and di-tert-butyl-, diisopropyl-, diethyl-azodicarboxylate or di-(4-chlorobenzyl)azodicarboxylate as reagents in solvents like toluene, dichloromethane or tetrahydrofuran preferably at ambient temperature to give adducts 120 or 121 (step n). Compounds 120 can be transformed by additional modifications into synthons 121, such modifications include oxidation at sulfur to the respective sulfoxide or sulfone e.g. by using m-chloroperbenzoic acid (step o).

Scheme 2b

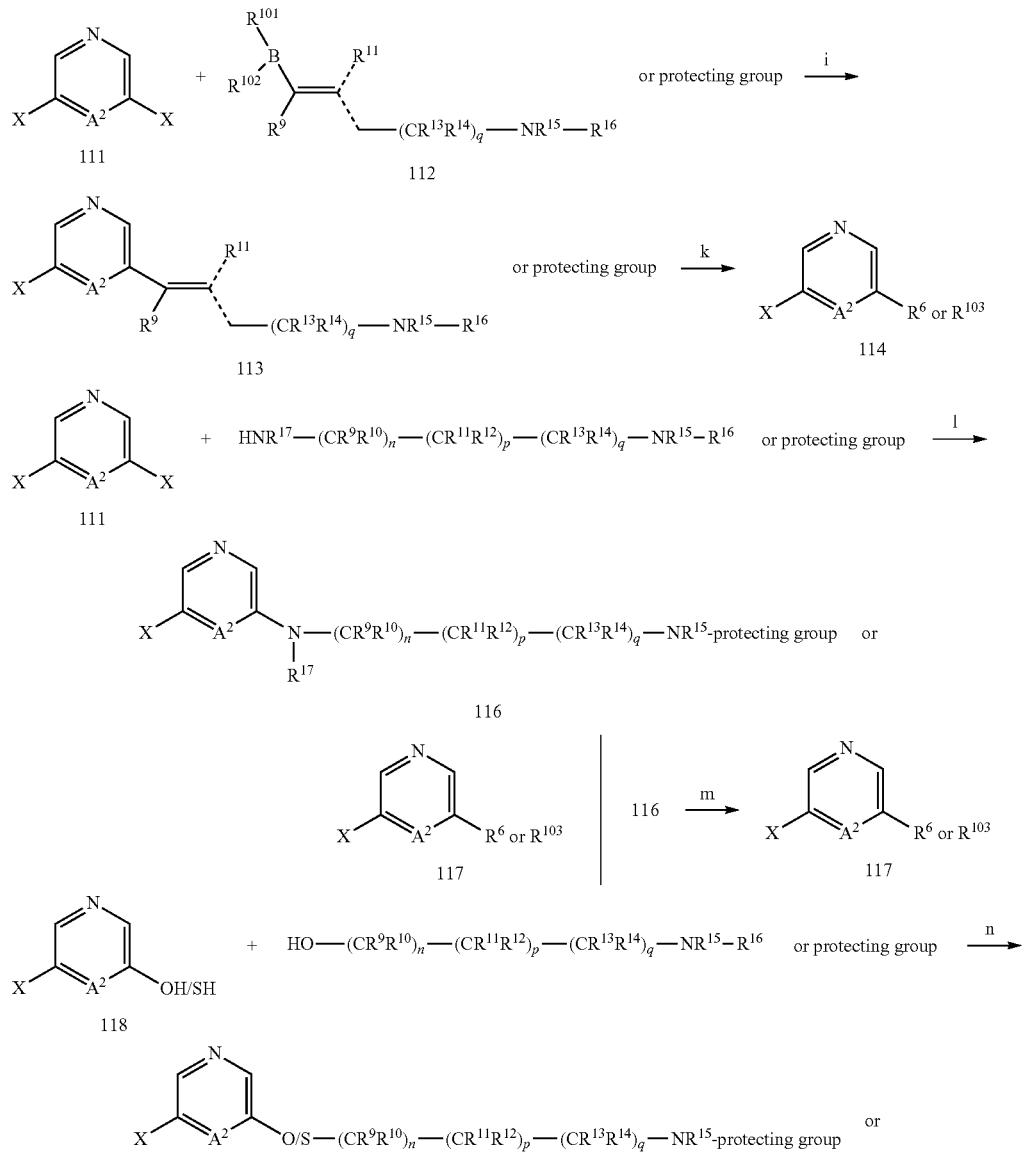

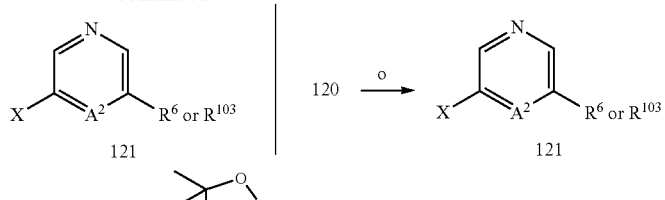

X is Halogen or $OSO_2CF_3$ $R^{101}$ and $R^{102}$ e.g. together with the boron atom to which they are attached form $R^{103}$ stands for substituents, which allow further transformation into $R^6$ at a later stage in the synthesis Also an embodiment of the present invention is a process to prepare a compound of formula (I) as defined above comprising the reaction of a compound of formula (II) in the presence of a compound of formula (III);

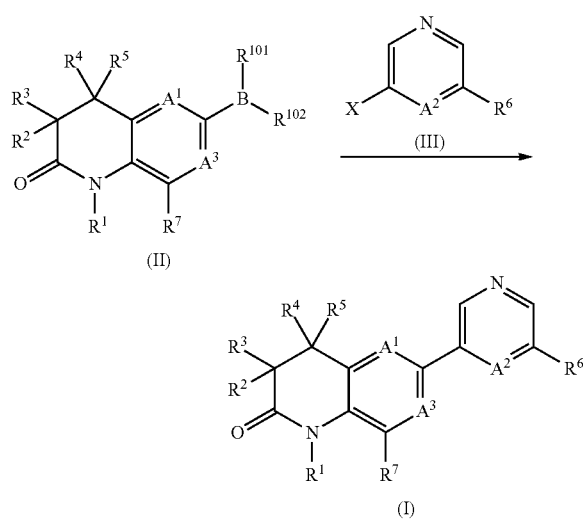

wherein $A^1$, $A^2$, $A^3$, $R^1$, $R^2$, $R^3$, $R^4$, $R^5$, $R^6$ and $R^7$ are as defined in claim 1 and wherein X is halogen or triflate, $R^{101}$ and $R^{102}$ are alkyl, cycloalkyl or together with the boron atom they are attached to form together a borolanyl.

In particular in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non-aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range particularly between room temperature and about 130°, wherein $A^1$, $A^2$, $A^3$, $R^1$, $R^2$, $R^3$, $R^4$, $R^5$, $R^6$ and $R^7$ are as defined in claim 1 and wherein X is halogen or triflate, $R^{103}$ and $R^{104}$ are alkyl, cycloalkyl or together with the boron atom they are attached to form together a borolanyl.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein. formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynomolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC(CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

| Example | EC50 human CYP11B2 µM | EC50 human CYP11B1 µM |
| --- | --- | --- |
| 1 | 0.170 | 3.70 |
| 2 | 0.430 | >3 |
| 3 | 0.715 | >3 |
| 4 | 0.011 | 0.35 |
| 5 | 0.019 | 1.08 |
| 6 | 0.098 | 3.34 |
| 7 | 0.056 | 0.57 |
| 8 | 0.049 | 2.33 |
| 9 | 0.829 | >10 |
| 10 | 0.020 | 0.17 |
| 11 | 0.076 | 0.41 |
| 12 | 0.002 | 0.05 |
| 13 | 0.319 | 17.89 |
| 14 | 0.308 | 1.57 |
| 15 | 0.019 | 1.20 |
| 16 | 0.011 | 0.86 |
| 17 | 4.649 | >10 |
| 18 | 0.058 | 0.75 |
| 19 | 0.023 | 0.80 |
| 20 | 0.003 | 0.02 |
| 21 | 0.021 | 0.26 |
| 22 | 0.025 | 0.10 |
| 23 | 0.032 | 0.39 |
| 24 | 0.007 | 0.22 |
| 25 | 0.005 | 0.11 |
| 26 | 0.018 | 0.57 |
| 27 | 0.007 | 0.27 |
| 28 | 0.121 | 0.78 |
| 29 | 0.260 | 5.56 |
| 30 | 0.170 | 10.22 |
| 31 | 0.172 | >3 |
| 32 | 1.293 | >10 |
| 33 | 1.256 | >10 |
| 34 | 0.416 | 29.22 |
| 35 | 0.325 | >10 |
| 36 | 0.071 | 2.57 |
| 37 | 0.044 | 1.59 |

-continued

| Example | EC50 human CYP11B2 µM | EC50 human CYP11B1 µM |
|---|---|---|
| 38 | 0.081 | 1.50 |
| 39 | 0.010 | 0.12 |
| 40 | 0.015 | 0.75 |
| 41 | 0.067 | 5.56 |
| 42 | 0.028 | 0.16 |
| 43 | 0.040 | 1.56 |
| 44 | 0.005 | 0.568 |
| 45 | 0.087 | 0.863 |
| 46 | 0.005 | 0.298 |
| 47 | 0.003 | 0.061 |
| 48 | 0.049 | 0.392 |
| 49 | 0.271 | 1.003 |
| 50 | 0.003 | 0.024 |
| 51 | 0.032 | 1.872 |
| 52 | 0.030 | 0.139 |
| 53 | 0.008 | 0.453 |
| 54 | n.d. | 3.855 |
| 55 | 0.682 | 11.133 |
| 56 | 0.040 | 0.587 |
| 57 | 0.026 | 0.393 |
| 59 | 0.033 | 0.710 |
| 60 | 0.685 | n.d. |
| 61 | 0.508 | 20.108 |
| 62 | 0.177 | 8.543 |
| 63 | 0.731 | 15.994 |
| 64 | 0.423 | 12.328 |
| 65 | 0.315 | 13.084 |
| 66 | 0.710 | n.d. |
| 67 | 0.160 | 7.675 |
| 68 | 0.350 | 33.719 |
| 69 | 0.411 | 3.492 |
| 70 | 0.202 | 15.608 |
| 71 | 0.081 | 2.497 |
| 72 | 0.007 | 0.101 |
| 73 | 0.017 | 0.575 |
| 74 | 0.286 | n.d. |
| 75 | 0.008 | 0.509 |
| 76 | 0.023 | 0.452 |
| 77 | 0.042 | 0.223 |
| 78 | 0.121 | 1.145 |
| 79 | 0.035 | 0.302 |
| 80 | 0.043 | 0.493 |
| 81 | 0.172 | 4.635 |
| 82 | 0.008 | 0.020 |
| 83 | 0.009 | 0.046 |
| 84 | 0.034 | 0.526 |
| 85 | 0.003 | 0.048 |
| 86 | 0.004 | 0.108 |
| 87 | 0.017 | 1.066 |
| 88 | 0.001 | 0.013 |
| 89 | 0.014 | 0.276 |
| 90 | 0.011 | 1.497 |
| 91 | 0.043 | 3.068 |
| 92 | 0.016 | 0.632 |
| 93 | 0.023 | 0.613 |
| 94 | 0.023 | 1.336 |
| 95 | 0.017 | 1.781 |
| 96 | 0.022 | 1.676 |
| 97 | 0.006 | 0.111 |
| 98 | 0.011 | 0.360 |
| 99 | 0.035 | 1.117 |
| 100 | 0.007 | 0.140 |
| 101 | 0.002 | 0.179 |
| 102 | 0.014 | 1.441 |
| 103 | 0.015 | 2.927 |
| 104 | 0.010 | 0.094 |
| 105 | 0.086 | 2.581 |
| 106 | 0.020 | 2.683 |
| 107 | 0.002 | 0.044 |
| 108 | 0.032 | 1.110 |
| 109 | 0.078 | 0.712 |
| 110 | 0.006 | 0.187 |
| 111 | 0.004 | 0.081 |
| 112 | 0.006 | 0.151 |
| 113 | 0.075 | 1.575 |
| 114 | 0.008 | 0.142 |
| 115 | 0.001 | 0.014 |
| 116 | 0.003 | 0.081 |
| 117 | 0.008 | 0.121 |
| 118 | 0.004 | 0.682 |
| 119 | 0.006 | 0.075 |
| 120 | 0.000 | 0.008 |
| 121 | 0.019 | 1.371 |
| 122 | 0.009 | 0.535 |
| 123 | 0.062 | 2.917 |
| 124 | 0.005 | 0.138 |
| 125 | 0.003 | 0.154 |
| 126 | 0.007 | 0.642 |
| 127 | 0.012 | 0.400 |
| 128 | 0.119 | 2.286 |
| 129 | 0.030 | 0.613 |
| 130 | 0.162 | 10.483 |
| 131 | 0.003 | 0.440 |
| 132 | 0.029 | 4.800 |
| 133 | 0.010 | 0.837 |
| 134 | 0.003 | 0.094 |
| 135 | 0.006 | 0.163 |
| 136 | 0.047 | 2.433 |
| 137 | 0.006 | 0.872 |
| 138 | 0.003 | 0.267 |
| 139 | 0.018 | 0.455 |
| 140 | 0.114 | 6.646 |
| 141 | 0.856 | 19.889 |
| 142 | 0.003 | 0.380 |
| 143 | 0.009 | 0.051 |
| 144 | 0.004 | 0.460 |
| 145 | 0.175 | 3.779 |
| 151 | 0.005 | 0.090 |
| 152 | 0.154 | 4.752 |
| 153 | 0.375 | 11.100 |
| 154 | 0.114 | 1.427 |
| 155 | 0.047 | 0.589 |
| 156 | 0.155 | 1.374 |
| 157 | 0.463 | 3.256 |
| 158 | 0.239 | 6.429 |
| 159 | 0.180 | 7.933 |
| 160 | 0.113 | 0.716 |
| 161 | 0.001 | 0.008 |
| 162 | 0.062 | 2.853 |
| 163 | 0.061 | 2.387 |
| 164 | 0.009 | 0.207 |
| 165 | 0.013 | 0.494 |
| 166 | 0.022 | 1.206 |
| 167 | 0.018 | 0.898 |
| 168 | 0.014 | 0.273 |
| 169 | 0.035 | 0.850 |
| 170 | 0.015 | 0.699 |
| 171 | 0.009 | 0.420 |
| 172 | 0.001 | 0.069 |
| 173 | 0.031 | 0.800 |
| 174 | 0.033 | 1.225 |
| 175 | 0.007 | 0.688 |
| 176 | 0.128 | n.d. |
| 177 | 0.117 | 8.464 |
| 178 | 0.010 | 0.535 |
| 179 | 0.012 | 0.169 |
| 180 | 0.033 | 1.891 |
| 181 | 0.025 | 2.320 |
| 182 | 0.006 | 0.302 |
| 183 | 0.004 | 0.268 |
| 184 | 0.227 | 9.741 |
| 185 | 0.633 | 9.289 |
| 186 | 0.011 | 0.199 |
| 187 | 0.027 | 0.705 |
| 188 | 0.014 | 0.572 |
| 189 | 0.002 | 0.093 |
| 190 | 0.007 | 0.442 |
| 191 | 0.010 | 0.777 |
| 192 | 0.029 | 1.981 |
| 193 | 0.022 | 1.009 |
| 194 | 0.041 | 1.704 |
| 195 | 0.001 | 0.056 |

-continued

| Example | EC50 human CYP11B2 µM | EC50 human CYP11B1 µM |
|---|---|---|
| 196 | 0.008 | 0.514 |
| 197 | 0.004 | 0.062 |
| 198 | 0.007 | 0.188 |
| 199 | 0.003 | 0.028 |
| 200 | 0.001 | 0.031 |
| 201 | 0.024 | 0.436 |
| 202 | 0.001 | 0.031 |
| 201 | 0.024 | 0.436 |
| 202 | 0.013 | 0.170 |
| 203 | 0.083 | 4.957 |
| 204 | 0.020 | 2.237 |
| 205 | 0.097 | 4.025 |
| 206 | 0.010 | 0.237 |
| 207 | 0.044 | 2.543 |
| 208 | 0.059 | 4.202 |
| 209 | 0.162 | 7.544 |
| 210 | 0.030 | 1.344 |
| 211 | 0.005 | 0.119 |
| 212 | 0.051 | 4.834 |
| 213 | 0.041 | 0.834 |
| 214 | 0.030 | 0.104 |
| 216 | 0.042 | 0.879 |
| 217 | 0.029 | 1.256 |
| 218 | 0.029 | 1.196 |
| 219 | 0.012 | 0.557 |
| 220 | 0.002 | 0.040 |
| 222 | 0.004 | 1.008 |
| 223 | 0.036 | 2.855 |
| 224 | 0.006 | 0.173 |
| 225 | 0.006 | 0.691 |
| 226 | 0.011 | 1.767 |
| 227 | 0.004 | 0.157 |
| 228 | 0.009 | 0.356 |
| 229 | 0.010 | 0.656 |
| 230 | 0.001 | 0.007 |
| 231 | 0.019 | 0.802 |
| 232 | 0.001 | 0.016 |
| 233 | 0.013 | 0.219 |
| 234 | 0.027 | 2.258 |
| 235 | 0.109 | 4.662 |
| 236 | 0.003 | 0.077 |
| 237 | 0.008 | 0.143 |
| 238 | 0.005 | 0.513 |
| 239 | 0.021 | 0.401 |
| 240 | 0.250 | 15.012 |
| 241 | 0.007 | 0.251 |
| 242 | 0.100 | 3.686 |
| 243 | 0.001 | 0.026 |
| 244 | 0.002 | 0.075 |
| 245 | 0.001 | 0.072 |
| 246 | 0.013 | 4.723 |
| 247 | 0.005 | 0.069 |
| 248 | 0.000 | 0.007 |
| 249 | 0.014 | 0.261 |
| 250 | 0.035 | 1.247 |
| 251 | 0.001 | 0.006 |
| 252 | 0.026 | 0.468 |
| 253 | 0.193 | 4.475 |
| 254 | 0.001 | 0.049 |
| 255 | 0.013 | 1.325 |
| 256 | 0.008 | 0.158 |
| 257 | 0.022 | 0.679 |
| 258 | 0.013 | 0.291 |
| 259 | 0.001 | 0.154 |
| 260 | 0.000 | 0.001 |
| 261 | 0.062 | 1.222 |
| 262 | 0.084 | 1.817 |
| 263 | 3.101 | n.d. |
| 264 | 0.024 | 2.921 |
| 265 | 0.009 | 0.623 |
| 266 | 0.054 | 0.623 |
| 267 | 0.001 | 0.236 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein display also variable inhibition of CYP11B1. These compounds may be used for the inhibition of CYP11B1 in combination with variable inhibition of CYP11B2. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), renal conditions, liver conditions, vascular conditions, inflammatory conditions, pain, retinopathy, neuropathy (such as peripheral neuropathy), insulinopathy, edema, endothelial dysfunction, baroreceptor dysfunction; fibrotic diseases, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, heart failure, hypertrophic cardiomyopathy, impaired arterial compliance, impaired diastolic filling, ischemia, left ventricular hypertrophy, myocardial and vascular fibrosis, myocardial infarction, myocardial necrotic lesions, myocardial necrotic lesions cardiac arrhythmias, prevention of sudden cardiac death, restenosis, stroke, vascular damage.

Renal conditions include acute and chronic renal failure, end-stage renal disease, decreased creatinine clearance, decreased glomerular filtration rate, diabetic nephropathy, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, nephropathy, proteinuria, reduced renal blood flow, renal arteriopathy, swelling and proliferation of intracapillary (endothelial and mesangial) and/or extracapillary cells (crescents).

Liver conditions include, but are not limited to, liver cirrhosis, liver ascites, hepatic congestion, nonalcoholic steatohepatitis and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, splenic congestion, liver ascites, respiratory or lung congestion, and the like.

Insulinopathies include, but are not limited to, insulin resistance, Type I diabetes mellitus, Type II diabetes mellitus, glucose sensitivity, pre-diabetic state, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In another embodiment, the cardiovascular condition is heart failure.

In another embodiment, the cardiovascular condition is left ventricular hypertrophy.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the compounds of formula (I) or their pharmaceutically acceptable salts and esters can be used for the treatment or prophylaxis Type II diabetes mellitus In another embodiment, the compounds of formula (I) or their pharmaceutically acceptable salts and esters can be used for the treatment or prophylaxis Type I diabetes mellitus The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate A-1

1-Methyl-6-(4,4,5,5-tetramethyl-[1,3,2]dioxaborolan-2-yl)-3,4-dihydro-1H-quinolin-2-one

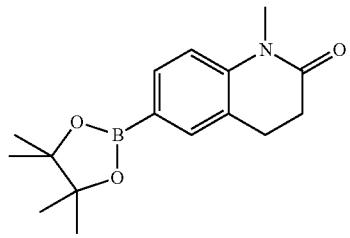 [SMILES: CN1C(=O)CCc2cc(B3OC(C)(C)C(C)(C)O3)ccc21]

[A]
6-Bromo-1-methyl-3,4-dihydro-1H-quinolin-2-one

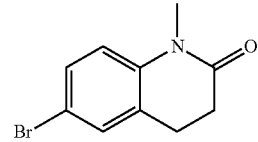

To a solution of 6-bromo-3,4-dihydroquinolin-2(1H)-one (5 g, 22.1 mmol) in DMF (100 mL) cooled to 0° C. was added potassium tert-butoxide (4.96 g, 44.2 mmol) portionwise and the reaction mixture was stirred at 0° C. for 15 min. Then, methyl iodide (4.08 g, 28.8 mmol) was added and the reaction mixture allowed to warm up to room temperature and stirring was continued over night. More MeI (1.25 g, 8.86 mmol) was added and the reaction mixture was heated to 40° C. until completion of the reaction. The mixture was diluted with EtOAc, poured into 100 mL of 1M HCl and the aqueous phase was extracted with EtOAc (2×200 mL). Combined organics were washed with brine, dried over $Na_2SO_4$, filtered and evaporated to dryness. The residue was purified by silica gel flash chromatography eluting with a 0 to 30% EtOAc-heptane gradient to give the title compound (4.23 g, 80%) as an off white solid. MS: 240.0, 242.1 (M+H$^+$).

[B] 1-Methyl-6-(4,4,5,5-tetramethyl-[1,3,2]dioxaborolan-2-yl)-3,4-dihydro-1H-quinolin-2-one

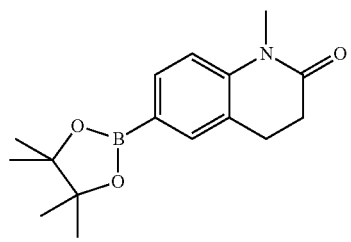 [SMILES: CN1C(=O)CCc2cc(B3OC(C)(C)C(C)(C)O3)ccc21]

A flask was charged with 6-bromo-1-methyl-3,4-dihydro-1H-quinolin-2-one (3 g, 12.5 mmol), 4,4,4',4',5,5,5',5'-octamethyl-2,2'-bi(1,3,2-dioxaborolane) (3.81 g, 15.0 mmol), potassium acetate (3.68 g, 37.5 mmol) and dioxane (48 mL). The mixture was purged with Ar, then dichloro[1,1'-bis(diphenylphosphino)-ferrocene]palladium(II) dichloromethane complex (1:1) [PdCl$_2$(DPPF)-CH$_2$Cl$_2$ adduct] (457 mg, 0.625 mmol) was added and the resulting mixture was heated to 80° C. over night. The reaction mixture was diluted with EtOAc, filtered through Dicalite and washed with EtOAc (2×150 mL). The resulting filtrate was washed with brine, dried over Na$_2$SO$_4$, filtered and evaporated to dryness. The residue was purified by silica gel flash chromatography eluting with a 0 to 40% EtOAc-heptane gradient to give the title compound (2.63 g, 73%) as an off white solid. MS: 288.0 (M+H$^+$).

Intermediate A-2

6-(5-Amino-pyridin-3-yl)-1-methyl-3,4-dihydro-1H-quinolin-2-one hydrochloride

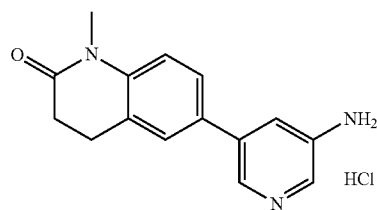

[A] 2,2-Dimethyl-N-[5-(1-methyl-2-oxo-1,2,3,4-tetrahydro-quinolin-6-yl)-pyridin-3-yl]-propionamide

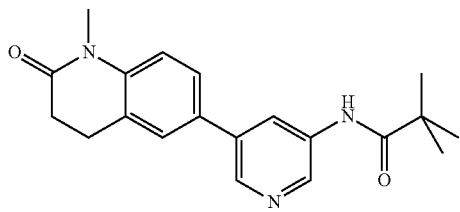 [SMILES: CN1C(=O)CCc2cc(-c3cncc(NC(=O)C(C)(C)C)c3)ccc21]

A microwave vial was charged with N-(5-bromopyridin-3-yl)pivalamide (0.2 g, 0.778 mmol), 1-methyl-6-(4,4,5,5-tetramethyl-[1,3,2]dioxaborolan-2-yl)-3,4-dihydro-1H-quinolin-2-one (intermediate A-1) (0.246 g, 0.856 mmol) and DMF (4 mL). The reaction mixture was purged with Argon; then, bis(triphenylphosphine)palladium(II)chloride (0.055 g, 0.078 mmol), followed by 1N aqueous Na$_2$CO$_3$ solution (2.33 mL, 2.33 mmol) were added and the reaction was heated in the microwave at 120° C. for 5 min. The reaction mixture was diluted with EtOAc, filtered through Dicalite and washed with EtOAc (2×20 mL). The resulting filtrate was washed with brine, dried over Na$_2$SO$_4$, filtered and evaporated to dryness. The residue was purified by silica gel flash chromatography eluting with a 0 to 5% MeOH-DCM gradient to give the title compound (0.195 g, 74%) as a white solid. MS: 338.2 (M+H$^+$).

[B] 6-(5-Amino-pyridin-3-yl)-1-methyl-3,4-dihydro-1H-quinolin-2-one hydrochloride

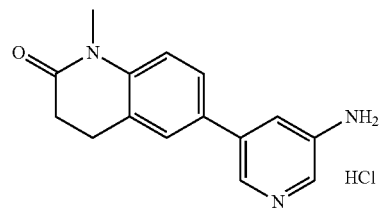 [SMILES: CN1C(=O)CCc2cc(-c3cncc(N)c3)ccc21 ; Cl]

A suspension of 2,2-dimethyl-N-[5-(1-methyl-2-oxo-1,2,3,4-tetrahydro-quinolin-6-yl)-pyridin-3-yl]-propionamide (0.195 g, 0.578 mmol) in 1N aqueous HCl (5.78 mL) was heated to 90° C. over night. The reaction mixture was evaporated to dryness and the resulting solid material was triturated in MeOH, filtered off and further dried in a the high vacuum to give the title compound (0.115 g, 69%) as an off white solid as the HCl salt. MS: 254.1 (M+H$^+$).

Intermediate A-3

6-{5-[(S)-2-(tert-Butyl-dimethyl-silanyloxymethyl)-pyrrolidin-1-yl]-pyridin-3-yl}-1-methyl-3,4-dihydro-1H-quinolin-2-one

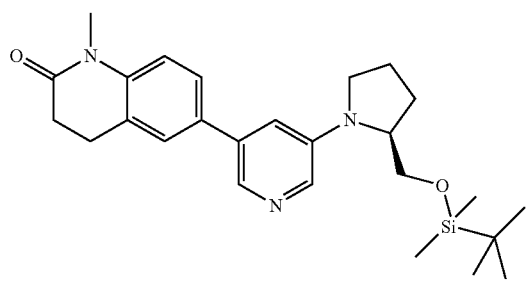 [SMILES: CN1C(=O)CCc2cc(-c3cncc(N4CCC[C@H]4CO[Si](C)(C)C(C)(C)C)c3)ccc21]

[A] (S)-2-(tert-Butyl-dimethyl-silanyloxymethyl)-pyrrolidine

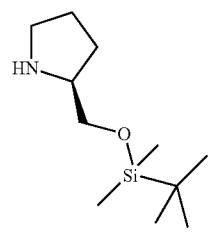

To a solution of (S)-pyrrolidin-2-yl-methanol (0.69 g, 6.82 mmol) in DCM (3 mL) cooled to 0° C. was added TEA (1.38 g, 13.6 mmol) followed by TBDMS-Cl (1.03 g, 6.82 mmol) in DCM (3 mL). The reaction mixture was then stirred at room temperature over night and poured into NH$_4$Cl (20 mL). The aqueous layer was extracted with DCM (2×50 mL). Combined organics were washed with brine, dried over Na₂SO₄, filtered and evaporated to dryness to give the title compound (1.11 g, 76%) as a yellow oil. MS: 216.2 (M+H⁺).

[B] 3-Bromo-5-[(S)-2-(tert-butyl-dimethyl-silanyloxymethyl)-pyrrolidin-1-yl]-pyridine

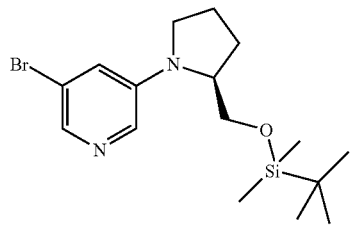 [SMILES: CC(C)(C)[Si](C)(C)OC[C@@H]1CCCN1c1cncc(Br)c1]

To a solution of (S)-2-((tert-butyldimethylsilyloxy)methyl)pyrrolidine (0.455 g, 2.11 mmol) in toluene (20 mL) were added tris(dibenzylideneacetone)dipalladium(0) (Pd₂(dba)₃) (0.039 g, 0.042 mmol) and rac-2,2'-bis(diphenylphosphino)-1,1'-binaphthalene (rac-BINAP) (0.066 g, 0.106 mmol). The solution was purged with Argon and heated to 85° C. for 10 min. After cooling to room temperature, sodium tert-butoxide (0.406 g, 4.22 mmol) and 3,5-dibromopyridine (0.5 g, 2.11 mmol) were added and the reaction mixture was then heated to 85° C. over night. The mixture was poured into sat. NH₄Cl (20 mL) and the aqueous layer was extracted with DCM (2×25 mL). Combined organics were washed with brine, dried over Na₂SO₄, filtered and evaporated to dryness. The residue was purified by silica gel flash chromatography eluting with a 0 to 5% MeOH-DCM gradient to give the title compound (0.412 g, 53%) as a yellow oil. MS: 371.0, 372.9 (M+H⁺).

[C] 6-{5-[(S)-2-(tert-Butyl-dimethyl-silanyloxymethyl)-pyrrolidin-1-yl]-pyridin-3-yl}-1-methyl-3,4-dihydro-1H-quinolin-2-one

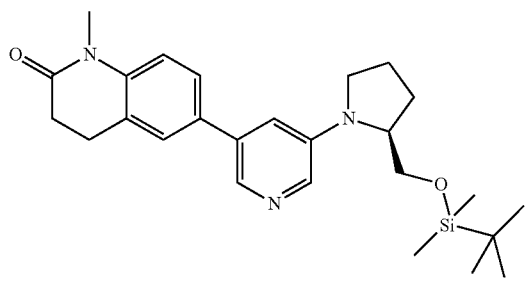 [SMILES: CN1C(=O)CCc2cc(-c3cncc(N4CCC[C@H]4CO[Si](C)(C)C(C)(C)C)c3)ccc21]

A microwave vial was charged with 3-bromo-5-[(S)-2-(tert-butyl-dimethyl-silanyloxymethyl)-pyrrolidin-1-yl]-pyridine (0.091 g, 0.245 mmol), 1-methyl-6-(4,4,5,5-tetramethyl-[1,3,2]dioxaborolan-2-yl)-3,4-dihydro-1H-quinolin-2-one (intermediate A-1, 0.077 g, 0.270 mmol) and DMF (1.5 mL). The reaction mixture was purged with Argon; then, bis(triphenylphosphine)palladium(II)chloride (0.017 g, 0.025 mmol), followed by a 1N Na₂CO₃ aqueous solution (0.980 mL, 0.980 mmol) were added and the reaction mixture was heated in the microwave at 120° C. for 30 min. The reaction mixture was diluted with EtOAc, poured into aq. NaHCO₃ (10 mL) and the aqueous layer was extracted with EtOAc (2×40 mL). Combined organics were washed with brine, dried over Na₂SO₄, filtered and evaporated. The residue was purified by silica gel flash chromatography eluting with a 0 to 5% MeOH-DCM gradient to give the title compound (0.1 g, 90%) as a white solid. MS: 452.1 (M+H⁺).

Intermediate A-4

6-{5-[(R)-2-(tert-Butyl-dimethyl-silanyloxymethyl)-pyrrolidin-1-yl]-pyridin-3-yl}-1-methyl-3,4-dihydro-1H-quinolin-2-one

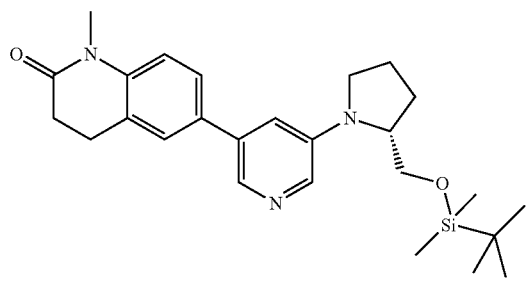 [SMILES: CN1C(=O)CCc2cc(-c3cncc(N4CCC[C@@H]4CO[Si](C)(C)C(C)(C)C)c3)ccc21]

[A] (R)-2-(tert-Butyl-dimethyl-silanyloxymethyl)-pyrrolidine

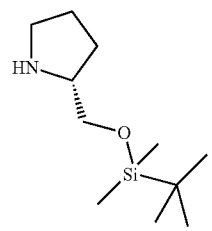

In analogy to the procedure described for the preparation of intermediate A-3 [A], (R)-pyrrolidin-2-yl-methanol was reacted with TBDMS-Cl in the presence of TEA to give the title compound as a yellow oil. MS: 216.3 (M+H⁺).

[B] 3-Bromo-5-[(R)-2-(tert-butyl-dimethyl-silanyloxymethyl)-pyrrolidin-1-yl]-pyridine

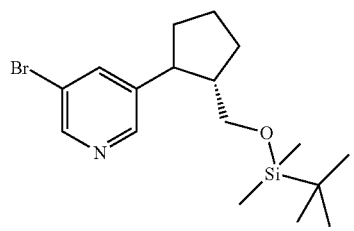 [SMILES: CC(C)(C)[Si](C)(C)OC[C@H]1CCCC1c1cncc(Br)c1]

In analogy to the procedure described for the preparation of intermediate A-3 [B], (R)-2-(tert-butyl-dimethyl-silanyloxymethyl)-pyrrolidine was reacted with 3,5-dibromopyridine in the presence of Pd$_2$(dba)$_3$, rac-BINAP and sodium tert-butoxide to give the title compound as a yellow oil. MS: 371.0, 372.9 (M+H$^+$).

[C] 6-{5-[(R)-2-(tert-Butyl-dimethyl-silanyloxymethyl)-pyrrolidin-1-yl]-pyridin-3-yl}-1-methyl-3,4-dihydro-1H-quinolin-2-one

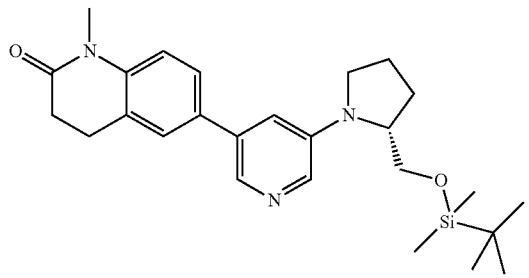 [SMILES: CN1C(=O)CCc2cc(-c3cncc(N4CCC[C@@H]4CO[Si](C)(C)C(C)(C)C)c3)ccc21]

In analogy to the procedure described for the preparation of intermediate A-3 [C], 1-methyl-6-(4,4,5,5-tetramethyl-[1,3,2]dioxaborolan-2-yl)-3,4-dihydro-1H-quinolin-2-one (intermediate A-1) has been coupled to 3-bromo-5-[(R)-2-(tert-butyl-dimethyl-silanyloxymethyl)-pyrrolidin-1-yl]-pyridine to give the title compound as a white solid. MS: 452.1 (M+H$^+$).

Intermediate A-5

3-Bromo-5-((S)-2-[1,2,4]triazol-1-ylmethyl-pyrrolidin-1-yl)-pyridine

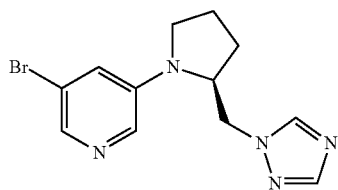 [SMILES: Brc1cncc(N2CCC[C@H]2Cn2cncn2)c1]

[A] [(S)-1-(5-Bromo-pyridin-3-yl)-pyrrolidin-2-yl]-methanol

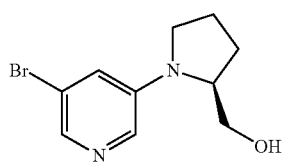 [SMILES: OC[C@@H]1CCCN1c1cncc(Br)c1]

To a solution of 3-bromo-5-[(S)-2-(tert-butyl-dimethyl-silanyloxymethyl)-pyrrolidin-1-yl]-pyridine (intermediate A-3 [B], 0.1 g, 0.269 mmol) in MeOH (2 mL) was added 4M HCl in dioxane (0.202 mL, 0.808 mmol) and the reaction mixture was stirred at room temperature for 1 h. The mixture was evaporated to dryness, the residue diluted with DCM, poured into aq. NaHCO$_3$ (10 mL) and extracted with DCM (25 mL). The organic layer was dried over Na$_2$SO$_4$, filtered and evaporated to give the title compound (0.060 g, 87%) as a yellow oil. MS: 257.0, 259.0 (M+H$^+$).

[B] 3-Bromo-5-((S)-2-chloromethyl-pyrrolidin-1-yl)-pyridine

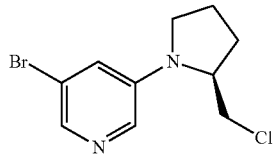 [SMILES: ClC[C@@H]1CCCN1c1cncc(Br)c1]

To a solution of (S)-(1-(5-bromopyridin-3-yl)pyrrolidin-2-yl)methanol (0.060 g, 0.233 mmol) in DCM (1 mL) cooled to 0° C. was added thionyl chloride (0.112 g, 0.932 mmol) dropwise. The reaction mixture was stirred at this temperature for 30 min and then allowed to warm up to room temperature and stirring was continued over night. The mixture was diluted with DCM, poured into aq. NaHCO$_3$ (10 mL) and the aqueous layer was extracted with DCM (2×20 mL). Combined organics were washed with brine, dried over Na$_2$SO$_4$, filtered and evaporated to dryness to give the title compound (0.055 g, 86%) as an orange oil. MS: 275.0, 277.0 (M+H$^+$).

[C] 3-Bromo-5-((S)-2-[1,2,4]triazol-1-ylmethyl-pyrrolidin-1-yl)-pyridine

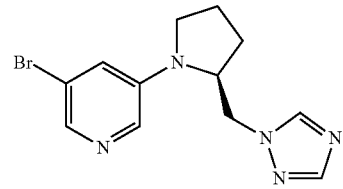 [SMILES: Brc1cncc(N2CCC[C@H]2Cn2cncn2)c1]

To a solution of NaH (0.011 g, 0.272 mmol) in DMF (1 mL) was added 1H-1,2,4-triazole (0.016 g, 0.236 mmol) and the reaction mixture was stirred at room temperature for 30 min. Then, 3-bromo-5-((S)-2-chloromethyl-pyrrolidin-1-yl)-pyridine (0.05 g, 0.181 mmol) in DMF (0.5 mL) was added to the reaction mixture which was heated to 80° C. over night. The mixture was diluted with DCM, poured into aq. NaHCO$_3$ (5 mL) and the aqueous layer was extracted with DCM (2×10 mL). Combined organics were dried over Na$_2$SO$_4$, filtered and evaporated to dryness to give the title compound (0.04 g, 72%) as a yellow oil. MS: 308.0, 310.0 (M+H$^+$).

Intermediate A-6

3-Bromo-5-((S)-2-methoxymethyl-pyrrolidin-1-yl)-pyridine

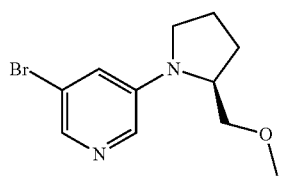

In analogy to the procedure described for the preparation of intermediate A-3 [B], (S)-2-methoxymethyl-pyrrolidine was reacted with 3,5-dibromopyridine in the presence of Pd$_2$ (dba)$_3$, rac-BINAP and sodium tert-butoxide to give the title compound as a yellow oil. MS: 271.1, 273.1 (M+H$^+$).

Intermediate A-7

[2-(5-Bromo-pyridin-3-yloxy)-ethyl]carbamic acid tert-butyl ester

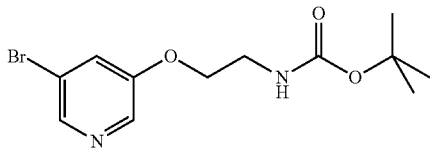 [SMILES: CC(C)(C)OC(=O)NCCOc1cncc(Br)c1]

To a solution of 5-bromopyridin-3-ol (0.5 g, 2.87 mmol) in THF (30 mL) cooled to 0° C. were added triphenylphosphine (0.829 g, 3.16 mmol) and tert-butyl 2-hydroxyethylcarbamate (0.51 g, 3.16 mmol) in THF (5 mL) followed by di-(4-chlorobenzyl)azodicarboxylate (1.16 g, 3.16 mmol), added portionwise, and the reaction mixture was then stirred at room temperature over night. The mixture was diluted with EtOAc, poured into aq. NaHCO$_3$ (50 mL) and the aqueous layer was extracted with EtOAc (2×100 mL). Combined organics were washed with brine, dried over Na$_2$SO$_4$, filtered and evaporated. The residue was taken up in diethyl ether (50 mL) and left to stand in the fridge for 2 h. After this time, the solid precipitate was filtered off and the resulting filtrate evaporated to dryness. The residue was purified by silica gel flash chromatography eluting with a 0 to 30% EtOAc-heptane gradient to give the title compound (0.57 g, 63%) as a white solid. MS: 317.0 and 319.0 (M+H$^+$).

Intermediate A-8

Benzyl-(5-bromo-pyridin-3-yl)-amine

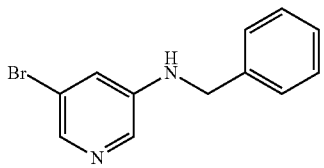

In analogy to the procedure described for the preparation of intermediate A-3 [B], benzylamine was reacted with 3,5-dibromopyridine in the presence of Pd$_2$(dba)$_3$, rac-BINAP and sodium tert-butoxide to give the title compound as a yellow solid. MS: 262.9, 264.9 (M+H$^+$).

Intermediate A-9

(S)-1-(5-Bromo-pyridin-3-yl)-5-hydroxymethyl-pyrrolidin-2-one

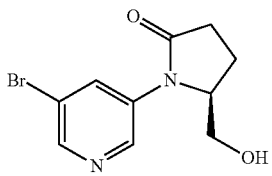

In a sealed tube, 3,5-dibromopyridine (0.5 g, 2.11 mmol) was combined with (S)-5-(hydroxymethyl)pyrrolidin-2-one (0.243 g, 2.11 mmol), copper (I) iodide (0.040 g, 0.021 mmol), potassium carbonate (0.583 g, 4.22 mmol) and N,N'-dimethylethylenediamine (0.037 g, 0.042 mmol) in 1,4-dioxane (20 mL). The reaction mixture was heated to 110° C. over night. The mixture was cooled to room temperature, filtered through Dicalite and washed with DCM. The residue was purified by silica gel flash chromatography eluting with a 0 to 10% MeOH-DCM gradient to give the title compound (0.140 g, 25%) as a light yellow oil. MS: 271.1, 273.1 (M+H$^+$).

Intermediate A-10

1-(5-Bromo-pyridin-3-yl)-pyrrolidin-2-one

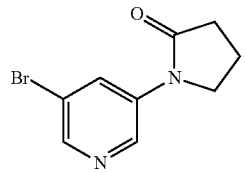 [SMILES: O=C1CCCN1c1cncc(Br)c1]

In analogy to the procedure described for the preparation of intermediate A-9, pyrrolidin-2-one has been coupled to 3,5-dibromopyridine to yield the title compound as a light yellow solid. MS: 241.0, 243.0 (M+H$^+$).

Intermediate A-11

Ethanesulfonic acid (5-bromo-pyridin-3-ylmethyl)-amide

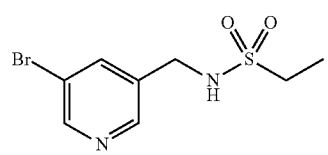

A flask was charged with 5-bromonicotinaldehyde (2.55 g, 13.7 mmol), ethanesulfonamide (2.99 g, 27.4 mmol) and toluene (250 mL), then titanium isopropoxide (5.84 g, 20.6 mmol) was added dropwise. The reaction mixture was heated to 115° C. over night and then concentrated in vacuo. The residue was taken up in DCM (200 mL) and MeOH (200 mL) and NaBH$_4$ (1.04 g, 27.4 mmol) was added portionwise at 0° C. The reaction mixture was stirred at 0° C. for 30 min and then poured into water (100 mL) and the resulting suspension was filtered through a pad of Dicalite and washed with DCM (3×100 mL). The aqueous layer was separated and extracted with DCM (2×200 mL). Combined organics were dried over Na$_2$SO$_4$, filtered and preadsorbed on silica gel. The residue was purified by silica gel flash chromatography eluting with a 0 to 5% MeOH-DCM gradient to give the title compound (3.01 g, 79%) as an orange solid. MS: 279.0, 281.0 (M+H$^+$).

Intermediate A-12

1-(5-Bromo-pyridin-3-ylmethyl)-pyrrolidin-2-one

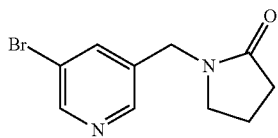 [SMILES: O=C1CCCN1Cc1cncc(Br)c1]

[A] 3-Bromo-5-chloromethyl-pyridine

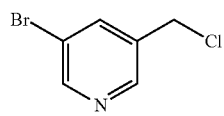

To a solution of (5-bromopyridin-3-yl)methanol (3 g, 16.0 mmol) in DCM (15 mL) cooled to 0° C. was added thionyl-chloride (7.59 g, 63.8 mmol) dropwise and the reaction mixture was stirred at room temperature over night. The mixture was poured onto ice/water (20 mL), basified with NaOH conc. (8 mL) and extracted with EtOAc (2×50 mL). Combined organics were dried over $Na_2SO_4$, filtered and evaporated to dryness. The residue was purified by silica gel flash chromatography eluting with a 0 to 40% EtOAc-Heptane gradient to give the title compound (3.08 g, 93%) as a white solid. MS: 206.0, 207.9 (M+H$^+$).

[B]
1-(5-Bromo-pyridin-3-ylmethyl)-pyrrolidin-2-one

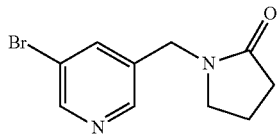 [SMILES: O=C1CCCN1Cc1cncc(Br)c1]

To a suspension of sodium hydride (60% in mineral oil, 0.044 g, 1.09 mmol) in DMF (2 mL) was added pyrrolidin-2-one (0.081 g, 0.945 mmol) and the reaction mixture was stirred at room temperature for 20 min. Then, 3-bromo-5-chloromethyl-pyridine (0.15 g, 0.727 mmol) was added and the resulting suspension was heated at 60° C. over night. The mixture was quenched with water (2 mL) and extracted with EtOAc (2×10 mL). Combined organics were dried over $Na_2SO_4$, filtered and concentrated in vacuo. The residue was purified by silica gel flash chromatography eluting with a 0 to 5% MeOH-DCM gradient to give the title compound (0.217 g, 87%) as a white solid. MS: 251.1, 257.1 (M+H$^+$).

Intermediate A-13

1-(5-Bromo-pyridin-3-ylmethyl)-piperidin-2-one

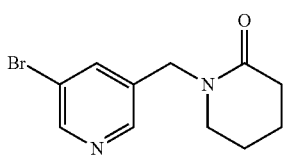 [SMILES: O=C1CCCCN1Cc1cncc(Br)c1]

In analogy to the procedure described for the preparation of intermediates A-12 [B], piperidin-2-one was reacted with 3-bromo-5-chloromethyl-pyridine (intermediate A-12 [A]) in the presence of NaH to give the title compound as a colorless oil. MS: 269.2, 271.2 (M+H$^+$).

Intermediate A-14

4-(5-Bromo-pyridin-3-ylmethyl)-thiomorpholine 1,1-dioxide

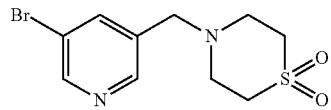 [SMILES: O=S1(=O)CCN(Cc2cncc(Br)c2)CC1]

In analogy to the procedure described for the preparation of intermediates A-12 [B], thiomorpholine 1,1-dioxide was reacted with 3-bromo-5-chloromethyl-pyridine (intermediate A-12 [A]) in the presence of NaH to give the title compound as a white solid. MS: 304.9, 307.0 (M+H$^+$).

Intermediate A-15

3-Bromo-5-((S)-2-methoxymethyl-pyrrolidin-1-ylmethyl)-pyridine

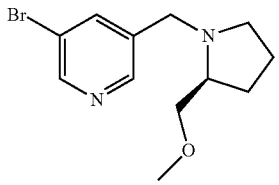 [SMILES: COC[C@@H]1CCCN1Cc1cncc(Br)c1]

In analogy to the procedure described for the preparation of intermediates A-12 [B], (S)-2-(methoxymethyl)pyrrolidine was reacted with 3-bromo-5-chloromethyl-pyridine (intermediate A-12 [A]) in presence of NaH to give the title compound as a yellow oil. MS: 285.0, 286.9 (M+H$^+$).

Intermediate A-16

6-{5-[(S)-2-(tert-Butyl-dimethyl-silanyloxymethyl)-pyrrolidin-1-ylmethyl]-pyridin-3-yl}-1-methyl-3,4-dihydro-1H-quinolin-2-one

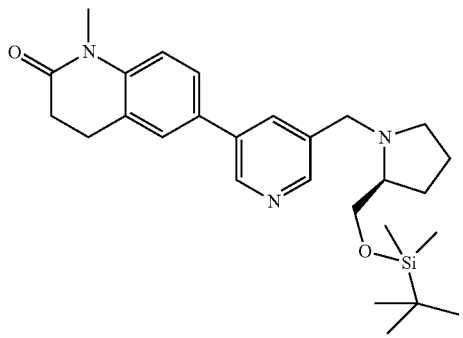 [SMILES: CN1C(=O)CCc2cc(-c3cncc(CN4CCC[C@H]4CO[Si](C)(C)C(C)(C)C)c3)ccc21]

[A] 3-Bromo-5-[(S)-2-(tert-butyl-dimethyl-silanyloxymethyl)-pyrrolidin-1-ylmethyl]-pyridine

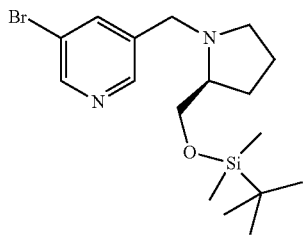 [SMILES: CC(C)(C)[Si](C)(C)OC[C@@H]1CCCN1Cc1cncc(Br)c1]

In analogy to the procedure described for the preparation of intermediates A-12 [B], (S)-2-(tert-butyl-dimethyl-silanyloxymethyl)-pyrrolidine (intermediate A-3 [A]) was reacted with 3-bromo-5-chloromethyl-pyridine (intermediate A-12 [A]) in presence of NaH to give the title compound as a yellow solid. MS: 385.2, 387.2 (M+H⁺).

[B] 6-{5-[(S)-2-(tert-Butyl-dimethyl-silanyloxymethyl)-pyrrolidin-1-ylmethyl]-pyridin-3-yl}-1-methyl-3,4-dihydro-1H-quinolin-2-one

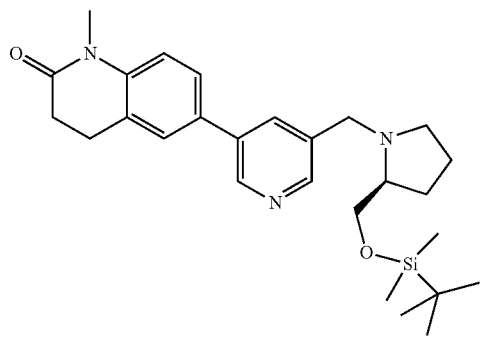 [SMILES: CN1C(=O)CCc2cc(-c3cncc(CN4CCC[C@H]4CO[Si](C)(C)C(C)(C)C)c3)ccc21]

In analogy to the procedure described for the preparation of intermediate A-3 [C], 1-methyl-6-(4,4,5,5-tetramethyl-[1,3,2]dioxaborolan-2-yl)-3,4-dihydro-1H-quinolin-2-one (intermediate A-1) has been coupled to 3-bromo-5-[(S)-2-(tert-butyl-dimethyl-silanyloxymethyl)-pyrrolidin-1-ylmethyl]-pyridine to give the title compound as an off white waxy solid. MS: 352.3 (M+H⁺).

Intermediate A-17

(S)-1-(5-Bromo-pyridin-3-ylmethyl)-pyrrolidine-2-carboxylic acid methyl ester

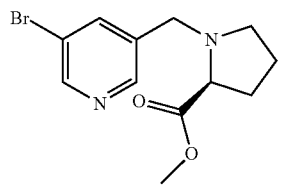 [SMILES: COC(=O)[C@@H]1CCCN1Cc1cncc(Br)c1]

In analogy to the procedure described for the preparation of intermediates A-12 [B], (S)-pyrrolidine-2-carboxylic acid methyl ester was reacted with 3-bromo-5-chloromethyl-pyridine (intermediate A-12 [A]) in presence of NaH to give the title compound as a light yellow oil. MS: 299.2, 301.1 (M+H⁺).

Intermediate A-18

6-{5-[(S)-2-(tert-Butyl-dimethyl-silanyloxymethyl)-5-oxo-pyrrolidin-1-ylmethyl]-pyridin-3-yl}-1-methyl-3,4-dihydro-1H-quinolin-2-one

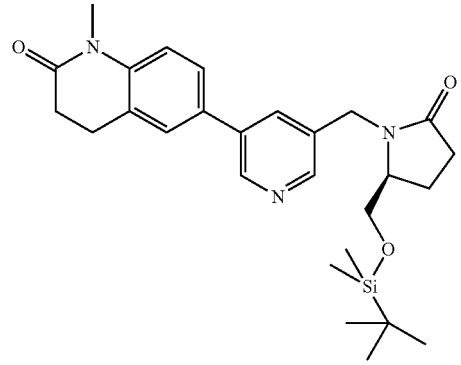 [SMILES: CN1C(=O)CCc2cc(-c3cncc(CN4C(=O)CC[C@H]4CO[Si](C)(C)C(C)(C)C)c3)ccc21]

[A] (S)-5-(tert-Butyl-dimethyl-silanyloxymethyl)-pyrrolidin-2-one

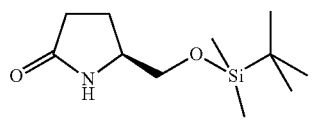

In analogy to the procedure described for the preparation of intermediate A-3 [A], (S)-5-hydroxymethyl-pyrrolidin-2-one was reacted with TBDMS-Cl in the presence of TEA to give the title compound as a colorless liquid. MS: 230.3 (M+H⁺).

[B] (S)-1-(5-Bromo-pyridin-3-ylmethyl)-5-(tert-butyl-dimethyl-silanyloxymethyl)-pyrrolidin-2-one

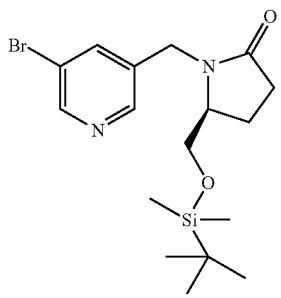 [SMILES: CC(C)(C)[Si](C)(C)OC[C@@H]1CCC(=O)N1Cc1cncc(Br)c1]

In analogy to the procedure described for the preparation of intermediates A-12 [B], (S)-5-(tert-butyl-dimethyl-silanyloxymethyl)-pyrrolidin-2-one was reacted with 3-bromo-5-chloromethyl-pyridine (intermediate A-12 [A]) in presence of NaH to give the title compound as a colorless oil. MS: 399.2, 401.2 (M+H$^+$).

[C] 6-{5-[(S)-2-(tert-Butyl-dimethyl-silanyloxymethyl)-5-oxo-pyrrolidin-1-ylmethyl]-pyridin-3-yl}-1-methyl-3,4-dihydro-1H-quinolin-2-one

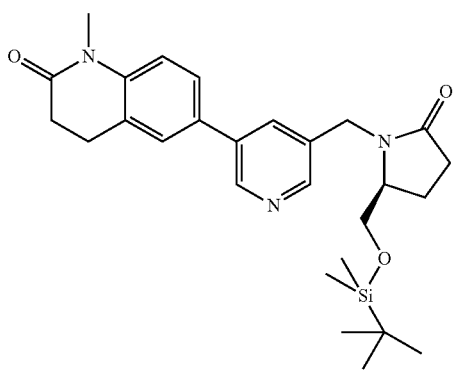 [SMILES: CN1C(=O)CCc2cc(-c3cncc(CN4C(=O)CC[C@H]4CO[Si](C)(C)C(C)(C)C)c3)ccc21]

In analogy to the procedure described for the preparation of intermediate A-3 [C], 1-methyl-6-(4,4,5,5-tetramethyl-[1,3,2]dioxaborolan-2-yl)-3,4-dihydro-1H-quinolin-2-one (intermediate A-1) has been coupled to (S)-1-(5-bromo-pyridin-3-ylmethyl)-5-(tert-butyl-dimethyl-silanyloxymethyl)-pyrrolidin-2-one to give the title compound as a brown foam. MS: 480.3 (M+H$^+$).

Intermediate A-19

3-Bromo-5-[(S)-2-(2,2,2-trifluoro-ethoxymethyl)-pyrrolidin-1-ylmethyl]-pyridine

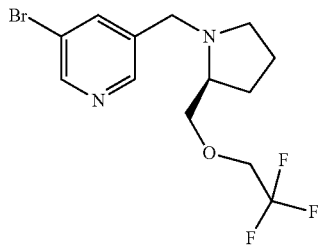 [SMILES: FC(F)(F)COC[C@@H]1CCCN1Cc1cncc(Br)c1]

[A] (S)-1-Benzyl-2-(2,2,2-trifluoro-ethoxymethyl)-pyrrolidine

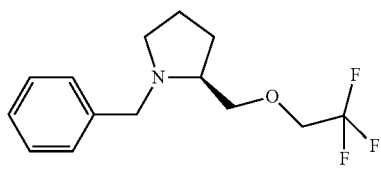 [SMILES: FC(F)(F)COC[C@@H]1CCCN1Cc1ccccc1]

To a suspension of sodium hydride (60% in mineral oil, 0.314 g, 7.84 mmol) in THF (20 mL) was added (S)-(1-benzyl-pyrrolidin-2-yl)-methanol (1.0 g, 5.23 mmol) and the reaction mixture was stirred at room temperature for 20 min. Then, 2,2,2-trifluoroethyl methanesulfonate (1.4 g, 7.84 mmol) was added and stirring was continued at room temperature over night. The reaction mixture was quenched with H$_2$O (10 mL) and extracted with EtOAc (2×50 mL). Combined organics were dried over Na$_2$SO$_4$, filtered and concentrated in vacuo. The residue was purified by silica gel flash chromatography eluting with a 0 to 5% MeOH(1% NH$_4$OH)-DCM gradient to give the title compound (0.706 g, 37%) as a light yellow liquid. MS: 274.3 (M+H$^+$).

[B] (S)-2-(2,2,2-Trifluoro-ethoxymethyl)-pyrrolidine

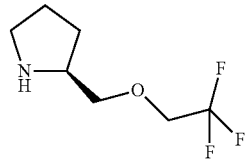 [SMILES: FC(F)(F)COC[C@@H]1CCCN1]

To a solution of (S)-1-benzyl-2-(2,2,2-trifluoroethoxymethyl)-pyrrolidine (0.5 g, 1.83 mmol) in MeOH (20 mL) was added Hunig's base (1.18 g, 9.15 mmol). The flask was purged three times with Ar and 10% Pd/C (0.487 g, 0.457 mmol) was added to the mixture. The flask was purged three times with hydrogen and the reaction mixture was stirred at room temperature for 1 h. The mixture was filtered through a pad of Celite, washed with MeOH (20 mL) and the resulting solution was concentrated in vacuo to give the title compound (0.250 g, 75%) as a colorless semi-solid. MS: 184.1 (M+H$^+$).

[C] 3-Bromo-5-[(S)-2-(2,2,2-trifluoro-ethoxymethyl)-pyrrolidin-1-ylmethyl]-pyridine

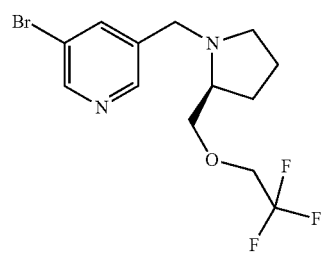 [SMILES: FC(F)(F)COC[C@@H]1CCCN1Cc1cncc(Br)c1]

In analogy to the procedure described for the preparation of intermediates A-12 [B], (S)-2-(2,2,2-trifluoro-ethoxymethyl)-pyrrolidine was reacted with 3-bromo-5-chloromethyl-pyridine (intermediate A-12 [A]) in presence of NaH to give the title compound as a yellow oil. MS: 353.1, 355.1 (M+H$^+$).

Intermediate A-20

2-(6-Chloro-pyrazin-2-ylamino)-ethanol

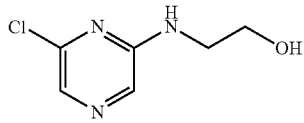 [SMILES: OCCNc1cncc(Cl)n1]

In a sealed tube, 2,6-dichloropyrazine (1 g, 6.71 mmol) was mixed with 2-aminoethanol (0.492 g, 8.05 mmol), Hunig's base (1.13 g, 8.73 mmol) in BuOH (7 mL) and the reaction mixture was heated to 80° C. over night. The mixture was concentrated in vacuo and the residue partitioned between NaHCO$_3$ (20 mL) and EtOAc (100 mL). The organic phase was separated, washed with brine, dried over Na$_2$SO$_4$, filtered and evaporated to dryness to give the title compound (0.583 g, 50%) as a light yellow foam. MS: 174.1 (M+H$^+$).

Intermediate A-21

Benzyl-(6-chloro-pyrazin-2-yl)-amine

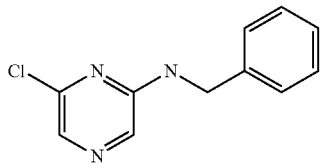 [SMILES: Clc1cncc(NCc2ccccc2)n1]

In analogy to the procedure described for the preparation of intermediates A-20, benzyl-amine was reacted with 2,6-dichloropyrazine in presence of Hunig's base to give the title compound as a light yellow foam. MS: 220.1 (M+H$^+$).

Intermediate A-22

7-Fluoro-1-methyl-6-(4,4,5,5-tetramethyl-[1,3,2]dioxaborolan-2-yl)-3,4-dihydro-1H-quinolin-2-one

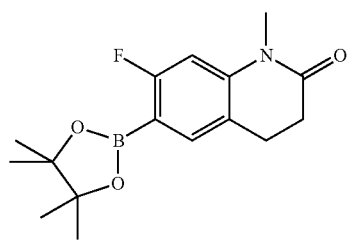 [SMILES: CN1C(=O)CCc2cc(B3OC(C)(C)C(C)(C)O3)c(F)cc21]

[A] 6-Bromo-7-fluoro-1-methyl-3,4-dihydro-1H-quinolin-2-one

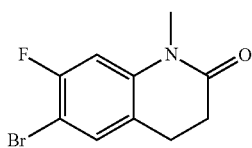

In analogy to the procedure described for the preparation of intermediates A-1 [A], 6-bromo-7-fluoro-3,4-dihydro-1H-quinolin-2-one was reacted with methyl iodide in presence of potassium tert-butoxide to give the title compound as a white foam. MS: 258.0, 259.9 (M+H$^+$).

[B] 7-Fluoro-1-methyl-6-(4,4,5,5-tetramethyl-[1,3,2]dioxaborolan-2-yl)-3,4-dihydro-1H-quinolin-2-one

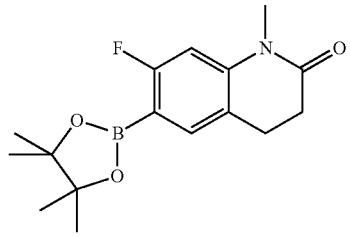 [SMILES: CN1C(=O)CCc2cc(B3OC(C)(C)C(C)(C)O3)c(F)cc21]

In analogy to the procedure described for the preparation of intermediates A-1 [B], 6-bromo-7-fluoro-1-methyl-3,4-dihydro-1H-quinolin-2-one was reacted with 4,4,4',4',5,5,5',5'-octamethyl-2,2'-bi(1,3,2-dioxaborolane) in presence of potassium acetate and PdCl$_2$(DPPF)-CH$_2$Cl$_2$ to give the title compound as a white solid. MS: 306.1 (M+H$^+$).

Intermediate A-23

1,4,4-Trimethyl-6-(4,4,5,5-tetramethyl-[1,3,2]dioxaborolan-2-yl)-3,4-dihydro-1H-quinolin-2-one

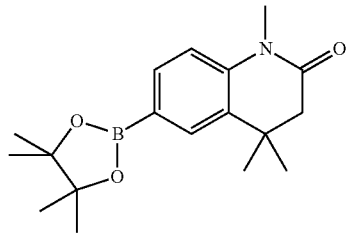 [SMILES: CN1C(=O)CC(C)(C)c2cc(B3OC(C)(C)C(C)(C)O3)ccc21]

In analogy to the procedure described for the preparation of intermediates A-1 [B], 6-bromo-1,4,4-trimethyl-3,4-dihydro-1H-quinolin-2-one was reacted with 4,4,4',4',5,5,5',5'-octamethyl-2,2'-bi(1,3,2-dioxaborolane) in presence of potassium acetate and PdCl$_2$(DPPF)-CH$_2$Cl$_2$ to give the title compound as an off-white solid. MS: 316.1 (M+H$^+$).

Intermediate A-24

6-(6-Chloro-pyrazin-2-yl)-2,6-diaza-spiro[3.3]heptane-2-carboxylic acid tert-butyl ester

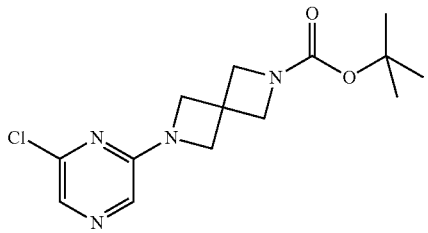 [SMILES: CC(C)(C)OC(=O)N1CC2(C1)CN(c1cncc(Cl)n1)C2]

In analogy to the procedure described for the preparation of intermediate A-20, 2,6-diaza-spiro[3.3]heptane-2-carboxylic acid tert-butyl ester was reacted with 2,6-dichloropyrazine in presence of Hunig's base to give the title compound as a white solid.

Intermediate A-25

6-(5-Bromo-pyridin-3-yl)-2,6-diaza-spiro[3.3]heptane-2-carboxylic acid tert-butyl ester

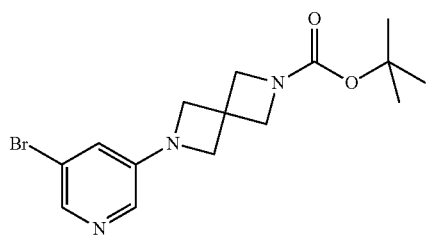

In analogy to the procedure described for the preparation of intermediate A-3 [B], 2,6-diaza-spiro[3.3]heptane-2-carboxylic acid tert-butyl ester was reacted with 3,5-dibromopyridine in the presence of Pd$_2$(dba)$_3$, rac-BINAP and sodium tert-butoxide to give the title compound as a white solid.

Intermediate A-26

(S)-2-(5-Bromo-pyridin-3-yloxymethyl)-azetidine-1-carboxylic acid tert-butyl ester

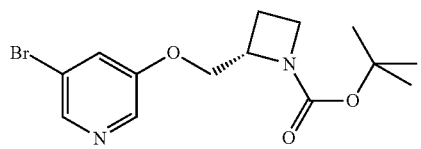 [SMILES: CC(C)(C)OC(=O)N1CC[C@H]1COc1cncc(Br)c1]

In analogy to the procedure described for the preparation of intermediate A-7, 5-bromopyridin-3-ol was reacted with (S)-2-hydroxymethyl-azetidine-1-carboxylic acid tert-butyl ester in presence of di-(4-chlorobenzyl)azodicarboxylate and triphenylphosphine to give the title compound as an amorphous colorless solid. MS: 343.1 and 345.1 (M+H$^+$).

Intermediate A-27

(R)-3-(5-Bromo-pyridin-3-yloxy)-pyrrolidine-1-carboxylic acid tert-butyl ester

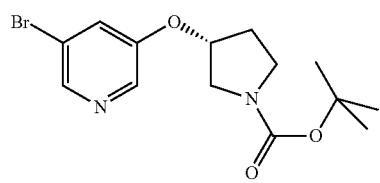 [SMILES: CC(C)(C)OC(=O)N1CC[C@@H](Oc2cncc(Br)c2)C1]

In analogy to the procedure described for the preparation of intermediate A-7, 5-bromopyridin-3-ol was reacted with (S)-3-hydroxy-pyrrolidine-1-carboxylic acid tert-butyl ester in presence of di-(4-chlorobenzyl)azodicarboxylate and triphenylphosphine to give the title compound as a white solid. MS: 343.1 and 345.1 (M+H$^+$).

Intermediate A-28

3-(5-Bromopyridin-3-yloxy)-azetidine-1-carboxylic acid tert-butyl ester

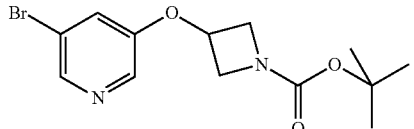

To a solution of 5-bromopyridin-3-ol (0.285 g, 1.64 mmol) in DMF (2.5 mL) was added K$_2$CO$_3$ (0.453 g, 3.28 mmol), followed by 3-bromo-azetidine-1-carboxylic acid tert-butyl ester (0.425 g, 1.8 mmol) in DMF (0.5 mL) and the reaction mixture was heated to 60° C. and stirred over night. The reaction mixture was diluted with EtOAc, poured into sat. NaHCO$_3$ solution (10 mL) and the aqueous layer was extracted EtOAc (2×20 mL). Combined organics were washed with brine, dried over Na$_2$SO$_4$, filtered and evaporated to dryness. The residue was purified by silica gel flash chromatography eluting with a 0 to 50% EtOAc-heptane gradient to give the title compound (0.539 g, 100%) as a colorless crystalline solid. MS: 329.1 (M+H$^+$).

Intermediate A-29

(S)-3-(5-Bromo-pyridin-3-yloxy)-pyrrolidine-1-carboxylic acid tert-butyl ester

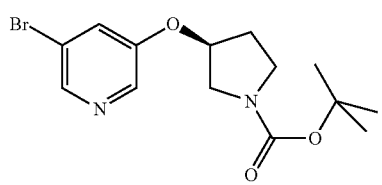 [SMILES: CC(C)(C)OC(=O)N1CC[C@H](Oc2cncc(Br)c2)C1]

In analogy to the procedure described for the preparation of intermediate A-7, 5-bromopyridin-3-ol was reacted with (R)-3-hydroxy-pyrrolidine-1-carboxylic acid tert-butyl ester in presence of di-(4-chlorobenzyl)azodicarboxylate and triphenylphosphine to give the title compound as a colorless oil. MS: 343.1 and 345.1 (M+H$^+$).

Intermediate A-30

(S)-3-(5-Bromopyridin-3-yloxy)-piperidine-1-carboxylic acid tert-butyl ester

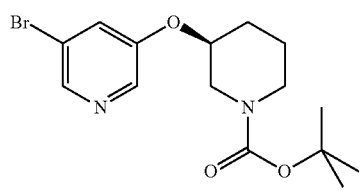 [SMILES: CC(C)(C)OC(=O)N1CCC[C@H](Oc2cncc(Br)c2)C1]

In analogy to the procedure described for the preparation of intermediate A-7, 5-bromopyridin-3-ol was reacted with (R)-3-hydroxy-piperidine-1-carboxylic acid tert-butyl ester in presence of di-(4-chlorobenzyl)azodicarboxylate and triphenylphosphine to give the title compound as a light yellow oil. MS: 357.1 and 359.1 (M+H$^+$).

Intermediate A-31

4-(5-Bromopyridin-3-yloxy)-piperidine-1-carboxylic acid tert-butyl ester

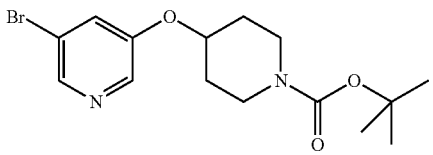 [SMILES: CC(C)(C)OC(=O)N1CCC(Oc2cncc(Br)c2)CC1]

In analogy to the procedure described for the preparation of intermediate A-7, 5-bromopyridin-3-ol was reacted with 4-hydroxy-piperidine-1-carboxylic acid tert-butyl ester in presence of di-(4-chlorobenzyl)azodicarboxylate and triphenylphosphine to give the title compound as a light yellow amorphous solid. MS: 357.0 and 359.0 (M+H$^+$).

Intermediate A-32

(S)-2-((5-Bromopyridin-3-yloxy)methyl)pyrrolidine-1-carboxylic acid tert-butyl ester

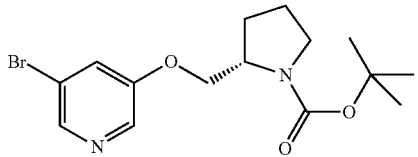 [SMILES: CC(C)(C)OC(=O)N1CCC[C@H]1COc1cncc(Br)c1]

In analogy to the procedure described for the preparation of intermediate A-7, 5-bromopyridin-3-ol was reacted with (S)-2-(hydroxymethyl)pyrrolidine-1-carboxylic acid tert-butyl ester in presence of di-(4-chlorobenzyl)azodicarboxylate and triphenylphosphine to give the title compound as a colorless oil. MS: 357.0 and 359.0 (M+H$^+$).

Intermediate A-33

(R)—N-(3-(5-Bromopyridin-3-yl)oxetan-3-yl)-2-methylpropane-2-sulfinamide

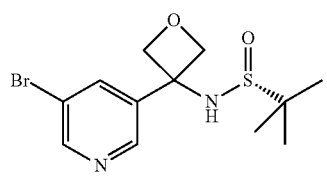 [SMILES: CC(C)(C)[S@@](=O)NC1(c2cncc(Br)c2)COC1]

[A] (R)-2-Methyl-N-(oxetan-3-ylidene)-propane-2-sulfinamide

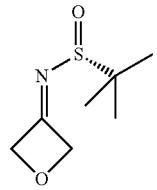

To a solution of Ti(OEt)$_4$ (2.02 g, 7.53 mmol) in THF (20 mL) was added (R)-2-methylpropane-2-sulfinamide (0.854 g, 7.05 mmol) followed by oxetan-3-one (0.493 g, 6.84 mmol) in THF (5 mL) and the reaction mixture was heated to 50° C. over night. After cooling, the reaction mixture was diluted with EtOAc (50 mL) and a saturated solution of brine (20 mL) was slowly added under stirring. After 15 min, the mixture was filtered through a plug of Dicalite and washed with EtOAc. The organic phase was separated, dried over Na$_2$SO$_4$ and evaporated to dryness. The residue was purified by silica gel flash chromatography eluting with a 0 to 40% EtOAc-heptane gradient to give the title compound (0.242 g, 20%) as a light yellow oil. MS: 176.2 (M+H$^+$).

[B] (R)—N-(3-(5-Bromopyridin-3-yl)oxetan-3-yl)-2-methylpropane-2-sulfinamide

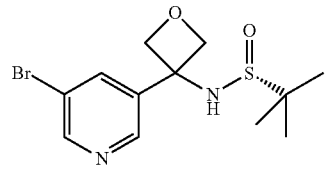 [SMILES: CC(C)(C)[S@@](=O)NC1(c2cncc(Br)c2)COC1]

To a solution of 3-bromo-5-iodopyridine (0.14 g, 0.493 mmol) in THF (2 mL) cooled at −78° C. was added nBuLi (462 µl, 0.74 mmol) dropwise over 5 min. The reaction mixture was stirred at −78° C. for 15 min, then (R)-2-methyl-N-(oxetan-3-ylidene)-propane-2-sulfinamide (0.1 g, 0.567 mmol) in THF (1 mL) was added dropwise. The reaction mixture was stirred at −78° C. for 10 min then allowed to warm up to RT. The mixture was quenched with water (2 mL) and extracted with EtOAc (2×10 mL). Combined organics were dried over Na$_2$SO$_4$, filtered and evaporated to dryness. The residue was purified by silica gel flash chromatography eluting with a 0 to 100% EtOAc-heptane gradient to give the title compound (0.096 g, 58%) as a light yellow oil. MS: 333.0 and 335.1 (M+H$^+$).

Intermediate A-34

6-(4,4,5,5-Tetramethyl-1,3,2-dioxaborolan-2-yl)-3,4-dihydroquinolin-2(1H)-one

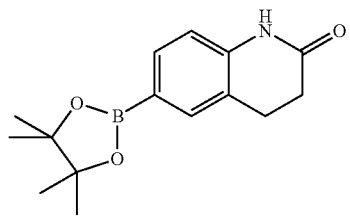 [SMILES: CC1(C)OB(c2ccc3c(c2)CCC(=O)N3)OC1(C)C]

In analogy to the procedure described for the preparation of intermediates A-1 [B], 6-bromo-3,4-dihydroquinolin-2(1H)-one was reacted with 4,4,4',4',5,5,5',5'-octamethyl-2,2'-bi(1, 3,2-dioxaborolane) in presence of potassium acetate and PdCl$_2$(DPPF)-CH$_2$Cl$_2$ to give the title compound as a colorless solid. MS: 274.4 (M+H$^+$).

Intermediate A-35

(R)-2-Methyl-propane-2-sulfinic acid [(S and R)-1-(5-bromo-pyridin-3-yl)-ethyl]amide

[A] (R, E)-N-(1-(5-Bromopyridin-3-yl)ethylidene)-2-methylpropane-2-sulfinamide

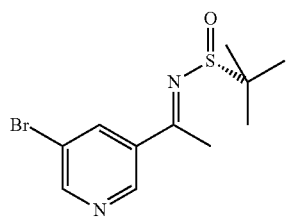 [SMILES: C/C(=N\[S@](=O)C(C)(C)C)c1cncc(Br)c1]

To a solution of 1-(5-bromopyridin-3-yl)ethanone (1.01 g, 5.04 mmol) in DCM (20 mL) was added (R)-2-methylpropane-2-sulfinamide (0.555 g, 4.58 mmol) followed by Ti(OEt)$_4$ (1.23 g, 4.58 mmol) dropwise and the reaction mixture was heated to 40° C. over night. After cooling, the solvent was removed under vacuum and the residue taken up in EtOAc (80 mL). This solution was vigorously stirred while a saturated solution of brine (20 mL) was slowly added. After 15 min, the mixture was filtered through a plug of Dicalite and washed with EtOAc. The organic phase was separated, dried over Na$_2$SO$_4$ and evaporated to dryness. The residue was purified by silica gel flash chromatography eluting with a 0 to 50% EtOAc-heptane gradient to give the title compound (0.964 g, 69%) as a yellow oil. MS: 303.1 and 305.0 (M+H$^+$).

[B] (R)-2-Methyl-propane-2-sulfinic acid [(S and R)-1-(5-bromo-pyridin-3-yl)-ethyl]-amide

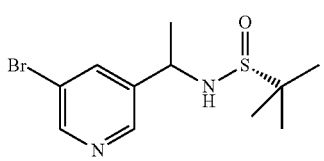

(S and R)

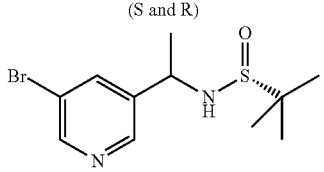

(R and S)

To a solution of (R, E)-N-(1-(5-bromopyridin-3-yl)ethylidene)-2-methylpropane-2-sulfinamide (0.3 g, 0.989 mmol) in MeOH (20 mL) cooled at 0° C. with an ice bath was added NaBH$_4$ (0.075 g, 1.98 mmol) portionwise and the reaction mixture was stirred at this temperature for 30 min and then at room temperature for another 30 min. The mixture was quenched with sat. ammonium chloride solution (10 mL), the organic solvent was evaporated and the resulting aqueous solution was extracted with EtOAc (2×25 mL). Combined organics were washed with brine, dried over Na$_2$SO$_4$, filtered and evaporated to dryness to give the title compound (0.293 g, 97%) as a colorless solid as a 2:1 mixture of both diastereoisomers. MS: 305.0 and 307.1 (M+H$^+$).

Intermediate A-36

6-(6-(2,6-Diazaspiro[3.3]heptan-2-yl)pyrazin-2-yl)-1-methyl-3,4-dihydroquinolin-2(1H)-one 2,2,2-trifluoroacetate

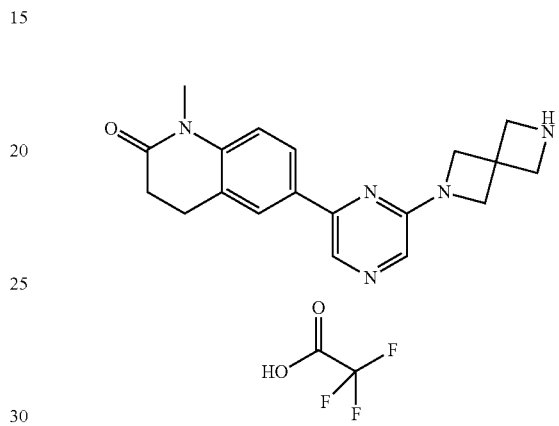

To a solution of 6-[6-(1-methyl-2-oxo-1,2,3,4-tetrahydro-quinolin-6-yl)-pyrazin-2-yl]-2,6-diaza-spiro[3.3]heptane-2-carboxylic acid tert-butyl ester (example 28, 0.231 g, 0.53 mmol) in DCM (3 mL) was added TFA (0.605 g, 5.3 mmol) and the reaction mixture was stirred at room temperature over night. The mixture was evaporated several times with toluene and then the residue was purified by reverse phase HPLC on a Gemini-NX column, eluting with a 20 to 98% MeOH—H$_2$O (0.05% TEA) gradient to give the title compound (0.203 g, 99%) as a yellow solid (TFA salt). MS: 336.3 (M+H$^+$).

Intermediate A-37

(rac)-N-(1-(5-Bromopyridin-3-yl)ethyl)ethanesulfonamide

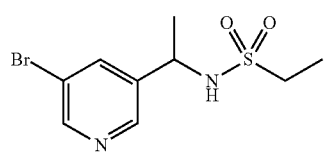

In analogy to the procedure described for the preparation of intermediate A-11, 1-(5-bromo-pyridin-3-yl)-ethanone was reacted with ethanesulfonamide in presence of titanium tetra-isopropoxide and then NaBH$_4$ to give the title compound as a light yellow oil. MS: 293.1 and 295.3 (M+H$^+$).

Intermediate A-38

(rac)-N-(1-(5-Bromopyridin-3-yl)propyl)ethanesulfonamide

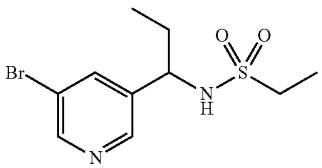 [SMILES: CCC(NS(=O)(=O)CC)c1cncc(Br)c1]

A flask was charged with 5-bromonicotinaldehyde (0.5 g, 2.69 mmol), ethanesulfonamide (0.367 g, 3.36 mmol) and toluene (25 mL), then titanium tetra-isopropoxide (1.53 g, 5.38 mmol) was added dropwise. The reaction mixture was heated to 110° C. over night and then concentrated in vacuo. The residue was dissolved in THF (25 mL) and cooled down to −40° C. A 3 M solution of ethylmagnesium bromide in ether (2.24 mL, 6.72 mmol) was added dropwise at this temperature and the resulting mixture was slowly warmed up to −20° C. and stirred for 2.5 h. The mixture was poured into a saturated NH$_4$Cl solution (15 mL), the resulting suspension was filtered and the filtrate was extracted with DCM (2×50 mL). Combined organics were dried over Na$_2$SO$_4$, filtered and evaporated to dryness. The residue was purified by silica gel flash chromatography eluting with a 0 to 5% MeOH-DCM gradient to give the title compound (0.5 g, 56%) as light yellow oil. MS: 307.1 and 308.9.

Intermediate A-39

(rac)-N-((5-Bromopyridin-3-yl)(cyclopropyl)methyl)ethanesulfonamide

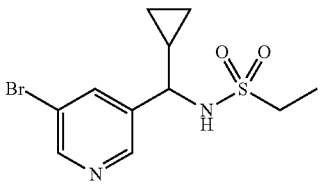 [SMILES: CCS(=O)(=O)NC(c1cncc(Br)c1)C1CC1]

In analogy to the procedure described for the preparation of intermediate A-38, 5-bromonicotinaldehyde was reacted with ethanesulfonamide in presence of titanium tetra-isopropoxide and then cyclopropylmagnesium bromide (0.5 M in THF) to give the title compound as a yellow oil. MS: 319.0 and 320.9 (M+H$^+$).

Intermediate A-40

(rac)-N-(1-(5-Bromopyridin-3-yl)-2-methylpropyl)ethanesulfonamide

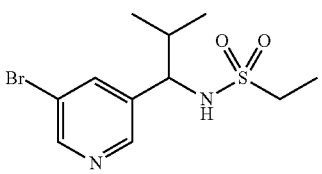 [SMILES: CCS(=O)(=O)NC(c1cncc(Br)c1)C(C)C]

In analogy to the procedure described for the preparation of intermediate A-38, 5-bromonicotinaldehyde was reacted with ethanesulfonamide in presence of titanium tetra-isopropoxide and then isopropylmagnesium chloride (2 M in THF) to give the title compound as a red oil. MS: 321.0 and 323.0 (M+H$^+$).

Intermediate A-41

N-((5-Bromopyridin-3-yl)methyl)-N-methylethanesulfonamide

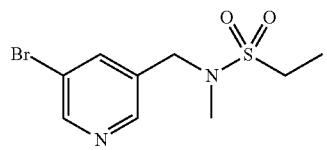

To a solution of ethanesulfonic acid (5-bromo-pyridin-3-ylmethyl)-amide (intermediate A-11, 0.21 g, 0.752 mmol) in DMF (6 mL) cooled at 0° C. with an ice bath was added 60% NaH in mineral oil (0.039 g, 0.98 mmol) and the mixture was stirred for 15 min. Then, MeI (0.136 g, 0.96 mmol) was added and the reaction was stirred at 0° C. for another 15 min before being quenched with aq. ammonia (2 mL). The mixture was further diluted with brine and then extracted with EtOAc (2×15 mL). Combined organics were dried over Na$_2$SO$_4$, filtered and evaporated to dryness to give the title compound (0.209 g, 85%) as a yellow oil which was used with no further purification. MS: 293.1 and 295.1 (M+H$^+$).

Intermediate A-42

N-((5-Bromopyridin-3-yl)methyl)-N-ethylethanesulfonamide

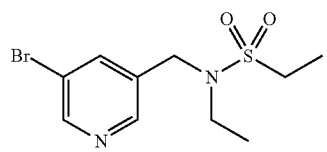 [SMILES: CCN(Cc1cncc(Br)c1)S(=O)(=O)CC]

To a solution of ethanesulfonic acid (5-bromo-pyridin-3-ylmethyl)-amide (intermediate A-11, 0.051 g, 0.182 mmol) in DMF (3 mL) cooled at 0° C. with an ice bath was added 60% NaH in mineral oil (0.011 g, 0.274 mmol) and the mixture was stirred at room temperature for 20 min. Then, iodoethane (0.045 g, 0.292 mmol) was added and the reaction mixture was stirred for 3 h before being quenched with water (5 mL). The aqueous solution was extracted with EtOAc (2×15 mL). Combined organics were dried over Na$_2$SO$_4$, filtered and evaporated to dryness to give the title compound (0.051 g, 82%) as orange oil which was used with no further purification. MS: 307.1 and 309.2 (M+H$^+$).

Intermediate A-43

N-((5-Bromopyridin-3-yl)methyl)-N-isopropylethanesulfonamide

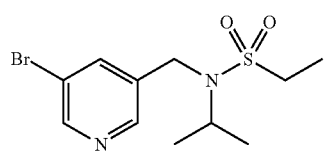 [SMILES: CCS(=O)(=O)N(Cc1cncc(Br)c1)C(C)C]

In analogy to the procedure described for the preparation of intermediate A-42, ethanesulfonic acid (5-bromo-pyridin-3-ylmethyl)-amide (intermediate A-11) was reacted with 2-iodopropane in presence of NaH (60% in mineral oil) to give the title compound as white solid after purification by reverse phase HPLC on a Gemini-NX column. MS: 323.1 (M+H⁺).

Intermediate A-44

N-((5-Bromopyridin-3-yl)methyl)-N-2-ethoxy-ethyl-ethanesulfonamide

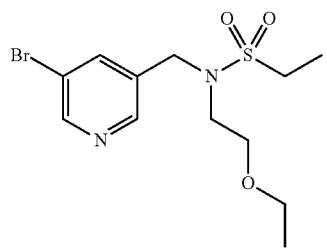 [SMILES: CCOCCN(Cc1cncc(Br)c1)S(=O)(=O)CC]

In analogy to the procedure described for the preparation of intermediate A-42, ethanesulfonic acid (5-bromo-pyridin-3-ylmethyl)-amide (intermediate A-11) was reacted with 2-bromoethyl ethyl ether in presence of NaH (60% in mineral oil) to give the title compound as yellow oil after purification by reverse phase HPLC on a Gemini-NX column. MS: 351.0 and 353.1 (M+H⁺).

Intermediate A-45

(rac)-N-(1-(5-Bromopyridin-3-yl)ethyl)-N-methyl-ethanesulfonamide

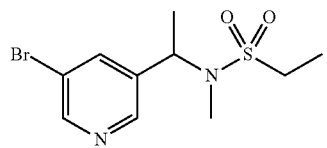 [SMILES: CCS(=O)(=O)N(C)C(C)c1cncc(Br)c1]

In analogy to the procedure described for the preparation of intermediate A-41, N-(1-(5-bromopyridin-3-yl)ethyl)ethanesulfonamide (intermediate A-37) was reacted with MeI in presence of NaH (60% in mineral oil) to give the title compound as a light yellow solid. MS: 307.1 and 309.2 (M+H⁺).

Intermediate A-46

(rac)-N-(1-(5-Bromopyridin-3-yl)ethyl)-N-ethyl-ethanesulfonamide

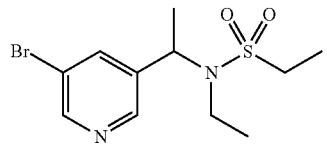 [SMILES: CCN(C(C)c1cncc(Br)c1)S(=O)(=O)CC]

In analogy to the procedure described for the preparation of intermediate A-42, N-(1-(5-bromopyridin-3-yl)ethyl)ethanesulfonamide (intermediate A-37) was reacted with iodoethane in presence of NaH (60% in mineral oil) to give the title compound as a yellow oil. MS: 321.0 and 323.1 (M+H⁺).

Intermediate A-47

1-Methyl-1H-pyrazole-4-carboxylic acid (5-bromo-pyridin-3-ylmethyl)-amide

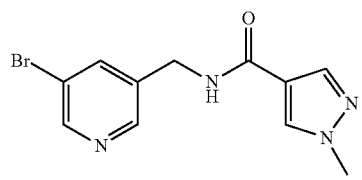 [SMILES: Cn1cc(C(=O)NCc2cncc(Br)c2)cn1]

In analogy to the procedure described for the preparation of example 75, coupling of (5-bromopyridin-3-yl)methanamine with 1-methyl-1H-pyrazole-4-carboxylic gave the title compound as a colorless solid. MS: 297.1 and 295.0 (M+H⁺).

Intermediate A-48

2-(5-Bromo-pyridin-3-ylmethyl)-isothiazolidine 1,1-dioxide

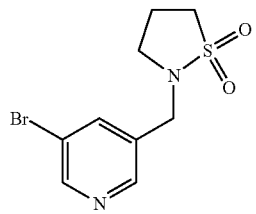

In analogy to the procedure described for the preparation of intermediate A-12 [B], isothiazolidine 1,1-dioxide was reacted with 3-bromo-5-chloromethyl-pyridine (intermediate A-12 [A]) in the presence of NaH to give the title compound as a light yellow oil. MS: 292.8 and 290.9 (M+H⁺).

Intermediate A-49

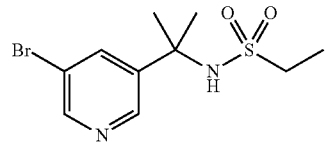 [SMILES: CCS(=O)(=O)NC(C)(C)c1cncc(Br)c1]

N-(2-(5-Bromopyridin-3-yl)propan-2-yl)ethanesulfonamide

A flask was charged with 1-(5-bromopyridin-3-yl)ethanone (0.5 g, 2.5 mmol), ethanesulfonamide (0.341 g, 3.12 mmol) and toluene (25 mL), then titanium tetra-isopropoxide (1.42 g, 5 mmol) was added dropwise. The reaction mixture was heated to 110° C. over night and then concentrated in vacuo to give the imine intermediate (0.73 g) as a light brown oil. A part of this the imine intermediate (0.4 g) was dissolved in THF (10 mL) and the mixture was cooled down to −78° C. A 3 M solution of methylmagnesium bromide in ether (1.14 mL, 3.43 mmol) was added dropwise at this temperature and the resulting mixture was stirred at −70° C. for 3 h. It was then allowed to warm up to 0° C. before being quenched with a saturated NH₄Cl solution (10 mL). The resulting suspension was filtered and the filtrate was extracted with DCM (2×30 mL). Combined organics were dried over Na₂SO₄, filtered and evaporated to dryness. The residue was purified by silica gel flash chromatography eluting with a 0 to 5% MeOH-DCM gradient to give the title compound (0.1 g, 17%) as a yellow oil which was used with no further purification. MS: 307.1 and 309.1 (M+H⁺).

Intermediate A-50

N-((5-Bromopyridin-3-yl)methyl)-N,3,5-trimethyl-isoxazole-4-carboxamide

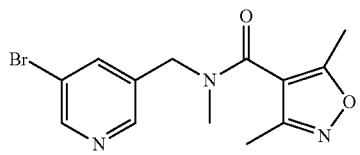 [SMILES: Cc1noc(C)c1C(=O)N(C)Cc1cncc(Br)c1]

In analogy to the procedure described for the preparation of intermediate A-41, 3,5-dimethyl-isoxazole-4-carboxylic acid (5-bromo-pyridin-3-ylmethyl)-methyl-amide (prepared as described for the preparation of intermediate A-47) was reacted with MeI in presence of NaH (60% in mineral oil) to give the title compound as a yellow solid. MS: 326.3 and 324.2 (M+H⁺).

Intermediate A-51

3-Bromo-5-[2-(1,1-dioxo-1λ⁶-isothiazolidin-2-yl)-ethoxy]-pyridine

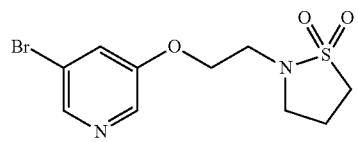

[A] 2-(2-Chloro-ethyl)-isothiazolidine-1,1-dioxide

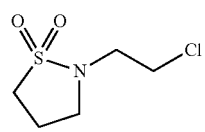

To a solution of 2-(1,1-dioxo-1λ⁶-isothiazolidin-2-yl)-ethanol (0.14 g, 0.847 mmol) in DCM (4 mL) was added SOCl₂ (0.151 g, 1.27 mmol) and the reaction mixture was heated to 40° C. for 2 h. The mixture was cooled to room temperature, diluted with DCM, poured into a sat. NaHCO₃ solution (10 mL) and the aqueous layer was extracted with DCM (2×20 mL). Combined organics were dried over Na₂SO₄, filtered and evaporated to dryness to give the title compound (0.046 g, 30%) as an orange oil which was used with no further purification. MS: 184.1 (M+H⁺).

[B] 3-Bromo-5-[2-(1,1-dioxo-1λ⁶-isothiazolidin-2-yl)-ethoxy]-pyridine

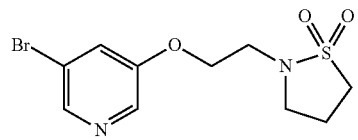

To a solution of 2-(2-chloro-ethyl)-isothiazolidine-1,1-dioxide (0.046 g, 0.253 mmol) and 5-bromopyridin-3-ol (0.04 g, 0.230 mmol) in DMF (1 mL) was added K₂CO₃ (0.064 g, 0.46 mmol), followed by KI (0.008 g, 0.046 mmol) and the reaction mixture was heated to 60° C. and stirred over night. The mixture was diluted with EtOAc, poured into a sat. NaHCO₃ solution (5 mL) and the aqueous layer was extracted with EtOAc (2×10 mL). Combined organics were washed with brine, dried over Na₂SO₄, filtered and evaporated to dryness. The residue was purified by silica gel flash chromatography eluting with a 0 to 5% MeOH-DCM gradient to give the title compound (0.015 g, 20%) as a yellow oil which was used with no further purification. MS: 321.3 and 323.2 (M+H⁺).

Intermediate A-52

N-((5-Bromo-4-methylpyridin-3-yl)methyl)ethane-sulfonamide

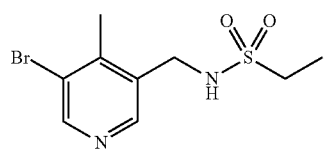

In analogy to the procedure described for the preparation of intermediate A-11, 5-bromo-4-methyl-pyridine-3-carbaldehyde has been reacted first with ethanesulfonamide, followed by reduction of the thus formed imine with NaBH₄ in MeOH to give the title compound as an off-white solid. MS: 293.1 and 295.3 (M+H⁺).

Intermediate A-53

N-((5-Bromo-4-chloropyridin-3-yl)methyl)ethane-sulfonamide

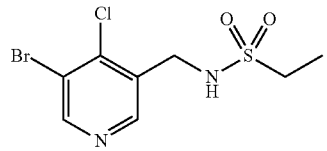

In analogy to the procedure described for the preparation of intermediate A-11, 5-bromo-4-chloro-pyridine-3-carbaldehyde has been reacted first with ethanesulfonamide, followed by reduction of the thus formed imine with NaBH₄ in MeOH to give the title compound as a light orange solid. MS: 313.2 and 315.1 (M+H⁺).

Intermediate A-54 tert-Butyl (trans)-4-(5-bromopyridin-3-yloxy)cyclohexylcarbamate

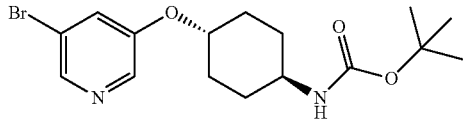 [SMILES: CC(C)(C)OC(=O)N[C@H]1CC[C@H](Oc2cncc(Br)c2)CC1]

In analogy to the procedure described for the preparation of intermediate A-7, 5-bromopyridin-3-ol was reacted with (cis)-(4-hydroxy-cyclohexyl)-carbamic acid tert-butyl ester in presence of di-(4-chlorobenzyl)azodicarboxylate and triphenylphosphine to give the title compound as a colorless solid. MS: 371.3 and 373.3 (M+H⁺).

Intermediate A-55

(R)-2-((5-Bromopyridin-3-yloxy)methyl)pyrrolidine-1-carboxylic acid tert-butyl ester

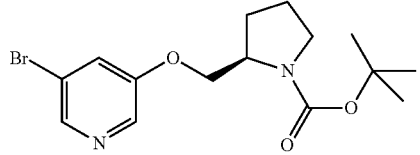 [SMILES: CC(C)(C)OC(=O)N1CCC[C@@H]1COc1cncc(Br)c1]

In analogy to the procedure described for the preparation of intermediate A-7, 5-bromopyridin-3-ol was reacted with (R)-2-(hydroxymethyl)pyrrolidine-1-carboxylic acid tert-butyl ester in presence of di-(4-chlorobenzyl)azodicarboxylate and triphenylphosphine to give the title compound as an orange oil. MS: 357.3 and 359.3 (M+H⁺).

Intermediate A-56

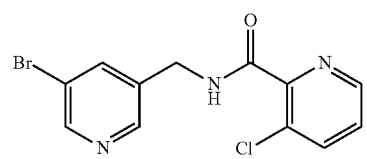 [SMILES: O=C(NCc1cncc(Br)c1)c1ncccc1Cl]

N-((5-Bromopyridin-3-yl)methyl)-3-chloropicolinamide

In analogy to the procedure described for the preparation of example 75, coupling of (5-bromopyridin-3-yl)methanamine with 3-chloro-pyridine-2-carboxylic acid gave the title compound as off-white solid. MS: 326.2 and 328.2 (M+H⁺).

Intermediate A-57

N-((5-Bromopyridin-3-yl)methyl)-3-chloro-N-methylpicolinamide

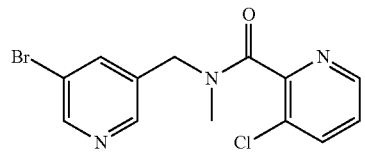 [SMILES: CN(Cc1cncc(Br)c1)C(=O)c1ncccc1Cl]

In analogy to the procedure described for the preparation of intermediate A-41, N-((5-bromopyridin-3-yl)methyl)-3-chloropicolinamide (intermediate A-56) was reacted with MeI in presence of NaH (60% in mineral oil) to give the title compound as a dark brown oil. MS: 340.2 and 342.2 (M+H⁺).

Intermediate A-58

(R)—N-((5-Bromo-4-chloropyridin-3-yl)methyl)-2-methylpropane-2-sulfinamide

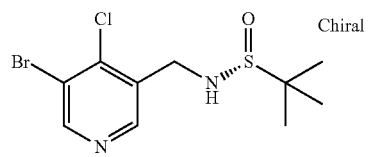 [SMILES: CC(C)(C)[S@@](=O)NCc1cncc(Br)c1Cl]

(R)-2-Methyl-propane-2-sulfinic acid 1-(5-bromo-4-chloro-pyridin-3-yl)-meth-(E)-ylideneamide, prepared from (R)-2-methylpropane-2-sulfinamide and 5-bromo-4-chloropyridine-3-carbaldehyde in analogy to procedure described for the preparation of intermediate A-35 [A], has been reduced with NaBH₄ in MeOH in analogy to the procedure described for the preparation of intermediate A-35 [B] to give the title compound as a yellow oil. MS: 325.2 (M+H⁺).

Intermediate A-59

(R)-2-Methyl-propane-2-sulfinic acid (5-bromo-4-methyl-pyridin-3-ylmethyl)-amide

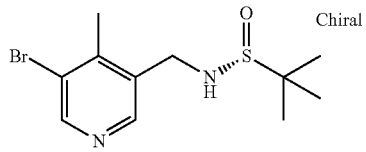

(R)-2-Methyl-propane-2-sulfinic acid 1-(5-bromo-4-methyl-pyridin-3-yl)-meth-(E)-ylideneamide, prepared from (R)-2-methylpropane-2-sulfinamide and 5-bromo-4-methylpyridine-3-carbaldehyde in analogy to procedure described for the preparation of intermediate A-35 [A], has been reduced with NaBH₄ in MeOH in analogy to the procedure described for the preparation of intermediate A-35 [B] to give the title compound as colorless solid. MS: 305.3 and 307.4 (M+H+).

Intermediate A-60

(R)-2-Methyl-propane-2-sulfinic acid [(R or S)-1-(5-bromo-4-methyl-pyridin-3-yl)-ethyl]-amide

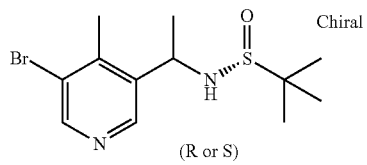

(R)-2-Methyl-propane-2-sulfinic acid 1-(5-bromo-4-methyl-pyridin-3-yl)-meth-(E)-ylideneamide, prepared from (R)-2-methylpropane-2-sulfinamide and 5-bromo-4-methyl-pyridine-3-carbaldehyde in analogy to procedure described for the preparation of intermediate A-35 [A], has been reacted with methylmagnesium bromide in analogy to the procedure described for the preparation of intermediate A-49 from the corresponding imine intermediate to give the title compound as light yellow amorphous solid. MS: 319.2 and 321.3 (M+H+).

Intermediate A-61

(R)-2-Methyl-propane-2-sulfinic acid [(R or S)-1-(5-bromo-4-chloro-pyridin-3-yl)-ethyl]-amide

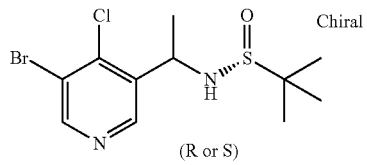 [SMILES: CC(N[S@](=O)C(C)(C)C)c1cncc(Br)c1Cl]

(R)-2-Methyl-propane-2-sulfinic acid 1-(5-bromo-4-chloro-pyridin-3-yl)-meth-(E)-ylideneamide, prepared from (R)-2-methylpropane-2-sulfinamide and 5-bromo-4-chloro-pyridine-3-carbaldehyde in analogy to procedure described for the preparation of intermediate A-35 [A], has been reacted with methylmagnesium bromide in analogy to the procedure described for the preparation of intermediate A-49 from the corresponding imine intermediate to give the title compound as orange oil. MS: 341.2 (M+H+).

Example 1

Ethanesulfonic acid [5-(1-methyl-2-oxo-1,2,3,4-tetrahydro-quinolin-6-yl)-pyridin-3-yl]-amide

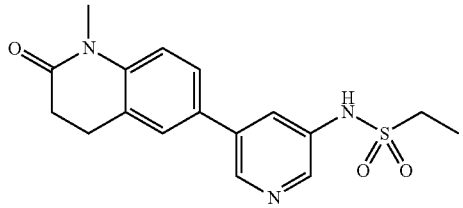 [SMILES: CCS(=O)(=O)Nc1cncc(-c2ccc3c(c2)CCC(=O)N3C)c1]

To a solution of 6-(5-amino-pyridin-3-yl)-1-methyl-3,4-dihydro-1H-quinolin-2-one (intermediate A-2, 0.02 g, 0.079 mmol) in DCM (0.5 mL) was added triethylamine (0.024 g, 0.237 mmol) followed by ethanesulfonyl chloride (0.01 g, 0.079 mmol) and the reaction mixture was stirred at room temperature for 1 h. The mixture was diluted with DCM, poured into water (5 mL) and the aqueous layer was extracted with DCM (2×20 mL). Combined organics were dried over Na₂SO₄, filtered and evaporated to dryness. The residue was purified by silica gel flash chromatography eluting with a 0 to 10% MeOH-DCM gradient to give the title compound (0.007 g, 23%) as a brown solid. MS: 346.0 (M+H+).

Example 2

Acetic acid [5-(1-methyl-2-oxo-1,2,3,4-tetrahydro-quinolin-6-yl)-pyridin-3-ylcarbamoyl]-methyl ester

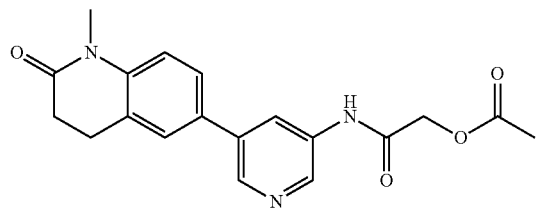 [SMILES: CC(=O)OCC(=O)Nc1cncc(-c2ccc3c(c2)CCC(=O)N3C)c1]

To a solution of 6-(5-amino-pyridin-3-yl)-1-methyl-3,4-dihydro-1H-quinolin-2-one hydrochloride (intermediate A-2, 0.045 g, 0.155 mmol) in DCM (1.5 mL) was added TEA (0.039 g, 0.388 mmol) followed by 2-chloro-2-oxoethyl acetate (0.017 g, 0.124 mmol) in DCM (1 mL) and the reaction mixture was stirred at room temperature for 2 h. The mixture was diluted with DCM, poured into aq. NaHCO₃ (10 mL) and the aqueous layer was extracted with DCM (2×25 mL). Combined organics were washed with brine, dried over Na₂SO₄, filtered and evaporated to dryness. The residue was purified by silica gel flash chromatography eluting with a 0 to 5% MeOH-DCM gradient to give the title compound (0.025 g, 46%) as a light brown solid. MS: 354.2 (M+H+).

Example 3

2-Hydroxy-N-[5-(1-methyl-2-oxo-1,2,3,4-tetrahydro-quinolin-6-yl)-pyridin-3-yl]-acetamide

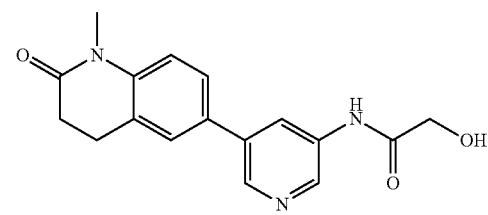 [SMILES: CN1C(=O)CCc2cc(-c3cncc(NC(=O)CO)c3)ccc21]

To a solution of acetic acid [5-(1-methyl-2-oxo-1,2,3,4-tetrahydro-quinolin-6-yl)-pyridin-3-ylcarbamoyl]-methyl ester (example 2, 0.025 g, 0.071 mmol) in MeOH (1 mL) was added a 1M aqueous solution of Na₂CO₃ (0.354 mL) and the reaction mixture was stirred at room temperature for 1 h. The mixture was evaporated to dryness, the residue dissolved in EtOAc (20 mL) and washed with aq. NaHCO₃ (5 mL). The organic layer was separated, dried over Na₂SO₄, filtered and

Example 4

6-[5-(2-Hydroxy-ethylamino)-pyridin-3-yl]-1-methyl-3,4-dihydro-1H-quinolin-2-one

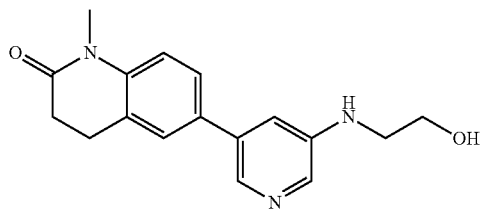 [SMILES: CN1C(=O)CCc2cc(-c3cncc(NCCO)c3)ccc21]

[A] 6-{5-[2-(tert-Butyl-dimethyl-silanyloxy)-ethylamino]-pyridin-3-yl}-1-methyl-3,4-dihydro-1H-quinolin-2-one

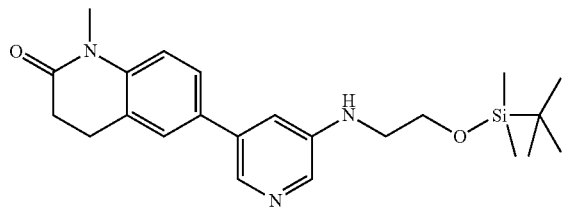 [SMILES: CN1C(=O)CCc2cc(-c3cncc(NCCO[Si](C)(C)C(C)(C)C)c3)ccc21]

To a solution of 6-(5-amino-pyridin-3-yl)-1-methyl-3,4-dihydro-1H-quinolin-2-one hydrochloride (intermediate A-2, 0.062 g, 0.214 mmol) in MeOH (1.5 mL) was added AcOH (0.154 g, 2.57 mmol), followed by 2-(tert-butyldimethylsilyloxy)acetaldehyde (0.039 g, 0.225 mmol) and the reaction mixture was stirred at room temperature for 1 h. Then, NaBH$_3$CN (0.027 g, 0.428 mmol) in THF (0.6 mL) was added to the reaction mixture and stirring at room temperature was continued for 2 h. The mixture was diluted with EtOAc, poured into aq. NaHCO$_3$ (10 mL) and the aqueous layer was extracted with EtOAc (2×25 mL). Combined organics were washed with brine, dried over Na$_2$SO$_4$, filtered and evaporated to dryness. The residue was purified by silica gel flash chromatography eluting with a 0 to 5% MeOH-DCM gradient to give the title compound (0.06 g, 68%) as a yellow solid. MS: 412.3 (M+H$^+$).

[B] 6-[5-(2-Hydroxy-ethylamino)-pyridin-3-yl]-1-methyl-3,4-dihydro-1H-quinolin-2-one

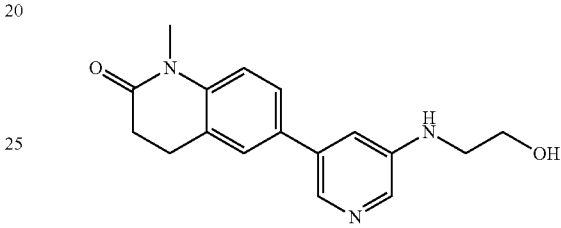

To solution of 6-{5-[2-(tert-butyl-dimethyl-silanyloxy)-ethylamino]-pyridin-3-yl}-1-methyl-3,4-dihydro-1H-quinolin-2-one (0.06 g, 0.146 mmol) in MeOH (2.5 mL) was added 4M HCl in dioxane (0.255 ml, 1.02 mmol) and the reaction mixture was stirred at room temperature for 2 h. The mixture was concentrated in vacuo, the residue dissolved in EtOAc (20 mL) and washed with aq. NaHCO$_3$ (5 mL). The organic layer was washed with brine, dried over Na$_2$SO$_4$, filtered and evaporated to dryness. The residue was purified by silica gel flash chromatography eluting with a 0 to 2% MeOH(1% NH$_4$OH)-DCM gradient to give the title compound (0.01 g, 22%) as an off white solid. MS: 298.3 (M+H$^+$).

The following compounds listed in Table 1 were prepared in analogy to the procedure described for the preparation of example 4 [B] using appropriate starting materials

TABLE 1

| Ex | Name and Structure | Starting Materials | Aspect | MS (M + H$^+$) |
|---|---|---|---|---|
| 5 | 6-[5-((S)-2-Hydroxymethyl-pyrrolidin-1-yl)-pyridin-3-yl]-1-methyl-3,4-dihydro-1H-quinolin-2-one | 6-{5-[(S)-2-(tert-Butyl-dimethyl-silanyloxymethyl)-pyrrolidin-1-yl]-pyridin-3-yl}-1-methyl-3,4-dihydro-1H-quinolin-2-one (intermediate A-3) | Light yellow solid | 338.2 |

TABLE 1-continued

| Ex | Name and Structure | Starting Materials | Aspect | MS (M + H⁺) |
|---|---|---|---|---|
| 6 | 6-[5-((R)-2-Hydroxymethyl-pyrrolidin-1-yl)-pyridin-3-yl]-1-methyl-3,4-dihydro-1H-quinolin-2-one | 6-{5-[(R)-2-(tert-Butyl-dimethyl-silanyloxymethyl)-pyrrolidin-1-yl]-pyridin-3-yl}-1-methyl-3,4-dihydro-1H-quinolin-2-one (intermediate A-4) | Light yellow solid | 338.2 |
| 7 | 6-[5-((S)-2-Hydroxymethyl-pyrrolidin-1-ylmethyl)-pyridin-3-yl]-1-methyl-3,4-dihydro-1H-quinolin-2-one | 6-{5-((S)-2-(tert-Butyl-dimethyl-silanyloxymethyl)-pyrrolidin-1-ylmethyl]-pyridin-3-yl}-1-methyl-3,4-dihydro-1H-quinolin-2-one (intermediate A-16) | Off white waxy solid | 352.3 |
| 8 | 6-[5-((S)-2-Hydroxymethyl-5-oxo-pyrrolidin-1-ylmethyl)-pyridin-3-yl]-1-methyl-3,4-dihydro-1H-quinolin-2-one | 6-{5-[(S)-2-(tert-Butyl-dimethyl-silanyloxymethyl)-5-oxo-pyrrolidin-1-ylmethyl]-pyridin-3-yl}-1-methyl-3,4-dihydro-1H-quinolin-2-one (intermediate A-18) | White Foam | 366.2 |

Example 9

6-[5-((S)-2-Ethylaminomethyl-pyrrolidin-1-yl)-pyridin-3-yl]-1-methyl-3,4-dihydro-1H-quinolin-2-one

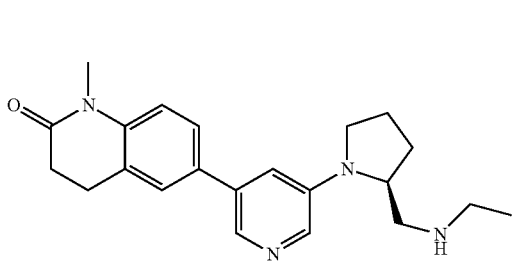 [SMILES: CCNC[C@@H]1CCCN1c1cncc(-c2ccc3c(c2)CCC(=O)N3C)c1]

[A] 6-[5-((S)-2-Chloromethyl-pyrrolidin-1-yl)-pyridin-3-yl]-1-methyl-3,4-dihydro-1H-quinolin-2-one

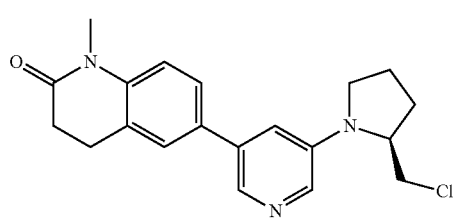 [SMILES: CN1C(=O)CCc2cc(-c3cncc(N4CCC[C@H]4CCl)c3)ccc21]

In analogy to the procedure described for the preparation of intermediate A-5 [B], 6-[5-((S)-2-hydroxymethyl-pyrrolidin-1-yl)-pyridin-3-yl]-1-methyl-3,4-dihydro-1H-quinolin- 2-one (example 5) has been reacted with thionyl chloride to give the title compound as an orange oil. MS: 356.1 (M+H⁺).

[B] 6-[5-((S)-2-Ethylaminomethyl-pyrrolidin-1-yl)-pyridin-3-yl]-1-methyl-3,4-dihydro-1H-quinolin-2-one

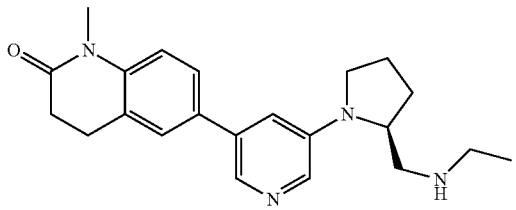 [SMILES: CCNC[C@@H]1CCCN1c1cncc(-c2ccc3c(c2)CCC(=O)N3C)c1]

In a sealed tube, a solution of 6-[5-((S)-2-chloromethyl-pyrrolidin-1-yl)-pyridin-3-yl]-1-methyl-3,4-dihydro-1H-quinolin-2-one (0.066 g, 0.185 mmol) in CH$_3$CN (2.5 mL) was mixed with K$_2$CO$_3$ (0.064 g, 0.464 mmol), TEA (0.188 g, 1.85 mmol), sodium iodide (0.028 g, 0.185 mmol) and ethanamine hydrochloride (0.151 g, 1.85 mmol). The reaction mixture was then heated to 80° C. overnight. The mixture was diluted with EtOAc, poured into aq. NaHCO$_3$ (10 mL) and the aqueous layer was extracted with EtOAc (2×20 mL). Combined organics were washed with brine, dried over Na$_2$SO$_4$, filtered and evaporated to dryness. The residue was purified by silica gel flash chromatography, eluting with a 0 to 15% MeOH(1% NH$_4$OH)-DCM gradient to give the title compound (0.02 g, 30%) as an orange gum. MS: 365.2 (M+H⁺).

Example 10

6-[5-((S)-2-Methoxymethyl-pyrrolidin-1-yl)-pyridin-3-yl]-1-methyl-3,4-dihydro-1H-quinolin-2-one

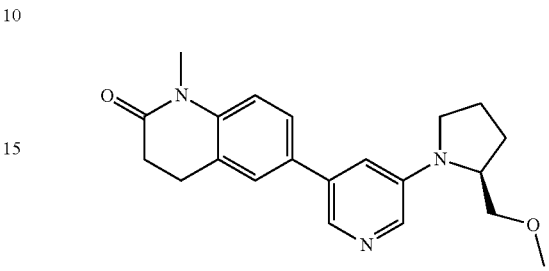

In analogy to the procedure described for the preparation of intermediate A-3 [C], 1-methyl-6-(4,4,5,5-tetramethyl-[1,3,2]dioxaborolan-2-yl)-3,4-dihydro-1H-quinolin-2-one (intermediate A-1) has been coupled to 3-bromo-5-((S)-2-methoxymethyl-pyrrolidin-1-yl)-pyridine (intermediate A-6) to give the title compound as a yellow oil. MS: 352.3 (M+H⁺).

The following compounds listed in Table 2 were prepared in analogy to the procedure described for the preparation of intermediate A-3 [C], using the appropriate starting materials.

TABLE 2

| Ex | Name | Starting Materials | Aspect | MS (M + H⁺) |
|---|---|---|---|---|
| 11 | 1-Methyl-6-[5-((S)-2-[1,2,4]triazol-1-ylmethyl-pyrrolidin-1-yl)-pyridin-3-yl]-3,4-dihydro-1H-quinolin-2-one | 3-Bromo-5-((S)-2-[1,2,4]triazol-1-ylmethyl-pyrrolidin-1-yl)-pyridine (intermediate A-5) and 1-methyl-6-(4,4,5,5-tetramethyl-[1,3,2]dioxaborolan-2-yl)-3,4-dihydro-1H-quinolin-2-one (intermediate A-1) | Light brown foam | 389.1 |
| 12 | 6-(5-Benzylamino-pyridin-3-yl)-1-methyl-3,4-dihydro-1H-quinolin-2-one | Benzyl-(5-bromo-pyridin-3-yl)-amine (intermediate A-8) and 1-methyl-6-(4,4,5,5-tetramethyl-[1,3,2]dioxaborolan-2-yl)-3,4-dihydro-1H-quinolin-2-one (intermediate A-1) | White solid | 344.1 |
| 13 | 6-[5-((S)-2-Hydroxymethyl-5-oxo-pyrrolidin-1-yl)-pyridin-3-yl]-1-methyl-3,4-dihydro-1H-quinolin-2-one | (S)-1-(5-Bromo-pyridin-3-yl)-5-hydroxymethyl-pyrrolidin-2-one (intermediate A-9) and 1-methyl-6-(4,4,5,5-tetramethyl-[1,3,2]dioxaborolan-2-yl)-3,4-dihydro-1H-quinolin-2-one (intermediate A-1) | White yellow foam | 352.3 |

TABLE 2-continued

| Ex | Name | Starting Materials | Aspect | MS (M + H⁺) |
|----|------|--------------------|--------|--------------|
| 14 | 1-Methyl-6-[5-(2-oxo-pyrrolidin-1-yl)-pyridin-3-yl]-3,4-dihydro-1H-quinolin-2-one | 1-(5-Bromo-pyridin-3-yl)-pyrrolidin-2-one (intermediate A-10) and 1-methyl-6-(4,4,5,5-tetramethyl-[1,3,2]dioxaborolan-2-yl)-3,4-dihydro-1H-quinolin-2-one (intermediate A-1) | White solid | 322.1 |
| 15 | Ethanesulfonic acid [5-(1-methyl-2-oxo-1,2,3,4-tetrahydro-quinolin-6-yl)-pyridin-3-ylmethyl]-amide | Ethanesulfonic acid (5-bromo-pyridin-3-ylmethyl)-amide (intermediate A-11) and 1-methyl-6-(4,4,5,5-tetramethyl-[1,3,2]dioxaborolan-2-yl)-3,4-dihydro-1H-quinolin-2-one (intermediate A-1) | White foam | 360.1 |
| 16 | Ethanesulfonic acid [5-(7-fluoro-1-methyl-2-oxo-1,2,3,4-tetrahydro-quinolin-6-yl)-pyridin-3-ylmethyl]-amide | Ethanesulfonic acid (5-bromo-pyridin-3-ylmethyl)-amide (intermediate A-11) and 7-fluoro-1-methyl-6-(4,4,5,5-tetramethyl-[1,3,2]dioxaborolan-2-yl)-3,4-dihydro-1H-quinolin-2-one (intermediate A-22) | White solid | 378.2 |
| 17 | Ethanesulfonic acid [5-(1,4,4-trimethyl-2-oxo-1,2,3,4-tetrahydro-quinolin-6-yl)-pyridin-3-ylmethyl]-amide | Ethanesulfonic acid (5-bromo-pyridin-3-ylmethyl)-amide (intermediate A-11) and 1,4,4-trimethyl-6-(4,4,5,5-tetramethyl-[1,3,2]dioxaborolan-2-yl)-3,4-dihydro-1H-quinolin-2-one (intermediate A-23) | Off white solid | 388.1 |
| 18 | 1-Methyl-6-[5-(2-oxo-pyrrolidin-1-ylmethyl)-pyridin-3-yl]-3,4-dihydro-1H-quinolin-2-one | 1-(5-Bromo-pyridin-3-ylmethyl)-pyrrolidin-2-one (intermediate A-12) and 1-methyl-6-(4,4,5,5-tetramethyl-[1,3,2]dioxaborolan-2-yl)-3,4-dihydro-1H-quinolin-2-one (intermediate A-1) | Brown foam | 336.4 |

TABLE 2-continued

| Ex | Name | Starting Materials | Aspect | MS (M + H⁺) |
|---|---|---|---|---|
| 19 | 1-Methyl-6-[5-(2-oxo-piperidin-1-ylmethyl)-pyridin-3-yl]-3,4-dihydro-1H-quinolin-2-one | 1-(5-Bromo-pyridin-3-ylmethyl)-piperidin-2-one (intermediate A-13) and 1-methyl-6-(4,4,5,5-tetramethyl-[1,3,2]dioxaborolan-2-yl)-3,4-dihydro-1H-quinolin-2-one (intermediate A-1) | White solid | 350.3 |
| 20 | 6-[5-(1,1-Dioxo-1λ⁶-thiomorpholin-4-ylmethyl)-pyridin-3-yl]-1-methyl-3,4-dihydro-1H-quinolin-2-one | 4-(5-Bromo-pyridin-3-ylmethyl)-thiomorpholine 1,1-dioxide (intermediate A-14) and 1-methyl-6-(4,4,5,5-tetramethyl-[1,3,2]dioxaborolan-2-yl)-3,4-dihydro-1H-quinolin-2-one (intermediate A-1) | White solid | 386.2 |
| 21 | 6-[5-(((S)-2-Methoxymethyl-pyrrolidin-1-ylmethyl)-pyridin-3-yl]-1-methyl-3,4-dihydro-1H-quinolin-2-one | 3-Bromo-5-(((S)-2-methoxymethyl-pyrrolidin-1-ylmethyl)-pyridine (intermediate A-15) and 1-methyl-6-(4,4,5,5-tetramethyl-[1,3,2]dioxaborolan-2-yl)-3,4-dihydro-1H-quinolin-2-one (intermediate A-1) | Colorless oil | 366.3 |
| 22 | (S)-1-[5-(1-Methyl-2-oxo-1,2,3,4-tetrahydro-quinolin-6-yl)-pyridin-3-ylmethyl]-pyrrolidine-2-carboxylic acid methyl ester | (S)-1-(5-Bromo-pyridin-3-ylmethyl)-pyrrolidine-2-carboxylic acid methyl ester (intermediate A-17) and 1-methyl-6-(4,4,5,5-tetramethyl-[1,3,2]dioxaborolan-2-yl)-3,4-dihydro-1H-quinolin-2-one (intermediate A-1) | Brown oil | 380.3 |

TABLE 2-continued

| Ex | Name | Starting Materials | Aspect | MS (M + H⁺) |
|----|------|-------------------|--------|-------------|
| 23 | 1-Methyl-6-{5-[(S)-2-(2,2,2-trifluoro-ethoxymethyl)-pyrrolidin-1-ylmethyl]-pyridin-3-yl}-3,4-dihydro-1H-quinolin-2-one | 3-Bromo-5-[(S)-2-(2,2,2-trifluoro-ethoxymethyl)-pyrrolidin-1-ylmethyl]-pyridine (intermediate A-19) and 1-methyl-6-(4,4,5,5-tetramethyl-[1,3,2]dioxaborolan-2-yl)-3,4-dihydro-1H-quinolin-2-one (intermediate A-1) | Colorless waxy solid | 434.4 |
| 24 | 6-[6-(2-Hydroxy-ethylamino)-pyrazin-2-yl]-1-methyl-3,4-dihydro-1H-quinolin-2-one | 2-(6-Chloro-pyrazin-2-ylamino)-ethanol (intermediate A-20) and 1-methyl-6-(4,4,5,5-tetramethyl-[1,3,2]dioxaborolan-2-yl)-3,4-dihydro-1H-quinolin-2-one (intermediate A-1) | Light brown solid | 299.2 |
| 25 | 6-(6-Benzylamino-pyrazin-2-yl)-1-methyl-3,4-dihydro-1H-quinolin-2-one | Benzyl-(6-chloro-pyrazin-2-yl)-amine (intermediate A-21) and 1-methyl-6-(4,4,5,5-tetramethyl-[1,3,2]dioxaborolan-2-yl)-3,4-dihydro-1H-quinolin-2-one (intermediate A-1) | Light yellow solid | 345.1 |
| 26 | 7-Fluoro-6-[6-(2-hydroxy-ethylamino)-pyrazin-2-yl]-1-methyl-3,4-dihydro-1H-quinolin-2-one | 2-(6-Chloro-pyrazin-2-ylamino)-ethanol (intermediate A-20) and 7-fluoro-1-methyl-6-(4,4,5,5-tetramethyl-[1,3,2]dioxaborolan-2-yl)-3,4-dihydro-1H-quinolin-2-one (intermediate A-22) | White solid | 317.1 |
| 27 | 6-(6-Benzylamino-pyrazin-2-yl)-7-fluoro-1-methyl-3,4-dihydro-1H-quinolin-2-one | Benzyl-(6-chloro-pyrazin-2-yl)-amine (intermediate A-21) and 7-fluoro-1-methyl-6-(4,4,5,5-tetramethyl-[1,3,2]dioxaborolan-2-yl)-3,4-dihydro-1H-quinolin-2-one (intermediate A-22) | Yellow solid | 362.9 |

TABLE 2-continued

| Ex | Name | Starting Materials | Aspect | MS (M + H+) |
|---|---|---|---|---|
| 28 | 6-[6-(1-Methyl-2-oxo-1,2,3,4-tetrahydro-quinolin-6-yl)-pyrazin-2-yl]-2,6-diaza-spiro[3.3]heptane-2-carboxylic acid tert-butyl ester | 6-(6-Chloro-pyrazin-2-yl)-2,6-diaza-spiro[3.3]heptane-2-carboxylic acid tert-butyl ester (intermediate 24) and 1-methyl-6-(4,4,5,5-tetramethyl-[1,3,2]dioxaborolan-2-yl)-3,4-dihydro-1H-quinolin-2-one (intermediate A-1) | Off white solid | 436.1 |
| 29 | 6-[5-(1-Methyl-2-oxo-1,2,3,4-tetrahydro-quinolin-6-yl)-pyridin-3-yl]-2,6-diaza-spiro[3.3]heptane-2-carboxylic acid tert-butyl ester | 6-(5-Bromo-pyridin-3-yl)-2,6-diaza-spiro[3.3]heptane-2-carboxylic acid tert-butyl ester (intermediate 25) and 1-methyl-6-(4,4,5,5-tetramethyl-[1,3,2]dioxaborolan-2-yl)-3,4-dihydro-1H-quinolin-2-one (intermediate A-1) | Brown waxy solid | 435.3 |

Example 30

6-[5-((R)-1-Hydroxymethyl-2-methyl-propylamino)-pyridin-3-yl]-1-methyl-3,4-dihydro-1H-quinolin-2-one

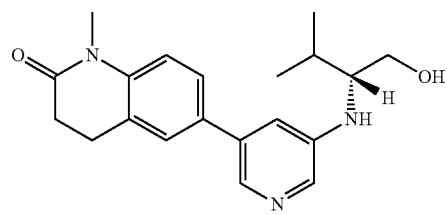 [SMILES: CC(C)[C@H](CO)Nc1cncc(-c2ccc3c(c2)CCC(=O)N3C)c1]

[A] 6-{5-[(R)-1-(tert-butyl-dimethyl-silanyloxymethyl)-2-methyl-propylamino]-pyridin-3-yl}-1-methyl-3,4-dihydro-1H-quinolin-2-one

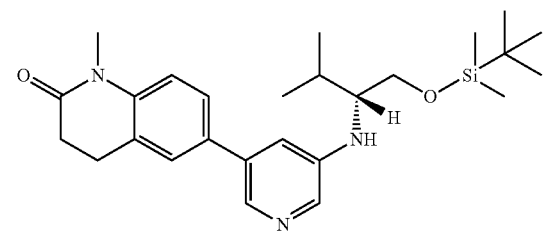 [SMILES: CC(C)[C@H](CO[Si](C)(C)C(C)(C)C)Nc1cncc(-c2ccc3c(c2)CCC(=O)N3C)c1]

In analogy to the procedures described for the preparation of intermediate A-3 [B] and A-3 [C]: i) (R)-1-(tert-butyl-dimethyl-silanyloxymethyl)-2-methyl-propylamine has been reacted with 3,5-dibromopyridine to give (5-bromo-pyridin-3-yl)-[(R)-1-(tert-butyl-dimethyl-silanyloxymethyl)-2-methyl-propyl]-amine; ii) subsequent condensation with 1-methyl-6-(4,4,5,5-tetramethyl-[1,3,2]dioxaborolan-2-yl)-3,4-dihydro-1H-quinolin-2-one (intermediate A-1) gave the title compound as light yellow amorphous solid. MS: 454.3 (M+H+).

[B] 6-[5-((R)-1-Hydroxymethyl-2-methyl-propylamino)-pyridin-3-yl]-1-methyl-3,4-dihydro-1H-quinolin-2-one

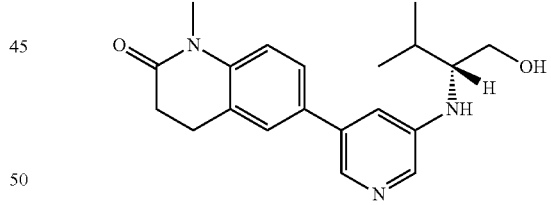

In a 10 mL round-bottomed flask, 6-{5-[(R)-1-(tert-butyl-dimethyl-silanyloxymethyl)-2-methyl-propylamino]-pyridin-3-yl}-1-methyl-3,4-dihydro-1H-quinolin-2-one (60 mg, 132 µmol) was dissolved in THF (1.5 mL) to give a light yellow solution and cooled down to 0° C. TBAF, 1 M sol. in THF (132 µl, 132 µmol) was added dropwise. The solution was stirred at 0° C. for 1.5 h and partitioned between aqueous sat. NaHCO₃ solution and AcOEt (3×). The organic layers were collected, dried over Na₂SO₄ and evaporated in vacuo. The crude material was purified by flash chromatography (silica gel, 20 g, 100% EtOAc followed by 1% MeOH in EtOAc) to give the title compound (22 mg, 49%) as a light yellow foam. MS: 340.2 (M+H+).

Example 31

6-[6-((R)-1-Hydroxymethyl-2-methyl-propylamino)-pyrazin-2-yl]-1-methyl-3,4-dihydro-1H-quinolin-2-one

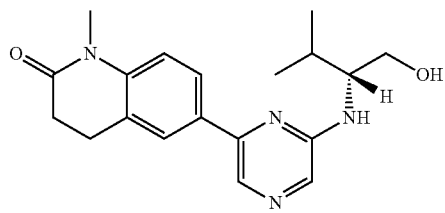 [SMILES: CC(C)[C@H](CO)Nc1cncc(-c2ccc3c(c2)CCC(=O)N3C)n1]

In analogy to the procedures described for the preparation of intermediate A-20 and A-3 [C]: i) (R)-2-amino-3-methyl-butan-1-ol has been reacted with 2,6-dichloropyrazine to give (R)-2-(6-chloro-pyrazin-2-ylamino)-3-methyl-butan-1-ol; ii) subsequent condensation with 1-methyl-6-(4,4,5,5-tetramethyl-[1,3,2]dioxaborolan-2-yl)-3,4-dihydro-1H-quinolin-2-one (intermediate A-1) gave the title compound as a light yellow solid. MS: 341.2 (M+H$^+$).

Example 32

Ethanesulfonic acid [5-(5-methyl-6-oxo-5,6,7,8-tetrahydro-[1,5]naphthyridin-2-yl)-pyridin-3-ylmethyl]-amide

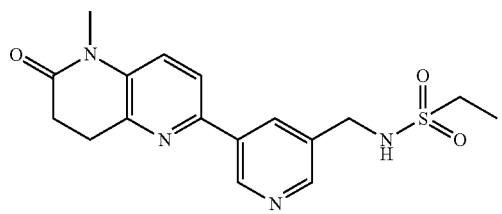 [SMILES: CCS(=O)(=O)NCc1cncc(-c2ccc3c(n2)CCC(=O)N3C)c1]

[A] 6-Bromo-3-nitro-2-(toluene-4-sulfonylmethyl)-pyridine

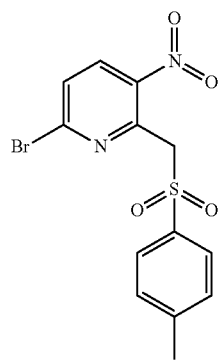

and 2-bromo-5-nitro-4-(toluene-4-sulfonylmethyl)-pyridine

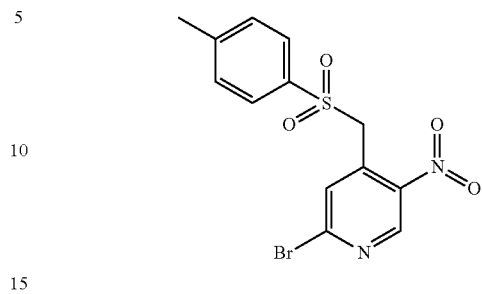

To a stirred solution of 2-bromo-5-nitro-pyridine (3.4 g, 25.0 mmol) and 1-chloromethanesulfonyl-4-methyl-benzene (3.4 g, 25 mmol) in THF (100 mL) was added t-BuOK solution (1.0 M in THF, 55 mL) at −78° C. After stirring for 30 minutes, AcOH (3.0 mL) was added to the above solution and the reaction mixture was allowed to warm up to RT and stirred for additional 20 minutes. After extraction of the reaction mixture with EtOAc, the organic layer was washed with brine, dried over anhy. Na$_2$SO$_4$, filtered and concentrated in vacuo to give a suspension (50 mL), which after filtration gave 2-bromo-5-nitro-4-(toluene-4-sulfonylmethyl)-pyridine as a pale white solid (3.25 g, 35%); the filtrate was concentrated in vacuo to afford 6-bromo-3-nitro-2-(toluene-4-sulfonylmethyl)-pyridine as a light yellow solid (4.2 g, 45%). MS: 371.1 & 373.1 (M+H$^+$).

[B] 3-(6-Bromo-3-nitro-pyridin-2-yl)-3-(toluene-4-sulfonyl)-propionic acid methyl ester

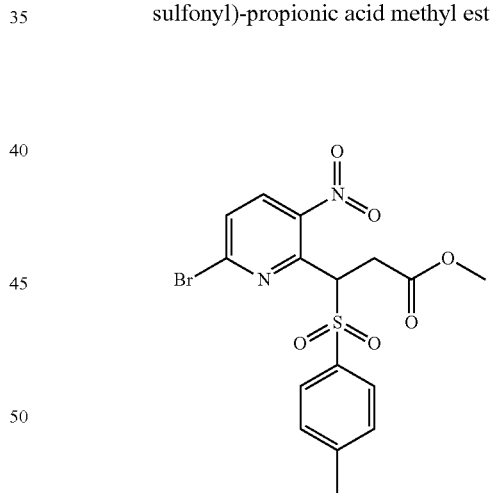

A mixture of 6-bromo-3-nitro-2-(toluene-4-sulfonylmethyl)-pyridine (3.3 g, 9.0 mmol), bromo-acetic acid methyl ester (2.1 mL, 22.5 mmol) and K$_2$CO$_3$ (8.4 g, 60.8 mmol) were suspended in DMF (18.0 mL) and stirred at 40° C. for 1 hour before pouring into water (50 mL). After extraction with EtOAc, the organic layer was washed with brine, dried over anhy. Na$_2$SO$_4$, filtered and concentrated in vacuo to give 3-(6-bromo-3-nitro-pyridin-2-yl)-3-(toluene-4-sulfonyl)-propionic acid methyl ester (3.9 g, quant.) as a light yellow solid. MS: 443.1 & 445.1 (M+H$^+$).

[C] 6-(2-Methoxycarbonyl-vinyl)-5-nitro-[2,3]bipyridinyl-5'-carboxylic acid methyl ester

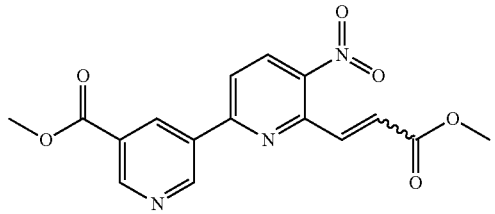

3-(6-Bromo-3-nitro-pyridin-2-yl)-3-(toluene-4-sulfonyl)-propionic acid methyl ester (1.2 g, 2.7 mmol), Pd(PPh$_3$)$_2$Cl$_2$ (190 mg, 0.27 mmol), Na$_2$CO$_3$ (572 mg, 5.4 mmol) and 3-(methoxycarbonyl)pyridine-5-boronic acid pinacol ester (926 mg, 3.5 mmol) were dissolved in 1,4-dioxane (4.0 mL) and the resulting reaction mixture was heated at 120° C. for 3 hours before it was poured into H$_2$O (50 mL). After extraction with EtOAc, the organic layer was washed with brine, dried over anhy. Na$_2$SO$_4$, filtered and concentrated in vacuo to give 6-(2-methoxycarbonyl-vinyl)-5-nitro-[2,3']bipyridinyl-5'-carboxylic acid methyl ester (926 mg, quant.) as a light yellow solid. MS: 344.1 (M+H$^+$).

[D] 5-(6-Oxo-5,6,7,8-tetrahydro-[1,5]naphthyridin-2-yl)-nicotinic acid methyl ester

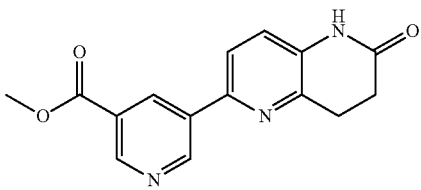 [SMILES: COC(=O)c1cncc(-c2ccc3c(n2)CCC(=O)N3)c1]

6-(2-Methoxycarbonyl-vinyl)-5-nitro-[2,3']bipyridinyl-5'-carboxylic acid methyl ester (926 mg, 2.7 mmol), 10% Pd/C (300 mg) and AcOH (1.3 mL) were suspended in methanol (300 mL) and the reaction mixture was stirred at 50° C. under 50 psi H$_2$ pressure for 13 hours. After filtration, the reaction mixture was concentrated in vacuo to give a crude product of 5-(6-oxo-5,6,7,8-tetrahydro-[1,5]naphthyridin-2-yl)-nicotinic acid methyl ester (500 mg, 65.4%) as a light yellow solid. MS: 284.1 (M+H$^+$).

[E] 5-(5-Methyl-6-oxo-5,6,7,8-tetrahydro-[1,5]naphthyridin-2-yl)-nicotinic acid methyl ester

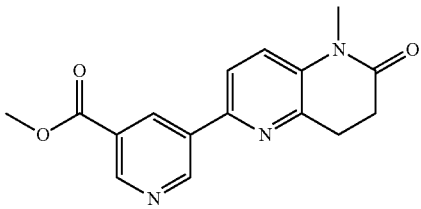 [SMILES: COC(=O)c1cncc(-c2ccc3c(n2)CCC(=O)N3C)c1]

To a stirred solution of 5-(6-oxo-5,6,7,8-tetrahydro-[1,5]naphthyridin-2-yl)-nicotinic acid methyl ester (430 mg, 1.52 mmol) in THF (15.0 mL) was added 60% NaH (91 mg, 2.28 mmol) at 0° C. and the reaction mixture was stirred at 2-5° C. for 0.5 h before CH$_3$I (0.3 mL, 4.56 mmol) was added. After stirring overnight at RT, it was poured into water (5.0 mL). After extraction with EtOAc, the organic layer was washed with brine, dried over anhy. Na$_2$SO$_4$, filtered and concentrated in vacuo to give 5-(5-methyl-6-oxo-5,6,7,8-tetrahydro-[1,5]naphthyridin-2-yl)-nicotinic acid methyl ester (383.7 mg, 85%) as a light yellow solid. MS: 298.1 (M+H$^+$).

[F] 6-(5-Hydroxymethyl-pyridin-3-yl)-1-methyl-3,4-dihydro-1H-[1,5]naphthyridin-2-one

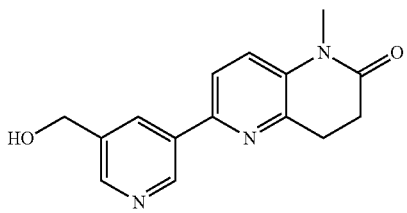 [SMILES: CN1C(=O)CCc2nc(-c3cncc(CO)c3)ccc21]

To a stirred solution of 5-(5-methyl-6-oxo-5,6,7,8-tetrahydro-[1,5]naphthyridin-2-yl)-nicotinic acid methyl ester (270 mg, 0.91 mmol) in MeOH (10 mL) was added sodium borohydride (300 mg, 8.0 mmol) at RT. After stirring overnight, the reaction mixture was quenched by adding water (5.0 mL). It was then concentrated in vacuo to give a light yellow oil. After extraction with EtOAc, the organic layer was washed with brine, dried over anhy. Na$_2$SO$_4$, filtered and concentrated in vacuo to give 6-(5-hydroxymethyl-pyridin-3-yl)-1-methyl-3,4-dihydro-1H-[1,5]naphthyridin-2-one (190 mg, 77.6%) as a white solid. MS: 270.1 (M+H$^+$).

[G] 6-(5-Chloromethyl-pyridin-3-yl)-1-methyl-3,4-dihydro-1H-[1,5]naphthyridin-2-one

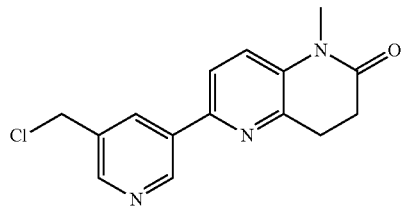 [SMILES: CN1C(=O)CCc2nc(-c3cncc(CCl)c3)ccc21]

At 0° C., 6-(5-hydroxymethyl-pyridin-3-yl)-1-methyl-3,4-dihydro-1H-[1,5]naphthyridin-2-one (170 mg, 0.63 mmol) in DCM (15 mL) was treated with thionyl chloride (0.32 mL, 4.0 mmol). After the addition, the reaction mixture was allowed to stir at 2-5° C. for 2 hours before it was poured into satd. aq. NaHCO$_3$ solution (50 mL). After extraction with EtOAc, the organic layer was washed with brine, dried over anhy. Na$_2$SO$_4$, filtered and concentrated in vacuo to give 6-(5-chloromethyl-pyridin-3-yl)-1-methyl-3,4-dihydro-1H-[1,5]naphthyridin-2-one (156 mg, 86.3%) as yellow oil. MS: 288.1 (M+H$^+$).

[H] Ethanesulfonic acid [5-(5-methyl-6-oxo-5,6,7,8-tetrahydro-[1,5]naphthyridin-2-yl)-pyridin-3-ylmethyl]-amide

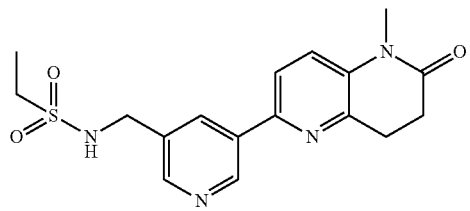 [SMILES: CCS(=O)(=O)NCc1cncc(-c2ccc3c(n2)CCC(=O)N3C)c1]

To a stirred solution of ethanesulfonic acid amide (118 mg, 1.08 mmol) in DMF (5.0 mL) was added 60% NaH (35 mg, 0.81 mmol) at RT and the resulting reaction mixture was stirred for 0.5 hour before 6-(5-chloromethyl-pyridin-3-yl)-1-methyl-3,4-dihydro-1H-[1,5]naphthyridin-2-one (156 mg, 0.54 mmol) was added. After continued stirring at RT for additional 2 hours, water (1.0 mL) was added. After extraction with EtOAc, the organic layer was washed with brine, dried over anhy. Na$_2$SO$_4$, filtered and concentrated in vacuo to give a crude product which was purified by prep-HPLC to give title compound (15 mg, 7.7%) as a light yellow solid. MS: 361.1 (M+H$^+$).

Example 33

6-Pyridin-3-yl-3,4-dihydro-1H-[1,5]naphthyridin-2-one

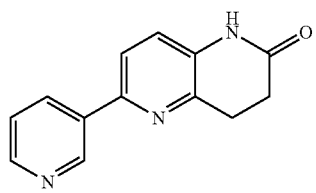 [SMILES: O=C1CCc2nc(-c3cccnc3)ccc2N1]

In analogy to the procedures described for the preparation of example 32 (steps [C] to [D]), the title compound was prepared using 3-(6-bromo-3-nitro-pyridin-2-yl)-3-(toluene-4-sulfonyl)-propionic acid methyl ester and 3-pyridine boronic acid as corresponding starting materials. MS: 226.1 (M+H$^+$).

Example 34

1-Methyl-6-pyridin-3-yl-3,4-dihydro-1H-[1,5]naphthyridin-2-one

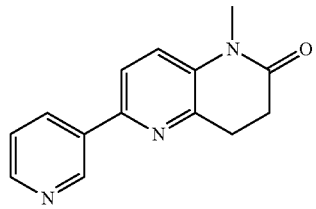 [SMILES: CN1C(=O)CCc2nc(-c3cccnc3)ccc21]

In analogy to the procedures described for the preparation of example 32 (step [E]), the title compound was prepared using 6-pyridin-3-yl-3,4-dihydro-1H-[1,5]naphthyridin-2-one (example 33) as corresponding starting material. MS: 240.2 (M+H$^+$).

Example 35

1-Methyl-6-pyridin-3-yl-3,4-dihydro-1H-[1,7]naphthyridin-2-one

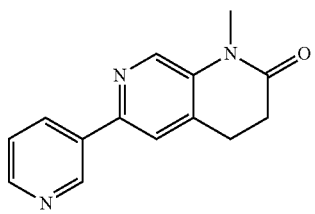 [SMILES: CN1C(=O)CCc2cc(-c3cccnc3)ncc21]

In analogy to the procedures described for the preparation of example 32 (steps [B] to [E]), the title compound was prepared using 2-bromo-5-nitro-4-(toluene-4-sulfonylmethyl)-pyridine (example 32 [A]) and 3-pyridine boronic acid as corresponding starting materials. MS: 240.1 (M+H$^+$).

Example 36

6-(5-Aminomethyl-pyridin-3-yl)-1-methyl-3,4-dihydro-1H-quinolin-2-one

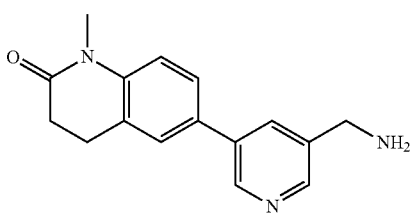 [SMILES: CN1C(=O)CCc2cc(-c3cncc(CN)c3)ccc21]

A round-bottomed flask was charged with 5-bromo-pyridin-3-yl-methylamine (0.5 g, 2.67 mmol), 1-methyl-6-(4,4,5,5-tetramethyl-[1,3,2]dioxaborolan-2-yl)-3,4-dihydro-1H-quinolin-2-one (intermediate A-1, 0.845 g, 2.94 mmol) and EtOH (48 mL). Then, tetrakis(triphenylphosphine)palladium (0) (0.093 g, 0.080 mmol), followed by aqueous Na$_2$CO$_3$ solution (8 mL, 0.312 g, 2.94 mmol) were added and the reaction mixture heated to 85° C. over night. The mixture was evaporated to dryness, the residue was taken up in EtOAc, filtered through Dicalite and washed with EtOAc (2×50 mL). The filtrate was evaporated to dryness. Then, the residue was purified by silica gel flash chromatography eluting with a 0 to 20% MeOH(1% NH$_4$OH)-DCM gradient to give the title compound (0.7 g, 94%) as an off white solid. MS: 268.2 (M+H$^+$).

Example 37

N-[5-(1-Methyl-2-oxo-1,2,3,4-tetrahydro-quinolin-6-yl)-pyridin-3-ylmethyl]-propionamide

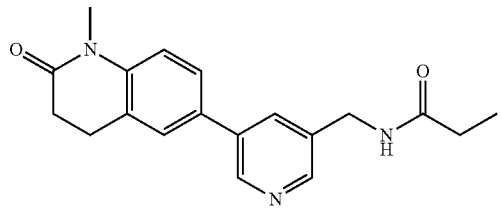

To a solution of 6-(5-aminomethyl-pyridin-3-yl)-1-methyl-3,4-dihydro-1H-quinolin-2-one (example 36, 0.05 g, 0.187 mmol) in dry DMF (1 mL) were added EDCI (0.039 g, 0.206 mmol), Hünig's base (0.060 g, 0.468 mmol) and propionic acid (0.021 g, 0.282 mmol) and the reaction mixture was stirred at room temperature over night. The reaction mixture was diluted with EtOAc, poured into sat. NH$_4$Cl solution (5 mL) and extracted with EtOAc (2×10 mL). Combined organics were dried over Na$_2$SO$_4$, filtered and evaporated to dryness. The residue was purified by silica gel flash chromatography eluting with a 0 to 10% MeOH(1% NH$_4$OH)-DCM gradient to give the title compound (0.029 g, 48%) as a white solid. MS: 324.4 (M+H$^+$).

Example 38

Propane-2-sulfonic acid [5-(1-methyl-2-oxo-1,2,3,4-tetrahydro-quinolin-6-yl)-pyridin-3-ylmethyl]-amide

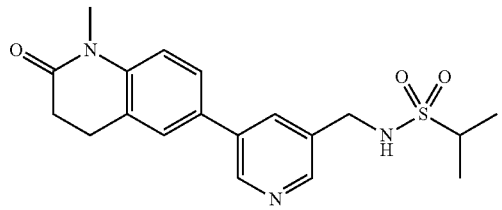 [SMILES: CC(C)S(=O)(=O)NCc1cncc(-c2ccc3c(c2)CCC(=O)N3C)c1]

To a solution of 6-(5-aminomethyl-pyridin-3-yl)-1-methyl-3,4-dihydro-1H-quinolin-2-one (example 36, 0.05 g, 0.187 mmol) in DCM (1 mL) cooled to 0° C. were added triethylamine (0.038 g, 0.374 mmol) and isopropylsulfonylchloride (0.029 g, 0.206 mmol). The resulting suspension was stirred at 0° C. for 4 h and then allowed to warm up to room temperature and stirring was continued for 2 h. The reaction mixture was diluted with DCM, poured into H$_2$O (5 mL) and extracted with DCM (2×10 mL). Combined organics were dried over Na$_2$SO$_4$, filtered and evaporated to dryness. The residue was purified by silica gel flash chromatography eluting with a 0 to 10% MeOH(1% NH$_4$OH)-DCM gradient to give the title compound (0.023 g, 33%) as a white foam. MS: 374.1 (M+H$^+$).

Example 39

{2-[5-(1-Methyl-2-oxo-1,2,3,4-tetrahydro-quinolin-6-yl)-pyridin-3-yloxy]-ethyl}-carbamic acid tert-butyl ester

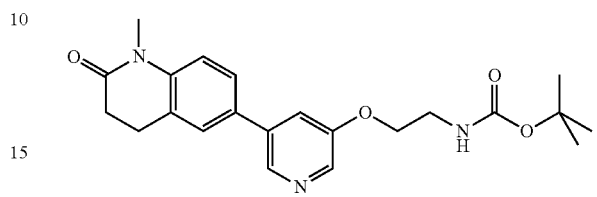

In analogy to the procedure described for the preparation of intermediate A-3 [C], 1-methyl-6-(4,4,5,5-tetramethyl-[1,3,2]dioxaborolan-2-yl)-3,4-dihydro-1H-quinolin-2-one (intermediate A-1) has been coupled to [2-(5-bromo-pyridin-3-yloxy)-ethyl]-carbamic acid tert-butyl ester (intermediate A-7) to give the title compound as a white solid. MS: 398.1 (M+H$^+$).

Example 40

3-Methoxy-isoxazole-5-carboxylic acid [5-(1-methyl-2-oxo-1,2,3,4-tetrahydro-quinolin-6-yl)-pyridin-3-ylmethyl]-amide

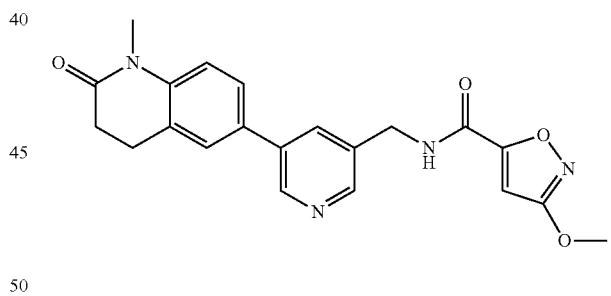

To a solution of 6-(5-aminomethyl-pyridin-3-yl)-1-methyl-3,4-dihydro-1H-quinolin-2-one (example 36, 0.05 g, 0.187 mmol) in dry DCM (1 mL) were added EDCI (0.039 g, 0.206 mmol), hydroxybenzotriazole (0.032 g, 0.206 mmol), Hünig's base (0.060 g, 0.468 mmol) and 3-methoxy-isoxazole-5-carboxylic acid (0.040 g, 0.281 mmol) and the resulting solution was stirred at room temperature over night. The reaction mixture was diluted with EtOAc, poured into sat. NaHCO$_3$ solution (5 mL) and extracted with EtOAc (2×10 mL). Combined organics were dried over Na$_2$SO$_4$, filtered and evaporated to dryness. The residue was purified by silica gel flash chromatography eluting with a 0 to 10% MeOH(1% NH$_4$OH)-DCM gradient to give the title compound (0.03 g, 41%) as a white solid. MS: 393.1 (M+H$^+$).

Example 41

Cyclopropanecarboxylic acid [5-(1-methyl-2-oxo-1,2,3,4-tetrahydro-quinolin-6-yl)-pyridin-3-ylmethyl]-amide

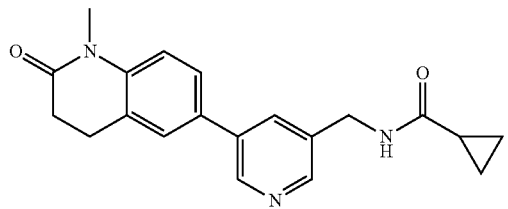 [SMILES: CN1C(=O)CCc2cc(-c3cncc(CNC(=O)C4CC4)c3)ccc21]

In analogy to the procedure described for the preparation of example 37, 6-(5-aminomethyl-pyridin-3-yl)-1-methyl-3,4-dihydro-1H-quinolin-2-one (example 36) has been reacted with cyclopropanecarboxylic acid to give the title compound as a white solid. MS: 336.3 (M+H$^+$).

Example 42

6-[5-(2-Amino-ethoxy)-pyridin-3-yl]-1-methyl-3,4-dihydro-1H-quinolin-2-one hydrochloride

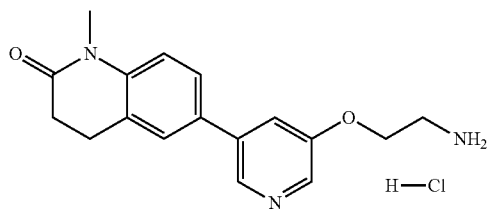

To a solution of {2-[5-(1-methyl-2-oxo-1,2,3,4-tetrahydro-quinolin-6-yl)-pyridin-3-yloxy]-ethyl}-carbamic acid tert-butyl ester (example 39, 0.06 g, 0.151 mmol) in MeOH (1 mL) was added 4M HCl in dioxane (0.151 mL, 0.604 mmol) and the reaction mixture was stirred at room temperature over night. The resulting suspension was filtered off and the solid material was triturated in diethyl ether, filtered off and further dried in a high vacuum to give the title compound (0.046 g, 91%) as a white solid. MS: 298.3 (M+H$^+$).

Example 43

N-{2-[5-(1-Methyl-2-oxo-1,2,3,4-tetrahydro-quinolin-6-yl)-pyridin-3-yloxy]-ethyl}-propionamide

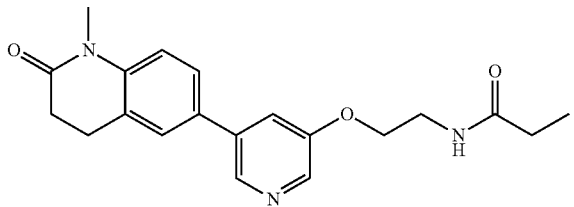 [SMILES: CCC(=O)NCCOc1cncc(-c2ccc3c(c2)CCC(=O)N3C)c1]

In analogy to the procedure described for the preparation of example 37, 6-[5-(2-amino-ethoxy)-pyridin-3-yl]-1-methyl-3,4-dihydro-1H-quinolin-2-one hydrochloride (example 42) has been reacted with propionic acid to give the title compound as a white solid. MS: 354.3 (M+H$^+$).

Example 44

6-[5-(1,1-Dioxo-1$\lambda^6$-[1,2]thiazinan-2-ylmethyl)-pyridin-3-yl]-1-methyl-3,4-dihydro-1H-quinolin-2-one

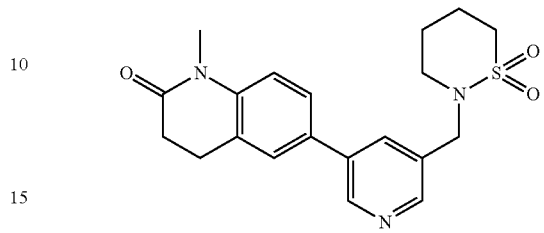

In analogy to the procedure described for the preparation of intermediate A-12 [B] and to the procedure described for the preparation of intermediate A-3 [C], [1,2]thiazinane 1,1-dioxide was reacted with 3-bromo-5-chloromethyl-pyridine (intermediate A-12 [A]) in the presence of NaH to give 2-(5-bromo-pyridin-3-ylmethyl)-[1,2]thiazinane 1,1-dioxide, which was subsequently reacted with 1-methyl-6-(4,4,5,5-tetramethyl-[1,3,2]dioxaborolan-2-yl)-3,4-dihydro-1H-quinolin-2-one (intermediate A-1) to give the title compound as an off-white solid. MS: 386.2 (M+H$^+$).

Example 45

(S)-2-[5-(1-Methyl-2-oxo-1,2,3,4-tetrahydro-quinolin-6-yl)-pyridin-3-yloxymethyl]-azetidine-1-carboxylic acid tert-butyl ester

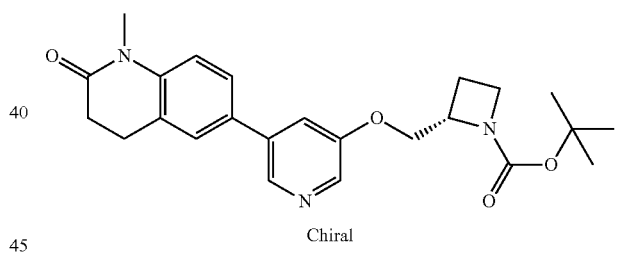

Chiral

A sealed tube was charged with (S)-2-(5-bromo-pyridin-3-yloxymethyl)-azetidine-1-carboxylic acid tert-butyl ester (intermediate A-26, 0.260 g, 0.76 mmol), 1-methyl-6-(4,4,5,5-tetramethyl-[1,3,2]dioxaborolan-2-yl)-3,4-dihydro-1H-quinolin-2-one (intermediate A-1, 0.239 g, 0.83 mmol) and DMF (3 mL). Then, bis(triphenylphosphine)palladium(II) chloride (0.053 g, 0.076 mmol), followed by 1N aqueous Na$_2$CO$_3$ solution (2.27 mL, 2.27 mmol) were added and the reaction was heated to 110° C. (pre-heated oil bath) for 1 h. The mixture was diluted with EtOAc, filtered through Dicalite and washed with EtOAc (20 mL). The resulting filtrate was poured into aq. NaHCO$_3$ (20 mL) and the aqueous layer was extracted with EtOAc (20 mL). Combined organics were washed with brine, dried over Na$_2$SO$_4$, filtered and evaporated. The residue was purified by silica gel flash chromatography eluting with a 0 to 100% EtOAc-heptane gradient to give the title compound (0.277 g, 86%) as a light brown foam. MS: 424.1 (M+H$^+$).

The following compounds listed in Table 3 were prepared in analogy to the procedure described for the preparation of example 45, using the appropriate starting materials.

TABLE 3

| Ex | Name | Starting Materials | Aspect | MS (M + H+) |
|---|---|---|---|---|
| 46 | (R)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester | (R)-3-(5-Bromo-pyridin-3-yloxy)-pyrrolidine-1-carboxylic acid tert-butyl ester (intermediate A-27) and 7-fluoro-1-methyl-6-(4,4,5,5-tetramethyl-[1,3,2]dioxaborolan-2-yl)-3,4-dihydro-1H-quinolin-2-one (intermediate A-22) | Colorless solid | 442.3 |
| 47 | 3-[5-(1-Methyl-2-oxo-1,2,3,4-tetrahydro-quinolin-6-yl)-pyridin-3-yloxy]-azetidine-1-carboxylic acid tert-butyl ester | 3-(5-Bromopyridin-3-yloxy)-azetidine-1-carboxylic acid tert-butyl ester (intermediate A-28) and 1-methyl-6-(4,4,5,5-tetramethyl-[1,3,2]dioxaborolan-2-yl)-3,4-dihydro-1H-quinolin-2-one (intermediate A-1) | Colorless solid | 410.5 |
| 48 | (S)-3-[5-(1-Methyl-2-oxo-1,2,3,4-tetrahydro-quinolin-6-yl)-pyridin-3-yloxy]-pyrrolidine-1-carboxylic acid tert-butyl ester | (S)-3-(5-Bromo-pyridin-3-yloxy)-pyrrolidine-1-carboxylic acid tert-butyl ester (intermediate A-29) and 1-methyl-6-(4,4,5,5-tetramethyl-[1,3,2]dioxaborolan-2-yl)-3,4-dihydro-1H-quinolin-2-one (intermediate A-1) | Colorless solid | 424.1 |
| 49 | (S)-3-[5-(1-Methyl-2-oxo-1,2,3,4-tetrahydro-quinolin-6-yl)-pyridin-3-yloxy]-piperidine-1-carboxylic acid tert-butyl ester | (S)-3-(5-Bromopyridin-3-yloxy)-piperidine-1-carboxylic acid tert-butyl ester (intermediate A-30) and 1-methyl-6-(4,4,5,5-tetramethyl-[1,3,2]dioxaborolan-2-yl)-3,4-dihydro-1H-quinolin-2-one (intermediate A-1) | Colorless oil | 438.3 |
| 50 | 4-[5-(1-Methyl-2-oxo-1,2,3,4-tetrahydro-quinolin-6-yl)-pyridin-3-yloxy]-piperidine-1-carboxylic acid tert-butyl ester | 4-(5-Bromopyridin-3-yloxy)-piperidine-1-carboxylic acid tert-butyl ester (intermediate A-31) and 1-methyl-6-(4,4,5,5-tetramethyl-[1,3,2]dioxaborolan-2-yl)-3,4-dihydro-1H-quinolin-2-one (intermediate A-1) | Colorless amorphous solid | 438.3 |

TABLE 3-continued

| Ex | Name | Starting Materials | Aspect | MS (M + H⁺) |
|---|---|---|---|---|
| 51 | (S)-2-[5-(1-Methyl-2-oxo-1,2,3,4-tetrahydro-quinolin-6-yl)-pyridin-3-yloxymethyl]-pyrrolidine-1-carboxylic acid tert-butyl ester | (S)-2-((5-Bromopyridin-3-yloxy)methyl)pyrrolidine-1-carboxylic acid tert-butyl ester (intermediate A-32) and 1-methyl-6-(4,4,5,5-tetramethyl-[1,3,2]dioxaborolan-2-yl)-3,4-dihydro-1H-quinolin-2-one (intermediate A-1) | Colorless solid | 438.5 |
| 52 | (S)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester | (S)-3-(5-Bromo-pyridin-3-yloxy)-pyrrolidine-1-carboxylic acid tert-butyl ester (intermediate A-29) and 7-fluoro-1-methyl-6-(4,4,5,5-tetramethyl-[1,3,2]dioxaborolan-2-yl)-3,4-dihydro-1H-quinolin-2-one (intermediate A-22) | Colorless solid | n.d. |
| 53 | (R)-3-[5-(1-Methyl-2-oxo-1,2,3,4-tetrahydro-quinolin-6-yl)-pyridin-3-yloxy]-pyrrolidine-1-carboxylic acid tert-butyl ester | (R)-3-(5-Bromo-pyridin-3-yloxy)-pyrrolidine-1-carboxylic acid tert-butyl ester (intermediate A-27) and 1-methyl-6-(4,4,5,5-tetramethyl-[1,3,2]dioxaborolan-2-yl)-3,4-dihydro-1H-quinolin-2-one (intermediate A-1) | Colorless solid | 424.2 |
| 54 | (R)-2-Methyl-propane-2-sulfinic acid {3-[5-(1-methyl-2-oxo-1,2,3,4-tetrahydro-quinolin-6-yl)-pyridin-3-yl]-oxetan-3-yl}-amide | (R)-N-(3-(5-Bromopyridin-3-yl)oxetan-3-yl)-2-methylpropane-2-sulfinamide (intermediate A-33) and 1-methyl-6-(4,4,5,5-tetramethyl-[1,3,2]dioxaborolan-2-yl)-3,4-dihydro-1H-quinolin-2-one (intermediate A-1) | Amorphous brown solid | 414.4 |
| 55 | Ethanesulfonic acid [5-(2-oxo-1,2,3,4-tetrahydro-quinolin-6-yl)-pyridin-3-ylmethyl]-amide | Ethanesulfonic acid (5-bromo-pyridin-3-ylmethyl)-amide (intermediate A-11) and 6-(4,4,5,5-tetramethyl-1,3,2-dioxaborolan-2-yl)-3,4-dihydroquinolin-2(1H)-one (intermediate A-34) | Amorphous colorless solid | 346.1 |

TABLE 3-continued

| Ex | Name | Starting Materials | Aspect | MS (M + H+) |
|---|---|---|---|---|
| 56 | (R)-2-Methyl-propane-2-sulfinic acid {(S or R)-1-[5-(1-methyl-2-oxo-1,2,3,4-tetrahydro-quinolin-6-yl)-pyridin-3-yl]-ethyl}-amide | (R)-2-Methyl-propane-2-sulfinic acid [(S and R)-1-(5-bromo-pyridin-3-yl)-ethyl]-amide (intermediate A-35) and 1-methyl-6-(4,4,5,5-tetramethyl-[1,3,2]dioxaborolan-2-yl)-3,4-dihydro-1H-quinolin-2-one (intermediate A-1) followed by HPLC separation. | Amorphous colorless solid | 386.1 |
| 57 | (R)-2-Methyl-propane-2-sulfinic acid {(R or S)-1-[5-(1-methyl-2-oxo-1,2,3,4-tetrahydro-quinolin-6-yl)-pyridin-3-yl]-ethyl}-amide | (R)-2-Methyl-propane-2-sulfinic acid [(S and R)-1-(5-bromo-pyridin-3-yl)-ethyl]-amide (intermediate A-35) and 1-methyl-6-(4,4,5,5-tetramethyl-[1,3,2]dioxaborolan-2-yl)-3,4-dihydro-1H-quinolin-2-one (intermediate A-1) followed by HPLC separation. | Amorphous colorless solid | 386.1 |
| 58 | {(trans)-4-[5-(1-Methyl-2-oxo-1,2,3,4-tetrahydro-quinolin-6-yl)-pyridin-3-yloxy]-cyclohexyl}-carbamic acid tert-butyl ester | tert-Butyl (trans)-4-(5-bromopyridin-3-yloxy)cyclohexylcarbamate (intermediate A-54) and 1-methyl-6-(4,4,5,5-tetramethyl-[1,3,2]dioxaborolan-2-yl)-3,4-dihydro-1H-quinolin-2-one (intermediate A-1). | Off-white solid | 452.5 |

Example 59

6-[5-(1-Amino-cyclopropyl)-pyridin-3-yl]-1-methyl-3,4-dihydro-1H-quinolin-2-one

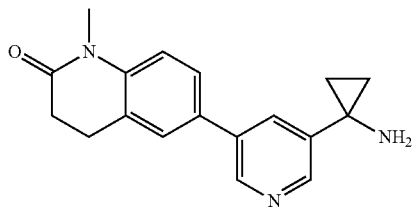 [SMILES: CN1C(=O)CCc2cc(-c3cncc(C4(N)CC4)c3)ccc21]

[A] Methyl 1-(5-bromopyridin-3-yl)cyclopropanecarboxylate

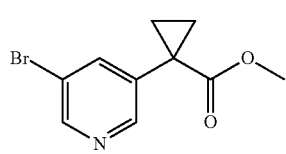

To a solution of methyl 2-(5-bromopyridin-3-yl)acetate (4 g, 17.4 mmol) in DMF (80 mL), cooled at 0° C. with an ice bath, was added 60% NaH in mineral oil (0.918 g, 38.3 mmol) and the reaction mixture was stirred at 0° C. for 15 min. Then, a solution of 1,2-dibromoethane (3.27 g, 17.4 mmol) in DMF (16 mL) was added at 0° C. After the addition, the mixture was stirred at room temperature for 1 h. Two other portions of 60% NaH in mineral oil (2×0.2 g) were added sequentially, until conversion was complete. Then, the reaction mixture was poured into H$_2$O (50 mL) and extracted with EtOAc (3×125 mL). The organic layers were combined, dried over Na$_2$SO$_4$, filtered and evaporated to dryness to give the title compound (4.764 g, 99%) as a brown oil, which was used with no further purification. MS: 256.0 and 258.0 (M+H+).

[B] Potassium 1-(5-bromopyridin-3-yl)cyclopropanecarboxylate

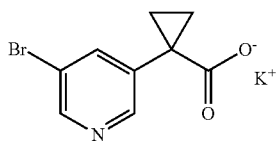 [SMILES: O=C([O-])C1(c2cncc(Br)c2)CC1 ; [K+]]

To a solution of methyl 1-(5-bromopyridin-3-yl)cyclopropanecarboxylate (4.764 g, 18.6 mmol) in THF (190 mL) was added 90% potassium trimethylsilanolate (2.65 g, 18.6 mmol) and the reaction mixture was stirred at room temperature over night. Then, the mixture was filtered and washed with THF to give the desired product (2.668 g) as a light

[C] 1-(5-(1-Methyl-2-oxo-1,2,3,4-tetrahydroquinolin-6-yl)pyridin-3-yl)cyclopropane-carboxylic acid

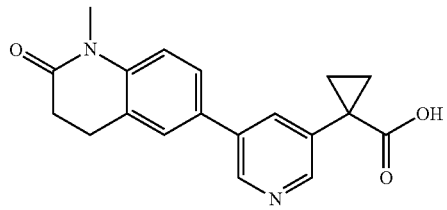 [SMILES: CN1C(=O)CCc2cc(-c3cncc(C4(C(=O)O)CC4)c3)ccc21]

A flask was charged with potassium 1-(5-bromopyridin-3-yl)cyclopropanecarboxylate (0.5 g, 1.52 mmol), 1-methyl-6-(4,4,5,5-tetramethyl-[1,3,2]dioxaborolan-2-yl)-3,4-dihydro-1H-quinolin-2-one (intermediate A-1, 0.479 g, 1.67 mmol) and DMF (7 mL). Then, bis(triphenylphosphine)palladium (II)chloride (0.106 g, 0.152 mmol), followed by 1N aqueous Na$_2$CO$_3$ solution (3.64 mL, 2.4 mmol) were added and the reaction was heated to 120° C. (pre-heated oil bath) for 1 h. The mixture was evaporated to dryness and the residue purified by silica gel flash chromatography eluting with a 0 to 15% MeOH-DCM gradient to give the title compound (0.551 g, 100%) as a brown solid. MS: 323.4 (M+H$^+$).

brown solid. The mother liquors were concentrated to around 50 mL of THF. Another portion of 90% potassium trimethylsilanolate (0.43 g) was added and stirring was continued for 5 h at room temperature. Then, the mixture was filtered and washed again with THF to give a second batch of desired product (0.953 g) which was combined with the first batch to give the title compound (3.621 g, 59.1%) as a light brown solid. MS:242.0 and 244.1 (M+H$^+$).

[D] 6-[5-(1-Amino-cyclopropyl)-pyridin-3-yl]-1-methyl-3,4-dihydro-1H-quinolin-2-one

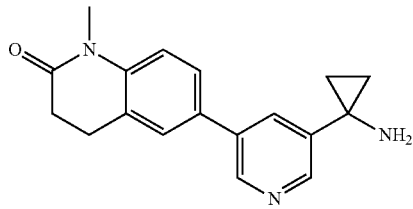 [SMILES: CN1C(=O)CCc2cc(-c3cncc(C4(N)CC4)c3)ccc21]

To solution of 1-(5-(1-methyl-2-oxo-1,2,3,4-tetrahydroquinolin-6-yl)pyridin-3-yl)cyclopropanecarboxylic acid (0.551 g, 1.52 mmol) in toluene (20 mL) were added TEA (0.185 g, 1.83 mmol) and diphenylphosphoryl azide (0.419 g, 1.52 mmol) and then the reaction mixture was heated to reflux for 4 h. After cooling to 0° C., a 1 M solution of sodium trimethylsilanoate in THF (3.04 mL, 3.04 mmol) was added and the mixture was stirred for 45 min at room temperature. After quenching with 0.1 M aq. HCl (40 mL), the aqueous solution was washed with ether (2 times), then basified with 1 M aq. NaOH and then extracted with DCM (2×100 mL). The combined organics were washed with brine, dried over Na$_2$SO$_4$, filtered and evaporated to dryness to give the title compound (0.333 g, 71%) as a yellow foam. MS: 294.4 (M+H$^+$).

The following compounds listed in Table 4 were prepared by treatment of the appropriate starting material with HCl in methanol in analogy to the procedure described for the preparation of example 42 (isolation of the compounds as HCl salts by direct evaporation or by basic extraction followed by silica gel or reverse phase chromatography):

TABLE 4

| Ex | Name | Starting Materials | Aspect | MS (M + H$^+$) |
|---|---|---|---|---|
| 60 | 1-Methyl-6-[5-((S)-pyrrolidin-3-yloxy)-pyridin-3-yl]-3,4-dihydro-1H-quinolin-2-one hydrochloride | (S)-3-[5-(1-Methyl-2-oxo-1,2,3,4-tetrahydro-quinolin-6-yl)-pyridin-3-yloxy]-pyrrolidine-1-carboxylic acid tert-butyl ester (example 48) | Yellow solid | 324.3 |
| 61 | 1-Methyl-6-[5-((S)-piperidin-3-yloxy)-pyridin-3-yl]-3,4-dihydro-1H-quinolin-2-one | (S)-3-[5-(1-Methyl-2-oxo-1,2,3,4-tetrahydro-quinolin-6-yl)-pyridin-3-yloxy]-piperidine-1-carboxylic acid tert-butyl ester (example 49) | Colorless amorphous solid | 338.3 |

TABLE 4-continued

| Ex | Name | Starting Materials | Aspect | MS (M + H+) |
|---|---|---|---|---|
| 62 | 1-Methyl-6-[5-(piperidin-4-yloxy)-pyridin-3-yl]-3,4-dihydro-1H-quinolin-2-one hydrochloride | 4-[5-(1-Methyl-2-oxo-1,2,3,4-tetrahydro-quinolin-6-yl)-pyridin-3-yloxy]-piperidine-1-carboxylic acid tert-butyl ester (example 50) | Light yellow solid | 338.4 |
| 63 | 6-[5-((S)-1-Azetidin-2-ylmethoxy)-pyridin-3-yl]-1-methyl-3,4-dihydro-1H-quinolin-2-one | (S)-2-[5-(1-Methyl-2-oxo-1,2,3,4-tetrahydro-quinolin-6-yl)-pyridin-3-yloxymethyl]-azetidine-1-carboxylic acid tert-butyl ester (example 45) | Light yellow oil | 324.2 |
| 64 | 6-[5-((S or R)-1-Amino-ethyl)-pyridin-3-yl]-1-methyl-3,4-dihydro-1H-quinolin-2-one hydrochloride | (R)-2-Methyl-propane-2-sulfinic acid {(S or R)-1-[5-(1-methyl-2-oxo-1,2,3,4-tetrahydro-quinolin-6-yl)-pyridin-3-yl]-ethyl}-amide (example 56) | Colorless solid | 282.1 |
| 65 | 6-[5-((R or S)-1-Amino-ethyl)-pyridin-3-yl]-1-methyl-3,4-dihydro-1H-quinolin-2-one hydrochloride | (R)-2-Methyl-propane-2-sulfinic acid {(R or S)-1-[5-(1-methyl-2-oxo-1,2,3,4-tetrahydro-quinolin-6-yl)-pyridin-3-yl]-ethyl}-amide (example 57) | Colorless solid | 282.1 |
| 66 | 1-Methyl-6-[5-((S)-1-pyrrolidin-2-ylmethoxy)-pyridin-3-yl]-3,4-dihydro-1H-quinolin-2-one hydrochloride | (S)-2-[5-(1-Methyl-2-oxo-1,2,3,4-tetrahydro-quinolin-6-yl)-pyridin-3-yloxymethyl]-pyrrolidine-1-carboxylic acid tert-butyl ester (example 51) | Yellow solid | 338.2 |

TABLE 4-continued

| Ex | Name | Starting Materials | Aspect | MS (M + H⁺) |
|----|------|-------------------|--------|-------------|
| 67 | 7-Fluoro-1-methyl-6-[5-[((R)-pyrrolidin-3-yloxy)-pyridin-3-yl]-3,4-dihydro-1H-quinolin-2-one hydrochloride | (R)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester (example 46) | Light yellow solid | 342.3 |
| 68 | 1-Methyl-6-[5-((R)-pyrrolidin-3-yloxy)-pyridin-3-yl]-3,4-dihydro-1H-quinolin-2-one hydrochloride | (R)-3-[5-(1-Methyl-2-oxo-1,2,3,4-tetrahydro-quinolin-6-yl)-pyridin-3-yloxy]-pyrrolidine-1-carboxylic acid tert-butyl ester (example 53) | Yellow solid | 324.5 |
| 69 | 6-[5-(3-Amino-oxetan-3-yl)-pyridin-3-yl]-1-methyl-3,4-dihydro-1H-quinolin-2-one hydrochloride | (R)-2-Methyl-propane-2-sulfinic acid {3-[5-(1-methyl-2-oxo-1,2,3,4-tetrahydro-quinolin-6-yl)-pyridin-3-yl]-oxetan-3-yl}-amide (example 54) | Light yellow solid | 310.2 |
| 70 | 6-[5-(Azetidin-3-yloxy)-pyridin-3-yl]-1-methyl-3,4-dihydro-1H-quinolin-2-one hydrochloride | 3-[5-(1-Methyl-2-oxo-1,2,3,4-tetrahydro-quinolin-6-yl)-pyridin-3-yloxy]-azetidine-1-carboxylic acid tert-butyl ester (example 47) | Yellow solid | 310.3 |
| 71 | 6-[5-((trans)-4-Amino-cyclohexyloxy)-pyridin-3-yl]-1-methyl-3,4-dihydro-1H-quinolin-2-one hydrochloride | {(trans)-4-[5-(1-Methyl-2-oxo-1,2,3,4-tetrahydro-quinolin-6-yl)-pyridin-3-yloxy]-cyclohexyl}-carbamic acid tert-butyl ester (example 58) | Yellow solid | 352.5 |

Example 72

6-[5-(1-Amino-1-methyl-ethyl)-pyridin-3-yl]-1-methyl-3,4-dihydro-1H-quinolin-2-one

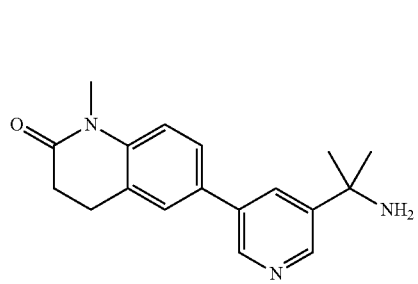 [SMILES: CN1C(=O)CCc2cc(-c3cncc(C(C)(C)N)c3)ccc21]

[A] Methyl 2-(5-bromopyridin-3-yl)-2-methylpropanoate

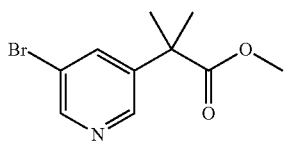

To a solution of methyl 2-(5-bromopyridin-3-yl)acetate (0.7 g, 3.04 mmol) in DMF (14 mL) cooled at 0° C. with an ice bath was added 60% NaH in mineral oil (0.244 g, 6.09 mmol) and the reaction mixture was stirred for 15 min. Then, a solution of MeI (0.864 g, 6.09 mmol) in DMF (16 mL) was added dropwise at 0° C. After the addition, the mixture was stirred at room temperature for 1 h. Another portion of 60% NaH in mineral oil (0.073 g) was added to the mixture which was stirred at room temperature for 1 h. The reaction mixture was poured into H$_2$O (15 mL) and the aqueous layer was extracted with EtOAc (3×50 mL). The organic layers were combined, dried over Na$_2$SO$_4$, filtered and evaporated to dryness to give the title compound (0.617 g, 75%) as a brown oil which was used with no further purification. MS: 258.2 and 260.3 (M+H$^+$).

[B] Potassium 2-(5-bromopyridin-3-yl)-2-methylpropanoate

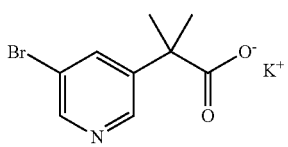

In analogy to the procedure described for the preparation of example 59 [B], methyl 2-(5-bromopyridin-3-yl)-2-methylpropanoate (example 72 [A]) was reacted with 90% potassium trimethylsilanolate to give the title compound as a light brown solid. MS: 244.3 (M+H$^+$).

[C] 2-Methyl-2-(5-(1-methyl-2-oxo-1,2,3,4-tetrahydroquinolin-6-yl)pyridin-3-yl)propan-oic acid

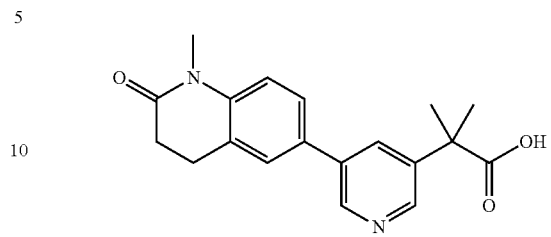

In analogy to the procedure described for the preparation of example 59 [C], potassium 2-(5-bromopyridin-3-yl)-2-methylpropanoate (example 72 [B]) was reacted with 1-methyl-6-(4,4,5,5-tetramethyl-[1,3,2]dioxaborolan-2-yl)-3,4-dihydro-1H-quinolin-2-one (intermediate A-1) in presence of bis(triphenylphosphine)palladium(II)chloride and Na$_2$CO$_3$ (1M aq. solution) to give the title compound as a brown foam. MS: 325.4 (M+H$^+$).

[D] 6-[5-(1-Amino-1-methyl-ethyl)-pyridin-3-yl]-1-methyl-3,4-dihydro-1H-quinolin-2-one

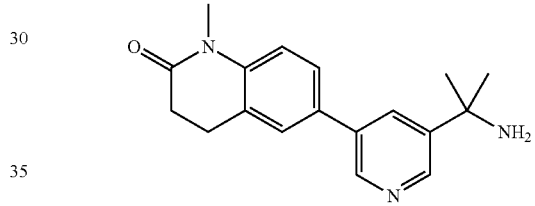

In analogy to the procedure described for the preparation of example 59 [D], 2-methyl-2-(5-(1-methyl-2-oxo-1,2,3,4-tetrahydroquinolin-6-yl)pyridin-3-yl)propanoic acid (example 72 [C]) was reacted with diphenylphosphoryl azide in presence of TEA and then sodium trimethylsilanoate (1 M in THF) to give the title compound as a light brown amorphous solid. MS: 296.5 (M+H$^+$).

Example 73

6-(5-Aminomethyl-pyridin-3-yl)-7-fluoro-1-methyl-3,4-dihydro-1H-quinolin-2-one

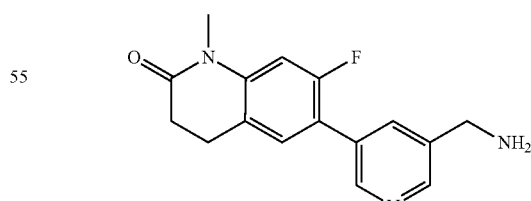

In analogy to the procedure described for the preparation of example 45, reaction of 3-aminomethyl-5-bromopyridine and 7-fluoro-1-methyl-6-(4,4,5,5-tetramethyl-[1,3,2]dioxaborolan-2-yl)-3,4-dihydro-1H-quinolin-2-one (intermediate A-22) gave the title compound as a light yellow solid. MS: 286.7 (M+H$^+$).

Example 74

6-{6-[6-(3-Methoxy-isoxazole-5-carbonyl)-2,6-diaza-spiro[3.3]hept-2-yl]-pyrazin-2-yl}-1-methyl-3,4-dihydro-1H-quinolin-2-one

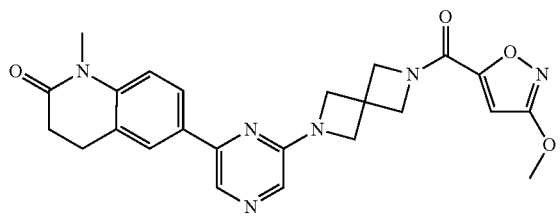 [SMILES: COc1cc(C(=O)N2CC3(C2)CN(c2cncc(-c4ccc5c(c4)CCC(=O)N5C)n2)C3)on1]

To a solution of 6-(6-(2,6-diazaspiro[3.3]heptan-2-yl)pyrazin-2-yl)-1-methyl-3,4-dihydroquinolin-2(1H)-one 2,2,2-trifluoroacetate (intermediate A-36, 0.030 g, 0.067 mmol) in DCM (1 mL) were added 3-methoxyisoxazole-5-carboxylic acid (0.014 g, 0.1 mmol) and TBTU (0.024 g, 0.073 mmol) followed by Hünig's base (0.022 g, 0.167 mmol) and the reaction mixture was stirred at room temperature over night. The reaction mixture was diluted with EtOAc, poured into sat. NaHCO₃ solution (5 mL) and extracted with EtOAc (2×10 mL). Combined organics were dried over Na₂SO₄, filtered and evaporated to dryness. The residue was purified by silica gel flash chromatography eluting with a 0 to 5% MeOH-DCM gradient to give the title compound (0.007 g, 20%) as a yellow solid. MS: 461.3 (M+H⁺).

Example 75

3,5-Dimethyl-isoxazole-4-carboxylic acid [5-(1-methyl-2-oxo-1,2,3,4-tetrahydro-quinolin-6-yl)-pyridin-3-ylmethyl]-amide

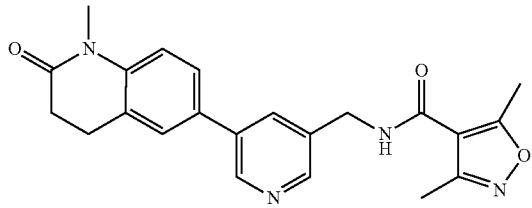 [SMILES: Cc1noc(C)c1C(=O)NCc1cncc(-c2ccc3c(c2)CCC(=O)N3C)c1]

To a solution of 6-(5-aminomethyl-pyridin-3-yl)-1-methyl-3,4-dihydro-1H-quinolin-2-one (example 36, 0.047 g, 0.177 mmol) in DMF (1 mL) were added 3,5-dimethylisoxazole-4-carboxylic acid (0.037 g, 0.266 mmol) and TBTU (0.063 g, 0.195 mmol) followed by Hünig's base (0.048 g, 0.372 mmol) and the reaction mixture was stirred at room temperature over night. The mixture was purified directly by reverse phase HPLC on a Gemini-NX column, eluting with a 20 to 98% MeOH—H2O (0.05% TEA) gradient to give the title compound (0.041 g, 59%) as a colorless solid. MS: 391.3 (M+H⁺).

Example 76

6-[5-((S)-1-Cyclopropanecarbonyl-pyrrolidin-3-yloxy)-pyridin-3-yl]-1-methyl-3,4-dihydro-1H-quinolin-2-one

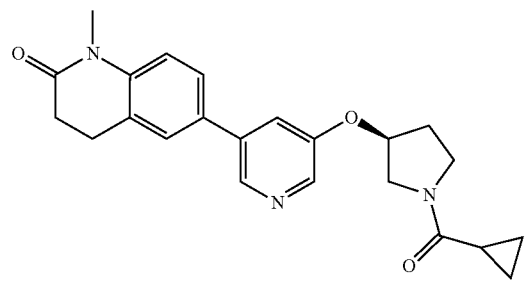 [SMILES: CN1C(=O)CCc2cc(-c3cncc(O[C@H]4CCN(C(=O)C5CC5)C4)c3)ccc21]

To a solution of 1-methyl-6-[5-((S)-pyrrolidin-3-yloxy)-pyridin-3-yl]-3,4-dihydro-1H-quinolin-2-one hydrochloride (example 60, 0.05 g, 0.139 mmol) in dry DCM (1.5 mL) was added cyclopropanecarbonyl chloride (0.015 g, 0.139 mmol) followed by TEA (0.035 g, 0.347 mmol) and the reaction mixture was stirred at room temperature for 1 h. Then, the reaction mixture was diluted with EtOAc, poured into sat. NaHCO₃ solution (10 mL) and extracted with EtOAc (2×20 mL). Combined organics were dried over Na₂SO₄, filtered and evaporated to dryness. The residue was purified by silica gel flash chromatography eluting with a 0 to 5% MeOH-DCM gradient to give the title compound (0.032 g, 59%) as a colorless foam. MS: 392.2 (M+H⁺).

The following compounds listed in Table 5 were prepared by treatment of the appropriate starting materials under the appropriate coupling conditions as described in examples 40, 74, 75 or 76.

TABLE 5

| Ex | Name | Starting Materials | Aspect Prep. by analogy to | MS (M + H⁺) |
|---|---|---|---|---|
| 77 | 3-Methyl-N-[5-(1-methyl-2-oxo-1,2,3,4-tetrahydro-quinolin-6-yl)-pyridin-3-ylmethyl]-butyramide | 6-(5-Aminomethyl-pyridin-3-yl)-1-methyl-3,4-dihydro-1H-quinolin-2-one (example 36) and 3-methyl-butyric acid | Colorless solid expl. 74 | 352.4 |

TABLE 5-continued

| Ex | Name | Starting Materials | Aspect Prep. by analogy to | MS (M + H$^+$) |
|---|---|---|---|---|
| 78 | 3,3,3-Trifluoro-N-[5-(1-methyl-2-oxo-1,2,3,4-tetrahydro-quinolin-6-yl)-pyridin-3-ylmethyl]-propionamide | 6-(5-Aminomethyl-pyridin-3-yl)-1-methyl-3,4-dihydro-1H-quinolin-2-one (example 36) and 3,3,3-trifluoro-propionic acid | Colorless solid expl. 74 | 378.3 |
| 79 | 2-Hydroxy-2-methyl-N-[5-(1-methyl-2-oxo-1,2,3,4-tetrahydro-quinolin-6-yl)-pyridin-3-ylmethyl]-propionamide | 6-(5-Aminomethyl-pyridin-3-yl)-1-methyl-3,4-dihydro-1H-quinolin-2-one (example 36) and 2-hydroxy-2-methyl-propionic acid | Colorless solid expl. 74 | 354.3 |
| 80 | 5-Methyl-[1,3,4]oxadiazole-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-methyl-[1,3,4]oxadiazole-2-carboxylic acid | Colorless solid expl. 75 | 378.3 |
| 81 | 1-Methyl-6-[5-((S)-1-propionyl-piperidin-3-yloxy)-pyridin-3-yl]-3,4-dihydro-1H-quinolin-2-one | 1-Methyl-6-[5-((S)-piperidin-3-yloxy)-pyridin-3-yl]-3,4-dihydro-1H-quinolin-2-one (example 61) and propionic acid | Orange amorphous solid expl. 74 | 394.1 |
| 82 | 2-Methoxy-pyrimidine-5-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 2-methoxy-pyrimidine-5-carboxylic acid | Colorless solid expl. 75 | 404.3 |

TABLE 5-continued

| Ex | Name | Starting Materials | Aspect Prep. by analogy to | MS (M + H⁺) |
|---|---|---|---|---|
| 83 | 1-Methyl-1H-imidazole-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 1-methyl-1H-imidazole-2-carboxylic acid | Colorless solid expl. 75 | 376.2 |
| 84 | 5-Trifluoromethyl-furan-3-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-trifluoromethyl-furan-3-carboxylic acid | Colorless amorphous solid expl. 75 | 430.4 |
| 85 | Pyridazine-3-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and pyridazine-3-carboxylic acid | Colorless solid expl. 75 | 374.3 |
| 86 | Pyrimidine-5-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and pyrimidine-5-carboxylic acid | Light brown solid expl. 75 | 374.3 |
| 87 | 1-Methyl-1H-pyrazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 1-methyl-1H-pyrazole-4-carboxylic acid | Colorless solid expl. 75 | 376.4 |

TABLE 5-continued

| Ex | Name | Starting Materials | Aspect Prep. by analogy to | MS (M + H⁺) |
|---|---|---|---|---|
| 88 | 1-Methyl-6-[5-(1-propionyl-piperidin-4-yloxy)-pyridin-3-yl]-3,4-dihydro-1H-quinolin-2-one | 1-Methyl-6-[5-(piperidin-4-yloxy)-pyridin-3-yl]-3,4-dihydro-1H-quinolin-2-one hydrochloride (example 62) and propionic acid | Orange amorphous solid expl. 74 | 394.1 |
| 89 | Pyridazine-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and pyridazine-4-carboxylic acid | Colorless amorphous solid expl. 75 | 374.3 |
| 90 | 1-Methyl-6-[5-((S)-1-propionyl-pyrrolidin-3-yloxy)-pyridin-3-yl]-3,4-dihydro-1H-quinolin-2-one | 1-Methyl-6-[5-((S)-pyrrolidin-3-yloxy)-pyridin-3-yl]-3,4-dihydro-1H-quinolin-2-one hydrochloride (example 60) and propionic acid | Light yellow oil expl. 74 | 380.3 |
| 91 | 6-[5-((S)-1-Cyclopropanecarbonyl-azetidin-2-ylmethoxy)-pyridin-3-yl]-1-methyl-3,4-dihydro-1H-quinolin-2-one | 6-[5-((S)-1-Azetidin-2-ylmethoxy)-pyridin-3-yl]-1-methyl-3,4-dihydro-1H-quinolin-2-one (example 63) and cyclopropanecarbonyl chloride | Off-white amorphous solid expl. 76 | 392.2 |
| 92 | 3-Methyl-isoxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-methyl-isoxazole-4-carboxylic acid | Light brown solid expl. 75 | 377.1 |

TABLE 5-continued

| Ex | Name | Starting Materials | Aspect Prep. by analogy to | MS (M + H⁺) |
|---|---|---|---|---|
| 93 | 4-Fluoro-2,6-dimethyl-N-[5-(1-methyl-2-oxo-1,2,3,4-tetrahydro-quinolin-6-yl)-pyridin-3-ylmethyl]-benzamide | 6-(5-Aminomethyl-pyridin-3-yl)-1-methyl-3,4-dihydro-1H-quinolin-2-one (example 36) and 4-fluoro-2,6-dimethyl-benzoic acid | Colorless solid expl. 75 | 418.3 |
| 94 | 1-Methyl-6-[5-((S)-1-propionyl-azetidin-2-ylmethoxy)-pyridin-3-yl]-3,4-dihydro-1H-quinolin-2-one | 6-[5-((S)-1-Azetidin-2-ylmethoxy)-pyridin-3-yl]-1-methyl-3,4-dihydro-1H-quinolin-2-one (example 63) and propionyl chloride | Light yellow oil expl. 76 | 380.3 |
| 95 | 3,6-Dichloro-pyridazine-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3,6-dichloro-pyridazine-4-carboxylic acid | Colorless amorphous solid expl. 75 | 442.3 |
| 96 | 3-Cyclopropyl-1-(2,2,2-trifluoro-ethyl)-1H-pyrazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-cyclopropyl-1-(2,2,2-trifluoro-ethyl)-1H-pyrazole-4-carboxylic acid | Colorless solid expl. 75 | 484.4 |
| 97 | Pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and pyridine-2-carboxylic acid | Colorless solid expl. 75 | 373.3 |

TABLE 5-continued

| Ex | Name | Starting Materials | Aspect Prep. by analogy to | MS (M + H⁺) |
|---|---|---|---|---|
| 98 | 1,3-Dimethyl-1H-pyrazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 1,3-dimethyl-1H-pyrazole-4-carboxylic acid | Colorless amorphous solid expl. 75 | 390.3 |
| 99 | Pyrimidine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and pyrimidine-2-carboxylic acid | Colorless solid expl. 75 | 374.3 |
| 100 | 6-Methoxy-pyridazine-3-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 6-methoxy-pyridazine-3-carboxylic acid | Colorless solid expl. 75 | 404.5 |
| 101 | 5-Methyl-isoxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-methyl-isoxazole-4-carboxylic acid | Colorless solid expl. 40 | 377.1 |
| 102 | 3,5-Dimethyl-isoxazole-4-carboxylic acid {2-[5-(1-methyl-2-oxo-1,2,3,4-tetrahydro-quinolin-6-yl)-pyridin-3-yloxy]-ethyl}-amide | 6-[5-(2-Amino-ethoxy)-pyridin-3-yl]-1-methyl-3,4-dihydro-1H-quinolin-2-one hydrochloride (example 42) and 3,5-dimethyl-isoxazole-4-carboxylic acid | Light yellow solid expl. 75 | 421.1 |

TABLE 5-continued

| Ex | Name | Starting Materials | Aspect Prep. by analogy to | MS (M + H⁺) |
|---|---|---|---|---|
| 103 | 1-Methyl-1H-pyrazole-4-carboxylic acid {2-[5-(1-methyl-2-oxo-1,2,3,4-tetrahydro-quinolin-6-yl)-pyridin-3-yloxy]-ethyl}-amide | 6-[5-(2-Amino-ethoxy)-pyridin-3-yl]-1-methyl-3,4-dihydro-1H-quinolin-2-one hydrochloride (example 42) and 1-methyl-1H-pyrazole-4-carboxylic acid | Colorless solid expl. 75 | 406.4 |
| 104 | 6-Chloro-pyridazine-3-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 6-chloro-pyridazine-3-carboxylic acid | Colorless solid expl. 40 | 408.3 |
| 105 | 3-Chloro-6-methyl-pyridazine-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-chloro-6-methyl-pyridazine-4-carboxylic acid | Colorless solid expl. 40 | 422.0 |
| 106 | 1-Methyl-6-[5-(((S)-1-propionyl-pyrrolidin-2-ylmethoxy)-pyridin-3-yl]-3,4-dihydro-1H-quinolin-2-one | 1-Methyl-6-[5-(((S)-1-pyrrolidin-2-ylmethoxy)-pyridin-3-yl]-3,4-dihydro-1H-quinolin-2-one hydrochloride (example 66) and propionyl chloride | Colorless amorphous solid expl. 76 | 394.3 |
| 107 | 5-Cyclopropyl-isoxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-cyclopropyl-isoxazole-4-carboxylic acid | Colorless amorphous solid expl. 75 | 403.3 |

TABLE 5-continued

| Ex | Name | Starting Materials | Aspect Prep. by analogy to | MS (M + H⁺) |
|---|---|---|---|---|
| 108 | 2-Methyl-5-trifluoromethyl-oxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 2-methyl-5-trifluoromethyl-oxazole-4-carboxylic acid | Colorless solid expl. 75 | 445.3 |
| 109 | 2-Methyl-oxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 2-methyl-oxazole-4-carboxylic acid | Off-white solid expl. 75 | 377.4 |
| 110 | 5-Cyclopropyl-oxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-cyclopropyl-oxazole-4-carboxylic acid | Colorless amorphous solid expl. 75 | 403.6 |
| 111 | 2,5-Dimethyl-oxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 2,5-dimethyl-oxazole-4-carboxylic acid | Colorless solid expl. 75 | 391.3 |
| 112 | 5-Methyl-oxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-methyl-oxazole-4-carboxylic acid | Colorless solid expl. 75 | 377.4 |

TABLE 5-continued

| Ex | Name | Starting Materials | Aspect Prep. by analogy to | MS (M + H+) |
|---|---|---|---|---|
| 113 | 3,5-Dimethyl-isoxazole-4-carboxylic acid {1-[5-(1-methyl-2-oxo-1,2,3,4-tetrahydro-quinolin-6-yl)-pyridin-3-yl]-cyclopropyl}-amide | 6-[5-(1-Amino-cyclopropyl)-pyridin-3-yl]-1-methyl-3,4-dihydro-1H-quinolin-2-one (example 59) and 3,5-dimethyl-isoxazole-4-carboxylic acid | Colorless solid expl. 40 | 417.4 |
| 114 | 6-Chloro-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 6-chloro-pyridine-2-carboxylic acid | Off-white solid expl. 75 | 407.2 |
| 115 | 3-Methyl-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-methyl-pyridine-2-carboxylic acid | Colorless solid expl. 75 | 387.2 |
| 116 | 3,6-Dichloro-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3,6-dichloro-pyridine-2-carboxylic acid | Colorless solid expl. 75 | 441.2 |
| 117 | 6-Methyl-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 6-methyl-pyridine-2-carboxylic acid | Colorless solid expl. 75 | 387.2 |

TABLE 5-continued

| Ex | Name | Starting Materials | Aspect Prep. by analogy to | MS (M + H$^+$) |
|---|---|---|---|---|
| 118 | 3-Chloro-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-chloro-pyridine-2-carboxylic acid | Off-white solid expl. 75 | 407.2 |
| 119 | 3-Fluoro-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-fluoro-pyridine-2-carboxylic acid | Colorless solid expl. 75 | 391.2 |
| 120 | 5-Chloro-3-methyl-pyridine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-chloro-3-methyl-pyridine-2-carboxylic acid | Off-white solid expl. 75 | 421.1 |
| 121 | 1-Methyl-6-[5-((R)-1-propionyl-pyrrolidin-3-yloxy)-pyridin-3-yl]-3,4-dihydro-1H-quinolin-2-one | 1-Methyl-6-[5-((R)-pyrrolidin-3-yloxy)-pyridin-3-yl]-3,4-dihydro-1H-quinolin-2-one hydrochloride (example 68) and propionyl chloride | Light yellow solid expl. 76 | 380.2 |
| 122 | 7-Fluoro-1-methyl-6-[5-((S)-1-propionyl-pyrrolidin-3-yloxy)-pyridin-3-yl]-3,4-dihydro-1H-quinolin-2-one | 7-Fluoro-1-methyl-6-[5-((S)-pyrrolidin-3-yloxy)-pyridin-3-yl]-3,4-dihydro-1H-quinolin-2-one (example 146) and propionyl chloride | Yellow solid expl. 76 | 398.2 |

TABLE 5-continued

| Ex | Name | Starting Materials | Aspect Prep. by analogy to | MS (M + H⁺) |
|---|---|---|---|---|
| 123 | 5-Trifluoromethyl-pyrimidine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-trifluoromethyl-pyrimidine-2-carboxylic acid | Colorless solid expl. 75 | 442.5 |
| 124 | 5-Methyl-pyrazine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-methyl-pyrazine-2-carboxylic acid | Colorless solid expl. 75 | 388.3 |
| 125 | 5-Chloro-pyrazine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-chloro-pyrazine-2-carboxylic acid | Colorless solid expl. 75 | 408.4 |
| 126 | 5-Trifluoromethyl-pyrazine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-trifluoromethyl-pyrazine-2-carboxylic acid | Colorless solid expl. 75 | 442.4 |
| 127 | 3,5-Dimethyl-isoxazole-4-carboxylic acid [5-(7-fluoro-1-methyl-2-oxo-1,2,3,4-tetrahydro-quinolin-6-yl)-pyridin-3-ylmethyl]-amide | 6-(5-Aminomethyl-pyridin-3-yl)-7-fluoro-1-methyl-3,4-dihydro-1H-quinolin-2-one (example 73) and 3,5-dimethyl-isoxazole-4-carboxylic acid | Colorless solid expl 40 | 409.5 |

TABLE 5-continued

| Ex | Name | Starting Materials | Aspect Prep. by analogy to | MS (M + H⁺) |
|---|---|---|---|---|
| 128 | 1-Methyl-6-[5-((R)-1-propionyl-pyrrolidin-2-ylmethoxy)-pyridin-3-yl]-3,4-dihydro-1H-quinolin-2-one | 1-Methyl-6-[5-((R)-1-pyrrolidin-2-ylmethoxy)-pyridin-3-yl]-3,4-dihydro-1H-quinolin-2-one hydrochloride (example 148) and propionyl chloride | Yellow solid expl. 76 | 394.5 |
| 129 | 1-Methyl-6-[5-(1-propionyl-azetidin-3-yloxy)-pyridin-3-yl]-3,4-dihydro-1H-quinolin-2-one | 6-[5-(Azetidin-3-yloxy)-pyridin-3-yl]-1-methyl-3,4-dihydro-1H-quinolin-2-one hydrochloride (example 70) and propionyl chloride | Colorless amorphous solid expl. 76 | 366.5 |
| 130 | N-{3-[5-(1-Methyl-2-oxo-1,2,3,4-tetrahydro-quinolin-6-yl)-pyridin-3-yl]-oxetan-3-yl}-propionamide | 6-[5-(3-Amino-oxetan-3-yl)-pyridin-3-yl]-1-methyl-3,4-dihydro-1H-quinolin-2-one hydrochloride (example 69) and propionyl chloride | Colorless amorphous solid expl. 76 | 366.1 |
| 131 | 3-Chloro-pyridine-2-carboxylic acid [5-(7-fluoro-1-methyl-2-oxo-1,2,3,4-tetrahydro-quinolin-6-yl)-pyridin-3-ylmethyl]-amide | 6-(5-Aminomethyl-pyridin-3-yl)-7-fluoro-1-methyl-3,4-dihydro-1H-quinolin-2-one (example 73) and 3-chloro-pyridine-2-carboxylic acid | Off-white solid expl. 75 | 425.4 |
| 132 | 3,6-Dichloro-pyridazine-4-carboxylic acid [5-(7-fluoro-1-methyl-2-oxo-1,2,3,4-tetrahydro-quinolin-6-yl)-pyridin-3-ylmethyl]-amide | 6-(5-Aminomethyl-pyridin-3-yl)-7-fluoro-1-methyl-3,4-dihydro-1H-quinolin-2-one (example 73) and 3,6-dichloro-pyridazine-4-carboxylic acid | Colorless amorphous solid expl. 40 | 460.3 |

TABLE 5-continued

| Ex | Name | Starting Materials | Aspect Prep. by analogy to | MS (M + H⁺) |
|---|---|---|---|---|
| 133 | 7-Fluoro-1-methyl-6-[5-((R)-1-propionyl-pyrrolidin-3-yloxy)-pyridin-3-yl]-3,4-dihydro-1H-quinolin-2-one | 7-Fluoro-1-methyl-6-[5-((R)-pyrrolidin-3-yloxy)-pyridin-3-yl]-3,4-dihydro-1H-quinolin-2-one hydrochloride (example 67) and propionyl chloride | Yellow solid expl. 76 | 398.5 |
| 134 | 5-Chloro-3-methoxy-pyrazine-2-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-chloro-3-methoxy-pyrazine-2-carboxylic acid | Yellow amorphous solid expl. 75 | 438.1 |
| 135 | 3,5-Dimethyl-isoxazole-4-carboxylic acid {(R or S)-1-[5-(1-methyl-2-oxo-1,2,3,4-tetrahydro-quinolin-6-yl)-pyridin-3-yl]-ethyl}-amide | 6-[5-((R or S)-1-Amino-ethyl)-pyridin-3-yl]-1-methyl-3,4-dihydro-1H-quinolin-2-one hydrochloride (example 65) and 3,5-dimethyl-isoxazole-4-carboxylic acid | Colorless solid expl. 74 | 405.5 |
| 136 | 3-Methyl-5-trifluoromethyl-isoxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3-methyl-5-trifluoromethyl-isoxazole-4-carboxylic acid | Off-white solid expl. 40 | 445.5 |
| 137 | 3-Chloro-pyridine-2-carboxylic acid {1-[5-(1-methyl-2-oxo-1,2,3,4-tetrahydro-quinolin-6-yl)-pyridin-3-yl]-cyclopropyl}-amide | 6-[5-(1-Amino-cyclopropyl)-pyridin-3-yl]-1-methyl-3,4-dihydro-1H-quinolin-2-one (example 59) and 3-chloro-pyridine-2-carboxylic acid | Off-white solid expl. 75 | 433.5 |

TABLE 5-continued

| Ex | Name | Starting Materials | Aspect Prep. by analogy to | MS (M + H+) |
|---|---|---|---|---|
| 138 | 3-Chloro-pyridine-2-carboxylic acid {1-methyl-1-[5-(1-methyl-2-oxo-1,2,3,4-tetrahydro-quinolin-6-yl)-pyridin-3-yl]-ethyl}-amide | 6-[5-(1-Amino-1-methyl-ethyl)-pyridin-3-yl]-1-methyl-3,4-dihydro-1H-quinolin-2-one (example 72) and 3-chloro-pyridine-2-carboxylic acid | Off-white amorphous solid expl. 75 | 435.5 |
| 139 | 3,5-Dimethyl-isoxazole-4-carboxylic acid {1-methyl-1-[5-(1-methyl-2-oxo-1,2,3,4-tetrahydro-quinolin-6-yl)-pyridin-3-yl]-ethyl}-amide | 6-[5-(1-Amino-1-methyl-ethyl)-pyridin-3-yl]-1-methyl-3,4-dihydro-1H-quinolin-2-one (example 72) and 3,5-dimethyl-isoxazole-4-carboxylic acid | Off-white solid expl. 40 | 419.5 |
| 140 | 3-Chloro-pyridine-2-carboxylic acid [5-(2-oxo-1,2,3,4-tetrahydro-quinolin-6-yl)-pyridin-3-ylmethyl]-amide | 6-(5-Aminomethyl-pyridin-3-yl)-3,4-dihydro-1H-quinolin-2-one (example 149) and 3-chloro-pyridine-2-carboxylic acid | Light yellow solid expl. 75 | 393.5 |
| 141 | 3,5-Dimethyl-isoxazole-4-carboxylic acid [5-(2-oxo-1,2,3,4-tetrahydro-quinolin-6-yl)-pyridin-3-ylmethyl]-amide | 6-(5-Aminomethyl-pyridin-3-yl)-3,4-dihydro-1H-quinolin-2-one (example 149) and 3,5-dimethyl-isoxazole-4-carboxylic acid | Colorless solid expl. 40 | 377.5 |
| 142 | 3-Chloro-pyridine-2-carboxylic acid {1-[5-(7-fluoro-1-methyl-2-oxo-1,2,3,4-tetrahydro-quinolin-6-yl)-pyridin-3-yl]-cyclopropyl}-amide | 6-[5-(1-Amino-cyclopropyl)-pyridin-3-yl]-7-fluoro-1-methyl-3,4-dihydro-1H-quinolin-2-one (example 150) and 3-chloro-pyridine-2-carboxylic acid | Light brown amorphous solid expl. 75 | 451.5 |

TABLE 5-continued

| Ex | Name | Starting Materials | Aspect Prep. by analogy to | MS (M + H+) |
|---|---|---|---|---|
| 143 | 3-Methyl-pyridine-2-carboxylic acid {1-[5-(1-methyl-2-oxo-1,2,3,4-tetrahydro-quinolin-6-yl)-pyridin-3-yl]-cyclopropyl}-amide | 6-[5-(1-Amino-cyclopropyl)-pyridin-3-yl]-1-methyl-3,4-dihydro-1H-quinolin-2-one (example 59) and 3-methyl-pyridine-2-carboxylic acid | Colorless solid expl. 75 | 413.5 |
| 144 | N-{(trans)-4-[5-(1-Methyl-2-oxo-1,2,3,4-tetrahydro-quinolin-6-yl)-pyridin-3-yloxy]-cyclohexyl}-propionamide | 6-[5-((trans)-4-Amino-cyclohexyloxy)-pyridin-3-yl]-1-methyl-3,4-dihydro-1H-quinolin-2-one hydrochloride (example 71) and propionyl chloride | Colorless solid expl. 76 | 408.5 |
| 145 | 5-Trifluoromethyl-isoxazole-4-carboxylic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 5-trifluoromethyl-isoxazole-4-carboxylic acid | Light brown amorphous solid expl. 40 | 431.5 |

Example 146

7-Fluoro-1-methyl-6-[5-((S)-pyrrolidin-3-yloxy)-pyridin-3-yl]-3,4-dihydro-1H-quinolin-2-one

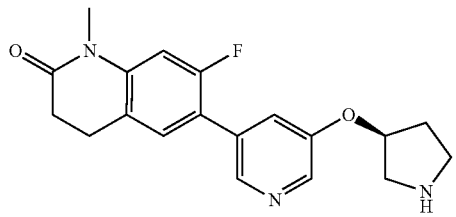 [SMILES: CN1C(=O)CCc2cc(-c3cncc(O[C@H]4CCNC4)c3)c(F)cc21]

In analogy to the procedure described for the preparation of example 42, reaction of (S)-3-[5-(7-fluoro-1-methyl-2-oxo-1,2,3,4-tetrahydro-quinolin-6-yl)-pyridin-3-yloxy]-pyrrolidine-1-carboxylic acid tert-butyl ester (example 52) with hydrogen chloride (in dioxane) in methanol gave the title compound as a yellow solid. MS: 342.1 (M+H+).

Example 147

(R)-2-[5-(1-Methyl-2-oxo-1,2,3,4-tetrahydro-quinolin-6-yl)-pyridin-3-yloxymethyl]-pyrrolidine-1-carboxylic acid tert-butyl ester

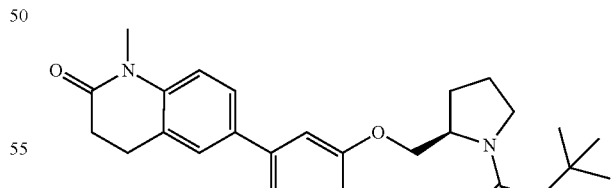

In analogy to the procedure described for the preparation of example 45, reaction of (R)-2-((5-bromopyridin-3-yloxy)methyl)pyrrolidine-1-carboxylic acid tert-butyl ester (intermediate A-55) and 1-methyl-6-(4,4,5,5-tetramethyl-[1,3,2]dioxaborolan-2-yl)-3,4-dihydro-1H-quinolin-2-one (intermediate A-1) gave the title compound as a colorless solid. MS: 438.6 (M+H+).

Example 148

1-Methyl-6-[5-((R)-1-pyrrolidin-2-ylmethoxy)-pyridin-3-yl]-3,4-dihydro-1H-quinolin-2-one hydrochloride

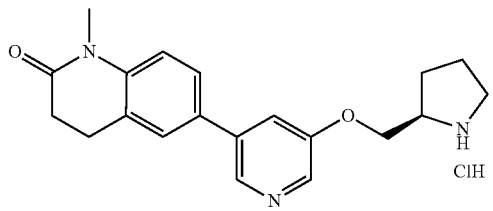 [SMILES: CN1C(=O)CCc2cc(-c3cncc(OC[C@H]4CCCN4)c3)ccc21 ; Cl]

In analogy to the procedure described for the preparation of example 42, reaction of (R)-2-[5-(1-methyl-2-oxo-1,2,3,4-tetrahydro-quinolin-6-yl)-pyridin-3-yloxymethyl]-pyrrolidine-1-carboxylic acid tert-butyl ester (example 147) with hydrogen chloride (in dixoane) in methanol gave the title compound as a yellow solid. MS: 338.2 (M+H$^+$).

Example 149

6-(5-Aminomethyl-pyridin-3-yl)-3,4-dihydro-1H-quinolin-2-one

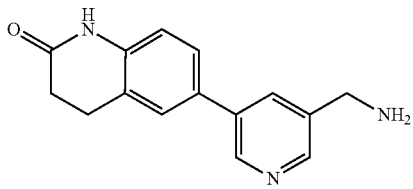 [SMILES: NCc1cncc(-c2ccc3c(c2)CCC(=O)N3)c1]

In analogy to the procedure described for the preparation of example 45, reaction of 3-aminomethyl-5-bromopyridine and 6-(4,4,5,5-tetramethyl-1,3,2-dioxaborolan-2-yl)-3,4-dihydroquinolin-2(1H)-one (intermediate A-34) gave the title compound as a light yellow amorphous solid. MS: 254.4 (M+H$^+$).

Example 150

6-[5-(1-Amino-cyclopropyl)-pyridin-3-yl]-7-fluoro-1-methyl-3,4-dihydro-1H-quinolin-2-one

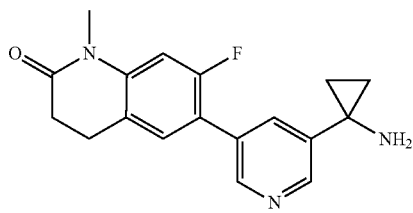 [SMILES: CN1C(=O)CCc2cc(-c3cncc(C4(N)CC4)c3)c(F)cc21]

In analogy to the procedures described for the preparation of example 59, potassium 1-(5-bromopyridin-3-yl)cyclopropanecarboxylate (example 59 [B]) has been reacted with 7-fluoro-1-methyl-6-(4,4,5,5-tetramethyl-[1,3,2]dioxaborolan-2-yl)-3,4-dihydro-1H-quinolin-2-one (intermediate A-22) and subsequently with diphenylphosphoryl azide and sodium trimethylsilanolate to give the title compound as a light yellow oil. MS: 312.5 (M+H$^+$).

The following compounds listed in Table 6 were prepared in analogy to the procedure described for the preparation of example 38, using the appropriate starting materials.

TABLE 6

| Ex | Name | Starting Materials | Aspect | MS (M + H$^+$) |
|---|---|---|---|---|
| 151 | Ethanesulfonic acid {2-[5-(1-methyl-2-oxo-1,2,3,4-tetrahydro-quinolin-6-yl)-pyridin-3-yloxy]-ethyl}-amide | 6-[5-(2-Amino-ethoxy)-pyridin-3-yl]-1-methyl-3,4-dihydro-1H-quinolin-2-one hydrochloride (example 42) and ethanesulfonyl chloride | Colorless oil | 390.1 |

TABLE 6-continued

| Ex | Name | Starting Materials | Aspect | MS (M + H+) |
|---|---|---|---|---|
| 152 | 3-Chloro-N-[5-(1-methyl-2-oxo-1,2,3,4-tetrahydro-quinolin-6-yl)-pyridin-3-ylmethyl]-benzenesulfonamide | 6-(5-Aminomethyl-pyridin-3-yl)-1-methyl-3,4-dihydro-1H-quinolin-2-one (example 36) and 3-chloro-benzenesulfonyl chloride | Light yellow solid | 442.2 |
| 153 | 6-Methoxy-pyridine-3-sulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 6-methoxy-pyridine-3-sulfonyl chloride | Light yellow solid | 439.3 |
| 154 | 3,5-Dimethyl-isoxazole-4-sulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 3,5-dimethyl-isoxazole-4-sulfonyl chloride | Yellow solid | 427.2 |
| 155 | Cyclopropanesulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and cyclopropanesulfonyl chloride | Off-white solid | 372.2 |

TABLE 6-continued

| Ex | Name | Starting Materials | Aspect | MS (M + H+) |
|---|---|---|---|---|
| 156 | 3,4-Dichloro-N-[5-(1-methyl-2-oxo-1,2,3,4-tetrahydro-quinolin-6-yl)-pyridin-3-ylmethyl]-benzenesulfonamide | 6-(5-Aminomethyl-pyridin-3-yl)-1-methyl-3,4-dihydro-1H-quinolin-2-one (example 36) and 3,4-dichloro-benzenesulfonyl chloride | Light yellow solid | 476.1 |
| 157 | 1-Methyl-1H-imidazole-4-sulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 1-methyl-1H-imidazole-4-sulfonyl chloride | Off-white solid | 412.3 |
| 158 | 6-Chloro-pyridine-3-sulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 6-chloro-pyridine-3-sulfonyl chloride | Light yellow solid | 443.2 |
| 159 | 1-Methyl-1H-pyrazole-4-sulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 1-methyl-1H-pyrazole-4-sulfonyl chloride | Light brown solid | 412.2 |

TABLE 6-continued

| Ex | Name | Starting Materials | Aspect | MS (M + H$^+$) |
|---|---|---|---|---|
| 160 | 6-[5-((S)-1-Ethanesulfonyl-piperidin-3-yloxy)-pyridin-3-yl]-1-methyl-3,4-dihydro-1H-quinolin-2-one | 1-Methyl-6-[5-((S)-piperidin-3-yloxy)-pyridin-3-yl]-3,4-dihydro-1H-quinolin-2-one (example 61) and ethanesulfonyl chloride | Colorless solid | 430.1 |
| 161 | 6-[5-(1-Ethanesulfonyl-piperidin-4-yloxy)-pyridin-3-yl]-1-methyl-3,4-dihydro-1H-quinolin-2-one | 1-Methyl-6-[5-(piperidin-4-yloxy)-pyridin-3-yl]-3,4-dihydro-1H-quinolin-2-one hydrochloride (example 62) and ethanesulfonyl chloride | Colorless amorphous solid | 430.1 |
| 162 | 2,2,2-Trifluoro-ethanesulfonic acid [5-(1-methyl-2-oxo-1,2,3,4-tetrahydro-quinolin-6-yl)-pyridin-3-ylmethyl]-amide | 6-(5-Aminomethyl-pyridin-3-yl)-1-methyl-3,4-dihydro-1H-quinolin-2-one (example 36) and 2,2,2-trifluoro-ethanesulfonyl chloride | Colorless solid | 414.1 |
| 163 | C,C,C-Trifluoro-N-[5-(1-methyl-2-oxo-1,2,3,4-tetrahydro-quinolin-6-yl)-pyridin-3-ylmethyl]-methanesulfonamide | 6-[5-Aminomethyl-pyridin-3-yl]-1-methyl-3,4-dihydro-1H-quinolin-2-one (example 36) and trifluoro-methanesulfonyl chloride | Colorless amorphous solid | 400.0 |

TABLE 6-continued

| Ex | Name | Starting Materials | Aspect | MS (M + H⁺) |
|---|---|---|---|---|
| 164 | 6-[5-((S)-1-Ethanesulfonyl-pyrrolidin-3-yloxy)-pyridin-3-yl]-1-methyl-3,4-dihydro-1H-quinolin-2-one | 1-Methyl-6-[5-((S)-pyrrolidin-3-yloxy)-pyridin-3-yl]-3,4-dihydro-1H-quinolin-2-one hydrochloride (example 60) and ethanesulfonyl chloride | Colorless amorphous solid | 416.1 |
| 165 | 6-[5-((S)-1-Ethanesulfonyl-azetidin-2-ylmethoxy)-pyridin-3-yl]-1-methyl-3,4-dihydro-1H-quinolin-2-one | 6-[5-((S)-1-Azetidin-2-ylmethoxy)-pyridin-3-yl]-1-methyl-3,4-dihydro-1H-quinolin-2-one (example 63) and ethanesulfonyl chloride | Colorless solid | 416.1 |
| 166 | Ethanesulfonic acid {1-[5-(1-methyl-2-oxo-1,2,3,4-tetrahydro-quinolin-6-yl)-pyridin-3-yl]-cyclopropyl}-amide | 6-[5-(1-Amino-cyclopropyl)-pyridin-3-yl]-1-methyl-3,4-dihydro-1H-quinolin-2-one (example 59) and ethanesulfonyl chloride | Off-white solid | 386.3 |
| 167 | 6-[5-((S)-1-Ethanesulfonyl-pyrrolidin-2-ylmethoxy)-pyridin-3-yl]-1-methyl-3,4-dihydro-1H-quinolin-2-one | 1-Methyl-6-[5-((S)-1-pyrrolidin-2-ylmethoxy)-pyridin-3-yl]-3,4-dihydro-1H-quinolin-2-one hydrochloride (example 66) and ethanesulfonyl chloride | Colorless amorphous solid | 430.5 |

TABLE 6-continued

| Ex | Name | Starting Materials | Aspect | MS (M + H+) |
|---|---|---|---|---|
| 168 | 6-[5-((R)-1-Ethanesulfonyl-pyrrolidin-3-yloxy)-pyridin-3-yl]-7-fluoro-1-methyl-3,4-dihydro-1H-quinolin-2-one | 7-Fluoro-1-methyl-6-[5-((R)-pyrrolidin-3-yloxy)-pyridin-3-yl]-3,4-dihydro-1H-quinolin-2-one hydrochloride (example 67) and ethanesulfonyl chloride | Off-white solid | 434.4 |
| 169 | 6-[5-((R)-1-Ethanesulfonyl-pyrrolidin-3-yloxy)-pyridin-3-yl]-1-methyl-3,4-dihydro-1H-quinolin-2-one | 1-Methyl-6-[5-((R)-pyrrolidin-3-yloxy)-pyridin-3-yl]-3,4-dihydro-1H-quinolin-2-one hydrochloride (example 68) and ethanesulfonyl chloride | Colorless oil | 416.4 |
| 170 | 6-[5-(1-Ethanesulfonyl-azetidin-3-yloxy)-pyridin-3-yl]-1-methyl-3,4-dihydro-1H-quinolin-2-one | 6-[5-(Azetidin-3-yloxy)-pyridin-3-yl]-1-methyl-3,4-dihydro-1H-quinolin-2-one hydrochloride (example 70) and ethanesulfonyl chloride | Colorless amorphous solid | 402.5 |
| 171 | Ethanesulfonic acid {1-[5-(7-fluoro-1-methyl-2-oxo-1,2,3,4-tetrahydro-quinolin-6-yl)-pyridin-3-yl]-cyclopropyl}-amide | 6-[5-(1-Amino-cyclopropyl)-pyridin-3-yl]-7-fluoro-1-methyl-3,4-dihydro-1H-quinolin-2-one (example 150) and ethanesulfonyl chloride | Brown amorphous solid | 404.5 |

TABLE 6-continued

| Ex | Name | Starting Materials | Aspect | MS (M + H+) |
|---|---|---|---|---|
| 172 | Ethanesulfonic acid {(trans)-4-[5-(1-methyl-2-oxo-1,2,3,4-tetrahydro-quinolin-6-yl)-pyridin-3-yloxy]-cyclohexyl}-amide | 6-[5-((trans)-4-Amino-cyclohexyloxy)-pyridin-3-yl]-1-methyl-3,4-dihydro-1H-quinolin-2-one hydrochloride (example 71) and ethanesulfonyl chloride | Yellow amorphous solid | 444.4 |
| 173 | Ethanesulfonic acid {(R or S)-1-[5-(1-methyl-2-oxo-1,2,3,4-tetrahydro-quinolin-6-yl)-pyridin-3-yl]-ethyl}-amide | 6-[5-((R or S)-1-Amino-ethyl)-pyridin-3-yl]-1-methyl-3,4-dihydro-1H-quinolin-2-one hydrochloride (example 65) and ethanesulfonyl chloride | Colorless amorphous solid | 374.1 |
| 174 | Ethanesulfonic acid {(S or R)-1-[5-(1-methyl-2-oxo-1,2,3,4-tetrahydro-quinolin-6-yl)-pyridin-3-yl]-ethyl}-amide | 6-[5-((S or R)-1-Amino-ethyl)-pyridin-3-yl]-1-methyl-3,4-dihydro-1H-quinolin-2-one hydrochloride (example 64) and ethanesulfonyl chloride | Colorless amorphous solid | 374.0 |

The following compounds listed in Table 7 were prepared in analogy to the procedure described for the preparation of example 45, using the appropriate starting materials.

TABLE 7

| Ex | Name | Starting Materials | Aspect | MS (M + H+) |
|---|---|---|---|---|
| 175 | 1-Methyl-1H-pyrazole-4-carboxylic acid [5-(7-fluoro-1-methyl-2-oxo-1,2,3,4-tetrahydro-quinolin-6-yl)-pyridin-3-ylmethyl]-amide | 1-Methyl-1H-pyrazole-4-carboxylic acid (5-bromo-pyridin-3-ylmethyl)-amide (intermediate A-47) and 7-fluoro-1-methyl-6-(4,4,5,5-tetramethyl-[1,3,2]dioxaborolan-2-yl)-3,4-dihydro-1H-quinolin-2-one (intermediate A-22) | Colorless solid | 394.0 |

TABLE 7-continued

| Ex | Name | Starting Materials | Aspect | MS (M + H+) |
|---|---|---|---|---|
| 176 | (rac)-Ethanesulfonic acid {2-methyl-1-[5-(1-methyl-2-oxo-1,2,3,4-tetrahydro-quinolin-6-yl)-pyridin-3-yl]-propyl}-amide | (rac)-N-(1-(5-Bromopyridin-3-yl)-2-methylpropyl) ethanesulfonamide (intermediate A-40) and 1-methyl-6-(4,4,5,5-tetramethyl-[1,3,2]dioxaborolan-2-yl)-3,4-dihydro-1H-quinolin-2-one (intermediate A-1) | Yellow solid | 402.5 |
| 177 | (rac)-Ethanesulfonic acid {cyclopropyl-[5-(1-methyl-2-oxo-1,2,3,4-tetrahydro-quinolin-6-yl)-pyridin-3-yl]-methyl}-amide | (rac)-N-((5-Bromopyridin-3-yl)(cyclopropyl)methyl) ethanesulfonamide (intermediate A-39) and 1-methyl-6-(4,4,5,5-tetramethyl-[1,3,2]dioxaborolan-2-yl)-3,4-dihydro-1H-quinolin-2-one (intermediate A-1) | Colorless amorphous solid | 400.3 |
| 178 | (rac)-Ethanesulfonic acid {1-[5-(7-fluoro-1-methyl-2-oxo-1,2,3,4-tetrahydro-quinolin-6-yl)-pyridin-3-yl]-ethyl}-amide | (rac)-N-(1-(5-Bromopyridin-3-yl)ethyl) ethanesulfonamide (intermediate A-37) and 7-fluoro-1-methyl-6-(4,4,5,5-tetramethyl-[1,3,2]dioxaborolan-2-yl)-3,4-dihydro-1H-quinolin-2-one (intermediate A-22) | Colorless amorphous solid | 392.1 |
| 179 | 6-[5-(1,1-Dioxo-1$\lambda^6$-isothiazolidin-2-ylmethyl)-pyridin-3-yl]-1-methyl-3,4-dihydro-1H-quinolin-2-one | 2-(5-Bromo-pyridin-3-ylmethyl)-isothiazolidine 1,1-dioxide (intermediate A-48) and 1-methyl-6-(4,4,5,5-tetramethyl-[1,3,2]dioxaborolan-2-yl)-3,4-dihydro-1H-quinolin-2-one (intermediate A-1) | Colorless solid | 372.1 |

TABLE 7-continued

| Ex | Name | Starting Materials | Aspect | MS (M + H+) |
|---|---|---|---|---|
| 180 | (rac)-Ethanesulfonic acid {1-[5-(1-methyl-2-oxo-1,2,3,4-tetrahydro-quinolin-6-yl)-pyridin-3-yl]-propyl}-amide | (rac)-N-(1-(5-Bromopyridin-3-yl)propyl) ethanesulfonamide (intermediate A-38) and 1-methyl-6-(4,4,5,5-tetramethyl-[1,3,2]dioxaborolan-2-yl)-3,4-dihydro-1H-quinolin-2-one (intermediate A-1) | Light yellow amorphous solid | 388.0 |
| 181 | Ethanesulfonic acid ethyl-[5-(1-methyl-2-oxo-1,2,3,4-tetrahydro-quinolin-6-yl)-pyridin-3-ylmethyl]-amide | N-((5-Bromopyridin-3-yl)methyl)-N-ethyl-ethanesulfonamide (intermediate A-42) and 1-methyl-6-(4,4,5,5-tetramethyl-[1,3,2]dioxaborolan-2-yl)-3,4-dihydro-1H-quinolin-2-one (intermediate A-1) | Light yellow amorphous solid | 388.2 |
| 182 | Ethanesulfonic acid methyl-[5-(1-methyl-2-oxo-1,2,3,4-tetrahydro-quinolin-6-yl)-pyridin-3-ylmethyl]-amide | N-((5-Bromopyridin-3-yl)methyl)-N-methyl-ethanesulfonamide (intermediate A-41) and 1-methyl-6-(4,4,5,5-tetramethyl-[1,3,2]dioxaborolan-2-yl)-3,4-dihydro-1H-quinolin-2-one (intermediate A-1) | Colorless solid | 374.1 |
| 183 | Ethanesulfonic acid {1-methyl-1-[5-(1-methyl-2-oxo-1,2,3,4-tetrahydro-quinolin-6-yl)-pyridin-3-yl]-ethyl}-amide | N-(2-(5-Bromopyridin-3-yl)propan-2-yl)ethanesulfonamide (intermediate A-49) and 1-methyl-6-(4,4,5,5-tetramethyl-[1,3,2]dioxaborolan-2-yl)-3,4-dihydro-1H-quinolin-2-one (intermediate A-1) | Colorless solid | 388.0 |

TABLE 7-continued

| Ex | Name | Starting Materials | Aspect | MS (M + H+) |
|---|---|---|---|---|
| 184 | Ethanesulfonic acid isopropyl-[5-(1-methyl-2-oxo-1,2,3,4-tetrahydro-quinolin-6-yl)-pyridin-3-ylmethyl]-amide | N-((5-Bromopyridin-3-yl)methyl)-N-isopropyl-ethanesulfonamide (intermediate A-43) and 1-methyl-6-(4,4,5,5-tetramethyl-[1,3,2]dioxaborolan-2-yl)-3,4-dihydro-1H-quinolin-2-one (intermediate A-1) | Colorless solid | 402.2 |
| 185 | Ethanesulfonic acid (2-ethoxy-ethyl)-[5-(1-methyl-2-oxo-1,2,3,4-tetrahydro-quinolin-6-yl)-pyridin-3-ylmethyl]-amide | N-((5-Bromopyridin-3-yl)methyl)-N-2-ethoxy-ethyl-ethanesulfonamide (intermediate A-44) and 1-methyl-6-(4,4,5,5-tetramethyl-[1,3,2]dioxaborolan-2-yl)-3,4-dihydro-1H-quinolin-2-one (intermediate A-1) | Colorless solid | 432.3 |
| 186 | (rac)-Ethanesulfonic acid methyl-{1-[5-(1-methyl-2-oxo-1,2,3,4-tetrahydro-quinolin-6-yl)-pyridin-3-yl]-ethyl}-amide | (rac)-N-(1-(5-Bromopyridin-3-yl)ethyl)-N-methyl-ethanesulfonamide (intermediate A-45) and 1-methyl-6-(4,4,5,5-tetramethyl-[1,3,2]dioxaborolan-2-yl)-3,4-dihydro-1H-quinolin-2-one (intermediate A-1) | Colorless amorphous solid | 388.4 |
| 187 | (rac)-Ethanesulfonic acid ethyl-{1-[5-(1-methyl-2-oxo-1,2,3,4-tetrahydro-quinolin-6-yl)-pyridin-3-yl]-ethyl}-amide | (rac)-N-(1-(5-Bromopyridin-3-yl)ethyl)-N-ethyl-ethanesulfonamide (intermediate A-46) and 1-methyl-6-(4,4,5,5-tetramethyl-[1,3,2]dioxaborolan-2-yl)-3,4-dihydro-1H-quinolin-2-one (intermediate A-1) | Colorless amorphous solid | 402.5 |

TABLE 7-continued

| Ex | Name | Starting Materials | Aspect | MS (M + H⁺) |
|---|---|---|---|---|
| 188 | 3,5-Dimethyl-isoxazole-4-carboxylic acid methyl-[5-(1-methyl-2-oxo-1,2,3,4-tetrahydro-quinolin-6-yl)-pyridin-3-ylmethyl]-amide | N-((5-Bromopyridin-3-yl)methyl)-N,3,5-trimethylisoxazole-4-carboxamide (intermediate A-50) and 1-methyl-6-(4,4,5,5-tetramethyl-[1,3,2]dioxaborolan-2-yl)-3,4-dihydro-1H-quinolin-2-one (intermediate A-1) | Colorless solid | 405.5 |
| 189 | 6-{5-[2-(1,1-Dioxo-1λ⁶-isothiazolidin-2-yl)-ethoxy]-pyridin-3-yl}-1-methyl-3,4-dihydro-1H-quinolin-2-one | 3-Bromo-5-[2-(1,1-dioxo-1λ⁶-isothiazolidin-2-yl)-ethoxy]-pyridine (intermediate A-51) and 1-methyl-6-(4,4,5,5-tetramethyl-[1,3,2]dioxaborolan-2-yl)-3,4-dihydro-1H-quinolin-2-one (intermediate A-1) | Light yellow oil | 402.4 |
| 190 | Ethanesulfonic acid {(R or S)-1-[5-(7-fluoro-1-methyl-2-oxo-1,2,3,4-tetrahydro-quinolin-6-yl)-pyridin-3-yl]-ethyl}-amide | (rac)-N-(1-(5-Bromopyridin-3-yl)ethyl)ethane-sulfonamide (intermediate A-37) and 7-fluoro-1-methyl-6-(4,4,5,5-tetramethyl-[1,3,2]dioxaborolan-2-yl)-3,4-dihydro-1H-quinolin-2-one (intermediate A-22) followed by separation with chiral phase HPLC. | Colorless amorphous solid | 392.1 |
| 191 | Ethanesulfonic acid {(S or R)-1-[5-(7-fluoro-1-methyl-2-oxo-1,2,3,4-tetrahydro-quinolin-6-yl)-pyridin-3-yl]-ethyl}-amide | (rac)-N-(1-(5-Bromopyridin-3-yl)ethyl)ethane-sulfonamide (intermediate A-37) and 7-fluoro-1-methyl-6-(4,4,5,5-tetramethyl-[1,3,2]dioxaborolan-2-yl)-3,4-dihydro-1H-quinolin-2-one (intermediate A-22) followed by separation with chiral phase HPLC. | Colorless amorphous solid | 392.1 |

TABLE 7-continued

| Ex | Name | Starting Materials | Aspect | MS (M + H+) |
|----|------|-------------------|--------|-------------|
| 192 | Ethanesulfonic acid [5-(7-fluoro-1-methyl-2-oxo-1,2,3,4-tetrahydro-quinolin-6-yl)-4-methyl-pyridin-3-ylmethyl]-amide | N-((5-Bromo-4-methylpyridin-3-yl)methyl) ethanesulfonamide (intermediate A-52) and 7-fluoro-1-methyl-6-(4,4,5,5-tetramethyl-[1,3,2]dioxaborolan-2-yl)-3,4-dihydro-1H-quinolin-2-one (intermediate A-22). | Colorless solid | 392.5 |
| 193 | Ethanesulfonic acid [4-chloro-5-(1-methyl-2-oxo-1,2,3,4-tetrahydro-quinolin-6-yl)-pyridin-3-ylmethyl]-amide | N-((5-Bromo-4-chloropyridin-3-yl)methyl) ethanesulfonamide (intermediate A-53) and 1-methyl-6-(4,4,5,5-tetramethyl-[1,3,2]dioxaborolan-2-yl)-3,4-dihydro-1H-quinolin-2-one (intermediate A-1) | Colorless solid | 394.3 |
| 194 | Ethanesulfonic acid [4-methyl-5-(1-methyl-2-oxo-1,2,3,4-tetrahydro-quinolin-6-yl)-pyridin-3-ylmethyl]-amide | N-((5-Bromo-4-methylpyridin-3-yl)methyl) ethanesulfonamide (intermediate A-52) and 1-methyl-6-(4,4,5,5-tetramethyl-[1,3,2]dioxaborolan-2-yl)-3,4-dihydro-1H-quinolin-2-one (intermediate A-1) | Grey solid | 374.4 |

Example 195

Ethanesulfonic acid methyl-{2-[5-(1-methyl-2-oxo-1,2,3,4-tetrahydro-quinolin-6-yl)-pyridin-3-yloxy]-ethyl}-amide

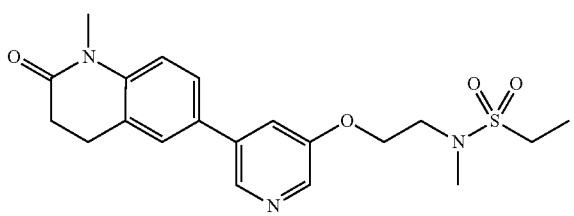 [SMILES: CCS(=O)(=O)N(C)CCOc1cncc(-c2ccc3c(c2)CCC(=O)N3C)c1]

To a solution of ethanesulfonic acid {2-[5-(1-methyl-2-oxo-1,2,3,4-tetrahydro-quinolin-6-yl)-pyridin-3-yloxy]-ethyl}-amide (example 151, 0.06 g, 0.154 mmol) in DMF (1.5 mL) cooled at 0° C. with an ice bath was added 60% NaH in mineral oil (0.008 g, 0.2 mmol) and the reaction mixture was stirred for 15 min. Then, MeI (0.026 g, 0.185 mmol) was added and the reaction mixture was stirred at 0° C. for another 30 min. The mixture was quenched with aq. ammonia (1 mL), diluted with brine (5 mL) and then extracted with EtOAc (2×20 mL). Combined organics were dried over $Na_2SO_4$, filtered and evaporated to dryness. The residue was purified by silica gel flash chromatography eluting with a 0 to 5% MeOH-DCM gradient to give the title compound (0.050 g, 80%) as a light yellow amorphous solid. MS: 404.4 (M+H+).

The following compounds listed in Table 8 were prepared in analogy to the procedure described for the preparation of example 195, using the appropriate starting materials.

TABLE 8

| Ex | Name | Starting Materials | Aspect | MS (M + H+) |
|---|---|---|---|---|
| 196 | 3-Chloro-pyridine-2-carboxylic acid methyl-[5-(1-methyl-2-oxo-1,2,3,4-tetrahydro-quinolin-6-yl)-pyridin-3-ylmethyl]-amide | 3-Chloro-pyridine-2-carboxylic acid [5-(1-methyl-2-oxo-1,2,3,4-tetrahydro-quinolin-6-yl)-pyridin-3-ylmethyl]-amide (example 118) | Colorless amorphous solid | 421.4 |
| 197 | N-Methyl-N-{2-[5-(1-methyl-2-oxo-1,2,3,4-tetrahydro-quinolin-6-yl)-pyridin-3-yloxy]-ethyl}-propionamide | N-{2-[5-(1-Methyl-2-oxo-1,2,3,4-tetrahydro-quinolin-6-yl)-pyridin-3-yloxy]-ethyl}-propionamide (example 43) | Colorless amorphous solid | 368.3 |
| 198 | 1-Methyl-1H-pyrazole-4-carboxylic acid methyl-[5-(1-methyl-2-oxo-1,2,3,4-tetrahydro-quinolin-6-yl)-pyridin-3-ylmethyl]-amide | 1-Methyl-1H-pyrazole-4-carboxylic acid [5-(1-methyl-2-oxo-1,2,3,4-tetrahydro-quinolin-6-yl)-pyridin-3-ylmethyl]-amide (example 87) | Colorless amorphous solid | 390.4 |
| 199 | 3-Methyl-pyridine-2-carboxylic acid methyl-[5-(1-methyl-2-oxo-1,2,3,4-tetrahydro-quinolin-6-yl)-pyridin-3-ylmethyl]-amide | 3-Methyl-pyridine-2-carboxylic acid [5-(1-methyl-2-oxo-1,2,3,4-tetrahydro-quinolin-6-yl)-pyridin-3-ylmethyl]-amide (example 115) | Colorless amorphous solid | 401.5 |

TABLE 8-continued

| Ex | Name | Starting Materials | Aspect | MS (M + H+) |
|---|---|---|---|---|
| 200 | 3-Chloro-pyridine-2-carboxylic acid [5-(7-fluoro-1-methyl-2-oxo-1,2,3,4-tetrahydro-quinolin-6-yl)-pyridin-3-ylmethyl]-methyl-amide | 3-Chloro-pyridine-2-carboxylic acid [5-(7-fluoro-1-methyl-2-oxo-1,2,3,4-tetrahydro-quinolin-6-yl)-pyridin-3-ylmethyl]-amide (example 131) | Off-white amorphous solid | 439.1 |
| 201 | 3-Chloro-pyridine-2-carboxylic acid methyl-{1-[5-(1-methyl-2-oxo-1,2,3,4-tetrahydro-quinolin-6-yl)-pyridin-3-yl]-cyclopropyl}-amide | 3-Chloro-pyridine-2-carboxylic acid {1-[5-(1-methyl-2-oxo-1,2,3,4-tetrahydro-quinolin-6-yl)-pyridin-3-yl]-cyclopropyl}-amide (example 137) | Colorless amorphous solid | 447.4 |
| 202 | 1-Methyl-1H-pyrazole-4-carboxylic acid [5-(7-fluoro-1-methyl-2-oxo-1,2,3,4-tetrahydro-quinolin-6-yl)-pyridin-3-ylmethyl]-methyl-amide | 1-Methyl-1H-pyrazole-4-carboxylic acid [5-(7-fluoro-1-methyl-2-oxo-1,2,3,4-tetrahydro-quinolin-6-yl)-pyridin-3-ylmethyl]-amide (example 175) | Light brown solid | 408.5 |

Example 203

Ethanesulfonic acid [5-(8-chloro-2-oxo-1,2,3,4-tetrahydro-quinolin-6-yl)-pyridin-3-ylmethyl]-amide

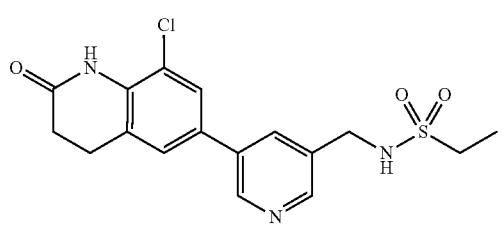 [SMILES: CCS(=O)(=O)NCc1cncc(-c2cc(Cl)c3c(c2)CCC(=O)N3)c1]

To a solution of ethanesulfonic acid [5-(2-oxo-1,2,3,4-tetrahydro-quinolin-6-yl)-pyridin-3-ylmethyl]-amide (example 55, 0.681 g, 0.197 mmol) in DMF (1 mL) heated to 65° C. was added N-chloro-succinimide (0.034 g, 0.256 mmol) and the reaction mixture was stirred at this temperature over night. The mixture was diluted with EtOAc, poured into water (5 mL) and extracted with EtOAc (2×10 mL). The combined organics were washed with brine, dried over $Na_2SO_4$, filtered and evaporated. The residue was purified by reverse phase HPLC on a Gemini-NX column, eluting with a MeOH—$H_2O$ (0.05% TEA) gradient to give the title compound (0.025 g, 33%) as a colorless amorphous solid. MS: 380.4 (M+H+).

The following compounds listed in Table 9 were prepared in analogy to the procedure described for the preparation of example 203, using the appropriate starting materials.

TABLE 9

| Ex | Name | Starting Materials | Aspect | MS (M + H+) |
|---|---|---|---|---|
| 204 | 3-Chloro-pyridine-2-carboxylic acid [5-(8-chloro-2-oxo-1,2,3,4-tetrahydro-quinolin-6-yl)-pyridin-3-ylmethyl]-amide | 3-Chloro-pyridine-2-carboxylic acid [5-(2-oxo-1,2,3,4-tetrahydro-quinolin-6-yl)-pyridin-3-ylmethyl]-amide (example 140) | Colorless solid | 427.4 |
| 205 | 3,5-Dimethyl-isoxazole-4-carboxylic acid [5-(8-chloro-2-oxo-1,2,3,4-tetrahydro-quinolin-6-yl)-pyridin-3-ylmethyl]-amide | 3,5-Dimethyl-isoxazole-4-carboxylic acid [5-(2-oxo-1,2,3,4-tetrahydro-quinolin-6-yl)-pyridin-3-ylmethyl]-amide (example 141) | Colorless solid | 411.4 |

Example 206

6-{5-[(3-Ethyl-oxetan-3-ylamino)-methyl]-pyridin-3-yl}-1-methyl-3,4-dihydro-1H-quinolin-2-one

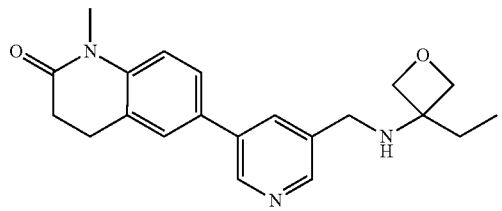 [SMILES: CCC1(NCc2cncc(-c3ccc4c(c3)CCC(=O)N4C)c2)COC1]

[A] 6-(5-Hydroxymethyl-pyridin-3-yl)-1-methyl-3,4-dihydro-1H-quinolin-2-one

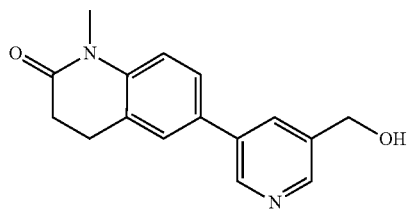 [SMILES: CN1C(=O)CCc2cc(-c3cncc(CO)c3)ccc21]

A microwave vial was charged with (5-bromo-pyridin-3-yl)-methanol (376 mg, 2.0 mmol), 1-methyl-6-(4,4,5,5-tetramethyl-[1,3,2]dioxaborolan-2-yl)-3,4-dihydro-1H-quinolin-2-one (intermediate A-1) (574 mg, 2.0 mmol) and DMF (4 mL). After purging the reaction mixture with argon, bis(triphenylphosphine)palladium(II)chloride (140 mg, 0.2 mmol) and 2 N aq. Na$_2$CO$_3$ solution (2.0 mL, 4 mmol) were added and the reaction was heated in the microwave at 120° C. for 50 min. The reaction mixture was diluted with EtOAc, filtered through Dicalite and washed with EtOAc (2×20 mL). The resulting filtrate was washed with brine, dried over anhydrous Na$_2$SO$_4$, filtered and evaporated to dryness. The residue was purified by silica gel flash chromatography eluting with a 0 to 5% MeOH-DCM gradient to give the title compound (198 mg, 74%) as a white solid. MS: 269.2 (M+H+).

[B] 6-(5-Chloromethyl-pyridin-3-yl)-1-methyl-3,4-dihydro-1H-quinolin-2-one

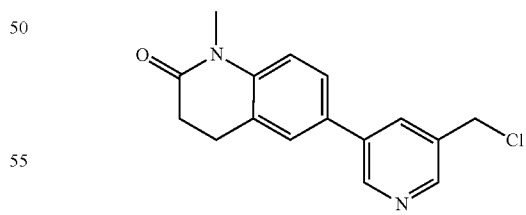

At 0° C., 6-(5-hydroxymethyl-pyridin-3-yl)-1-methyl-3,4-dihydro-1H-quinolin-2-one (190 mg, 0.7 mmol) in DCM (15 mL) was treated slowly with thionyl chloride (0.32 mL, 4.0 mmol). After the addition, the reaction mixture was allowed to stir at 2-5° C. for 2 hours before it was poured into satd. aq. NaHCO$_3$ solution (50 mL). After extraction with EtOAc, the organic layer was washed with brine, dried over anhydrous Na$_2$SO$_4$, filtered and concentrated in vacuo to give title compound (190 mg, 93.5%) as yellow oil. MS: 287.1 (M+H+).

[C] 6-{5-[(3-Ethyl-oxetan-3-ylamino)-methyl]-pyridin-3-yl}-1-methyl-3,4-dihydro-1H-quinolin-2-one

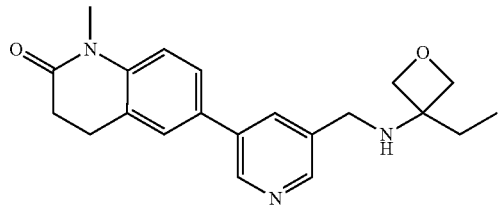 [SMILES: CCC1(NCc2cncc(-c3ccc4c(c3)CCC(=O)N4C)c2)COC1]

To a stirred solution of 6-(5-chloromethyl-pyridin-3-yl)-1-methyl-3,4-dihydro-1H-quinolin-2-one (190 mg, 0.66 mmol) in DMF (5.0 mL) was added $K_2CO_3$ (276 mg, 2.0 mmol) and 3-ethyl-oxetan-3-ylamine (415 mg, 3.0 mmol) at room temperature and the resulting reaction mixture was stirred at room temperature for additional 12 hours. After extraction with EtOAc, the organic layer was washed with brine, dried over anhydrous $Na_2SO_4$, filtered and concentrated in vacuo to give a crude product which was purified by prep-HPLC to give title compound (35 mg, 17.2%) as a light yellow solid. MS: 352.1 $(M+H^+)$.

Example 207

Ethanesulfonic acid [5-(7-chloro-1-methyl-2-oxo-1,2,3,4-tetrahydro-quinolin-6-yl)-pyridin-3-ylmethyl]-amide

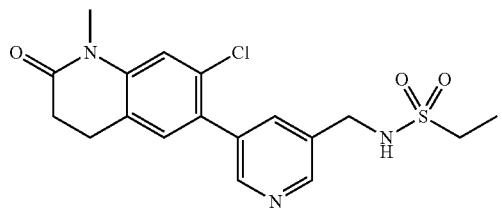 [SMILES: CCS(=O)(=O)NCc1cncc(-c2cc3c(cc2Cl)N(C)C(=O)CC3)c1]

[A] N-(4-Bromo-3-chloro-phenyl)-3-chloro-propionamide

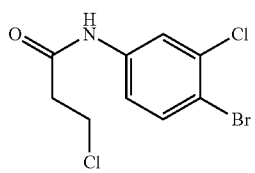 [SMILES: O=C(CCCl)Nc1ccc(Br)c(Cl)c1]

To a solution of 4-bromo-3-chloroaniline (6.0 g, 29.1 mmol) and pyridine (3.45 g, 43.6 mmol) in 1,2-dichloroethane (50 mL) was added 3-chloropropionyl chloride (5.53 g, 43.6 mmol) dropwise at 15° C. After stirring for 2 hours at room temperature, the mixture was washed with water and then hydrochloric acid (2 N, aqueous). The organic layer was dried over anhydrous sodium sulfate. After filtration, the solvent was removed under reduced pressure. The product N-(4-bromo-3-chloro-phenyl)-3-chloro-propionamide (8.20 g, yield: 95%) was obtained as an oil. MS: 298.0 $(M+H^+)^+$.

[B] 6-Bromo-7-chloro-3,4-dihydro-1H-quinolin-2-one

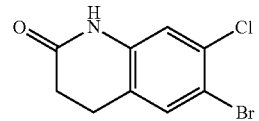 [SMILES: O=C1CCc2cc(Br)c(Cl)cc2N1]

A flame-dried 50-mL flask equipped with a magnetic stirring bar was charged with N-(4-bromo-3-chloro-phenyl)-3-chloro-propionamide (1.0 g, 3.36 mmol) and aluminium chloride (0.67 g, 5.04 mmol). In a pre-heated oil bath, the flask was heated at 135~140° C. for 2 hours. After cooling to room temperature, the reaction mixture was treated slowly with ice-water, then extracted with EtOAc. The organic layer was washed with water and brine in sequence and dried over anhydrous $Na_2SO_4$. After evaporation of the solvent, the residue was purified by recrystallization from EtOAc (2 mL) which gave title compound (0.44 g, 50%) as a solid. MS: 260.0 $(M+H^+)^+$.

[C] 6-Bromo-7-chloro-1-methyl-3,4-dihydro-1H-quinolin-2-one

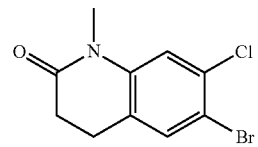

Potassium tert-butoxide (0.45 g, 4.0 mmol) was added to a solution of 6-bromo-7-chloro-3,4-dihydro-1H-quinolin-2-one (0.52 g, 2.0 mmol) in DMF (5 mL) at 0° C. Then, the reaction mixture was stirred at 0° C. for 30 min and methyl iodide (0.18 g, 1.29 mmol) was added. The resulting mixture was stirred for 2 hours before water was added. After extraction of the reaction mixture with EtOAc, the organic layer was washed with water and brine in sequence. Then, it was dried over anhydrous $Na_2SO_4$ and the solvent was removed under reduced pressure to give a crude product (0.49 g, 90%) as a white solid. MS: 274.0 $(M+H^+)^+$.

[D] 7-Chloro-1-methyl-6-(4,4,5,5-tetramethyl-[1,3,2]dioxaborolan-2-yl)-3,4-dihydro-1H-quinolin-2-one

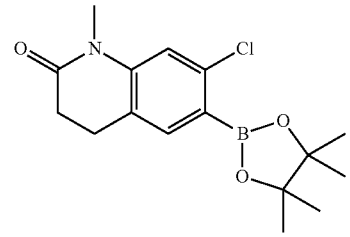 [SMILES: CN1C(=O)CCc2cc(B3OC(C)(C)C(C)(C)O3)c(Cl)cc21]

A mixture of 6-bromo-7-chloro-1-methyl-3,4-dihydro-1H-quinolin-2-one (0.1 g, 0.36 mmol), bis(pinacolato)diboron (0.13 g, 0.55 mmol), 1,1'-bis(diphenylphosphino) ferrocenedichloro-palladium (II) (14.7 mg, 0.018 mmol) and potassium acetate (0.11 g, 1.08 mmol) in dioxane (3 mL) was heated in a microwave at 100° C. for 3 hours. The mixture was diluted with EtOAc, washed with water, dried over anhydrous Na$_2$SO$_4$, and concentrated in vacuo. The residue was purified by flash chromatography (silica gel, 30% ethyl acetate in hexane) to afford the title compound (82 mg, 70%) as a white solid. MS: 322.1 (M+H$^+$)$^+$.

[E] Ethanesulfonic acid [5-(7-chloro-1-methyl-2-oxo-1,2,3,4-tetrahydro-quinolin-6-yl)-pyridin-3-ylmethyl]-amide

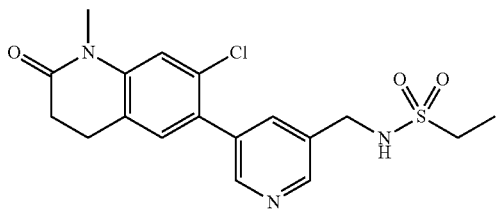 [SMILES: CCS(=O)(=O)NCc1cncc(-c2cc3c(cc2Cl)N(C)C(=O)CC3)c1]

A mixture of 7-chloro-1-methyl-6-(4,4,5,5-tetramethyl-[1,3,2]dioxaborolan-2-yl)-3,4-dihydro-1H-quinolin-2-one (20 mg, 0.06 mmol), ethanesulfonic acid (5-bromo-pyridin-3-ylmethyl)-amide (intermediate A-11, 26 mg, 0.09 mmol), bis(triphenylphosphine)-palladium(II) chloride (4.2 mg, 0.006 mmol) and sodium carbonate (2 N aq., 0.06 mL) in DMF (1 mL) was heated in a microwave at 120° C. for 30 minutes. The mixture was diluted with EtOAc, washed with water, dried over anhydrous Na$_2$SO$_4$ and concentrated in vacuo. The residue was purified by prep-HPLC to afford the title product (7.1 mg, 30%) as a white solid. MS, 394.2 (M+H$^+$)$^+$.

Example 208

Ethanesulfonic acid [5-(8-fluoro-1-methyl-2-oxo-1,2,3,4-tetrahydro-quinolin-6-yl)-pyridin-3-ylmethyl]-amide

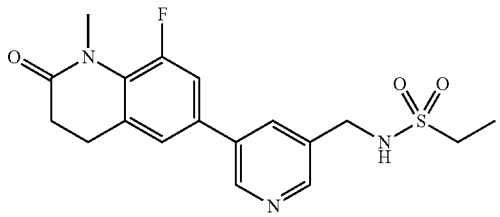 [SMILES: CCS(=O)(=O)NCc1cncc(-c2cc(F)c3c(c2)CCC(=O)N3C)c1]

[A] 3-Chloro-N-(2-fluoro-phenyl)-propionamide

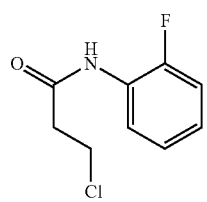 [SMILES: O=C(CCCl)Nc1ccccc1F]

To a solution of 2-fluoroaniline (6.67 g, 60 mmol) and pyridine (5.21 g, 66 mmol) in 1,2-dichloroethane (50 mL) was added 3-chloropropionyl chloride (8.38 g, 66 mmol) dropwise at 15° C. After stirring at room temperature for 2 hours, the mixture was washed with water and then hydrochloric acid (2 N, aqueous). The organic layer was dried over anhydrous Na$_2$SO$_4$, filtered, and concentrated in vacuo to afford title compound (10.9 g, yield: 90%) as an oil. MS: 202.1 (M+H$^+$)$^+$.

[B] 8-Fluoro-3,4-dihydro-1H-quinolin-2-one

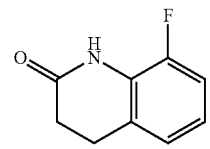 [SMILES: O=C1CCc2cccc(F)c2N1]

A flame-dried 50-mL flask equipped with a magnetic stirring bar was charged with 3-chloro-N-(2-fluoro-phenyl)-propionamide (5.33 g, 26.5 mmol) and aluminium chloride (5.30 g, 39.7 mmol). In a pre-heated oil bath, the flask was heated at 160° C. for 1.5 hours. After cooling to room temperature, the mixture was treated slowly with ice-water and extracted with EtOAc. The organic layer was washed with water and brine in sequence, dried over anhydrous Na$_2$SO$_4$, filtered, and concentrated in vacuo. The resulting residue was then purified by flash chromatography (silica gel, 30% ethyl acetate in hexane) to afford title compound (3.1 g, 70%) as a solid. MS: 166.0 (M+H$^+$)$^+$.

[C] 6-Bromo-8-fluoro-3,4-dihydro-1H-quinolin-2-one

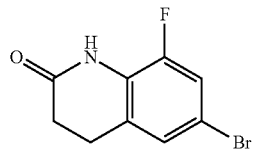

At 0° C., NBS (0.62 g, 3.5 mmol) was added dropwise to a solution of 8-fluoro-3,4-dihydro-1H-quinolin-2-one (0.52 g, 3.2 mmol) in DMF (5 mL). The resulting reaction mixture was stirred at room temperature for 12 hours before it was treated with water. The precipitated solid was collected through filtration, washed with ether, and dried in a vacuum to afford title compound (0.65 g, 85%) as a white solid. MS: 244.1 (M+H$^+$)$^+$.

[D] 6-Bromo-8-fluoro-1-methyl-3,4-dihydro-1H-quinolin-2-one

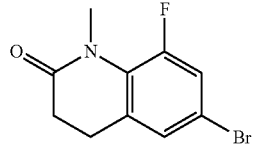

A solution of 6-bromo-8-fluoro-3,4-dihydro-1H-quinolin-2-one (0.21 g, 0.86 mmol) in DMF (2 mL) was treated with potassium tert-butoxide (0.19 g, 1.72 mmol) at 0° C. The resulting mixture was stirred at 0° C. for 30 minutes before methyl iodide (0.18 g, 1.29 mmol) was added. After stirring for 2 hours, the reaction mixture was treated with water, extracted with EtOAc, washed with water and brine in sequence, and dried over anhydrous Na$_2$SO$_4$. After removal of solvent under reduced pressure, the crude product (0.18 g, 80%) was obtained as a white solid. MS: 258.0 (M+H$^+$)$^+$.

[E] 8-Fluoro-1-methyl-6-(4,4,5,5-tetramethyl-[1,3,2]dioxaborolan-2-yl)-3,4-dihydro-1H-quinolin-2-one

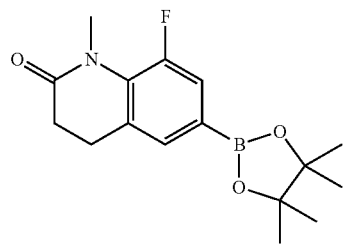 [SMILES: CN1C(=O)CCc2cc(B3OC(C)(C)C(C)(C)O3)cc(F)c21]

A mixture of 6-bromo-8-fluoro-1-methyl-3,4-dihydro-1H-quinolin-2-one (0.18 g, 0.36 mmol), bis(pinacolato)diboron (0.25 g, 1.05 mmol), 1,1'-bis(diphenylphosphino)ferrocene-dichloropalladium (II) (28.6 mg, 0.035 mmol) and potassium acetate (0.21 g, 2.1 mmol) in dioxane (3 mL) was heated in a microwave at 100° C. for 3 hours. After dilution with EtOAc, the organic layer was washed with water, dried over anhydrous Na$_2$SO$_4$ and concentrated in vacuo. The residue was then purified by flash chromatography (silica gel, 30% ethyl acetate in hexane) to afford the title compound (0.15 g, 70%) as a white solid. MS: 306.2 (M+H$^+$)$^+$.

[F] Ethanesulfonic acid [5-(8-fluoro-1-methyl-2-oxo-1,2,3,4-tetrahydro-quinolin-6-yl)-pyridin-3-ylmethyl]-amide

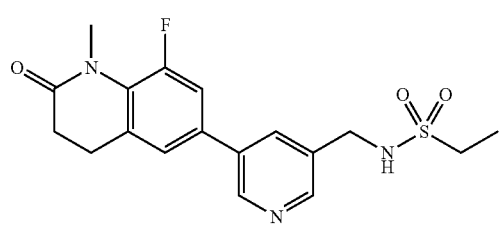 [SMILES: CCS(=O)(=O)NCc1cncc(-c2cc(F)c3c(c2)CCC(=O)N3C)c1]

A mixture of 8-fluoro-1-methyl-6-(4,4,5,5-tetramethyl-[1,3,2]dioxaborolan-2-yl)-3,4-dihydro-1H-quinolin-2-one (20 mg, 0.066 mmol), ethanesulfonic acid (5-bromo-pyridin-3-ylmethyl)-amide (intermediate A-11, 27.4 mg, 0.098 mmol), bis(triphenylphosphine)-palladium(II) chloride (4.6 mg, 0.0066 mmol) and aq. sodium carbonate solution (2 N, 0.07 mL) in DMF (1 mL) was heated in a microwave at 120° C. for 30 min. The resulting reaction mixture was then diluted with EtOAc, washed with water, dried over sodium sulfate and concentrated in vacuo. The residue was purified by prep-HPLC to afford the title compound (12.4 mg, 50%) as a white solid. MS: 378.1 (M+H$^+$)$^+$.

Example 209

Ethanesulfonic acid [5-(8-chloro-1-methyl-2-oxo-1,2,3,4-tetrahydro-quinolin-6-yl)-pyridin-3-ylmethyl]-amide

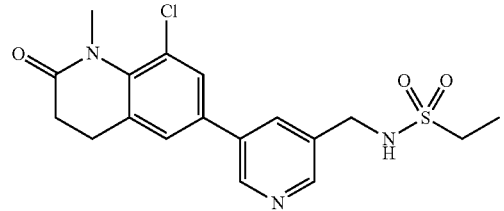 [SMILES: CCS(=O)(=O)NCc1cncc(-c2cc(Cl)c3c(c2)CCC(=O)N3C)c1]

[A] N-(4-Bromo-2-chloro-phenyl)-3-chloro-propionamide

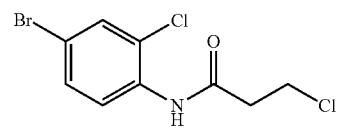 [SMILES: O=C(CCCl)Nc1ccc(Br)cc1Cl]

To a solution of 4-bromo-2-chloro-phenylamine (32 g, 0.15 mol) and pyridine (13.45 g, 0.17 mol) in DCM (200 mL) was added 3-chloropropionyl chloride (21.65 g, 0.17 mol) dropwise at 15° C. After stirring at room temperature for 1 hour, the mixture was washed with water and then hydrochloric acid (2 N, aqueous). The organic layer was dried over anhydrous Na$_2$SO$_4$, filtered, and concentrated in vacuo to afford title compound (10.9 g, yield: 90%) as a white solid.

[B] 6-Bromo-8-chloro-3,4-dihydro-1H-quinolin-2-one

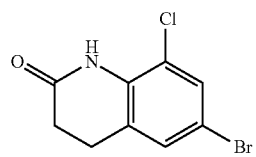 [SMILES: O=C1CCc2cc(Br)cc(Cl)c2N1]

A flame-dried 500-mL flask equipped with a magnetic stirring bar was charged with N-(4-bromo-2-chloro-phenyl)-3-chloro-propionamide (29.7 g, 0.1 mol) and aluminium chloride (53.3 g, 0.4 mol). In a pre-heated oil bath, the flask was heated at 140° C. for 1 hour. After cooling to room temperature, the mixture was treated slowly with ice-water and extracted with EtOAc. The organic layer was washed with water and brine in sequence, dried over anhydrous Na$_2$SO$_4$, filtered, and concentrated in vacuo. The resulting residue was then purified by flash chromatography (silica gel, 30% ethyl acetate in hexane) to afford the title compound (7.0 g, 27%) as a white solid.

[C] 6-Bromo-8-chloro-1-methyl-3,4-dihydro-1H-quinolin-2-one

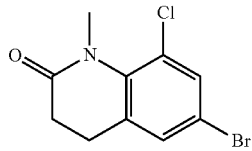

A solution of 6-bromo-8-chloro-3,4-dihydro-1H-quinolin-2-one (7.0 g, 26.9 mmol) in DMF (100 mL) was treated with potassium tert-butoxide (6.0 g, 53.8 mmol) at 0° C. portionwise. The resulting mixture was stirred at 0° C. for 30 minutes before methyl iodide (5.0 g, 35.0 mmol) was added. After stirred for 12 hours, the reaction mixture was treated with water, extracted with EtOAc, washed with water and brine in sequence, and dried over anhydrous $Na_2SO_4$. After removal of solvent under reduced pressure, the crude product (3.3 g, 45%) was obtained as a white solid.

[D] 8-Chloro-1-methyl-6-(4,4,5,5-tetramethyl-[1,3,2]dioxaborolan-2-yl)-3,4-dihydro-1H-quinolin-2-one

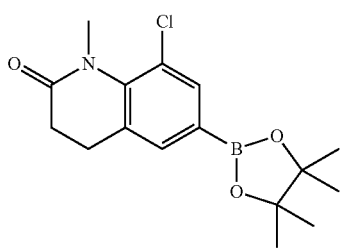

A mixture of 6-bromo-8-chloro-1-methyl-3,4-dihydro-1H-quinolin-2-one (0.23 g, 0.84 mmol), bis(pinacolato)diboron (0.255 g, 1.01 mmol), 1,1'-bis(diphenylphosphino)-ferrocene-dichloropalladium (II) (30.7 mg, 0.04 mmol) and potassium acetate (0.247 g, 2.52 mmol) in dioxane (5 mL) was heated in a microwave at 80° C. over night. After dilution with EtOAc, the organic layer was washed with water, dried over anhydrous $Na_2SO_4$ and concentrated in vacuo. The residue was then purified by flash chromatography (silica gel, 30% ethyl acetate in hexane) to afford the title compound (0.17 g, 63%) as a white solid.

[E] Ethanesulfonic acid [5-(8-chloro-1-methyl-2-oxo-1,2,3,4-tetrahydro-quinolin-6-yl)-pyridin-3-ylmethyl]-amide

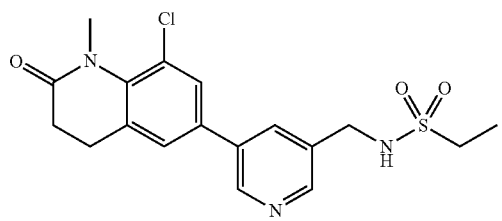 [SMILES: CCS(=O)(=O)NCc1cncc(-c2cc(Cl)c3c(c2)CCC(=O)N3C)c1]

Under argon protection, bis(triphenylphosphine)palladium(II)chloride (4 mg, 0.05 mmol) followed by 1 N aqueous $Na_2CO_3$ solution (1 mL), was added to a solution of 8-chloro-1-methyl-6-(4,4,5,5-tetramethyl-[1,3,2]-dioxaborolan-2-yl)-3,4-dihydro-1H-quinolin-2-one (160 mg, 0.5 mmol) and ethanesulfonic acid (5-bromo-pyridin-3-ylmethyl)-amide (intermediate A-11, 158 mg, 0.6 mmol) in DMF (3 mL). The resulting reaction mixture was then heated in a microwave at 110° C. for 45 min. After cooling to room temperature, the reaction mixture was diluted with EtOAc (5 mL) and poured into a satd. aq. solution of $NaHCO_3$ (10 mL). The aqueous layer was extracted with EtOAc (3×5 mL). Combined organics were washed with water and brine (20 mL), dried over anhydrous $Na_2SO_4$, filtered and concentrated in vacuo to give a crude product which was then purified by prep-HPLC to give title compound (65 mg, 45%) as a white solid. MS: 394.1 $(M+H^+)^+$.

Example 210

Ethanesulfonic acid [5-(5-fluoro-1-methyl-2-oxo-1,2,3,4-tetrahydro-quinolin-6-yl)-pyridin-3-ylmethyl]-amide

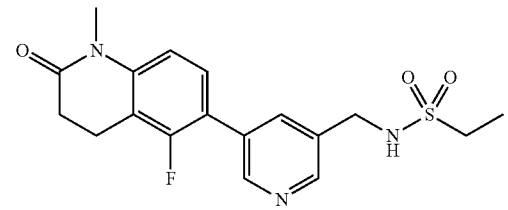 [SMILES: CCS(=O)(=O)NCc1cncc(-c2ccc3c(c2F)CCC(=O)N3C)c1]

[A] 3-Chloro-N-(3-fluoro-phenyl)-propionamide

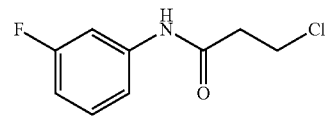 [SMILES: O=C(CCCl)Nc1cccc(F)c1]

To a solution of 3-fluoroanilline (10 mL, 104.02 mmol) in DCM (100 mL) was added pyridine (21 mL, 260.2 mmol) and 3-chloropropionyl chloride (12 mL, 124.4 mmol). The reaction mixture was stirred for 3 hours at room temperature until all starting material had disappeared as shown by LC-MS analysis. The reaction mixture was then diluted with $H_2O$ and extracted with EtOAc. The organic layer was dried over anhydrous $Na_2SO_4$ and concentrated in vacuo to afford the title compound as a solid. It was used in the next step without further purification.

[B] 7-Fluoro-3,4-dihydro-1H-quinolin-2-one (compound A) and 5-fluoro-3,4-dihydro-1H-quinolin-2-one (compound B)

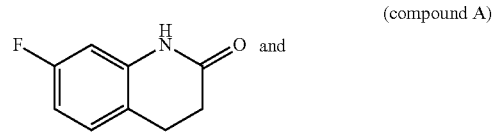

(compound A)

-continued (compound B)

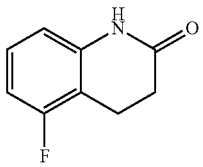

A flame-dried 50-mL flask equipped with a magnetic stirring bar was charged with 3-chloro-N-(3-fluoro-phenyl)-propionamide (10 g, 49.6 mmol) and AlCl$_3$ (23.1 g, 173.6 mmol). On a pre-heated oil bath, the flask was heated at 120~125° C. for 2 hours until LC-MS indicated the reaction was complete. After cooling to room temperature, the mixture was treated slowly with ice-water. After extraction with EtOAc, the combined organic layers were washed with water and brine in sequence. The organic layer was dried over anhydrous Na$_2$SO$_4$, filtered and concentrated in vacuo to afford a white solid as a crude mixture of two regioisomeric products (A:B) in a ratio of 5.3:1. (7.63 g, 93.2%).

[C] 7-Fluoro-1-methyl-3,4-dihydro-1H-quinolin-2-one and 5-fluoro-1-methyl-3,4-dihydro-1H-quinolin-2-one (compound A)

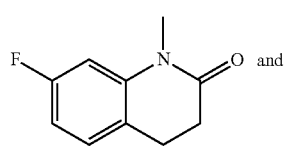

and (compound B)

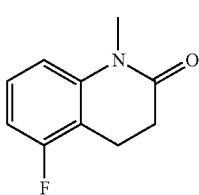

To an ice cold solution of a mixture of 7-fluoro-3,4-dihydro-1H-quinolin-2-one and 5-fluoro-3,4-dihydro-1H-quinolin-2-one (16.5 g, 0.1 mol) in DMF (200 mL) was added potassium tert-butoxide (22.4 g, 0.2 mol) in 2 portions. The reaction mixture was stirred at 0° C. for 30 min before MeI (25.4 g, 0.18 mol) was added. After the addition, the reaction mixture was allowed to warm up to RT slowly and stirred at RT over night. It was then diluted with EtOAc (500 mL) and poured into 200 mL of 1 M aq. HCl. After extraction with EtOAc (200 mL, 3×), the combined organic layers were washed with brine, dried over anhydrous Na$_2$SO$_4$, filtered and concentrated in vacuo to give the crude title compounds as oil (16.0 g, 89%). It was used in the next step without further purification.

[D] 6-Bromo-7-fluoro-1-methyl-3,4-dihydro-1H-quinolin-2-one and 6-bromo-5-fluoro-1-methyl-3,4-dihydro-1H-quinolin-2-one (compound A)

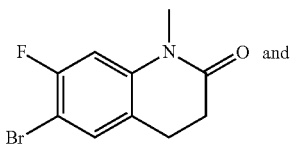

(compound B)

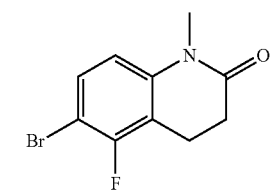

To an ice cold solution of the mixture of 7-fluoro-1-methyl-3,4-dihydro-1H-quinolin-2-one and 5-fluoro-1-methyl-3,4-dihydro-1H-quinolin-2-one (16.0 g, 89.4 mmol) in DMF (200 mL) was added NBS (16.0 g, 89.4 mmol). After the addition, the reaction mixture was warmed up to RT and stirred for 3 hours. When LC-MS indicated the completion of the reaction, the mixture was diluted with EtOAc (500 mL) and poured into 500 mL of water. The aqueous layer was then extracted with EtOAc (200 mL, 3×). Combined organic layers were washed with brine, dried over Na$_2$SO$_4$, filtered and concentrated in vacuo to give the crude title compound as oil (18.0 g, 78%). It was used in the next step without further purification.

[E] Ethanesulfonic acid [5-(5-fluoro-1-methyl-2-oxo-1,2,3,4-tetrahydro-quinolin-6-yl)-pyridin-3-ylmethyl]-amide

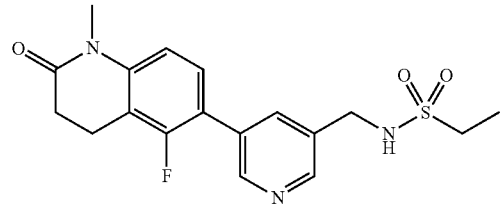 [SMILES: CCS(=O)(=O)NCc1cncc(-c2ccc3c(c2F)CCC(=O)N3C)c1]

In analogy to the procedure described for the preparation of intermediates A-1 [B], the mixture of 6-bromo-7-fluoro-1-methyl-3,4-dihydro-1H-quinolin-2-one and 6-bromo-5-fluoro-1-methyl-3,4-dihydro-1H-quinolin-2-one was reacted with 4,4,4',4',5,5,5',5'-octamethyl-2,2'-bi(1,3,2-dioxaborolane) in the presence of potassium acetate and PdCl$_2$(DPPF)-CH$_2$Cl$_2$ and the reaction product was subsequently reacted with ethanesulfonic acid (5-bromo-pyridin-3-ylmethyl)-amide (intermediate A-11) in analogy to the procedure described for the preparation of example 45. The crude reaction product has been separated by preparative HPLC to give ethanesulfonic acid [5-(7-fluoro-1-methyl-2-oxo-1,2,3,4-tetrahydro-quinolin-6-yl)-pyridin-3-ylmethyl]-amide (example 16) as well as the title compound as a white solid. MS: 378.1 (M+H$^+$)$^+$.

Example 211

Ethanesulfonic acid [5-(7-fluoro-1-methyl-2-oxo-1,2,3,4-tetrahydro-quinolin-6-yl)-pyridin-3-ylmethyl]-methyl-amide

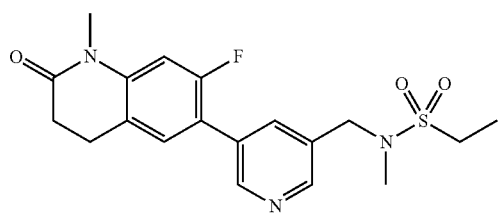 [SMILES: CCS(=O)(=O)N(C)Cc1cncc(-c2cc3c(cc2F)N(C)C(=O)CC3)c1]

To a solution of ethanesulfonic acid [5-(7-fluoro-1-methyl-2-oxo-1,2,3,4-tetrahydro-quinolin-6-yl)-pyridin-3-ylmethyl]-amide (example 16, 0.15 g, 0.39 mmol) in DMF (5 mL) was added potassium tert-butoxide (67.2 mg, 0.60 mmol) at 0° C. The resulting mixture was stirred for 30 minutes at 0° C. before methyl iodide (84.6 mg, 0.6 mmol) was added dropwise. After stirring for 2 hours, the mixture was treated with water, and extracted with EtOAc. The combined organic layers were then washed with water and brine in sequence, dried over anhydrous $Na_2SO_4$ and concentrated in vacuo. The residue was then purified by flash chromatography (silica gel, 5% methanol in dichloromethane) to afford the title compound (93 mg, 60%) as a white solid. MS: 392.1 $(M+H^+)^+$.

Example 212

N-[5-(7-Fluoro-1-methyl-2-oxo-1,2,3,4-tetrahydro-quinolin-6-yl)-pyridin-3-ylmethyl]-propionamide

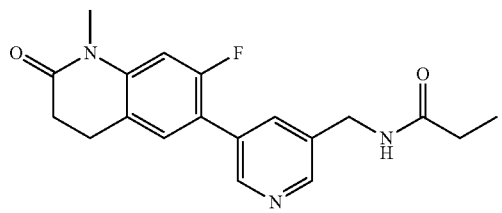 [SMILES: CCC(=O)NCc1cncc(-c2cc3c(cc2F)N(C)C(=O)CC3)c1]

[A] N-(5-Bromo-pyridin-3-ylmethyl)-propionamide

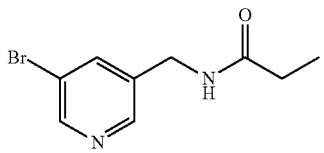

To a solution of propionamide (146 mg, 2.0 mmol) in DMF (10 mL) was added NaH (61 mg, 2.4 mmol) at 0° C. and reaction mixture was stirred for 10 min before the addition of 3-bromo-5-chloromethyl-pyridine (intermediate A-12 [A], 412 mg, 2.0 mmol). The resulting reaction mixture was stirred at room temperature for 1 hour before water was added. Then, the reaction mixture was extracted with EtOAc and combined organic layers were dried by anhydrous $Na_2SO_4$, filtered and concentrated in vacuo. The residue was then purified by flash chromatography to give title compound (400 mg, 82%) as a solid.

[B] N-[5-(7-Fluoro-1-methyl-2-oxo-1,2,3,4-tetrahydro-quinolin-6-yl)-pyridin-3-ylmethyl]-propionamide

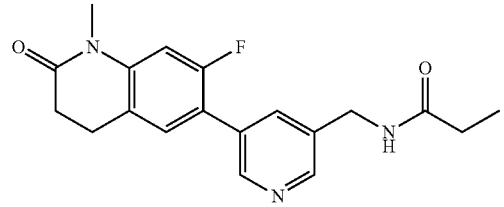 [SMILES: CCC(=O)NCc1cncc(-c2cc3c(cc2F)N(C)C(=O)CC3)c1]

To a mixture of 7-fluoro-1-methyl-6-(4,4,5,5-tetramethyl-[1,3,2]dioxaborolan-2-yl)-3,4-dihydro-1H-quinolin-2-one (intermediate A-22, 168 g, 0.55 mmol) and N-(5-bromo-pyridin-3-ylmethyl)-propionamide (122 mg, 0.5 mmol) in DMF (3 mL), purged with argon for 1 min, was added bis(triphenylphosphine)palladium (II)chloride (38 mg, 0.054 mmol) and 1 N aq. $Na_2CO_3$ (2.5 mL). Then, the resulting reaction mixture was heated in a microwave at 110° C. for 45 min. After cooling to room temperature, it was diluted with EtOAc (5 mL) and poured into a satd. aq. solution of $NaHCO_3$ (10 mL). The aqueous layer was extracted with EtOAc (3×5 mL) and combined organics were washed with water and brine (20 mL), dried over anhydrous $Na_2SO_4$, filtered and concentrated in vacuo. The residue was then purified by prep-HPLC to afford the title compound (30 mg, 18%) as a white solid. MS: 342.1 $(M+H^+)^+$.

Example 213

(rac)-N-{1-[5-(7-Fluoro-1-methyl-2-oxo-1,2,3,4-tetrahydro-quinolin-6-yl)-pyridin-3-yl]-ethyl}-propionamide

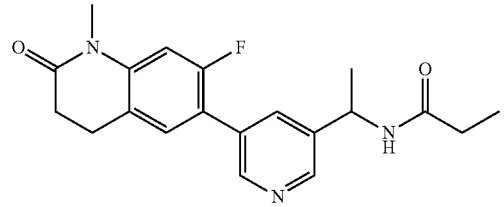 [SMILES: CCC(=O)NC(C)c1cncc(-c2cc3c(cc2F)N(C)C(=O)CC3)c1]

[A] 5-Bromo-N-methoxy-N-methyl-nicotinamide

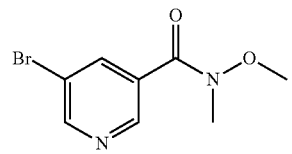

To a solution of 5-bromo-nicotinic acid (2.02 g, 10 mmol) and O,N-dimethyl-hydroxylamine (670 mg, 11 mmol) in DMF (100 mL) was added HOBt (400 mg, 0.3 mmol), EDCI (2.09 g, 11 mmol) and Et₃N (1.11 g, 11 mmol). The resulting mixture was stirred at room temperature for 1 hour. Water was added to the reaction mixture and it was extracted with EtOAc. The organic layer was washed with brine, dried by anhydrous Na₂SO₄, filtered and concentrated in vacuo. The residue was then purified by flash chromatography to give the title compound (2.08 g, 85%) as a solid.

[B] 1-(5-Bromo-pyridin-3-yl)-ethanone

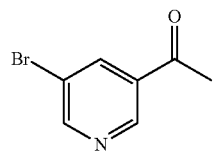

To a solution of 5-bromo-N-methoxy-N-methyl-nicotinamide (2.08 g, 8.5 mmol) in THF (20 mL) was added MeMgBr (1.52 g, 12.75 mmol) at −78° C. After the addition, the reaction mixture was stirred at room temperature for 2 hours before quenching with water. After extraction with EtOAC, the organic layer was washed with brine, dried over anhydrous Na₂SO₄, filtered and concentrated in vacuo. The residue was then purified by flash column chromatography to afford the title compound (1.5 g, 88%).

[C] (rac)-1-(5-Bromo-pyridin-3-yl)-ethylamine

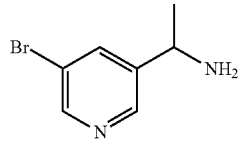

To a solution of 1-(5-bromo-pyridin-3-yl)-ethanone (400 mg, 2 mmol) in methanolic ammonia (10 mL) was added Ti(O-iPr)₄ (1.14 g, 4 mmol). The resulting reaction mixture was heated to reflux and stirred over night. After cooling at 0° C., NaBH₄ was added into the mixture and it was allowed to warm up to room temperature and stirred for 3 hours. Water was added and the reaction mixture was extracted with EtOAc. The organic layer was washed with water and brine, dried over anhydrous Na₂SO₄, filtered and concentrated in vacuo. It was directly used in the next step without further purification.

[D] (rac)-N-[1-(5-Bromo-pyridin-3-yl)-ethyl]-propionamide

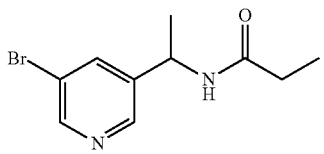

At 0° C., propionyl chloride (138 mg, 1.5 mmol) was added dropwise to a solution of (rac)-1-(5-bromo-pyridin-3-yl)-ethylamine (201 mg, 1 mmol) and Et₃N (153 mg, 1.5 mmol) in DCM (10 mL). The reaction mixture was stirred at room temperature for 1 hour before it was concentrated to dryness. The residue was redissolved in EtOAc and washed with water and brine, dried over anhydrous Na₂SO₄, filtered and concentrated in vacuo. The residue was purified by flash column chromatography to give the title compound (200 mg, 78%).

[E] (rac)-N-{1-[5-(7-Fluoro-1-methyl-2-oxo-1,2,3,4-tetrahydro-quinolin-6-yl)-pyridin-3-yl]-ethyl}-propionamide

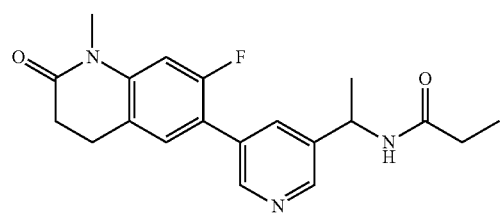 [SMILES: CCC(=O)NC(C)c1cncc(-c2cc3c(cc2F)N(C)C(=O)CC3)c1]

To a mixture of 7-fluoro-1-methyl-6-(4,4,5,5-tetramethyl-[1,3,2]dioxaborolan-2-yl)-3,4-dihydro-1H-quinolin-2-one (intermediate A-22, 168 g, 0.55 mmol) and (rac)-N-[1-(5-bromo-pyridin-3-yl)-ethyl]-propionamide (125 mg, 0.5 mmol) in DMF (3 mL), purged with argon for 1 min, was added bis(triphenylphosphine)palladium(II)chloride (38 mg, 0.054 mmol) and 1 N aq. Na₂CO₃ (2.5 mL). Then, the resulting reaction mixture was heated in a microwave at 100° C. for 45 min. After cooling to room temperature, it was diluted with EtOAc (5 mL), and poured into satd. aq. solution of NaHCO₃ (10 mL). The aqueous layer was extracted with EtOAc (3×5 mL) and combined organics were washed with water and brine (20 mL), dried over anhydrous Na₂SO₄, filtered and concentrated in vacuo. The residue was the purified by prep-HPLC to give the title compound (35 mg, 20%) as a white solid. MS: 356.3 (M+H⁺)⁺.

Example 214

(S)-3-[5-(2-oxo-1,2,3,4-tetrahydro-quinolin-6-yl)-pyridin-3-yloxy]-pyrrolidine-1-carboxylic acid tert-butyl ester

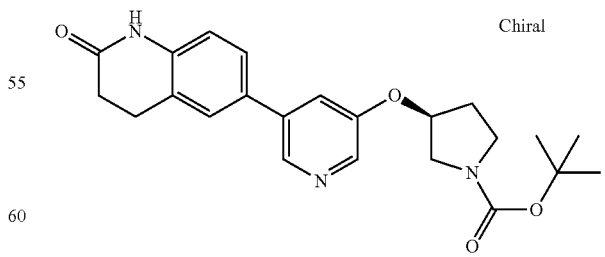

In analogy to the procedure described for the preparation of example 45, 6-(4,4,5,5-tetramethyl-1,3,2-dioxaborolan-2-yl)-3,4-dihydroquinolin-2(1H)-one (intermediate A-34) has been coupled to (S)-3-(5-bromo-pyridin-3-yloxy)-pyrrolidine-1-carboxylic acid tert-butyl ester (intermediate A-29) to give the title compound as a dark grey amorphous solid. MS: 410.6 (M+H+).

Example 215

3-Chloro-pyridine-2-carboxylic acid methyl-[5-(2-oxo-1,2,3,4-tetrahydro-quinolin-6-yl)-pyridin-3-ylmethyl]-amide

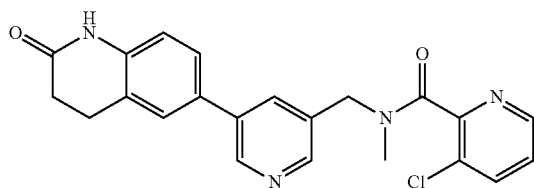 [SMILES: CN(Cc1cncc(-c2ccc3c(c2)CCC(=O)N3)c1)C(=O)c1ncccc1Cl]

In analogy to the procedure described for the preparation of example 45, 6-(4,4,5,5-tetramethyl-1,3,2-dioxaborolan-2-yl)-3,4-dihydroquinolin-2(1H)-one (intermediate A-34) has been coupled to N-((5-bromopyridin-3-yl)methyl)-3-chloro-N-methylpicolinamide (intermediate A-57) to give the title compound as a light brown amorphous solid. MS: 407.5 (M+H+).

Example 216

3-Chloro-pyridine-2-carboxylic acid [5-(8-chloro-2-oxo-1,2,3,4-tetrahydro-quinolin-6-yl)-pyridin-3-ylmethyl]-methyl-amide

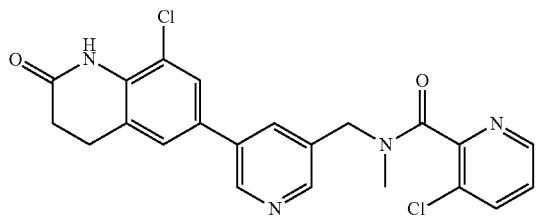 [SMILES: CN(Cc1cncc(-c2cc(Cl)c3c(c2)CCC(=O)N3)c1)C(=O)c1ncccc1Cl]

In analogy to the procedure described for the preparation of example 203, 3-chloro-pyridine-2-carboxylic acid methyl-[5-(2-oxo-1,2,3,4-tetrahydro-quinolin-6-yl)-pyridin-3-ylmethyl]-amide (example 215) was reacted with N-chloro-succinimide to give the title compound as a light brown solid. MS: 441.5 (M+H+).

Example 217

(R)-2-Methyl-propane-2-sulfinic acid [4-chloro-5-(1-methyl-2-oxo-1,2,3,4-tetrahydro-quinolin-6-yl)-pyridin-3-ylmethyl]-amide

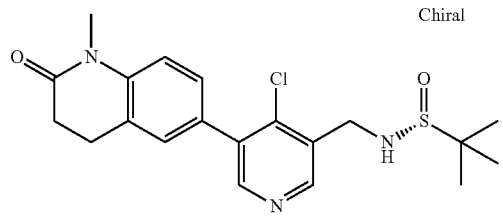 [SMILES: CN1C(=O)CCc2cc(-c3cncc(CN[S@](=O)C(C)(C)C)c3Cl)ccc21]

In analogy to the procedure described for the preparation of example 45, 1-methyl-6-(4,4,5,5-tetramethyl-[1,3,2]dioxaborolan-2-yl)-3,4-dihydro-1H-quinolin-2-one (intermediate A-1) has been coupled to (R)—N-((5-bromo-4-chloropyridin-3-yl)methyl)-2-methylpropane-2-sulfinamide (intermediate A-58) to give the title compound as an orange solid. MS: 406.4 (M+H+).

Example 218

6-(5-Aminomethyl-4-chloro-pyridin-3-yl)-1-methyl-3,4-dihydro-1H-quinolin-2-one hydrochloride

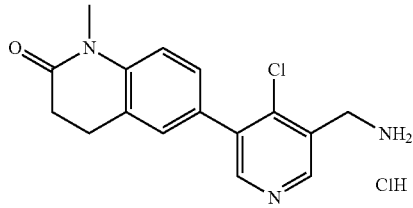 [SMILES: CN1C(=O)CCc2cc(-c3cncc(CN)c3Cl)ccc21 ; Cl]

In analogy to the procedure described for the preparation of example 42, reaction of (R)-2-methyl-propane-2-sulfinic acid [4-chloro-5-(1-methyl-2-oxo-1,2,3,4-tetrahydro-quinolin-6-yl)-pyridin-3-ylmethyl]-amide (example 217) with hydrogen chloride (in dixoane) in methanol gave the title compound as a yellow solid. MS: 302.4 (M+H+).

Example 219

3,5-Dimethyl-isoxazole-4-carboxylic acid [4-chloro-5-(1-methyl-2-oxo-1,2,3,4-tetrahydro-quinolin-6-yl)-pyridin-3-ylmethyl]-amide

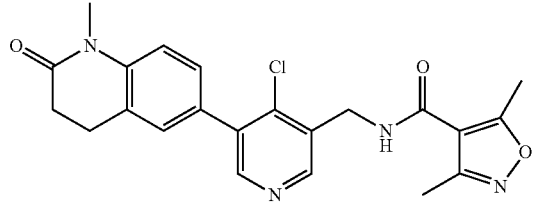 [SMILES: Cc1noc(C)c1C(=O)NCc1cncc(-c2ccc3c(c2)CCC(=O)N3C)c1Cl]

To a solution of 6-(5-aminomethyl-4-chloro-pyridin-3-yl)-1-methyl-3,4-dihydro-1H-quinolin-2-one hydrochloride (example 218, 0.05 g, 0.148 mmol) in dry DMF (1 mL) were added EDCI (0.034 g, 0.077 mmol), hydroxybenzotriazole (0.017 g, 0.077 mmol), Hünig's base (0.057 g, 0.443 mmol) and 3,5-dimethyl-isoxazole-4-carboxylic acid (0.021 g, 0.148 mmol) and the resulting solution was stirred at room temperature for 2 h. The reaction mixture was diluted with EtOAc, poured into sat. NaHCO3 solution (10 mL) and extracted with EtOAc (2×20 mL). Combined organics were dried over Na2SO4, filtered and evaporated to dryness. The residue was purified by silica gel flash chromatography eluting with a 0 to 5% MeOH-DCM gradient to give the title compound (0.03 g, 48%) as a colorless solid. MS: 425.4 (M+H+).

Example 220

3-Chloro-pyridine-2-carboxylic acid [4-chloro-5-(1-methyl-2-oxo-1,2,3,4-tetrahydro-quinolin-6-yl)-pyridin-3-ylmethyl]-amide

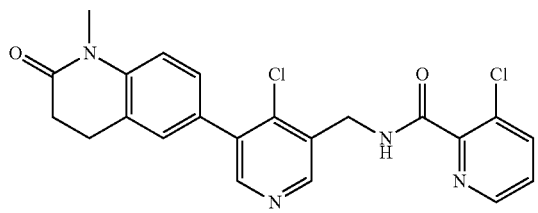

In analogy to the procedure described for the preparation of example 75, 6-(5-aminomethyl-4-chloro-pyridin-3-yl)-1-methyl-3,4-dihydro-1H-quinolin-2-one hydrochloride (example 218) has been coupled with 3-chloro-pyridine-2-carboxylic acid to give the title compound as an off-white solid. MS: 441.3 (M+H$^+$).

Example 221

(R)-2-Methyl-propane-2-sulfinic acid [4-methyl-5-(1-methyl-2-oxo-1,2,3,4-tetrahydro-quinolin-6-yl)-pyridin-3-ylmethyl]-amide

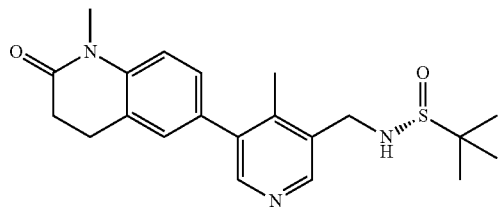 [SMILES: Cc1c(CN[S@](=O)C(C)(C)C)cncc1-c1ccc2c(c1)CCC(=O)N2C]

In analogy to the procedure described for the preparation of example 45, 1-methyl-6-(4,4,5,5-tetramethyl-[1,3,2]dioxaborolan-2-yl)-3,4-dihydro-1H-quinolin-2-one (intermediate A-1) has been coupled to (R)-2-methyl-propane-2-sulfinic acid (5-bromo-4-methyl-pyridin-3-ylmethyl)-amide (intermediate A-59) to give the title compound as a colorless amorphous solid. MS: 386.5 (M+H$^+$).

Example 222

6-(5-Aminomethyl-4-methyl-pyridin-3-yl)-1-methyl-3,4-dihydro-1H-quinolin-2-one hydrochloride

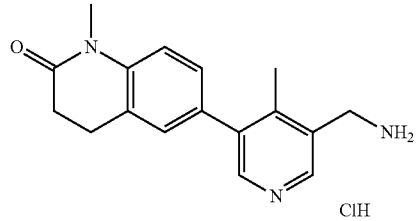 [SMILES: Cc1c(CN)cncc1-c1ccc2c(c1)CCC(=O)N2C ; Cl]

In analogy to the procedure described for the preparation of example 42, reaction of (R)-2-methyl-propane-2-sulfinic acid [4-methyl-5-(1-methyl-2-oxo-1,2,3,4-tetrahydro-quinolin-6-yl)-pyridin-3-ylmethyl]-amide (example 221) with hydrogen chloride (in dixoane) in methanol gave the title compound as a yellow solid. MS: 282.5 (M+H$^+$).

Example 223

3,5-Dimethyl-isoxazole-4-carboxylic acid [4-methyl-5-(1-methyl-2-oxo-1,2,3,4-tetrahydro-quinolin-6-yl)-pyridin-3-ylmethyl]-amide

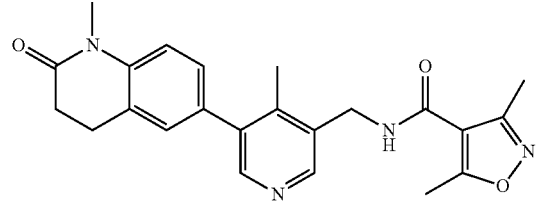 [SMILES: Cc1noc(C)c1C(=O)NCc1cncc(-c2ccc3c(c2)CCC(=O)N3C)c1C]

In analogy to the procedure described for the preparation of example 219, 6-(5-aminomethyl-4-methyl-pyridin-3-yl)-1-methyl-3,4-dihydro-1H-quinolin-2-one hydrochloride (example 222) has been coupled with 3,5-dimethyl-isoxazole-4-carboxylic acid to give the title compound as an off-white solid. MS: 405.5 (M+H$^+$).

Example 224

3-Chloro-pyridine-2-carboxylic acid [4-methyl-5-(1-methyl-2-oxo-1,2,3,4-tetrahydro-quinolin-6-yl)-pyridin-3-ylmethyl]-amide

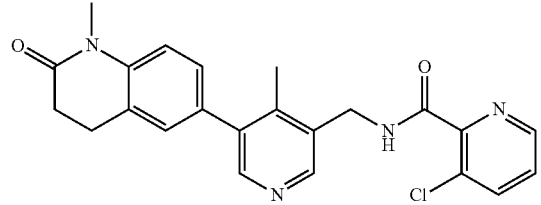 [SMILES: Cc1c(CNC(=O)c2ncccc2Cl)cncc1-c1ccc2c(c1)CCC(=O)N2C]

In analogy to the procedure described for the preparation of example 75, 6-(5-aminomethyl-4-methyl-pyridin-3-yl)-1-methyl-3,4-dihydro-1H-quinolin-2-one hydrochloride (example 222) has been coupled with 3-chloro-pyridine-2-carboxylic acid to give the title compound as a colorless solid. MS: 421.5 (M+H$^+$).

Example 225

(R)-2-Methyl-propane-2-sulfinic acid [5-(7-fluoro-1-methyl-2-oxo-1,2,3,4-tetrahydro-quinolin-6-yl)-4-methyl-pyridin-3-ylmethyl]-amide

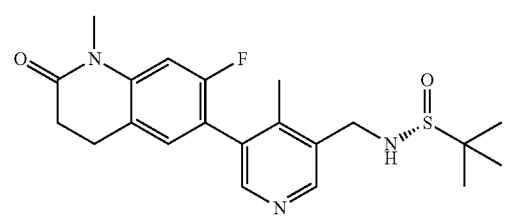 [SMILES: Cc1c(CN[S@](=O)C(C)(C)C)cncc1-c1cc2c(cc1F)N(C)C(=O)CC2]

In analogy to the procedure described for the preparation of example 45, 7-fluoro-1-methyl-6-(4,4,5,5-tetramethyl-[1,3,2]dioxaborolan-2-yl)-3,4-dihydro-1H-quinolin-2-one (intermediate A-22) has been coupled to (R)-2-methyl-propane-2-sulfinic acid (5-bromo-4-methyl-pyridin-3-ylmethyl)-amide (intermediate A-59) to give the title compound as a brown amorphous solid. MS: 404.5 (M+H⁺).

Example 226

6-(5-Aminomethyl-4-methyl-pyridin-3-yl)-7-fluoro-1-methyl-3,4-dihydro-1H-quinolin-2-one hydrochloride

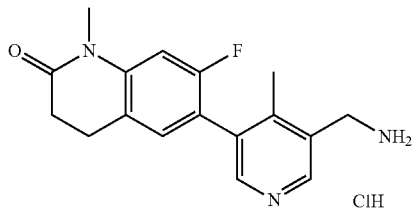 [SMILES: Cc1c(CN)cncc1-c1cc2c(cc1F)N(C)C(=O)CC2 ; Cl]

In analogy to the procedure described for the preparation of example 42, reaction of (R)-2-methyl-propane-2-sulfinic acid [5-(7-fluoro-1-methyl-2-oxo-1,2,3,4-tetrahydro-quinolin-6-yl)-4-methyl-pyridin-3-ylmethyl]-amide (example 225) with hydrogen chloride (in dixoane) in methanol gave the title compound as a light brown solid. MS: 300.5 (M+H⁺).

Example 227

3-Chloro-pyridine-2-carboxylic acid [5-(7-fluoro-1-methyl-2-oxo-1,2,3,4-tetrahydro-quinolin-6-yl)-4-methyl-pyridin-3-ylmethyl]-amide

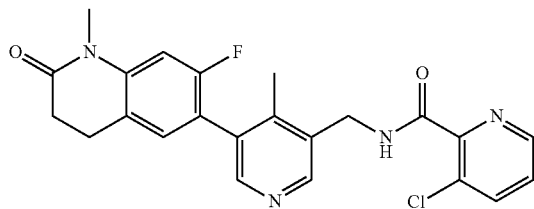 [SMILES: Cc1c(CNC(=O)c2ncccc2Cl)cncc1-c1cc2c(cc1F)N(C)C(=O)CC2]

In analogy to the procedure described for the preparation of example 75, 6-(5-aminomethyl-4-methyl-pyridin-3-yl)-7-fluoro-1-methyl-3,4-dihydro-1H-quinolin-2-one hydrochloride (example 226) has been coupled with 3-chloro-pyridine-2-carboxylic acid to give the title compound as a colorless solid. MS: 439.4 (M+H⁺).

Example 228

3-Chloro-pyridine-2-carboxylic acid [4-chloro-5-(1-methyl-2-oxo-1,2,3,4-tetrahydro-quinolin-6-yl)-pyridin-3-ylmethyl]-methyl-amide

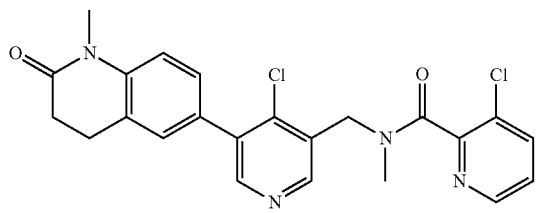 [SMILES: CN(Cc1cncc(-c2ccc3c(c2)CCC(=O)N3C)c1Cl)C(=O)c1ncccc1Cl]

In analogy to the procedure described for the preparation of example 195, 3-chloro-pyridine-2-carboxylic acid [4-chloro-5-(1-methyl-2-oxo-1,2,3,4-tetrahydro-quinolin-6-yl)-pyridin-3-ylmethyl]-amide (example 220) has been reacted with sodium hydride and methyl iodide to give the title compound as off-white solid. MS: 455.1 (M+H⁺).

Example 229

3-Chloro-pyridine-2-carboxylic acid methyl-[4-methyl-5-(1-methyl-2-oxo-1,2,3,4-tetrahydro-quinolin-6-yl)-pyridin-3-ylmethyl]-amide

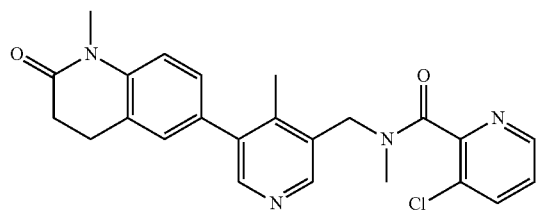 [SMILES: Cc1c(CN(C)C(=O)c2ncccc2Cl)cncc1-c1ccc2c(c1)CCC(=O)N2C]

In analogy to the procedure described for the preparation of example 195, 3-chloro-pyridine-2-carboxylic acid [4-methyl-5-(1-methyl-2-oxo-1,2,3,4-tetrahydro-quinolin-6-yl)-pyridin-3-ylmethyl]-amide (example 224) has been reacted with sodium hydride and methyl iodide to give the title compound as light brown amorphous solid. MS: 435.5 (M+H⁺).

Example 230

3-Chloro-pyridine-2-carboxylic acid {(R or S)-1-[5-(1-methyl-2-oxo-1,2,3,4-tetrahydro-quinolin-6-yl)-pyridin-3-yl]-ethyl}-amide

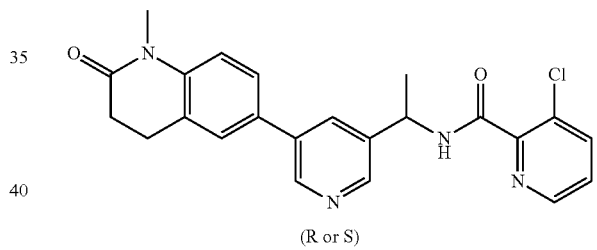

(R or S)

In analogy to the procedures described for the preparation of example 74, 6-[5-((R or S)-1-amino-ethyl)-pyridin-3-yl]-1-methyl-3,4-dihydro-1H-quinolin-2-one hydrochloride (example 65) has been coupled with 3-chloro-pyridine-2-carboxylic acid to give the title compound as a colorless solid. MS: 421.4 (M+H⁺).

Example 231

5'-(1-Methyl-2-oxo-1,2,3,4-tetrahydro-quinolin-6-yl)-5,6-dihydro-4H-[3,3']bipyridinyl-1-carboxylic acid tert-butyl ester

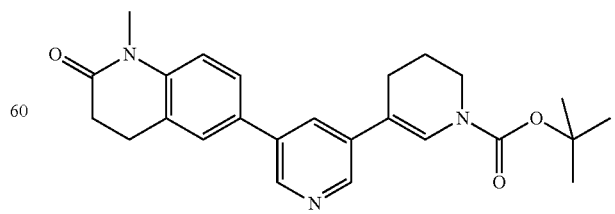

In analogy to the procedure described for the preparation of example 45, 6-(5-bromo-pyridin-3-yl)-1-methyl-3,4-dihydro-1H-quinolin-2-one (prepared from 1-methyl-6-(4,4,5,5- tetramethyl-[1,3,2]dioxaborolan-2-yl)-3,4-dihydro-1H-quinolin-2-one (intermediate A-1) and 3,5-dibromo pyridine also with a procedure as used for the preparation of example 45) has been coupled to 5-(4,4,5,5-tetramethyl-[1,3,2]dioxaborolan-2-yl)-3,4-dihydro-2H-pyridine-1-carboxylic acid tert-butyl ester to give the title compound as an amorphous colorless solid. MS: 420.5 (M+H$^+$).

Example 232

{2-[5-(7-Fluoro-1-methyl-2-oxo-1,2,3,4-tetrahydro-quinolin-6-yl)-pyridin-3-yloxy]-ethyl}-carbamic acid tert-butyl ester

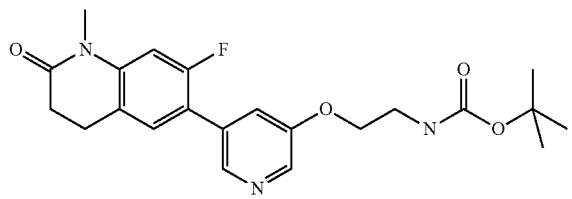 [SMILES: CN1C(=O)CCc2cc(-c3cncc(OCCNC(=O)OC(C)(C)C)c3)c(F)cc21]

In analogy to the procedure described for the preparation of example 45, 7-fluoro-1-methyl-6-(4,4,5,5-tetramethyl-[1,3,2]dioxaborolan-2-yl)-3,4-dihydro-1H-quinolin-2-one (intermediate A-22) has been coupled to [2-(5-bromo-pyridin-3-yloxy)-ethyl]-carbamic acid tert-butyl ester (intermediate A-7) to give the title compound as a yellow waxy solid. MS: 416.4 (M+H$^+$).

Example 233

3-Chloro-pyridine-2-carboxylic acid {2-[5-(1-methyl-2-oxo-1,2,3,4-tetrahydro-quinolin-6-yl)-pyridin-3-yloxy]-ethyl}-amide

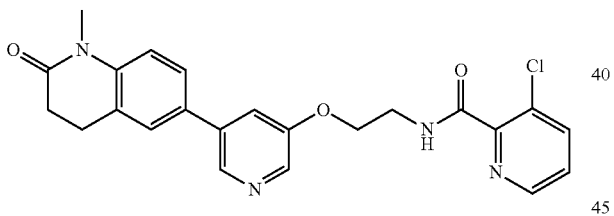

In analogy to the procedure described for the preparation of example 75, 6-[5-(2-amino-ethoxy)-pyridin-3-yl]-1-methyl-3,4-dihydro-1H-quinolin-2-one hydrochloride (example 42) has been coupled with 3-chloro-pyridine-2-carboxylic acid to give the title compound as a light yellow viscous oil. MS: 437.4 (M+H$^+$).

Example 234

Ethanesulfonic acid [5-(4-oxo-1,2,5,6-tetrahydro-4H-pyrrolo[3,2,1-ij]quinolin-8-yl)-pyridin-3-ylmethyl]-amide

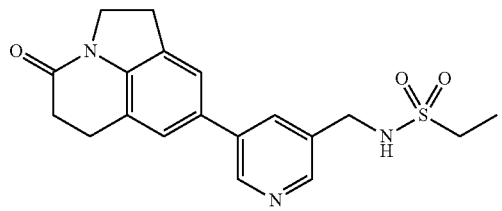 [SMILES: CCS(=O)(=O)NCc1cncc(-c2cc3c4c(c2)CCN4C(=O)CC3)c1]

In analogy to the procedure described for the preparation of example 45, 8-(4,4,5,5-tetramethyl-1,3,2-dioxaborolan-2-yl)-5,6-dihydro-1H-pyrrolo[3,2,1-ij]quinolin-4(2H)-one has been coupled to ethanesulfonic acid (5-bromo-pyridin-3-ylmethyl)-amide (intermediate A-11) to give the title compound as a colorless amorphous solid. MS: 372.2 (M+H$^+$).

Example 235

Ethanesulfonic acid [5-(3-oxo-2,3,6,7-tetrahydro-1H,5H-pyrido[3,2,1-ij]quinolin-9-yl)-pyridin-3-ylm-ethyl]-amide

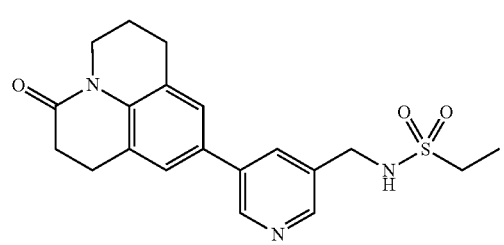 [SMILES: CCS(=O)(=O)NCc1cncc(-c2cc3c4c(c2)CCC(=O)N4CCC3)c1]

In analogy to the procedure described for the preparation of example 45, 9-(4,4,5,5-tetramethyl-1,3,2-dioxaborolan-2-yl)-1,2,6,7-tetrahydropyrido[3,2,1-ij]quinolin-3(5H)-one (prepared from 9-bromo-1,2,6,7-tetrahydropyrido[3,2,1-ij]quinolin-3(51H)-one and 4,4,4',4',5,5,5',5'-octamethyl-2,2'-bi(1,3,2-dioxaborolane) in analogy to the procedure described for the preparation of intermediate A-1 [B]) has been coupled to ethanesulfonic acid (5-bromo-pyridin-3-ylmethyl)-amide (intermediate A-11) to give the title compound as an off-white amorphous solid. MS: 386.2 (M+H$^+$).

Example 236

3-Chloro-pyridine-2-carboxylic acid [5-(4-oxo-1,2,5,6-tetrahydro-4H-pyrrolo[3,2,1-ij]quinolin-8-yl)-pyridin-3-ylmethyl]-amide

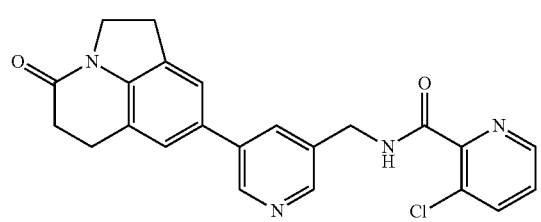 [SMILES: O=C(NCc1cncc(-c2cc3c4c(c2)CCN4C(=O)CC3)c1)c1ncccc1Cl]

In analogy to the procedure described for the preparation of example 45, 8-(4,4,5,5-tetramethyl-1,3,2-dioxaborolan-2-yl)-5,6-dihydro-1H-pyrrolo[3,2,1-ij]quinolin-4(2H)-one has been coupled to N-((5-bromopyridin-3-yl)methyl)-3-chloropicolinamide (intermediate A-56) to give the title compound as off-white solid. MS: 419.3 (M+H$^+$).

Example 237

3-Chloro-pyridine-2-carboxylic acid methyl-[5-(4-oxo-1,2,5,6-tetrahydro-4H-pyrrolo[3,2,1-ij]quinolin-8-yl)-pyridin-3-ylmethyl]-amide

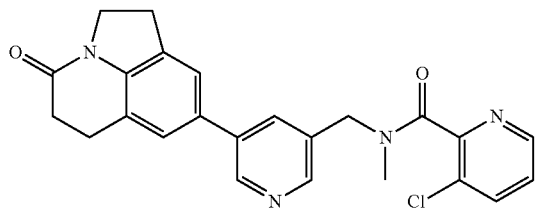 [SMILES: CN(Cc1cncc(-c2cc3c4c(c2)CCN4C(=O)CC3)c1)C(=O)c1ncccc1Cl]

In analogy to the procedure described for the preparation of example 195, N-methylation of 3-chloro-pyridine-2-carboxylic acid [5-(4-oxo-1,2,5,6-tetrahydro-4H-pyrrolo[3,2,1-ij]quinolin-8-yl)-pyridin-3-ylmethyl]-amide (example 236) gave the title compound as a light yellow solid. MS: 433.4 (M+H$^+$).

Example 238

6-[5-(2-Amino-ethoxy)-pyridin-3-yl]-7-fluoro-1-methyl-3,4-dihydro-1H-quinolin-2-one hydrochloride

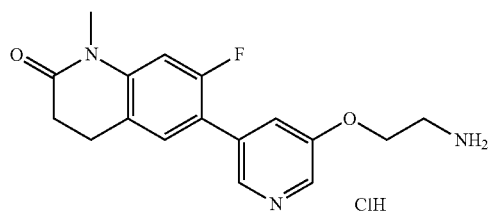 [SMILES: CN1C(=O)CCc2cc(-c3cncc(OCCN)c3)c(F)cc21 ; Cl]

In analogy to the procedure described for the preparation of example 42, reaction of {2-[5-(7-fluoro-1-methyl-2-oxo-1,2,3,4-tetrahydro-quinolin-6-yl)-pyridin-3-yloxy]-ethyl}-carbamic acid tert-butyl ester (example 232) with hydrogen chloride (in dixoane) in methanol gave the title compound as light yellow solid. MS: 316.5 (M+H$^+$).

Example 239

(R)-2-Methyl-propane-2-sulfinic acid {(R or S)-1-[4-methyl-5-(1-methyl-2-oxo-1,2,3,4-tetrahydro-quinolin-6-yl)-pyridin-3-yl]-ethyl}-amide

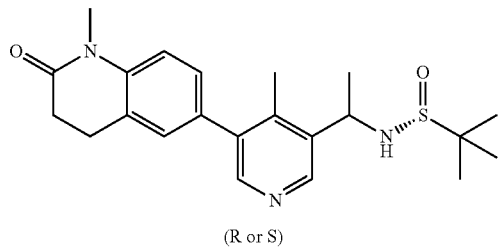 [SMILES: Cc1c(-c2ccc3c(c2)CCC(=O)N3C)cncc1C(C)N[S@](=O)C(C)(C)C]

In analogy to the procedure described for the preparation of example 45, reaction of 1-methyl-6-(4,4,5,5-tetramethyl-[1,3,2]dioxaborolan-2-yl)-3,4-dihydro-1H-quinolin-2-one (intermediate A-1) with (R)-2-methyl-propane-2-sulfinic acid [(R or S)-1-(5-bromo-4-methyl-pyridin-3-yl)-ethyl]-amide (intermediate A-60) gave the title compound as a dark brown amorphous solid. MS: 400.5 (M+H$^+$).

Example 240

6-[5-((R or S)-1-Amino-ethyl)-4-methyl-pyridin-3-yl]-1-methyl-3,4-dihydro-1H-quinolin-2-one hydrochloride

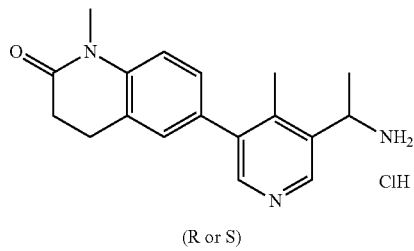 [SMILES: Cc1c(-c2ccc3c(c2)CCC(=O)N3C)cncc1C(C)N ; Cl]

In analogy to the procedure described for the preparation of example 42, reaction of (R)-2-methyl-propane-2-sulfinic acid {(R or S)-1-[4-methyl-5-(1-methyl-2-oxo-1,2,3,4-tetrahydro-quinolin-6-yl)-pyridin-3-yl]-ethyl}-amide (example 239) with hydrogen chloride (in dixoane) in methanol gave the title compound as light brown solid. MS: 296.5 (M+H$^+$).

Example 241

3-Chloro-pyridine-2-carboxylic acid {(R or S)-1-[4-methyl-5-(1-methyl-2-oxo-1,2,3,4-tetrahydro-quinolin-6-yl)-pyridin-3-yl]-ethyl}-amide

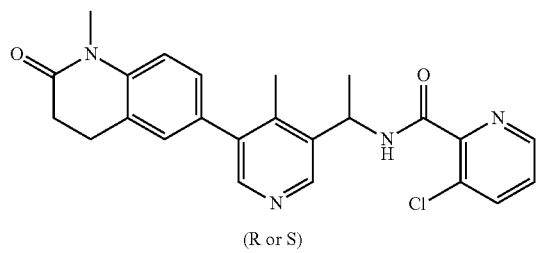 [SMILES: Cc1c(-c2ccc3c(c2)CCC(=O)N3C)cncc1C(C)NC(=O)c1ncccc1Cl]

In analogy to the procedure described for the preparation of example 75, 6-[5-((R or S)-1-amino-ethyl)-4-methyl-pyridin-3-yl]-1-methyl-3,4-dihydro-1H-quinolin-2-one hydrochloride (example 240) has been coupled with 3-chloro-pyridine-2-carboxylic acid to give the title compound as a colorless solid. MS: 435.6 (M+H$^+$).

Example 242

3,5-Dimethyl-isoxazole-4-carboxylic acid {(R or S)-1-[4-methyl-5-(1-methyl-2-oxo-1,2,3,4-tetrahydro-quinolin-6-yl)-pyridin-3-yl]-ethyl}-amide

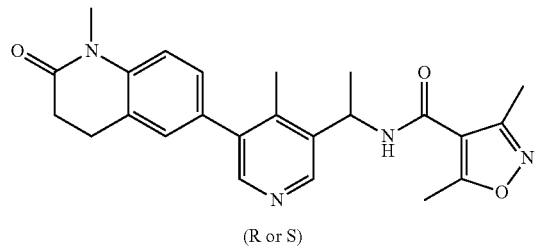 [SMILES: Cc1noc(C)c1C(=O)NC(C)c1cncc(-c2ccc3c(c2)CCC(=O)N3C)c1C]

In analogy to the procedure described for the preparation of example 219, 6-[5-((R or S)-1-amino-ethyl)-4-methyl-pyridin-3-yl]-1-methyl-3,4-dihydro-1H-quinolin-2-one hydrochloride (example 240) has been coupled with 3,5-dimethylisoxazole-4-carboxylic acid to give the title compound as a colorless amorphous solid. MS: 419.6 (M+H⁺).

Example 243

Ethanesulfonic acid {2-[5-(7-fluoro-1-methyl-2-oxo-1,2,3,4-tetrahydro-quinolin-6-yl)-pyridin-3-yloxy]-ethyl}-amide

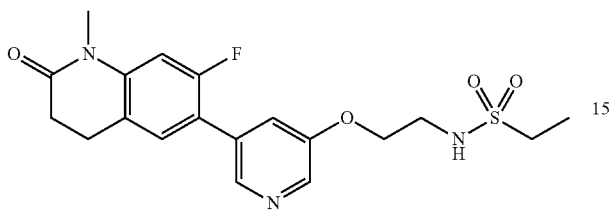

In analogy to the procedure described for the preparation of example 38, 6-[5-(2-amino-ethoxy)-pyridin-3-yl]-7-fluoro-1-methyl-3,4-dihydro-1H-quinolin-2-one hydrochloride (example 238) and ethanesulfonyl chloride gave the title compound as an orange amorphous solid. MS: 408.4 (M+H⁺).

Example 244

3-Chloro-pyridine-2-carboxylic acid {2-[5-(7-fluoro-1-methyl-2-oxo-1,2,3,4-tetrahydro-quinolin-6-yl)-pyridin-3-yloxy]-ethyl}-amide

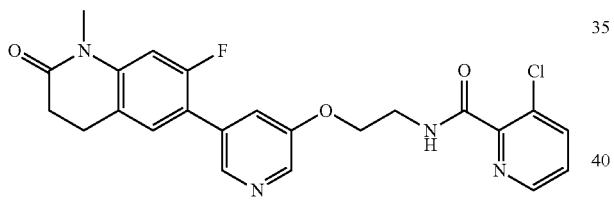

In analogy to the procedure described for the preparation of example 75, 6-[5-(2-amino-ethoxy)-pyridin-3-yl]-7-fluoro-1-methyl-3,4-dihydro-1H-quinolin-2-one hydrochloride (example 238) has been coupled with 3-chloro-pyridine-2-carboxylic acid to give the title compound as an off-white solid. MS: 455.3 (M+H⁺).

Example 245

N-{(trans)-4-[5-(1-Methyl-2-oxo-1,2,3,4-tetrahydro-quinolin-6-yl)-pyridin-3-yloxy]-cyclohexyl}-methanesulfonamide

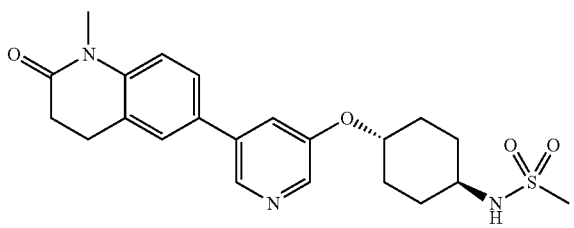 [SMILES: CN1C(=O)CCc2cc(-c3cncc(O[C@H]4CC[C@H](NS(C)(=O)=O)CC4)c3)ccc21]

In analogy to the procedure described for the preparation of example 38, 6-[5-((trans)-4-amino-cyclohexyloxy)-pyridin-3-yl]-1-methyl-3,4-dihydro-1H-quinolin-2-one hydrochloride (example 71) and methanesulfonyl chloride gave the title compound as a light yellow amorphous solid. MS: 430.4 (M+H⁺).

Example 246

3,5-Dimethyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide

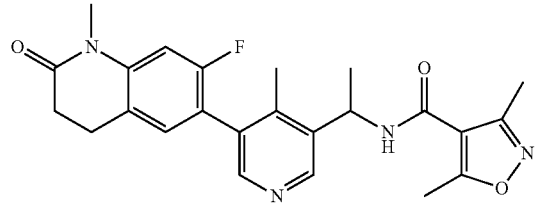 [SMILES: Cc1noc(C)c1C(=O)NC(C)c1cncc(-c2cc3c(cc2F)N(C)C(=O)CC3)c1C]

In analogy to the procedure described for the preparation of example 219, 6-(5-aminomethyl-4-methyl-pyridin-3-yl)-7-fluoro-1-methyl-3,4-dihydro-1H-quinolin-2-one hydrochloride (example 226) has been coupled with 3,5-dimethyl-isoxazole-4-carboxylic acid to give the title compound as a colorless solid. MS: 423.6 (M+H⁺).

Example 247

5-(1-Methyl-2-oxo-1,2,3,4-tetrahydro-quinolin-6-yl)-3',6'-dihydro-2'H-[3,4']bipyridinyl-1'-carboxylic acid tert-butyl ester

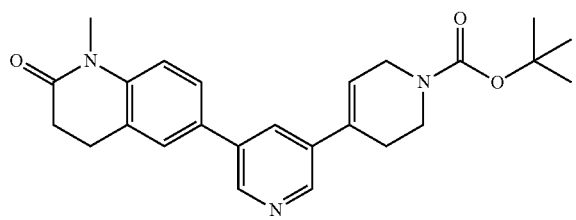

In analogy to the procedure described for the preparation of example 45, 6-(5-bromo-pyridin-3-yl)-1-methyl-3,4-dihydro-1H-quinolin-2-one (prepared from 1-methyl-6-(4,4,5,5-tetramethyl-[1,3,2]dioxaborolan-2-yl)-3,4-dihydro-1H-quinolin-2-one (intermediate A-1) and 3,5-dibromo pyridine also with a procedure as used for the preparation of example 45) has been coupled to 4-(4,4,5,5-tetramethyl-[1,3,2]dioxaborolan-2-yl)-3,6-dihydro-2H-pyridine-1-carboxylic acid tert-butyl ester to give the title compound as light yellow amorphous solid. MS: 420.5 (M+H⁺).

Example 248

Ethanesulfonic acid {2-[5-(7-fluoro-1-methyl-2-oxo-1,2,3,4-tetrahydro-quinolin-6-yl)-pyridin-3-yloxy]-ethyl}-methyl-amide

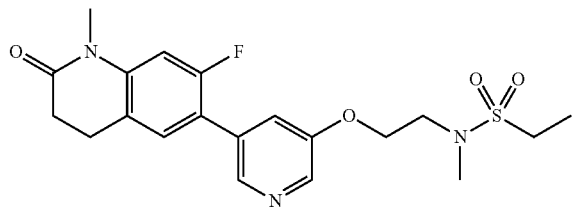 [SMILES: CCS(=O)(=O)N(C)CCOc1cncc(-c2cc3c(cc2F)N(C)C(=O)CC3)c1]

In analogy to the procedure described for the preparation of example 195, ethanesulfonic acid {2-[5-(7-fluoro-1-methyl-2-oxo-1,2,3,4-tetrahydro-quinolin-6-yl)-pyridin-3-yloxy]-ethyl}-amide (example 243) has been reacted with sodium hydride and methyl iodide to give the title compound as orange amorphous solid. MS: 422.4 (M+H$^+$).

Example 249

(R)-2-Methyl-propane-2-sulfinic acid {(R or S)-1-[4-chloro-5-(1-methyl-2-oxo-1,2,3,4-tetrahydro-quinolin-6-yl)-pyridin-3-yl]-ethyl}-amide

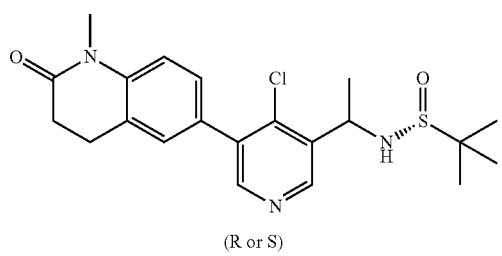 [SMILES: CC(N[S@](=O)C(C)(C)C)c1cncc(-c2ccc3c(c2)CCC(=O)N3C)c1Cl]
(R or S)

In analogy to the procedure described for the preparation of example 45, reaction of 1-methyl-6-(4,4,5,5-tetramethyl-[1,3,2]dioxaborolan-2-yl)-3,4-dihydro-1H-quinolin-2-one (intermediate A-1) with (R)-2-methyl-propane-2-sulfinic acid [(R or S)-1-(5-bromo-4-chloro-pyridin-3-yl)-ethyl]-amide (intermediate A-61) gave the title compound as a colorless amorphous solid. MS: 420.4 (M+H$^+$).

Example 250

6-[5-((R or S)-1-Amino-ethyl)-4-chloro-pyridin-3-yl]-1-methyl-3,4-dihydro-1H-quinolin-2-one hydrochloride

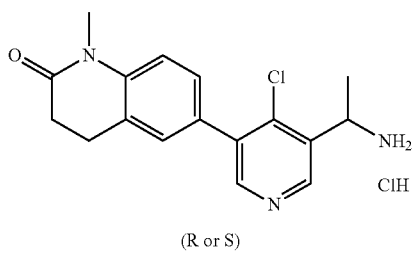 [SMILES: CC(N)c1cncc(-c2ccc3c(c2)CCC(=O)N3C)c1Cl ; Cl]
(R or S)

In analogy to the procedure described for the preparation of example 42, reaction of (R)-2-methyl-propane-2-sulfinic acid {(R or S)-1-[4-chloro-5-(1-methyl-2-oxo-1,2,3,4-tetrahydro-quinolin-6-yl)-pyridin-3-yl]-ethyl}-amide (example 249) with hydrogen chloride (in dioxane) in methanol gave the title compound as yellow solid. MS: 316.4 (M+H$^+$).

Example 251

3-Chloro-pyridine-2-carboxylic acid {(R or S)-1-[4-chloro-5-(1-methyl-2-oxo-1,2,3,4-tetrahydro-quinolin-6-yl)-pyridin-3-yl]-ethyl}-amide

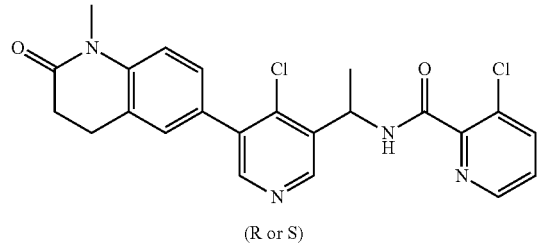 [SMILES: CC(NC(=O)c1ncccc1Cl)c1cncc(-c2ccc3c(c2)CCC(=O)N3C)c1Cl]
(R or S)

In analogy to the procedure described for the preparation of example 75, 6-[5-((R or S)-1-amino-ethyl)-4-chloro-pyridin-3-yl]-1-methyl-3,4-dihydro-1H-quinolin-2-one hydrochloride (example 250) has been coupled with 3-chloro-pyridine-2-carboxylic acid to give the title compound as a colorless solid. MS: 455.5 (M+H$^+$).

Example 252

(R)-2-Methyl-propane-2-sulfinic acid {(R or S)-1-[5-(7-fluoro-1-methyl-2-oxo-1,2,3,4-tetrahydro-quinolin-6-yl)-4-methyl-pyridin-3-yl]-ethyl}-amide

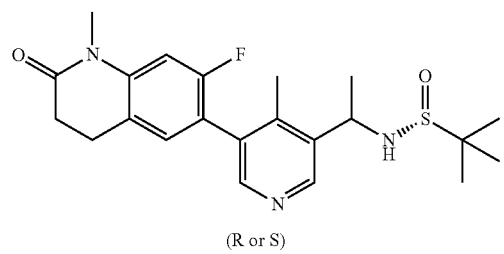 [SMILES: Cc1c(-c2cc3c(cc2F)N(C)C(=O)CC3)cncc1C(C)N[S@](=O)C(C)(C)C]
(R or S)

In analogy to the procedure described for the preparation of example 45, reaction of 7-fluoro-1-methyl-6-(4,4,5,5-tetramethyl-[1,3,2]dioxaborolan-2-yl)-3,4-dihydro-1H-quinolin-2-one (intermediate A-22) with (R)-2-methyl-propane-2-sulfinic acid [(R or S)-1-(5-bromo-4-methyl-pyridin-3-yl)-ethyl]-amide (intermediate A-60) gave the title compound as a yellow amorphous solid. MS: 418.5 (M+H$^+$).

Example 253

6-[5-((R or S)-1-Amino-ethyl)-4-methyl-pyridin-3-yl]-7-fluoro-1-methyl-3,4-dihydro-1H-quinolin-2-one hydrochloride

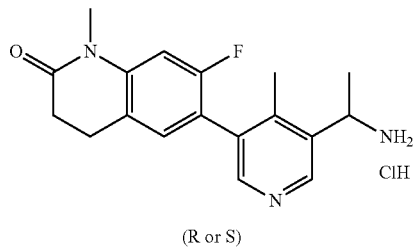 [SMILES: Cc1c(-c2cc3c(cc2F)N(C)C(=O)CC3)cncc1C(C)N ; Cl]
(R or S)

In analogy to the procedure described for the preparation of example 42, reaction of (R)-2-methyl-propane-2-sulfinic acid {(R or S)-1-[5-(7-fluoro-1-methyl-2-oxo-1,2,3,4-tetrahydro-quinolin-6-yl)-4-methyl-pyridin-3-yl]-ethyl}-amide (example 252) with hydrogen chloride (in dixoane) in methanol gave the title compound as light brown solid. MS: 314.5 (M+H⁺).

Example 254

6-[5-((S)-1-Acetyl-pyrrolidin-3-yloxy)-pyridin-3-yl]-1-methyl-3,4-dihydro-1H-quinolin-2-one

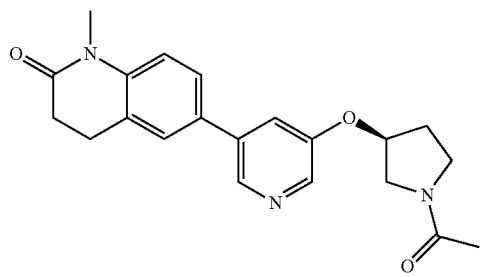 [SMILES: CC(=O)N1CC[C@H](Oc2cncc(-c3ccc4c(c3)CCC(=O)N4C)c2)C1]

In analogy to the procedure described in example 76, 1-methyl-6-[5-((S)-pyrrolidin-3-yloxy)-pyridin-3-yl]-3,4-dihydro-1H-quinolin-2-one hydrochloride (example 60) has been reacted with acetyl chloride to give the title compound as a colorless solid. MS: 366.4 (M+H⁺).

Example 255

1-Methyl-6-{5-[(S)-1-(1-methyl-1H-pyrazole-4-carbonyl)-pyrrolidin-3-yloxy]-pyridin-3-yl}-3,4-dihydro-1H-quinolin-2-one

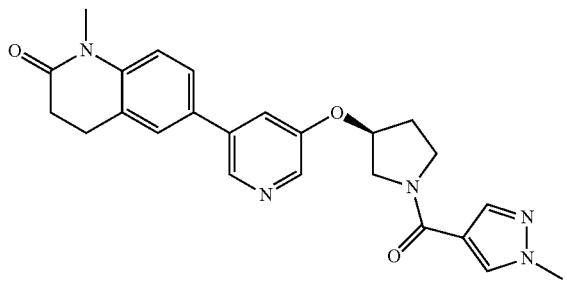 [SMILES: CN1C(=O)CCc2cc(-c3cncc(O[C@H]4CCN(C(=O)c5cnn(C)c5)C4)c3)ccc21]

To a solution of 1-methyl-6-[5-((S)-pyrrolidin-3-yloxy)-pyridin-3-yl]-3,4-dihydro-1H-quinolin-2-one hydrochloride (0.04 g, 0.111 mmol, example 60), 1-methyl-1H-pyrazole-4-carboxylic acid (0.021 g, 0.167 mmol) and Hunig's base (0.036 g, 0.278 mmol) in EtOAc (2 mL) was added propylphosphonic acid anhydride (cyclic trimer) solution (50% in EtOAc, 0.177 mL, 0.25 mmol) dropwise and the reaction mixture was stirred at room temperature over night. The mixture was diluted with EtOAc, poured into a sat. NaHCO₃ solution (5 mL) and extracted with EtOAc (2×20 mL). Combined organics were dried over Na₂SO₄, filtered and evaporated. The residue was purified by silica gel flash chromatography eluting with a 0 to 10% MeOH-DCM gradient to give the title compound (0.036 g, 75.1%) as a colorless amorphous solid. MS: 432.4 (M+H⁺).

Example 256

(S)-3-[5-(1-Methyl-2-oxo-1,2,3,4-tetrahydro-quinolin-6-yl)-pyridin-3-yloxy]-pyrrolidine-1-carboxylic acid ethyl ester

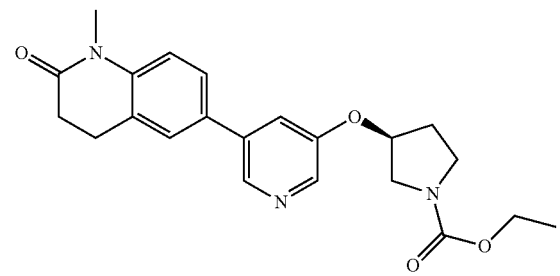 [SMILES: CCOC(=O)N1CC[C@H](Oc2cncc(-c3ccc4c(c3)CCC(=O)N4C)c2)C1]

In analogy to the procedure described in example 76, 1-methyl-6-[5-((S)-pyrrolidin-3-yloxy)-pyridin-3-yl]-3,4-dihydro-1H-quinolin-2-one hydrochloride (example 60) has been reacted with chloroformic acid ethyl ester to give the title compound as a light yellow amorphous solid. MS: 396.5 (M+H⁺).

Example 257

3,5-Dimethyl-isoxazole-4-carboxylic acid {(R or S)-1-[4-chloro-5-(1-methyl-2-oxo-1,2,3,4-tetrahydro-quinolin-6-yl)-pyridin-3-yl]-ethyl}-amide

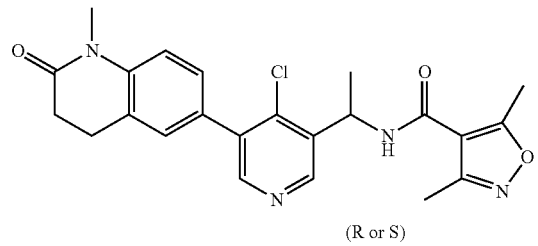 [SMILES: Cc1noc(C)c1C(=O)NC(C)c1cncc(-c2ccc3c(c2)CCC(=O)N3C)c1Cl]

(R or S)

In analogy to the procedure described for the preparation of example 219, 6-[5-((R or S)-1-amino-ethyl)-4-chloro-pyridin-3-yl]-1-methyl-3,4-dihydro-1H-quinolin-2-one hydrochloride (example 250) has been coupled with 3,5-dimethyl-isoxazole-4-carboxylic acid to give the title compound as an off-white amorphous solid. MS: 439.4 (M+H⁺).

Example 258

3-Chloro-pyridine-2-carboxylic acid {(R or S)-1-[5-(7-fluoro-1-methyl-2-oxo-1,2,3,4-tetrahydro-quinolin-6-yl)-4-methyl-pyridin-3-yl]ethyl}-amide

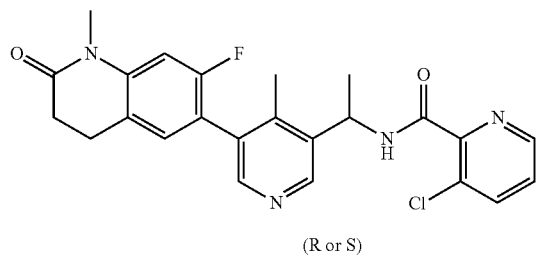 [SMILES: Cc1c(-c2cc3c(cc2F)N(C)C(=O)CC3)cncc1C(C)NC(=O)c1ncccc1Cl]

(R or S)

In analogy to the procedure described for the preparation of example 75, 6-[5-((R or S)-1-amino-ethyl)-4-methyl-pyridin-3-yl]-7-fluoro-1-methyl-3,4-dihydro-1H-quinolin-2-one hydrochloride (example 253) has been coupled with 3-chloro-pyridine-2-carboxylic acid to give the title compound as an off-white solid. MS: 453.4 (M+H⁺).

Example 259

5-Methyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide

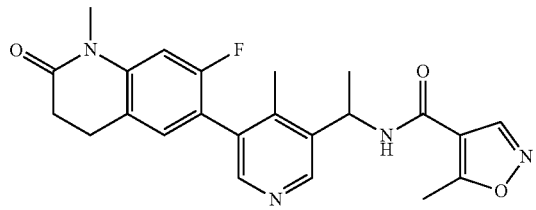 [SMILES: Cc1oncc1C(=O)NC(C)c1cncc(-c2cc3c(cc2F)N(C)C(=O)CC3)c1C]

In analogy to the procedure described for the preparation of example 219, 6-(5-aminomethyl-4-methyl-pyridin-3-yl)-7-fluoro-1-methyl-3,4-dihydro-1H-quinolin-2-one hydrochloride (example 226) has been coupled with 5-methyl-isoxazole-4-carboxylic acid to give the title compound as an off-white solid. MS: 409.6 (M+H⁺).

Example 260

5-(1-Methyl-2-oxo-1,2,3,4-tetrahydro-quinolin-6-yl)-3',4',5',6'-tetrahydro-2'H-[3,4']bipyridinyl-1'-carboxylic acid tert-butyl ester

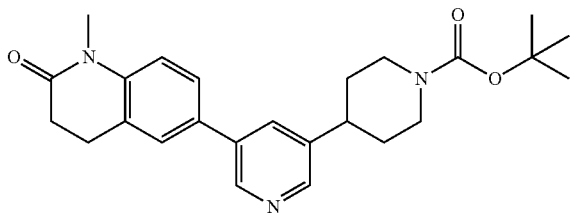 [SMILES: CN1C(=O)CCc2cc(-c3cncc(C4CCN(C(=O)OC(C)(C)C)CC4)c3)ccc21]

5-(1-Methyl-2-oxo-1,2,3,4-tetrahydro-quinolin-6-yl)-3',6'-dihydro-2'H-[3,4']bipyridinyl-1'-carboxylic acid tert-butyl ester (example 247, 0.128 g, 0.305 mmol) in MeOH (50 mL) was run through the H-cube for 2 h (flow rate: 0.5 mL/min; temperature: 60° C.; catalyst: 10% Pd/C (THS 01111); full hydrogen mode). The resulting solution was evaporated to dryness to give the title compound (0.106 g, 74%) as a yellow amorphous solid. MS: 422.5 (M+H⁺).

Example 261

N-{(R or S)-1-[4-Chloro-5-(1-methyl-2-oxo-1,2,3,4-tetrahydro-quinolin-6-yl)-pyridin-3-yl]-ethyl}-propionamide

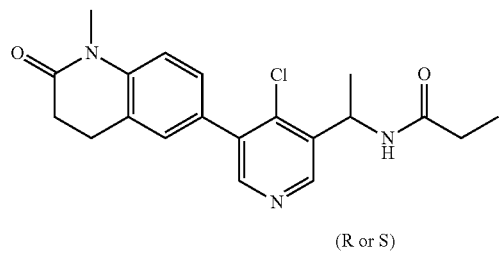 [SMILES: CCC(=O)NC(C)c1cncc(-c2ccc3c(c2)CCC(=O)N3C)c1Cl]

(R or S)

In analogy to the procedure described in example 76, 6-[5-((R or S)-1-amino-ethyl)-4-chloro-pyridin-3-yl]-1-methyl-3,4-dihydro-1H-quinolin-2-one hydrochloride (example 250) has been reacted with propionyl chloride to give the title compound as a colorless solid. MS: 372.5 (M+H⁺).

Example 262

6-[5-(1-Amino-cyclopropyl)-pyridin-3-yl]-1-methyl-1H-quinolin-2-one

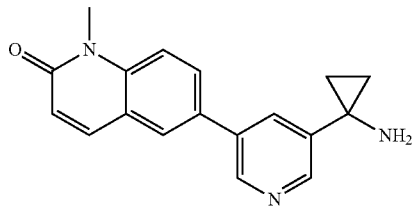 [SMILES: Cn1c(=O)ccc2cc(-c3cncc(C4(N)CC4)c3)ccc21]

To solution of 1-(5-(1-methyl-2-oxo-1,2,3,4-tetrahydroquinolin-6-yl)pyridin-3-yl)cyclopropanecarboxylic acid (example 59 [C], 0.3 g, 0.931 mmol) in toluene (15 mL) were added TEA (0.141 g, 1.4 mmol) and diphenylphosphoryl azide (0.384 g, 1.4 mmol) and then the reaction mixture was heated to reflux for 4 h. The mixture was concentrated in vacuo, the residue was dissolved in THF (30 mL) and the solution cooled to 0° C. Then, a solution of KOtBu (0.627 g, 5.58 mmol) in THF (13 mL) was added and the mixture was stirred for 1 h at 0° C. and then over night at room temperature. The mixture was concentrated in vacuo, the residue was preadsorbed on silica gel and purified by silica gel flash chromatography eluting with a 0 to 10% MeOH-DCM gradient to give a yellow amorphous solid (0.104 g). This material was then further purified by reverse phase HPLC on a Gemini-NX column, eluting with a MeOH—H₂O (0.05% TEA) gradient to give the title compound (0.02 g, 7%) as a colorless amorphous solid. MS: 292.3 (M+H⁺).

Example 263

Ethanesulfonic acid [5-(8-fluoro-1-methyl-2-oxo-1,2-dihydro-quinolin-6-yl)-pyridin-3-ylmethyl]-amide

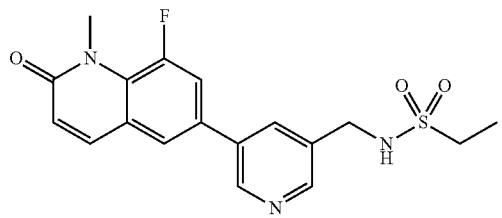 [SMILES: CCS(=O)(=O)NCc1cncc(-c2cc(F)c3c(ccc(=O)n3C)c2)c1]

A mixture of 8-fluoro-1-methyl-6-(4,4,5,5-tetramethyl-[1,3,2]dioxaborolan-2-yl)-3,4-dihydro-1H-quinolin-2-one (example 208 [E], 20 mg, 0.066 mmol), ethanesulfonic acid (5-bromo-pyridin-3-ylmethyl)-amide (intermediate A-11, 27.4 mg, 0.098 mmol), bis(triphenylphosphine)-palladium (II) chloride (4.6 mg, 0.0066 mmol), and aq. sodium carbonate solution (2 N, 0.07 mL) in DMF (1 mL) was heated in a microwave at 120° C. for 30 minutes. After dilution of the reaction mixture with EtOAc, the organic layer was washed with water, dried over anhydrous $Na_2SO_4$ and concentrated in vacuo. The residue was then purified by prep-HPLC to afford the title compound (2.5 mg, 10%) as a white solid. MS: 376.3 $(M+H^+)^+$.

Example 264

N-{(R or S)-1-[5-(7-Fluoro-1-methyl-2-oxo-1,2,3,4-tetrahydro-quinolin-6-yl)-4-methyl-pyridin-3-yl]ethyl}-propionamide

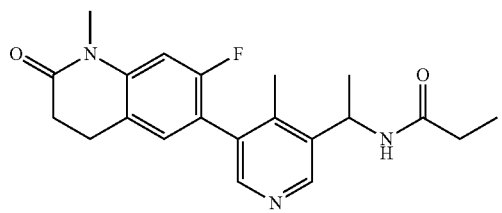 [SMILES: CCC(=O)NC(C)c1cncc(-c2cc3c(cc2F)N(C)C(=O)CC3)c1C]

In analogy to the procedure described in example 76, 6-[5-((R or S)-1-amino-ethyl)-4-methyl-pyridin-3-yl]-7-fluoro-1-methyl-3,4-dihydro-1H-quinolin-2-one hydrochloride (example 253) has been reacted with propionyl chloride to give the title compound as a colorless amorphous solid. MS: 370.6 $(M+H^+)$.

Example 265

N-[4-Chloro-5-(1-methyl-2-oxo-1,2,3,4-tetrahydro-quinolin-6-yl)-pyridin-3-ylmethyl]-propionamide

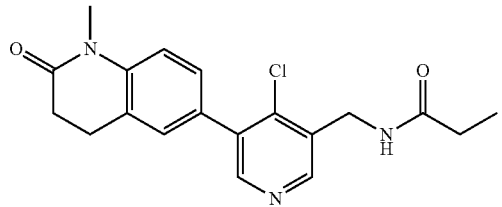 [SMILES: CCC(=O)NCc1cncc(-c2ccc3c(c2)CCC(=O)N3C)c1Cl]

In analogy to the procedure described in example 76, 6-(5-aminomethyl-4-chloro-pyridin-3-yl)-1-methyl-3,4-dihydro-1H-quinolin-2-one hydrochloride (example 218) has been reacted with propionyl chloride to give the title compound as an off-white solid. MS: 358.4 $(M+H^+)$.

Example 266

N-{(R or S)-1-[4-Methyl-5-(1-methyl-2-oxo-1,2,3,4-tetrahydro-quinolin-6-yl)-pyridin-3-yl]-ethyl}-propionamide

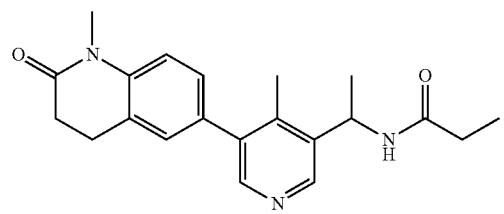 [SMILES: CCC(=O)NC(C)c1cncc(-c2ccc3c(c2)CCC(=O)N3C)c1C]

In analogy to the procedure described in example 76, 6-[5-((R or S)-1-amino-ethyl)-4-methyl-pyridin-3-yl]-1-methyl-3,4-dihydro-1H-quinolin-2-one hydrochloride (example 240) has been reacted with propionyl chloride to give the title compound as a colorless amorphous solid. MS: 352.5 $(M+H^+)$.

Example 267

3,5-Dimethyl-isoxazole-4-carboxylic acid {2-[5-(7-fluoro-1-methyl-2-oxo-1,2,3,4-tetrahydro-quinolin-6-yl)-pyridin-3-yloxy]-ethyl}-amide

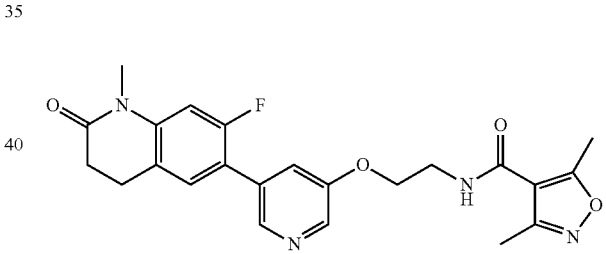

In analogy to the procedure described for the preparation of example 219, 6-[5-(2-amino-ethoxy)-pyridin-3-yl]-7-fluoro-1-methyl-3,4-dihydro-1H-quinolin-2-one hydrochloride (example 238) has been coupled with 3,5-dimethyl-isoxazole-4-carboxylic acid to give the title compound as a colorless solid. MS: 439.4 $(M+H^+)$.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound according to formula (I),

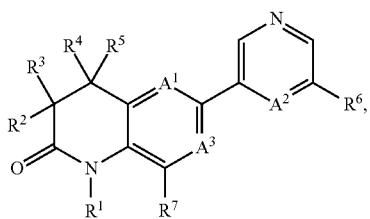

(I)

wherein:
$R^1$ is H, alkyl, haloalkyl, cycloalkyl or halocycloalkyl;
$R^2$ is H, alkyl, haloalkyl, cycloalkyl or halocycloalkyl;
$R^3$ is H, alkyl, haloalkyl, cycloalkyl or halocycloalkyl;
$R^4$ is H, alkyl, haloalkyl, cycloalkyl or halocycloalkyl;
or $R^3$ and $R^4$ together with the carbon atoms to which they are attached form a double bond;
$R^5$ is H, alkyl, haloalkyl, cycloalkyl or halocycloalkyl;
$R^6$ is H or $R^8$;
$R^7$ is H, halogen, alkyl, haloalkyl, cycloalkyl or halocycloalkyl;
or $R^1$ and $R^7$ together with the nitrogen and carbon atoms to which they are attached form a heterocycloalkyl substituted with one to three substituents independently selected from H, alkyl, haloalkyl, cycloalkyl or halocycloalkyl;
$R^8$ is $-O_m-(CR^9R^{10})_n-(C^{11}R^{12})_p-(CR^{13}R^{14})_q-NR^{15}R^{16}$,
$-N_mR^{17}-(CR^9R^{10})_n-(CR^{11}R^{12})_p-(CR^{13}R^{14})_q-NR^{15}R^{16}$ or
$-S_m(O)_r-(CR^9R^{10})_n-(CR^{11}R^{12})_p-(CR^{13}R^{14})_q-NR^{15}R^{16}$;
$R^9$ is H, alkyl, haloalkyl, cycloalkyl or halocycloalkyl;
$R^{10}$ is H, alkyl, haloalkyl, cycloalkyl or halocycloalkyl;
$R^{11}$ is H, alkyl, haloalkyl, cycloalkyl or halocycloalkyl;
or $R^{10}$ and $R^{11}$ together with the carbon atoms to which they are attached form a double bond;
$R^{12}$ is H, alkyl, haloalkyl, cycloalkyl or halocycloalkyl;
or $R^{11}$ and $R^{12}$ together with the carbon atom to which they are attached form a cycloalkyl or a heterocycloalkyl;
$R^{13}$ is H, alkyl, haloalkyl, cycloalkyl or halocycloalkyl;
$R^{14}$ is H, alkyl, haloalkyl, cycloalkyl or halocycloalkyl;
or $R^{10}$ and $R^{14}$ together form $-(CH_2)_t-$;
$R^{15}$ is H, alkyl, haloalkyl, cycloalkyl, halocycloalkyl, alkoxyalkyl, haloalkoxyalkyl or hydroxyalkyl;
$R^{16}$ is H, alkyl, haloalkyl, cycloalkyl, halocycloalkyl, hydroxyalkyl, alkoxyalkyl, haloalkoxyalkyl, phenylalkyl, substituted phenylalkyl, aryl, substituted aryl, heterocycloalkyl, substituted heterocycloalkyl, heteroaryl, substituted heteroaryl, $-S(O)_2R^{18}$, $-S(O)R^{18}$, $-S(O)_2OR^{18}$, $-S(O)_2NR^{18}R^{19}$, $-C(O)R^{18}$, $-C(O)OR^{18}$ or $-C(O)NR^{18}R^{19}$, wherein substituted phenylalkyl, substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl, wherein in case $R^{15}$ is H or alkyl and $R^{16}$ is H or alkyl, then the sum of n, p and q is at least 1;
or $R^{15}$ and $R^{16}$ together with the nitrogen atom to which they are attached form a substituted heterocycloalkyl or a substituted heteroaryl, wherein substituted heterocycloalkyl and substituted heteroaryl are substituted with $R^{23}$, $R^{24}$ and $R^{25}$;
or $R^{13}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;
or $R^{11}$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;
or $R^9$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$;
$R^{17}$ is H, alkyl, haloalkyl, cycloalkyl or halocycloalkyl;
$R^{18}$ is alkyl, cycloalkyl, haloalkyl, halocycloalkyl, hydroxyalkyl, halohydroxyalkyl, alkoxyalkyl, haloalkoxyalkyl, alkylcarbonyloxyalkyl, aryl, substituted aryl, heterocycloalkyl, substituted heterocycloalkyl, heteroaryl, substituted heteroaryl, wherein substituted aryl, substituted heterocycloalkyl and substituted heteroaryl are substituted with one to three substituents independently selected from alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

$R^{19}$ is H, alkyl, haloalkyl, cycloalkyl or halocycloalkyl;

$A^1$ is $CR^{20}$;

$A^2$ is $CR^{21}$ or N;

$A^3$ is $CR^{22}$;

$R^{20}$ is H, halogen, alkyl, haloalkyl, cycloalkyl or halocycloalkyl;

$R^{21}$ is H, halogen, alkyl, haloalkyl, cycloalkyl or halocycloalkyl;

$R^{22}$ is H, halogen, alkyl, haloalkyl, cycloalkyl or halocycloalkyl;

$R^{23}$, $R^{24}$ and $R^{25}$ are each independently selected from H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, —S(O)$_2$R$^{18}$, —C(O)R$^{18}$, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein substituted amino, substituted aminoalkyl and substituted aminocarbonyl are substituted on the nitrogen atom with one to two substituents independently selected from alkyl, cycloalkyl, alkylcycloalkyl, cycloalkylalkyl, alkylcycloalkylalkyl, hydroxyalkyl and alkoxyalkyl;

wherein in case m is zero and $R^9$ and $R^{15}$, or $R^{11}$ and $R^{15}$ or $R^{13}$ and $R^{15}$ or $R^{15}$ and $R^{16}$ together with the nitrogen and carbon atoms to which they are attached form a substituted heterocycloalkyl or a substituted heteroaryl, then at least one of $R^{23}$, $R^{24}$, $R^{25}$ and $R^{16}$ is different from H, alkyl, haloalkyl, alkoxy, haloalkoxy, halogen, hydroxy, cyano, amino, substituted amino, aminocarbonyl, substituted aminocarbonyl, wherein substituted amino and substituted aminocarbonyl are substituted on the nitrogen atom with one to two alkyl, and —C(O)R$^{18}$, —S(O)$_2$R$^{18}$, wherein R$^{18}$ is alkyl, haloalkyl, hydroxyalkyl, halohydroxyalkyl, alkoxyalkyl or haloalkoxyalkyl;

m is zero or 1, wherein in case m is 1, then the sum of n and p is 2, 3 or 4;

n is zero, 1 or 2;

p is zero, 1 or 2;

q is zero, 1 or 2;

r is zero, 1 or 2, wherein in case m is zero then r is zero; and t is zero, 1 or 2;

or a pharmaceutically acceptable salt or ester thereof.

2. The compound according to claim 1, wherein $R^1$ is H or alkyl.

3. The compound according to claim 1, wherein $R^2$ is H.

4. The compound according to claim 1, wherein $R^3$ is H.

5. The compound according to claim 1, wherein $R^4$ is H or alkyl.

6. The compound according to claim 1, wherein $R^5$ is H or alkyl.

7. The compound according to claim 1, wherein $R^7$ is H.

8. The compound according to claim 1, wherein is $R^8$ is —O$_m$—(CR$^9$R$^{10}$)$_n$—(CR$^{11}$R$^{12}$)$_p$—(CR$^{13}$R$^{14}$)$_q$—NR$^{15}$R$^{16}$.

9. The compound according to claim 1, wherein $R^9$ is H, alkyl or cycloalkyl.

10. The compound according to claim 1, wherein $R^{10}$ is H or alkyl.

11. The compound according to claim 1, wherein $R^{11}$ is H.

12. The compound according to claim 1, wherein $R^{12}$ is H.

13. The compound according to claim 1, wherein $R^{13}$ is H.

14. The compound according to claim 1, wherein $R^{14}$ is H.

15. The compound according to claim 1, wherein $R^{15}$ is H, alkyl or alkoxyalkyl.

16. The compound according to claim 1, wherein $R^9$ and $R^{15}$ together with the nitrogen and carbon atoms to which they are attached form a substituted heterocycloalkyl, wherein substituted heterocycloalkyl is substituted with $R^{23}$, $R^{24}$ and $R^{25}$.

17. The compound according to claim 1, wherein $R^{16}$ is H, hydroxyalkyl, phenylalkyl, heterocycloalkyl substituted with alkyl, —S(O)R$^{18}$, —S(O)$_2$R$^{18}$, —C(O)R$^{18}$ or —C(O)OR$^{18}$, wherein in case R$^{15}$ is H or alkyl and R$^{16}$ is H or alkyl, then the sum of n, p and q is at least 1.

18. The compound according to a claim 1, wherein $R^{16}$ is hydroxyalkyl, —S(O)$_2$R$^{18}$, —C(O)R$^{18}$ or —C(O)OR$^{18}$.

19. The compound according to claim 1, wherein $R^{15}$ and $R^{16}$ together with the nitrogen atom to which they are attached form a substituted heterocycloalkyl wherein substituted heterocycloalkyl is substituted with one to three substituents independently selected from hydroxyalkyl, alkoxyalkyl, haloalkoxyalkyl, alkoxycarbonyl, oxo, triazolylalkyl and substituted aminoalkyl, wherein substituted aminoalkyl is substituted on the nitrogen atom with one to two alkyl.

20. The compound according to claim 1, wherein $R^{18}$ is alkyl, cycloalkyl, haloalkyl, hydroxyalkyl, alkylcarbonyloxyalkyl, aryl, substituted aryl, heterocycloalkyl, substituted heterocycloalkyl, heteroaryl, substituted heteroaryl, wherein substituted aryl, substituted heterocycloalkyl and substituted heteroaryl are substituted with one to three substituents independently selected from alkyl, hydroxyalkyl, haloalkyl, cycloalkyl and halogen.

21. The compound according to claim 1, wherein $R^{23}$, $R^{24}$ and $R^{25}$ are each independently selected from hydrogen, hydroxyalkyl, alkoxy, alkoxyalkyl, haloalkoxyalkyl, alkoxycarbonyl, oxo, triazolylalkyl and substituted aminoalkyl, wherein substituted aminoalkyl is substituted on the nitrogen atom with one to two alkyl.

22. The compound according to claim 1, selected from the group consisting of:

Ethanesulfonic acid [5-(1-methyl-2-oxo-1,2,3,4-tetrahydro-quinolin-6-yl)-pyridin-3-yl]-amide;

Acetic acid [5-(1-methyl-2-oxo-1,2,3,4-tetrahydro-quinolin-6-yl)-pyridin-3-ylcarbamoyl]-methyl ester;

2-Hydroxy-N-[5-(1-methyl-2-oxo-1,2,3,4-tetrahydro-quinolin-6-yl)-pyridin-3-yl]-acetamide;

6-[5-(2-Hydroxy-ethylamino)-pyridin-3-yl]-1-methyl-3,4-dihydro-1H-quinolin-2-one;

6-[5-((S)-2-Hydroxymethyl-pyrrolidin-1-yl)-pyridin-3-yl]-1-methyl-3,4-dihydro-1H-quinolin-2-one;

6-[5-((R)-2-Hydroxymethyl-pyrrolidin-1-yl)-pyridin-3-yl]-1-methyl-3,4-dihydro-1H-quinolin-2-one;

6-[5-((S)-2-Hydroxymethyl-pyrrolidin-1-ylmethyl)-pyridin-3-yl]-1-methyl-3,4-dihydro-1H-quinolin-2-one;

6-[5-((S)-2-Hydroxymethyl-5-oxo-pyrrolidin-1-ylmethyl)-pyridin-3-yl]-1-methyl-3,4-dihydro-1H-quinolin-2-one;

6-[5-((S)-2-Ethylaminomethyl-pyrrolidin-1-yl)-pyridin-3-yl]-1-methyl-3,4-dihydro-1H-quinolin-2-one;

6-[5-((S)-2-Methoxymethyl-pyrrolidin-1-yl)-pyridin-3-yl]-1-methyl-3,4-dihydro-1H-quinolin-2-one;

1-Methyl-6-[5-((S)-2-[1,2,4]triazol-1-ylmethyl-pyrrolidin-1-yl)-pyridin-3-yl]-3,4-dihydro-1H-quinolin-2-one;
6-(5-Benzylamino-pyridin-3-yl)-1-methyl-3,4-dihydro-1H-quinolin-2-one;
6-[5-((S)-2-Hydroxymethyl-5-oxo-pyrrolidin-1-yl)-pyridin-3-yl]-1-methyl-3,4-dihydro-1H-quinolin-2-one;
1-Methyl-6-[5-(2-oxo-pyrrolidin-1-yl)-pyridin-3-yl]-3,4-dihydro-1H-quinolin-2-one, and
Ethanesulfonic acid [5-(1-methyl-2-oxo-1,2,3,4-tetrahydro-quinolin-6-yl)-pyridin-3-ylmethyl]-amide;
and pharmaceutically acceptable salts thereof.

23. The compound according to claim 1, selected from the group consisting of:
Ethanesulfonic acid [5-(7-fluoro-1-methyl-2-oxo-1,2,3,4-tetrahydro-quinolin-6-yl)-pyridin-3-ylmethyl]-amide;
Ethanesulfonic acid [5-(1,4,4-trimethyl-2-oxo-1,2,3,4-tetrahydro-quinolin-6-yl)-pyridin-3-ylmethyl]-amide;
1-Methyl-6-[5-(2-oxo-pyrrolidin-1-ylmethyl)-pyridin-3-yl]-3,4-dihydro-1H-quinolin-2-one;
1-Methyl-6-[5-(2-oxo-piperidin-1-ylmethyl)-pyridin-3-yl]-3,4-dihydro-1H-quinolin-2-one;
6-[5-(1,1-Dioxo-1$\lambda^6$-thiomorpholin-4-ylmethyl)-pyridin-3-yl]-1-methyl-3,4-dihydro-1H-quinolin-2-one;
6-[S—((S)-2-Methoxymethyl-pyrrolidin-1-ylmethyl)-pyridin-3-yl]-1-methyl-3,4-dihydro-1H-quinolin-2-one;
(S)-1-[5-(1-Methyl-2-oxo-1,2,3,4-tetrahydro-quinolin-6-yl)-pyridin-3-ylmethyl]-pyrrolidine-2-carboxylic acid methyl ester;
1-Methyl-6-{5-[(S)-2-(2,2,2-trifluoro-ethoxymethyl)-pyrrolidin-1-ylmethyl]-pyridin-3-yl}-3,4-dihydro-1H-quinolin-2-one;
6-[5-(1-Methyl-2-oxo-1,2,3,4-tetrahydro-quinolin-6-yl)-pyridin-3-yl]-2,6-diaza-spiro[3.3]heptane-2-carboxylic acid tert-butyl ester; and
6-[S—((R)-1-Hydroxymethyl-2-methyl-propylamino)-pyridin-3-yl]-1-methyl-3,4-dihydro-1H-quinolin-2-one;
and pharmaceutically acceptable salts thereof.

24. The compound according to claim 1, selected from the group consisting of:
6-[6-((R)-1-Hydroxymethyl-2-methyl-propylamino)-pyrazin-2-yl]-1-methyl-3,4-dihydro-1H-quinolin-2-one;
6-(5-Aminomethyl-pyridin-3-yl)-1-methyl-3,4-dihydro-1H-quinolin-2-one;
N-[5-(1-Methyl-2-oxo-1,2,3,4-tetrahydro-quinolin-6-yl)-pyridin-3-ylmethyl]-propionamide;
Propane-2-sulfonic acid [5-(1-methyl-2-oxo-1,2,3,4-tetrahydro-quinolin-6-yl)-pyridin-3-ylmethyl]-amide;
{2-[5-(1-Methyl-2-oxo-1,2,3,4-tetrahydro-quinolin-6-yl)-pyridin-3-yloxy]-ethyl}-carbamic acid tert-butyl ester;
3-Methoxy-isoxazole-5-carboxylic acid [5-(1-methyl-2-oxo-1,2,3,4-tetrahydro-quinolin-6-yl)-pyridin-3-ylmethyl]-amide;
Cyclopropanecarboxylic acid [5-(1-methyl-2-oxo-1,2,3,4-tetrahydro-quinolin-6-yl)-pyridin-3-ylmethyl]-amide;
6-[5-(2-Amino-ethoxy)-pyridin-3-yl]-1-methyl-3,4-dihydro-1H-quinolin-2-one hydrochloride;
N-{2-[5-(1-Methyl-2-oxo-1,2,3,4-tetrahydro-quinolin-6-yl)-pyridin-3-yloxy]-ethyl}-propionamide; and
6-[5-(1,1-Dioxo-1$\lambda^6$-[1,2]thiazinan-2-ylmethyl)-pyridin-3-yl]-1-methyl-3,4-dihydro-1H-quinolin-2-one;
and pharmaceutically acceptable salts thereof.

25. The compound according to claim 1, selected from the group consisting of:
(S)-2-(5-(1-Methyl-2-oxo-1,2,3,4-tetrahydro-quinolin-6-yl)-pyridin-3-yloxymethyl)-azetidine-1H-carboxylic acid tert-butyl ester;
(R)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester;
3-[5-(1-Methyl-2-oxo-1,2,3,4-tetrahydro-quinolin-6-yl)-pyridin-3-yloxy]-azetidine-1-carboxylic acid tert-butyl ester;
(S)-3-[5-(1-Methyl-2-oxo-1,2,3,4-tetrahydro-quinolin-6-yl)-pyridin-3-yloxy]-pyrrolidine-1-carboxylic acid tert-butyl ester;
(S)-3-[5-(1-Methyl-2-oxo-1,2,4-tetrahydro-quinolin-6-yl)-pyridin-3-yloxy]-piperidine-1-carboxylic acid tert-butyl ester;
4-[5-(1-Methyl-2-oxo-1,2,3,4-tetrahydro-quinolin-6-yl)-pyridin-3-yloxy]-piperidine-1-carboxylic acid tert-butyl ester;
(S)-2-[5-(1-Methyl-2-oxo-1,2,3,4-tetrahydro-quinolin-6-yl)-pyridin-3-yloxymethyl]-pyrrolidine-1-carboxylic acid tert-butyl ester;
(S)-3-[5-(7-Fluoro-1-methyl-2-oxo-1,2,3,4-tetrahydro-quinolin-6-yl)-pyridin-3-yloxy]-pyrrolidine-1-carboxylic acid tert-butyl ester;
(R)-3-[5-(1-Methyl-2-oxo-1,2,3,4-tetrahydro-quinolin-6-yl)-pyridin-3-yloxy]-pyrrolidine-1-carboxylic acid tert-butyl ester;
(R)-2-Methyl-propane-2-sulfinic acid {3-[5-(1-methyl-2-oxo-1,2,3,4-tetrahydro-quinolin-6-yl)-pyridin-3-yl]-oxetan-3-yl}-amide;
Ethanesulfonic acid [5-(2-oxo-1,2,3,4-tetrahydro-quinolin-6-yl)-pyridin-3-ylmethyl]-amide;
(R)-2-Methyl-propane-2-sulfinic acid {(S or R)-1-[5-(1-methyl-2-oxo-1,2,3,4-tetrahydro-quinolin-6-yl)-pyridin-3-yl]-ethyl}-amide;
(R) 2-Methyl-propane-2-sulfinic acid {(R or S)-1-[5-(1-methyl-2-oxo-1,2,3,4-tetrahydro-quinolin-6-yl)-pyridin-3-yl]-ethyl}-amide;
{(trans)-4-[5-(1-Methyl-2-oxo-1,2,3,4-tetrahydro-quinolin-6-yl)-pyridin-3-yloxy]-cyclohexyl}-carbamic acid tert-butyl ester; and
6-[5-(1-Amino-cyclopropyl)-pyridin-3-yl]-1-methyl-3,4-dihydro-1H-quinolin-2-one;
and pharmaceutically acceptable salts thereof.

26. The compound according to claim 1, selected from the group consisting of:
1-Methyl-6-[5-((S)-pyrrolidin-3-yloxy)-pyridin-3-yl]-3,4-dihydro-1H-quinolin-2-one hydrochloride;
1-Methyl-6-[5-((S)-piperidin-3-yloxy)-pyridin-3-yl]-3,4-dihydro-1H-quinolin-2-one;
1-Methyl-6-[5(piperidin-4-yloxy)-pyridin-3-yl]-3,4-dihydro-1H-quinolin-2-one hydrochloride;
6-[5-((S)-1-Azetidin-2-ylmethoxy)-pyridin-3-yl]-1-methyl-3,4-dihydro-1H-quinolin-2-one;
6-[5-((S or R)-1-Amino-ethyl)-pyridin-3-yl]-1-methyl-3,4-dihydro-1H-quinolin-2-one hydrochloride;
6-[5-((R or S)-1-Amino-ethyl)-pyridin-3-yl]-1-methyl-3,4-dihydro-1H-quinolin-2-one hydrochloride;
1-Methyl-6-[5-((S)-1-pyrrolidin-2-ylmethoxy)-pyridin-3-yl]-3,4-dihydro-1H-quinolin-2-one hydrochloride;
7-Fluoro-1-methyl-6-[5-((R)-pyrrolidin-3-yloxy)-pyridin-3-yl]-3,4-dihydro-1H-quinolin-2-one hydrochloride;
1-Methyl-6-[5-((R)-pyrrolidin-3-yloxy)-pyridin-3-yl]-3,4-dihydro-1H-quinolin-2-one hydrochloride;

6-[5-(3-Amino-oxetan-3-yl)-pyridin-3-yl]-1-methyl-3,4-dihydro-1H-quinolin-2-one hydrochloride;
6-[5-(Azetidin-3-yloxy)-pyridin-3-yl]-1-methyl-3,4-dihydro-1H-quinolin-2-one hydrochloride;
6-[5-((trans)-4-Amino-cyclohexyloxy)-pyridin-3-yl]-1-methyl-3,4-dihydro-1H-quinolin-2-one hydrochloride;
6-[5-(1-Amino-1-methyl-ethyl)-pyridin-3-yl]-1-methyl-3,4-dihydro-1H-quinolin-2-one;
6-(5-Aminomethyl-pyridin-3-yl)-7-fluoro-1-methyl-3,4-dihydro-1H-quinolin-2-one; and
6-{6-[6-(3-Methoxy-isoxazole-5-carbonyl)-2,6-diazaspiro[3,3]hept-2-yl]-pyrazin-2-yl}-1-methyl-3,4-dihydro-1H-quinolin-2-one:
and pharmaceutically acceptable salts thereof.

27. The compound according to claim 1, selected from the group consisting of:
3,5-Dimethyl-isoxazole-4-carboxylic acid [5-(1-methyl-2-oxo-1,2,3,4-tetrahydro-quinolin-6-yl)-pyridin-3-ylmethyl]-amide;
6-[5-((S)-1-Cyclopropanecarbonyl-pyrrolidin-3-yloxy)-pyridin-3-yl]-1-methyl-3,4-dihydro-1H-quinolin-2-one;
3-Methyl-N-[5-(1-methyl-2-oxo-1,2,3,4-tetrahydro-quinolin-6-yl)-pyridin-3-ylmethyl]-butyramide;
3,3,3-Trifluoro-N-[5-(1-methyl-2-oxo-1,2,3,4-tetrahydro-quinolin-6-yl)-pyridin-3-ylmethyl]-propionamide;
2-Hydroxy-2-methyl-N-[5-(1-methyl-2-oxo-1,2,3,4-tetrahydro-quinolin-6-yl)-pyridin-3-ylmethyl]-propionamide;
5-Methyl-[1,3,4]oxadiazole-2-carboxylic acid [5-(1-methyl-2-oxo-1,2,3,4-tetrahydro-quinolin-6-yl)-pyridin-3-ylmethyl]-amide;
1-Methyl-6-[5-((S)-1-propionyl-piperidin-3-yloxy)-pyridin-3-yl]-3,4-dihydro-1H-quinolin-2-one;
2-Methoxy-pyrimidine-5-carboxylic acid [5-(1-methyl-2-oxo-1,2,3,4-tetrahydro-quinolin-6-yl)-pyridin-3-ylmethyl]-amide,
1-Methyl-1H-imidazole-2-carboxylic acid [5-(1-methyl-2-oxo-1,2,3,4-tetrahydro-quinolin-6-yl)-pyridin-3-ylmethyl]-amide;
5-Trifluoromethyl-furan-3-carboxylic acid [5-(1-methyl-2-oxo-1,2,3,4-tetrahydro-quinolin-6-yl)-pyridin-3-ylmethyl]-amide;
Pyridazine-3-carboxylic acid [5-(1-methyl-2-oxo-1,2,3,4-tetrahydro-quinolin-6-yl)-pyridin-3-ylmethyl]-amide;
Pyrimidine-5-carboxylic acid [5-(1-methyl-2-oxo-1,2,3,4-tetrahydro-quinolin-6-yl)-pyridin-3-ylmethyl]-amide;
1-Methyl-1H-pyrazole-4-carboxylic acid [5-(1-methyl-2-oxo-1,2,3,4-tetrahydro-quinolin-6-yl)-pyridin-3-ylmethyl]-amide;
1-Methyl-6-[5-(1-propionyl-piperidin-4-yloxy)-pyridin-3-yl]-3,4-dihydro-1H-quinolin-2-one; and
Pyridazine-4-carboxylic acid [5-(1-methyl-2-oxo-1,2,3,4-tetrahydro-quinolin-6-yl)-pyridin-3-ylmethyl]-amide;
and pharmaceutically acceptable salts thereof.

28. The compound according to claim 1, selected from the group consisting of:
1-Methyl-6-[5-((S)-1-propionyl-pyrrolidin-3-yloxy)-pyridin-3-yl]-3,4-dihydro-1H-quinolin-2-one;
6-[5-((S)-1-Cyclopropanecarbonyl-azetidin-2-ylmethoxy)-pyridin-3-yl]-1-methyl-3,4-dihydro-1H-quinolin-2-one;
3-Methyl-isoxazole-4-carboxylic acid [5-(1-methyl-2-oxo-1,2,3,4-tetrahydro-quinolin-6-yl)-pyridin-3-ylmethyl]-amide;
4-Fluoro-2,6-dimethyl-N-[5-(1-methyl-2-oxo-1,2,3,4-tetrahydro-quinolin-6-yl)-pyridin-3-ylmethyl]-benzamide;
1-Methyl-6-[5-((S)-1-propionyl-azetidin-2-ylmethoxy)-pyridin-3-yl]-3,4-dihydro-1H-quinolin-2-one;
3,6-Dichloro-pyridazine-4-carboxylic acid [5-(1-methyl-2-oxo-1,2,3,4-tetrahydro-quinolin-6-yl)-pyridin-3-ylmethyl]-amide;
3-Cyclopropyl-1-(2,2,2-trifluoro-ethyl)-1H-pyrazole-4-carboxylic acid [5-(1-methyl-2-oxo-1,2,3,4-tetrahydro-quinolin-6-yl)-pyridin-3-ylmethyl]-amide;
Pyridine-2-carboxylic acid [5-(1-methyl-2-oxo-1,2,3,4-tetrahydro-quinolin-6-yl)-pyridin-3-ylmethyl]-amide;
1,3-Dimethyl-1H-pyrazole-4-carboxylic acid [5-(1-methyl-2-oxo-1,2,3,4-tetrahydro-quinolin-6-yl)-pyridin-3-ylmethyl]-amide;
Pyrimidine-2-carboxylic acid [5-(1-methyl-2-oxo-1,2,3,4-tetrahydro-quinolin-6-yl)-pyridin-3-ylmethyl]-amide;
6-Methoxy-pyridazine-3-carboxylic acid [5-(1-methyl-2-oxo-1,2,3,4-tetrahydro-quinolin-6-yl)-pyridin-3-ylmethyl]-amide;
5-Methyl-isoxazole-4-carboxylic acid [5-(1-methyl-2-oxo-1,2,3,4-tetrahydro-quinolin-6-yl)-pyridin-3-ylmethyl]-amide;
3,5-Dimethyl-isoxazole-4-carboxylic acid {2-[5-(1-methyl-2-oxo-1,2,3,4-tetrahydro-quinolin-6-yl)-pyridin-3-yloxy]-ethyl}-amide;
1 Methyl-1H-pyrazole-4-carboxylic acid {2-[5-(1-methyl-2-oxo-1,2,3,4-tetrahydro-quinolin-6-yl)-pyridin-3-yloxy]-ethyl}-amide; and
6-Chloro-pyridazine-3-carboxylic acid [5-(1-methyl-2-oxo-1,2,3,4-tetrahydro-quinolin-6-yl)-pyridin-3-ylmethyl]-amide;
and pharmaceutically acceptable salts thereof.

29. The compound according to claim 1, selected from the group consisting of:
3-Chloro-6-methyl-pyridazine-4-carboxylic acid [5-(1-methyl-2-oxo-1,2,3,4-tetrahydro-quinolin-6-yl)-pyridin-3-ylmethyl]-amide;
1-Methyl-6-[5-((S)-1-propionyl-pyrrolidin-2-ylmethoxy)-pyridin-3-yl]-3,4-dihydro-1H-quinolin-2-one;
5-Cyclopropyl-isoxazole-4-carboxylic acid [5-(1-methyl-2-oxo-1,2,3,4-tetrahydro-quinolin-6-yl)-pyridin-3-ylmethyl]-amide;
2-Methyl-5-trifluoromethyl-oxazole-4-carboxylic acid [5-(1-methyl-2-oxo-1,2,3,4-tetrahydro-quinolin-6-yl)-pyridin-3-ylmethyl]-amide;
2-Methyl-oxazole-4-carboxylic acid [5-(1-methyl-2-oxo-1,2,3,4-tetrahydro-quinolin-6-yl)-pyridin-3-ylmethyl]-amide;
5-Cyclopropyl-oxazole-4-carboxylic acid [5-(1-methyl-2-oxo-1,2,3,4-tetrahydro-quinolin-6-yl)-pyridin-3-ylmethyl]-amide;
2,5-Dimethyl-oxazole-4-carboxylic acid [5-(1-methyl-2-oxo-1,2,3,4-tetrahydro-quinolin-6-yl)-pyridin-3-ylmethyl]-amide;
5-Methyl-oxazole-4-carboxylic acid [5-(1-methyl-2-oxo-1,2,3,4-tetrahydro-quinolin-6-yl)-pyridin-3-ylmethyl]-amide;
3,5-Dimethyl-isoxazole-4-carboxylic acid {1-[5-(1-methyl-2-oxo-1,2,3,4-tetrahydro-quinolin-6-yl)-pyridin-3-yl]-cyclopropyl}-amide;
6-Chloro-pyridine-2-carboxylic acid [5-(1-methyl-2-oxo-1,2,3,4-tetrahydro-quinolin-6-yl)-pyridin-3-ylmethyl]-amide;

3-Methyl-pyridine-2-carboxylic acid [5(1-methyl-2-oxo-1,2,3,4-tetrahydro-quinolin-6-yl)-pyridin-3-ylmethyl]-amide;

3,6-Dichloro-pyridine-2-carboxylic acid [5-(1-methyl-2-oxo-1,2,3,4-tetrahydro-quinolin-6-yl)-pyridin-3-ylmethyl]-amide;

6-Methyl-pyridine-2-carboxylic acid [5-(1-methyl-2-oxo-1,2,3,4-tetrahydro-quinolin-6-yl)-pyridin-3-ylmethyl]-amide;

3-Chloro-pyridine-2-carboxylic acid [5-(1-methyl-2-oxo-1,2,3,4-tetrahydro-quinolin-6-yl)-pyridin-3-ylmethyl]-amide; and 3-Fluoro-pyridine-2-carboxylic acid [5-(1-methyl-2-oxo-1,2,3,4-tetrahydro-quinolin-6-yl)-pyridin-3-ylmethyl]-amide;

and pharmaceutically acceptable salts thereof.

30. The compound according to claim 1, selected from the group consisting of:

5-Chloro-3-methyl-pyridine-2-carboxylic acid [5-(1-methyl-2-oxo-1,2,3,4-tetrahydro-quinolin-6-yl)-pyridin-3-ylmethyl]-amide;

1-Methyl-6-[5-((R)-1-propionyl-pyrrolidin-3-yloxy)-pyridin-3-yl]-3,4-dihydro-1H-quinolin-2-one;

7-Fluoro-1-methyl-6-[5-((S)-1-propionyl-pyrrolidin-3-yloxy)-pyridin-3-yl]-3,4-dihydro-1H-quinolin-2-one;

5-Trifluoromethyl-pyrimidine-2-carboxylic acid [5-(1-methyl-2-oxo-1,2,3,4-tetrahydro-quinolin-6-yl)-pyridin-3-ylmethyl]-amide;

5-Methyl-pyrazine-2-carboxylic acid [5-(1-methyl-2-oxo-1,2,3,4-tetrahydro-quinolin-6-yl)-pyridin-3-ylmethyl]-amide;

5-Chloro-pyrazine-2-carboxylic acid [5-(1-methyl-2-oxo-1,2,3,4-tetrahydro-quinolin-6-yl)-pyridin-3-ylmethyl]-amide;

5-Trifluoromethyl-pyrazine-2-carboxylic acid [5-(1-methyl-2-oxo-1,2,3,4-tetrahydro-quinolin-6-yl)-pyridin-3-ylmethyl]-amide;

3,5-Dimethyl-isoxazole-4-carboxylic acid [5-(7-fluoro-1-methyl-2-oxo-1,2,3,4-tetrahydro-quinolin-6-yl)-pyridin-3-ylmethyl]-amide;

1-Methyl-6-[5-((R)-1-propionyl-pyrrolidin-2-ylmethoxy)-pyridin-3-yl]-3,4-dihydro-1H-quinolin-2-one;

1-Methyl-6-[5-(1I-propionyl-azetidin-3-yloxy)-pyridin-3-yl]-3,4-dihydro-1H-quinolin-2-one;

N-3-[5-(1-Methyl-2-oxo-1,2,3,4-tetrahydro-quinolin-6-yl)-pyridin-3-yl]-oxetan-3-yl)-propionamide;

3-Chloro-pyridine-2-carboxylic acid [5-(7-fluoro-1-methyl-2-oxo-1,2,3,4-tetrahydro-quinolin-6-yl)-pyridin-3-ylmethyl]-amide;

3,6-Dichloro-pyridazine-4-carboxylic acid [5-(7-fluoro-1-methyl-2-oxo-1,2,3,4-tetrahydro-quinolin-6-yl)-pyridin-3-ylmethyl]-amide;

7-Fluoro-1-methyl-6-[5-((R)-1-propionyl-pyrrolidin-3-yloxy)-pyridin-3-yl]-3,4-dihydro-1H-quinolin-2-one;

5-Chloro-3-methoxy-pyrazine-2-carboxylic acid [5-(1-methyl-2-oxo-1,2,3,4-tetrahydro-quinolin-6-yl)-pyridin-3-ylmethyl]-amide; and 3,5-Dimethyl-isoxazole-4-carboxylic acid {(R or S)-1-[5-(1-methyl-2-oxo-1,2,3,4-tetrahydro-quinolin-6-yl)-pyridin-3-yl]-ethyl}-amide;

and pharmaceutically acceptable salts thereof.

31. The compound according to claim 1, selected from the group consisting of:

3-Methyl-5-trifluoromethyl-isoxazole-4-carboxylic acid [5-(1-methyl-2-oxo-1,2,3,4-tetrahydro-quinolin-6-yl)-pyridin-3-ylmethyl]-amide;

3-Chloro-pyridine-2-carboxylic acid {1-[5-(1-methyl-2-oxo-1,2,3,4-tetrahydro-quinolin-6-yl)-pyridin-3-yl]-cyclopropyl}-amide;

3-Chloro-pyridine-2-carboxylic acid {1-methyl-1-[5-(1-methyl-2-oxo-1,2,3,4-tetrahydro-quinolin-6-yl)-pyridin-3-yl]-ethyl}-amide;

3,5-Dimethyl-isoxazole-4-carboxylic acid {1-methyl-1-[5-(1-methyl-2-oxo-1,2,3,4-tetrahydro-quinolin-6-yl)-pyridin-3-yl]-ethyl}-amide;

3-Chloro-pyridine-2-carboxylic acid [5-(2-oxo-1,2,3,4-tetrahydro-quinolin-6-yl)-pyridin-3-ylmethyl]-amide;

3,5-Dimethyl-isoxazole-4-carboxylic acid [5-(2-oxo-1,2,3,4-tetrahydro-quinolin-6-yl)-pyridin-3-ylmethyl]-amide;

3-Chloro-pyridine-2-carboxylic acid {1-[5-(7-fluoro-1-methyl-2-oxo-1,2,3,4-tetrahydro-quinolin-6-yl)-pyridin-3-yl]-cyclopropyl}-amide;

3-Methyl-pyridine-2-carboxylic acid {1-[5-(1-methyl-2-oxo-1,2,3,4-tetrahydro-quinolin-6-yl)-pyridin-3-yl]-cyclopropyl}-amide;

N-{(trans)-4-[5-(1-Methyl-2-oxo-1,2,3,4-tetrahydro-quinolin-6-yl)-pyridin-3-yloxy]-cyclohexyl}-propionamide;

5-Trifluoromethyl-isoxazole-4-carboxylic acid [5-(1-methyl-2-oxo-1,2,3,4-tetrahydro-quinolin-6-yl)-pyridin-3-ylmethyl]-amide;

7-Fluoro-1-methyl-6-[5-((S)-pyrrolidin-3-yloxy)-pyridin-3-yl]-3,4-dihydro-1H-quinolin-2-one;

(R)-2-[5-(1-Methyl-2-oxo-1,2,3,4-tetrahydro-quinolin-6-yl)-pyridin-3-yloxymethyl]-pyrrolidine-1-carboxylic acid tert-butyl ester;

1-Methyl-6-[5-((R)-1-pyrrolidin-2-ylmethoxy)-pyridin-3-yl]-3,4-dihydro-1H-quinolin-2-one hydrochloride;

6-(5-Aminomethyl-pyridin-3-yl)-3,4-dihydro-1H-quinolin-2-one; and

6-[5-(1-Amino-cyclopropyl)-pyridin-3-yl]-7-fluoro-1-methyl-3,4-dihydro-1H-quinolin-2-one;

and pharmaceutically acceptable salts thereof.

32. The compound according to claim 1, selected from the group consisting of:

Ethanesulfonic acid {2-[5-(1-methyl-2-oxo-1,2,3,4-tetrahydro-quinolin-6-yl)-pyridin-3-yloxy]-ethyl}-amide;

3-Chloro-N-[5-(1-methyl-2-oxo-1,2,3,4-tetrahydro-quinolin-6-yl)-pyridin-3-ylmethyl]-benzenesulfonamide;

6-Methoxy-pyridin-3-sulfonic acid [5-(1-methyl-2-oxo-1,2,3,4-tetrahydro-quinolin-6-yl)-pyridin-3-ylmethyl]-amide;

3,5-Dimethyl-isoxazole-4-sulfonic acid [5-(1-methyl-2-oxo-1,2,3,4-tetrahydro-quinolin-6-yl)-pyridin-3-ylmethyl]-amide;

Cyclopropanesulfonic acid [5-(1-methyl-2-oxo-1,2,3,4-tetrahydro-quinolin-6-yl)-pyridin-3-ylmethyl]-amide;

3,4-Dichloro-N-[5-(1-methyl-2-oxo-1,2,3,4-tetrahydro-quinolin-6-yl)-pyridin-3-ylmethyl]-benzenesulfonamide;

1-Methyl-1H-imidazole-4-sulfonic acid [5-(1-methyl-2-oxo-1,2,3,4-tetrahydro-quinolin-6-yl)-pyridin-3-ylmethyl]-amide;

6-Chloro-pyridine-3-sulfonic acid [5-(1-methyl-2-oxo-1,2,3,4-tetrahydro-quinolin-6-yl)-pyridin-3-ylmethyl]-amide;

1-Methyl-1H-pyrazole-4-sulfonic acid [5-(1-methyl-2-oxo-1,2,3,4-tetrahydro-quinolin-6-yl)-pyridin-3-ylmethyl]-amide;

6-[5-((S)-1-Ethanesulfonyl-piperidin-3-yloxy)-pyridin-3-yl]-1-methyl-3,4-dihydro-1H-quinolin-2-one;

6-[5-(1-Ethanesulfonyl-piperidin-4-yloxy)-pyridin-3-yl]-1-methyl-3,4-dihydro-1H-quinolin-2-one;
2,2,2-Trifluoro-ethanesulfonic acid [5-(1-methyl-2-oxo-1,2,3,4-tetrahydro-quinolin-6-yl)-pyridin-3-ylmethyl]-amide;
C,C,C-Trifluoro-N-[5-(1-methyl-2-oxo-1,2,3,4-tetrahydro-quinolin-6-yl)-pyridin-3-ylmethyl]-methanesulfonamide;
6-[5-((S)-1-Ethanesulfonyl-pyrrolidin-3-yloxy)-pyridin-3-yl]-1-methyl-3,4-dihydro-1H-quinolin-2-one; and
6-[5-((S)-1-Ethanesulfonyl-azetidin-2-ylmethoxy)-pyridin-3-yl]-1-methyl-3,4-dihydro-1H-quinolin-2-one:
and pharmaceutically acceptable salts thereof.

33. The compound according to claim 1, selected from the group consisting of:
Ethanesulfonic acid {1-[5-(1-methyl-2-oxo-1,2,3,4-tetrahydro-quinolin-6-yl)-pyridin-3-yl]-cyclopropyl}-amide;
6-[5-((S)-1-Ethanesulfonyl-pyrrolidin-2-ylmethoxy)-pyridin-3-yl]-1-methyl-3,4-dihydro-1H-quinolin-2-one;
6-[5-((R)-1-Ethanesulfonyl-pyrrolidin-3-yloxy)-pyridin-3-yl]-7-fluoro-1-methyl-3,4-dihydro-1H-quinolin-2-one;
6-[5-((R)-1-Ethanesulfonyl-pyrrolidin-3-yloxy)-pyridin-3-yl]-1-methyl-3,4-dihydro-1H-quinolin-2-one;
6-[5-(1-Ethanesulfonyl-azetidin-3-yloxy)-pyridin-3-yl]-1-methyl-3,4-dihydro-1H-quinolin-2-one,
Ethanesulfonic acid {1-[5-(7-fluoro-1-methyl-2-oxo-1,2,3,4-tetrahydro-quinolin-6-yl)-pyridin-3-yl]-cyclopropyl}-amide;
Ethanesulfonic acid {(trans)-4-[5-(1-methyl-2-oxo-1,2,3,4-tetrahydro-quinolin-6-yl)-pyridin-3-yloxy]-cyclohexyl}-amide;
Ethanesulfonic acid {(R or S)-1-[5-(1-methyl-2-oxo-1,2,3,4-tetrahydro-quinolin-6-yl)-pyridin-3-yl]-ethyl}-amide;
Ethanesulfonic acid {(S or R)-1-[5-(1-methyl-2-oxo-1,2,3,4-tetrahydro-quinolin-6-yl)-pyridin-3-yl]-ethyl}-amide;
1-Methyl-1H-pyrazole-4-carboxylic acid [5-(7-fluoro-1-methyl-2-oxo-1,2,3,4-tetrahydro-quinolin-6-yl)-pyridin-3-ylmethyl]-amide;
(rac)-Ethanesulfonic acid {2-methyl-1-[5-(1-methyl-2-oxo-1,2,3,4-tetrahydro-quinolin-6-yl)-pyridin-3-yl]-propyl}-amide;
(rac)-Ethanesulfonic acid {cyclopropyl-[5-(1-methyl-2-oxo-1,2,3,4-tetrahydro-quinolin-6-yl)-pyridin-3-yl]-methyl}-amide;
(rac)-Ethanesulfonic acid {1-[5-(7-fluoro-1-methyl-2-oxo-1,2,3,4-tetrahydro-quinolin-6-yl)-pyridin-3-yl]-ethyl}-amide;
6-[5-(1,1-Dioxo-1λ6-isothiazolidin-2-ylmethyl)-pyridin-3-yl]-1-methyl-3,4-dihydro-1H-quinolin-2-one; and
(rac)-Ethanesulfonic acid {1-[5-(1-methyl-2-oxo-1,2,3,4-tetrahydro-quinolin-6-yl)-pyridin-3-yl]-propyl}-amide;
and pharmaceutically acceptable salts thereof.

34. The compound according to claim 1, selected from the group consisting of:
Ethanesulfonic acid ethyl-[5-(1-methyl-2-oxo-1,2,3,4-tetrahydro-quinolin-6-yl)-pyridin-3-ylmethyl]-amide;
Ethanesulfonic acid methyl-[5-(1-methyl-2-oxo-1,2,3,4-tetrahydro-quinolin-6-yl)-pyridin-3-ylmethyl]-amide;
Ethanesulfonic acid {1-methyl-1-[5-(1-methyl-2-oxo-1,2,3,4-tetrahydro-quinolin-6-yl)-pyridin-3-yl]-ethyl}-amide;
Ethanesulfonic acid isopropyl-[5-(1-methyl-2-oxo-1,2,3,4-tetrahydro-quinolin-6-yl)-pyridin-3-ylmethyl]-amide;
Ethanesulfonic acid (2-ethoxy-ethyl)-[5-(1-methyl-2-oxo-1,2,3,4-tetrahydro-quinolin-6-yl)-pyridin-3-ylmethyl]-amide;
(rac)-Ethanesulfonic acid methyl-{1-[5-(1-methyl-2-oxo-1,2,3,4-tetrahydro-quinolin-6-yl)-pyridin-3-yl]-ethyl}-amide;
(rac)-Ethanesulfonic acid ethyl-{1-[5-(1-methyl-2-oxo-1,2,3,4-tetrahydro-quinolin-6-yl)-pyridin-3-yl]-ethyl}-amide;
3,5-Dimethyl-isoxazole-4-carboxylic acid methyl-[5-(1-methyl-2-oxo-1,2,3,4-tetrahydro-quinolin-6-yl)-pyridin-3-ylmethyl]-amide;
6-{5-[2-(1,1-Dioxo-1λ6-isothiazolidin-2-yl)-ethoxy]-pyridin-3-yl}-1-methyl-3,4-dihydro-1H-quinolin-2-one;
Ethanesulfonic acid {(R or S)-1-[5-(7-fluoro-1-methyl-2-oxo-1,2,3,4-tetrahydro-quinolin-6-yl)-pyridin-3-yl]-ethyl}-amide;
Ethanesulfonic acid {(S or R)-1-[5-(7-fluoro-1-methyl-2-oxo-1,2,3,4-tetrahydro-quinolin-6-yl)-pyridin-3-yl]-ethyl}-amide;
Ethanesulfonic acid [5-(7-fluoro-1-methyl-2-oxo-1,2,3,4-tetrahydro-quinolin-6-yl)-4-methyl-pyridin-3-ylmethyl]-amide;
Ethanesulfonic acid [4-chloro-5-(1-methyl-2-oxo-1,2,3,4-tetrahydro-quinolin-6-yl)-pyridin-3-ylmethyl]-amide;
Ethanesulfonic acid [4-methyl-5-(1-methyl-2-oxo-1,2,3,4-tetrahydro-quinolin-6-yl)-pyridin-3-ylmethyl]-amide; and
Ethanesulfonic acid methyl-{2-[5-(1-methyl-2-oxo-1,2,3,4-tetrahydro-quinolin-6-yl)-pyridin-3-yloxy]-ethyl}-amide;
and pharmaceutically acceptable salts thereof.

35. The compound according to claim 1, selected from the group consisting of:
3-Chloro-pyridine-2-carboxylic acid methyl-[5-(1-methyl-2-oxo-1,2,3,4-tetrahydro-quinolin-6-yl)-pyridin-3-ylmethyl]-amide;
N-Methyl-N-{2-[5-(1-methyl-2-oxo-1,2,3,4-tetrahydro-quinolin-6-yl)-pyridin-3-yloxy]-ethyl}-propionamide;
1-Methyl-1H-pyrazole-4-carboxylic acid methyl-[5-(1-methyl-2-oxo-1,2,3,4-tetrahydro-quinolin-6-yl)-pyridin-3-ylmethyl]-amide;
3-Methyl-pyridine-2-carboxylic acid methyl-[5-(1-methyl-2-oxo-1,2,3,4-tetrahydro-quinolin-6-yl)-pyridin-3-ylmethyl]-amide;
3-Chloro-pyridine-2-carboxylic acid [5-(7-fluoro-1-methyl-2-oxo-1,2,3,4-tetrahydro-quinolin-6-yl)-pyridin-3-ylmethyl]-methyl-amide;
3-Chloro-pyridine-2-carboxylic acid methyl-{1-[5-(1-methyl-2-oxo-1,2,3,4-tetrahydro-quinolin-6-yl)-pyridin-3-yl]-cyclopropyl}-amide;
1-Methyl-1H-pyrazole-4-carboxylic acid [5-(7-fluoro-1-methyl-2-oxo-1,2,3,4-tetrahydro-quinolin-6-yl)-pyridin-3-ylmethyl]-methyl-amide;
Ethanesulfonic acid [5-(8-chloro-2-oxo-1,2,3,4-tetrahydro-quinolin-6-yl)-pyridin-3-ylmethyl]-amide;
3-Chloro-pyridine-2-carboxylic acid [5-(8-chloro-2-oxo-1,2,3,4-tetrahydro-quinolin-6-yl)-pyridin-3-ylmethyl]-amide;
3,5-Dimethyl-isoxazole-4-carboxylic acid [5-(8-chloro-2-oxo-1,2,3,4-tetrahydro-quinolin-6-yl)-pyridin-3-ylmethyl]-amide;
6-{5-[(3-Ethyl-oxetan-3-ylamino)-methyl]-pyridin-3-yl}-1-methyl-3,4-dihydro-1H-quinolin-2-one;

Ethanesulfonic acid [5-(7-chloro-1-methyl-2-oxo-1,2,3,4-tetrahydro-quinolin-6-yl)-pyridin-3-ylmethyl]-amide;
Ethanesulfonic acid [5-(8-fluoro-1-methyl-2-oxo-1,2,3,4-tetrahydro-quinolin-6-yl)-pyridin-3-ylmethyl]-amide;
Ethanesulfonic acid [5-(8-chloro-1-methyl-2-oxo-1,2,3,4-tetrahydro-quinolin-6-yl)-pyridin-3-ylmethyl]-amide; and
Ethanesulfonic acid [5-(5-fluoro-1-methyl-2-oxo-1,2,3,4-tetrahydro-quinolin-6-yl)-pyridin-3-ylmethyl]-amide;
and pharmaceutically acceptable salts thereof.

36. The compound according to claim 1, selected from the group consisting of:
Ethanesulfonic acid [5-(7-fluoro-1-methyl-2-oxo-1,2,3,4-tetrahydro-quinolin-6-yl)-pyridin-3-ylmethyl]-methyl-amide;
N-[5-(7-Fluoro-1-methyl-2-oxo-1,2,3,4-tetrahydro-quinolin-6-yl)-pyridin-3-ylmethyl]-propionamide;
(rac)-N-{1-[5-(7-Fluoro-1-methyl-2-oxo-1,2,3,4-tetrahydro-quinolin-6-yl)-pyridin-3-yl]-ethyl}-propionamide;
(S)-3-[5-(2-Oxo-1,2,3,4-tetrahydro-quinolin-6-yl)-pyridin-3-yloxy]-pyrrolidine-1-carboxylic acid tert-butyl ester;
3-Chloro-pyridine-2-carboxylic acid methyl-[5-(2-oxo-1,2,3,4-tetrahydro-quinolin-6-yl)-pyridin-3-ylmethyl]-amide;
3-Chloro-pyridine-2-carboxylic acid [5-(8-chloro-2-oxo-1,2,3,4-tetrahydro-quinolin-6-yl)-pyridin-3-ylmethyl]-methyl-amide;
(R)-2-Methyl-propane-2-sulfinic acid [4-chloro-5-(1-methyl-2-oxo-1,2,3,4-tetrahydro-quinolin-6-yl)-pyridin-3-ylmethyl]-amide;
6-(5-Aminomethyl-4-chloro-pyridin-3-yl)-1-methyl-3,4-dihydro-1H-quinolin-2-one hydrochloride;
3,5-Dimethyl-isoxazole-4-carboxylic acid [4-chloro-5-(1-methyl-2-oxo-1,2,3,4-tetrahydro-quinolin-6-yl)-pyridin-3-ylmethyl]-amide;
3-Chloro-pyridine-2-carboxylic acid [4-chloro-5-(1-methyl-2-oxo-1,2,3,4-tetrahydro-quinolin-6-yl)-pyridin-3-ylmethyl]-amide;
(R)-2-Methyl-propane-2-sulfinic acid [4-methyl-5-(1-methyl-2-oxo-1,2,3,4-tetrahydro-quinolin-6-yl)-pyridin-3-ylmethyl]1-amide;
6-(5-Aminomethyl-4-methyl-pyridin-3-yl)-1-methyl-3,4-dihydro-1H-quinolin-2-one hydrochloride;
3,5-Dimethyl-isoxazole-4-carboxylic acid [4-methyl-5-(1-methyl-2-oxo-1,2,3,4-tetrahydro-quinolin-6-yl)-pyridin-3-ylmethyl]-amide;
3-Chloro-pyridine-2-carboxylic acid [4-methyl-5-(1-methyl-2-oxo-1,2,3,4-tetrahydro-quinolin-6-yl)-pyridin-3-ylmethyl]-amide; and
(R)-2-Methyl-propane-2-sulfinic acid [5-(7-fluoro-1-methyl-2-oxo-1,2,3,4-tetrahydro-quinolin-6-yl)-4-methyl-pyridin-3-ylmethyl]-amide;
and pharmaceutically acceptable suits thereof.

37. The compound according to claim 1, selected from the group consisting of:
6-(5-Aminomethyl-4-methyl-pyridin-3-yl)-7-fluoro-1-methyl-3,4-dihydro-1H-quinolin-2-one hydrochloride;
3-Chloro-pyridine-2-carboxylic acid [5-(7-fluoro-1-methyl-2-oxo-1,2,3,4-tetrahydro-quinolin-6-yl)-4-methyl-pyridin-3-ylmethyl]-amide;
3-Chloro-pyridine-2-carboxylic acid [4-chloro-5-(1-methyl-2-oxo-1,2,3,4-tetrahydro-quinolin-6-yl)-pyridin-3-ylmethyl]-methyl-amide;
3-Chloro-pyridine-2-carboxylic acid methyl-[4-methyl-5-(1-methyl-2-oxo-1,2,3,4-tetrahydro-quinolin-6-yl)-pyridin-3-ylmethyl]-amide;
3-Chloro-pyridine-2-carboxylic acid {(R or S)-1-[5-(1-methyl-2-oxo-1,2,3,4-tetrahydro-quinolin-6-yl)-pyridin-3-yl]-ethyl}-amide;
5'-(1-Methyl-2-oxo-1,2,3,4-tetrahydro-quinolin-6-yl)-5,6-dihydro-4H-[3,3']bipyridinyl-1-carboxylic acid tert-butyl ester;
{2-[5-(7-Fluoro-1-methyl-2-oxo-1,2,3,4-tetrahydro-quinolin-6-yl)-pyridin-3-yloxy]-ethyl}-carbamic acid tert-butyl ester;
3-Chloro-pyridine-2-carboxylic acid {2-[5-(1-methyl-2-oxo-1,2,3,4-tetrahydro-quinolin-6-yl)-pyridin-3-yloxy]-ethyl}-amide;
Ethanesulfonic acid [5-(4-oxo-1,2,5,6-tetrahydro-4H-pyrrolo[3,2,1-ij]quinolin-8-yl)-pyridin-3-ylmethyl]-amide;
Ethanesulfonic acid [5-(3-oxo-2,3,6,7-tetrabydro-1H,5H-pyrido[3,2,1-ij]quinolin-9-yl)-pyridin-3-ylmethyl]-amide;
3-Chloro-pyridine-2-carboxylic acid [5-(4-oxo-1,2,5,6-tetrahydro-4H-pyrrolo[3,2,1-ij]quinolin-8-yl)-pyridin-3-ylmethyl]-amide;
3-Chloro-pyridine-2-carboxylic acid methyl-[5-(4-oxo-1,2,5,6-tetrahydro-4H-pyrrolo[3,2,1-ij]quinolin-8-yl)-pyridin-3-ylmethyl]-amide;
6-[5-(2-Amino-ethoxy)-pyridin-3-yl]-7-fluoro-1-methyl-3,4-dihydro-1H-quinolin-2-one hydrochloride;
(R)-2-Methyl-propane-2-sulfinic acid {(R or S)-1-[4-methyl-5-(1-methyl-2-oxo-1,2,3,4-tetrahydro-quinolin-6-yl)-pyridin-3-yl]-ethyl}-amide; and
6-[5-((R or S)-1-Amino-ethyl)-4-methyl-pyridin-3-yl]-1-methyl-3,4-dihydro-1H-quinolin-2-one hydrochloride;
and pharmaceutically acceptable salts thereof.

38. The compound according to claim 1, selected from the group consisting of:
3-Chloro-pyridine-2-carboxylic acid {(R or S)-1-[4-methyl-5-(1-methyl-2-oxo-1,2,3,4-tetrahydro-quinolin-6-yl)-pyridin-3-yl]-ethyl}-amide;
3,5-Dimethyl-isoxazole-4-carboxylic acid {(R or S)-1-[4-methyl-5-(1-methyl-2-oxo-1,2,3,4-tetrahydro-quinolin-6-yl)-pyridin-3-yl]-ethyl}-amide;
Ethanesulfonic acid {2-[5-(7-fluoro-1-methyl-2-oxo-1,2,3,4-tetrahydro-quinolin-6-yl)-pyridin-3-yloxy]-ethyl}-amide;
3-Chloro-pyridine-2-carboxylic acid {2-[5-(7-fluoro-1-methyl-2-oxo-1,2,3,4-tetrahydro-quinolin-6-yl)-pyridin-3-yloxy]-ethyl}-amide;
N-(trans)-4-[5-(1-Methyl-2-oxo-1,2,3,4-tetrahydro-quinolin-6-yl)-pyridin-3-yloxy]-cyclohexyl)-methane-sulfonamide;
3,5-Dimethyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide;
5-(1-Methyl-2-oxo-1,2,3,4-tetrahydro-quinolin-6-yl)-3',6'-dihydro-2'H-[3,4']bipyridinyl-1'-carboxylic acid tert-butyl ester;
Ethanesulfonic acid {2-[5-(7-fluoro-1-methyl-2-oxo-1,2,3,4-tetrahydro-quinolin-6-yl)-pyridin-3-yloxy]-ethyl}-methyl-amide;
(R)-2-Methyl-propane-2-sulfinic acid {(R or S)-1-[4-chloro-5-(1-methyl-2-oxo-1,2,3,4-tetrabydro-quinolin-6-yl)-pyridin-3-yl]-ethyl}-amide;
6-[5-(R or S)-1-Amino-ethyl)-4-chloro-pyridin-3-yl]-1-methyl-3,4-dihydro-1H-quinolin-2-one hydrochloride;
3-Chloro-pyridine-2-carboxylic acid {(R or S)-1-[4-chloro-5-(1-methyl-2-oxo-1,2,3,4-tetrahydro-quinolin-6-yl)-pyridin-3-yl]-ethyl}-amide;

(R)-2-Methyl-propane-2-sulfinic acid {(R or S)-1-[5-(7-fluoro-1-methyl-2-oxo-1,2,3,4-tetrahydro-quinolin-6-yl)-4-methyl-pyridin-3-yl]-ethyl}-amide;

6-[5-((R or S)-1-Amino-ethyl)-4-methyl-pyridin-3-yl]-7-fluoro-1-methyl-3,4-dihydro-1H-quinolin-2-one hydrochloride;

6-[5-((S)-1-Acetyl-pyrrolidin-3-yloxy)-pyridin-3-yl]-1-methyl-3,4-dihydro-1H-quinolin-2-one; and 1-Methyl-6-{5-[(S)-1-(1-methyl-1H-pyrazole-4-carbonyl)-pyrrolidin-3-yloxy]-pyridin-3-yl}-3,4-dihydro-1H-quinolin-2-one;

and pharmaceutically acceptable salts thereof.

39. The compound according to claim 1, selected from the group consisting of:

(S)-3-[5-(1-Methyl-2-oxo-1,2,3,4-tetrahydro-quinolin-6-yl)-pyridin-3-yloxy]-pyrrolidine-1-carboxylic acid ethyl ester;

3,5-Dimethyl-isoxazole-4-carboxylic acid {(R or S)-1-[4-chloro-5-(1-methyl-2-oxo-1,2,3,4-tetrahydro-quinolin-6-yl)-pyridin-3-yl]-ethyl}-amide;

3-Chloro-pyridine-2-carboxylic acid {(R or S)-1-[5-(7-fluoro-1-methyl-2-oxo-1,2,3,4-tetrahydro-quinolin-6-yl)-4-methyl-pyridin-3-yl]-ethyl}-amide;

5-Methyl-isoxazole-4-carboxylic acid [5-(7-fluoro-1-methyl-2-oxo-1,2,34-tetrahydro-quinolin-6-yl)-4-methyl-pyridin-3-ylmethyl]-amide;

5-(1-Methyl-2-oxo-1,2,3,4-tetrahydro-quinolin-6-yl)-3',4',5',6'-tetrahydro-2'H-[3,4']bipyridinyl-1'-carboxylic acid tert-butyl ester;

N-{(R or S)-1-[4-Chloro-5-(1-methyl-2-oxo-1,2,3,4-tetrahydro-quinolin-6-yl)-pyridin-3-yl]-ethyl}-propionamide;

6-[5-(1-Amino-cyclopropyl)-pyridin-3-yl]-1-methyl-1H-quinolin-2-one;

Ethanesulfonic acid [5-(8-fluoro-1-methyl-2-oxo-1,2-dihydro-quinolin-6-yl)-pyridin-3-ylmethyl]-amide;

N-{(R or S)-1-[5-(7-Fluoro-1-methyl-2-oxo-1,2,3,4-tetrabydro-quinolin-6-yl)-4-methyl-pyridin-3-yl]-ethyl}-propionamide;

N-[4-Chloro-5-(1-methyl-2-oxo-1,2,3,4-tetrahydro-quinolin-6-yl)-pyridin-3-ylmethyl]-propionamide;

N-{(R or S)-1-[4-Methyl-5-(1-methyl-2-oxo-1,2,3,4-tetrahydro-quinolin-6-yl)-pyridin-3-yl]-ethyl}-propionamide; and 3,5-Dimethyl-isoxazole-4-carboxylic acid {2-[5-(7-fluoro-1-methyl-2-oxo-1,2,3,4-tetrahydro-quinolin-6-yl)-pyridin-3-yloxy]-ethyl}-amide;

and pharmaceutically acceptable salts thereof.

40. The compound according to claim 1 selected from the group consisting of:

6-[5-(2-Hydroxy-ethylamino)-pyridin-3-yl]-1-methyl-3,4-dihydro-1H-quinolin-2-one;

6-[5-((S)-2-Hydroxymethyl-pyrrolidin-1-yl)-pyridin-3-yl]-1-methyl-3,4-dihydro-1H-quinolin-2-one;

6-[5-((S)-2-Hydroxymethyl-pyrrolidin-1-ylmethyl)-pyridin-3-yl]-1-methyl-3,4-dihydro-1H-quinolin-2-one;

6-[5-((S)-2-Hydroxymethyl-5-oxo-pyrrolidin-1-ylmethyl)-pyridin-3-yl]-1-methyl-3,4-dihydro-1H-quinolin-2-one;

Ethanesulfonic acid [5-(1-methyl-2-oxo-1,2,3,4-tetrahydro-quinolin-6-yl)-pyridin-3-ylmethyl]-amide;

Ethanesulfonic acid [5-(7-fluoro-1-methyl-2-oxo-1,2,3,4-tetrahydro-quinolin-6-yl)-pyridin-3-ylmethyl]-amide; and 1-Methyl-6-[5-(2-oxo-pyrrolidin-1-ylmethyl)-pyridin-3-yl]-3,4-dihydro-1H-quinolin-2-one;

6-[5-((R)-1-Hydroxymethyl-2-methyl-propylamino)-pyridin-3-yl]-1-methyl-3,4-dihydro-1H-quinolin-2-one;

and pharmaceutically acceptable salts thereof.

41. The compound according to claim 1 selected from the group consisting of:

3,5-Dimethyl-isoxazole-4-carboxylic acid [5-(1-methyl-2-oxo-1,2,3,4-tetrahydro-quinolin-6-yl)-pyridin-3-ylmethyl]-amide;

1-Methyl-6-[5-((S)-1-propionyl-pyrrolidin-3-yloxy)-pyridin-3-yl]-3,4-dihydro-1H-quinolin-2-one;

5-Methyl-isoxazole-4-carboxylic acid [5-(1-methyl-2-oxo-1,2,3,4-tetrahydro-quinolin-6-yl)-pyridin-3-ylmethyl]-amide;

3,5-Dimethyl-isoxazole-4-carboxylic acid {2-[5-(1-methyl-2-oxo-1,2,3,4-tetrahydro-quinolin-6-yl)-pyridin-3-yloxy]-ethyl}-amide;

1-Methyl-1H-pyrazole-4-carboxylic acid {2-[5-(1-methyl-2-oxo-1,2,3,4-tetrahydro-quinolin-6-yl)-pyridin-3-yloxy]-ethyl}-amide;

3-Chloro-pyridine-2-carboxylic acid [5-(1-methyl-2-oxo-1,2,3,4-tetrahydro-quinolin-6-yl)-pyridin-3-ylmethyl]-amide;

3-Chloro-pyridine-2-carboxylic acid [5-(7-fluoro-1-methyl-2-oxo-1,2,3,4-tetrahydro-quinolin-6-yl)-pyridin-3-ylmethyl]-amide;

7-Fluoro-1-methyl-6-[5-((R)-1-propionyl-pyrrolidin-3-yloxy)-pyridin-3-yl]-3,4-dihydro-1H-quinolin-2-one;

3-Chloro-pyridine-2-carboxylic acid {1-[5-(1-methyl-2-oxo-1,2,3,4-tetrahydro-quinolin-6-yl)-pyridin-3-yl]-cyclopropyl}-amide;

3-Chloro-pyridine-2-carboxylic acid {1-methyl-1-[5-(1-methyl-2-oxo-1,2,3,4-tetrahydro-quinolin-6-yl)-pyridin-3-yl]-ethyl}-amide;

3-Chloro-pyridine-2-carboxylic acid {1-[5-(7-fluoro-1-methyl-2-oxo-1,2,3,4-tetrahydro-quinolin-6-yl)-pyridin-3-yl]-cyclopropyl}-amide;

Ethanesulfonic acid {(trans)-4-[5-(1-methyl-2-oxo-1,2,3,4-tetrahydro-quinolin-6-yl)-pyridin-3-yloxy]-cyclohexyl}-amide;

1-Methyl-1H-pyrazole-4-carboxylic acid [5-(7-fluoro-1-methyl-2-oxo-1,2,3,4-tetrahydro-quinolin-6-yl)-pyridin-3-ylmethyl]-amide;

Ethanesulfonic acid {1-methyl-1-[5(1-methyl-2-oxo-1,2,3,4-tetrahydro-quinolin-6-yl)-pyridin-3-yl]-ethyl}-amide; and 6-{5-[2-(1,1-Dioxo-1λ6-isothiazolidin-2-yl)-ethoxy]-pyridin-3-yl}-1-methyl-3,4-dihydro-1H-quinolin-2-one;

and pharmaceutically acceptable salts thereof.

42. The compound according to claim 1 selected from the group consisting of: Ethanesulfonic acid {(R or S)-1-[5-(7-fluoro-1-methyl-2-oxo-1,2,3,4-tetrahydro-quinolin-6-yl)-pyridin-3-yl]-ethyl}-amide;

Ethanesulfonic acid {(S or R)-1-[5-(7-fluoro-1-methyl-2-oxo-1,2,3,4-tetrahydro-quinolin-6-yl)-pyridin-3-yl]-ethyl}-amide;

Ethanesulfonic acid methyl-{2-[5-(1-methyl-2-oxo-1,2,3,4-tetrahydro-quinolin-6-yl)-pyridin-3-yloxy]-ethyl}-amide;

Ethanesulfonic acid [5-(4-oxo-1,2,5,6-tetrahydro-4H-pyrrolo[3,2,1-ij]quinolin-8-yl)-pyridin-3-ylmethyl]-amide;

N-{(trans)-4-[5-(1-Methyl-2-oxo-1,2,3,4-tetrahydro-quinolin-6-yl)-pyridin-3-yloxy]-cyclohexyl}-methanesulfonamide;

3,5-Dimethyl-isoxazole-4-carboxylic acid [5-(7-fluoro-1-methyl-2-oxo-1,2,3,4-tetrahydro-quinolin-6-yl)-4-methyl-pyridin-3-ylmethyl]-amide;

5-(1-Methyl-2-oxo-1,2,3,4-tetrahydro-quinolin-6-yl)-3',6'-dihydro-2'H-[3,4']bipyridinyl-1'-carboxylic acid tert-butyl ester;

Ethanesulfonic acid {2-[5-(7-fluoro-1-methyl-2-oxo-1,2,3,4-tetrahydro-quinolin-6-yl)-pyridin-3-yloxy]-ethyl}-methyl-amide;

3,5-Dimethyl-isoxazole-4-carboxylic acid {2-[5-(7-fluoro-1-methyl-2-oxo-1,2,3,4-tetrahydro-quinolin-6-yl)-pyridin-3-yloxy]-ethyl}-amide; and 1-Methyl-6-{5-[(S)-1-(1-methyl-1H-pyrazole-4-carbonyl)-pyrrolidin-3-yloxy]-pyridin-3-yl}-3,4-dihydro-1H-quinolin-2-one;

and pharmaceutically acceptable salts thereof.

43. A pharmaceutical composition, comprising a therapeutically effective amount of a compound according to claim 1, or a pharmaceutically acceptable salt thereof, and a pharmaceutically acceptable excipient.

\* \* \* \* \*